United States Patent
Pellicciari et al.

(10) Patent No.: US 11,254,644 B2
(45) Date of Patent: *Feb. 22, 2022

(54) INHIBITORS OF ALPHA-AMINO-BETA-CARBOXYMUCONIC ACID SEMIALDEHYDE DECARBOXYLASE

(71) Applicant: TES Pharma S.r.l., Corciano (IT)

(72) Inventors: Roberto Pellicciari, Perugia (IT); Johan Auwerx, Buchillon (CH); Nadia Raffaelli, Ancona (IT)

(73) Assignee: TES PHARMA S.R.L., Corciano (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/670,676

(22) Filed: Oct. 31, 2019

(65) Prior Publication Data
US 2020/0207721 A1    Jul. 2, 2020

Related U.S. Application Data

(60) Continuation of application No. 15/612,877, filed on Jun. 2, 2017, now Pat. No. 10,513,499, which is a division of application No. 14/839,209, filed on Aug. 28, 2015, now Pat. No. 9,708,272.

(60) Provisional application No. 62/043,853, filed on Aug. 29, 2014.

(51) Int. Cl.
| | | |
|---|---|---|
| *C07D 239/38* | (2006.01) |
| *C07D 403/12* | (2006.01) |
| *C07D 233/68* | (2006.01) |
| *C07D 233/84* | (2006.01) |
| *C07D 233/96* | (2006.01) |
| *C07D 407/12* | (2006.01) |
| *C07D 409/12* | (2006.01) |
| *A61K 31/505* | (2006.01) |
| *A61K 31/513* | (2006.01) |
| *C07D 239/56* | (2006.01) |
| *C07D 401/04* | (2006.01) |
| *C07D 405/04* | (2006.01) |
| *C07D 409/04* | (2006.01) |
| *C07D 409/14* | (2006.01) |
| *C07D 413/14* | (2006.01) |
| *C07D 417/04* | (2006.01) |

(52) U.S. Cl.
CPC .......... *C07D 239/38* (2013.01); *A61K 31/505* (2013.01); *A61K 31/513* (2013.01); *C07D 233/68* (2013.01); *C07D 233/84* (2013.01); *C07D 233/96* (2013.01); *C07D 239/56* (2013.01); *C07D 401/04* (2013.01); *C07D 403/12* (2013.01); *C07D 405/04* (2013.01); *C07D 407/12* (2013.01); *C07D 409/04* (2013.01); *C07D 409/12* (2013.01); *C07D 409/14* (2013.01); *C07D 413/14* (2013.01); *C07D 417/04* (2013.01)

(58) Field of Classification Search
CPC .. C07D 413/14; C07D 409/14; C07D 409/04; C07D 417/04; C07D 401/04; C07D 239/56; C07D 239/38; C07D 405/04; C07D 403/12; C07D 233/68; C07D 233/84; C07D 233/96; C07D 407/12; C07D 409/12; A61K 31/505; A61K 31/513
See application file for complete search history.

(56) References Cited

U.S. PATENT DOCUMENTS

| | | |
|---|---|---|
| 3,914,250 A | 10/1975 | Kim |
| 3,980,781 A | 9/1976 | Snell et al. |
| 4,000,138 A | 12/1976 | Snell et al. |
| 4,062,950 A | 12/1977 | Frommer et al. |
| 4,174,439 A | 11/1979 | Rauenbusch et al. |
| 4,189,438 A | 2/1980 | Umezawa et al. |
| 4,242,453 A | 12/1980 | Umezawa et al. |
| 4,254,256 A | 3/1981 | Otani et al. |
| 4,273,765 A | 6/1981 | Suhara et al. |
| 4,278,793 A | 7/1981 | Durckheimer et al. |
| 4,399,131 A | 8/1983 | Durckheimer et al. |
| 4,405,644 A | 9/1983 | Kabbet et al. |
| 4,451,455 A | 5/1984 | Vertesy et al. |
| 4,452,813 A | 6/1984 | Fujii et al. |
| 4,598,089 A | 7/1986 | Hadvary et al. |
| 4,623,714 A | 11/1986 | Vertesy et al. |

(Continued)

FOREIGN PATENT DOCUMENTS

| | | |
|---|---|---|
| CN | 1161202 | 10/1997 |
| CN | 102617480 | 8/2012 |

(Continued)

OTHER PUBLICATIONS

Shibata et al., "Phthalate Esters Enhance Quinolinate Production by Inhibiting Amino-Carboxymuconate-Semialdehyde Decarboxylase (ACMSD), a key Enzyme of the Tryptophan-Niacin Pathway," International Congress Series 1304:184-194 (2007).

International Search Report and Written Opinion issued by the International Searching Authority for Application PCT/EP2015/069808, dated Nov. 25, 2015, 15 pages.

(Continued)

*Primary Examiner* — Deepak R Rao
(74) *Attorney, Agent, or Firm* — Cooley LLP

(57) ABSTRACT

The present disclosure discloses compounds capable of modulating the activity of α-amino-β-carboxymuconic acid semialdehyde decarboxylase (ACMSD), which are useful for the prevention and/or the treatment of diseases and disorders associated with defects in NAD⁺ biosynthesis, e.g., metabolic disorders, neurodegenerative diseases, chronic inflammatory diseases, kidney diseases, and diseases associated with ageing. The present application also discloses pharmaceutical compositions comprising said compounds and the use of such compounds as a medicament.

17 Claims, 10 Drawing Sheets

(56) References Cited

U.S. PATENT DOCUMENTS

| | | |
|---|---|---|
| 4,634,765 A | 1/1987 | Liu |
| 4,639,436 A | 1/1987 | Junge et al. |
| 4,701,559 A | 10/1987 | Horii et al. |
| 4,713,313 A | 12/1987 | Bartels-Keith et al. |
| 4,746,680 A | 5/1988 | Jeffery et al. |
| 4,751,237 A | 6/1988 | Chabala et al. |
| 4,758,556 A | 7/1988 | Durckheimer et al. |
| 4,780,126 A | 10/1988 | Diehr et al. |
| 4,791,114 A | 12/1988 | Constansa et al. |
| 4,806,147 A | 2/1989 | Fest et al. |
| 4,806,564 A | 2/1989 | Chabala et al. |
| 4,806,570 A | 2/1989 | Jeffery et al. |
| 4,816,477 A | 3/1989 | Girotra |
| 4,847,271 A | 7/1989 | Chabala et al. |
| 4,921,954 A | 5/1990 | Witkamp et al. |
| 4,927,454 A | 5/1990 | Fest et al. |
| 4,956,366 A | 9/1990 | Nimmesgern et al. |
| 4,973,587 A | 11/1990 | Ward et al. |
| 4,983,597 A | 1/1991 | Yang et al. |
| 4,990,637 A | 2/1991 | Fest et al. |
| 5,013,837 A | 5/1991 | Ward et al. |
| 5,081,122 A | 1/1992 | Ward |
| 5,091,418 A | 2/1992 | Sawada et al. |
| 5,091,524 A | 2/1992 | Vertesy et al. |
| 5,112,820 A | 5/1992 | Ward |
| 5,120,729 A | 6/1992 | Chabla et al. |
| 5,157,116 A | 10/1992 | Ducep et al. |
| 5,164,494 A | 11/1992 | Witkamp et al. |
| 5,182,298 A | 1/1993 | Helms et al. |
| 5,192,772 A | 3/1993 | Yoshikuni et al. |
| 5,217,877 A | 6/1993 | Sawada et al. |
| 5,236,917 A | 8/1993 | Dunlap et al. |
| 5,256,675 A | 10/1993 | Matsuo et al. |
| 5,292,736 A | 3/1994 | Kumar et al. |
| 5,359,058 A | 10/1994 | Verweij et al. |
| 5,366,982 A | 11/1994 | Dereu et al. |
| 5,369,107 A | 11/1994 | Matsuo et al. |
| 5,371,074 A | 12/1994 | Dunlap et al. |
| 5,391,571 A | 2/1995 | Mewshaw et al. |
| 5,436,272 A | 7/1995 | Scheinbaum |
| 5,444,061 A | 8/1995 | Bisset et al. |
| 5,451,677 A | 9/1995 | Fisher et al. |
| 5,462,960 A | 10/1995 | Barth et al. |
| 5,468,743 A | 11/1995 | Janssens et al. |
| 5,472,967 A | 12/1995 | Hoornaert et al. |
| 5,492,915 A | 2/1996 | Dereu et al. |
| 5,504,078 A | 4/1996 | Ducep et al. |
| 5,512,565 A | 4/1996 | Mewshaw et al. |
| 5,521,283 A | 5/1996 | DiMarchi et al. |
| 5,532,237 A | 7/1996 | Gallant et al. |
| 5,552,522 A | 9/1996 | DiMarchi et al. |
| 5,552,523 A | 9/1996 | Basinski et al. |
| 5,552,524 A | 9/1996 | Basinski et al. |
| 5,595,988 A | 1/1997 | Janssens et al. |
| 5,596,012 A | 1/1997 | Dunlap et al. |
| 5,602,151 A | 2/1997 | Mewshaw et al. |
| 5,624,941 A | 4/1997 | Barth et al. |
| 5,629,308 A | 5/1997 | Janssens et al. |
| 5,633,379 A | 5/1997 | Allgeier |
| 5,650,422 A | 7/1997 | Dunlap et al. |
| 5,705,515 A | 1/1998 | Fisher et al. |
| 5,710,146 A | 1/1998 | Durckheimer et al. |
| 5,724,115 A | 3/1998 | Sakai et al. |
| 5,739,106 A | 4/1998 | Rink et al. |
| 5,760,038 A | 6/1998 | Mumgesan et al. |
| 5,780,473 A | 7/1998 | Mumgesan et al. |
| 5,789,408 A | 8/1998 | Kleinman et al. |
| 5,874,432 A | 2/1999 | Dunlap et al. |
| 5,888,420 A | 3/1999 | Sakai et al. |
| 5,932,569 A | 8/1999 | Janssens et al. |
| 5,962,457 A | 10/1999 | Chenard et al. |
| 6,001,836 A | 12/1999 | Poindexter et al. |
| 6,028,084 A | 2/2000 | Barth et al. |
| 6,140,343 A | 10/2000 | DeNinno et al. |
| 6,140,354 A | 10/2000 | Dax et al. |
| 6,147,089 A | 11/2000 | DeNinno et al. |
| 6,147,090 A | 11/2000 | DeNinno et al. |
| 6,159,964 A | 12/2000 | Ali et al. |
| 6,191,160 B1 | 2/2001 | Gao et al. |
| 6,197,786 B1 | 3/2001 | DeNinno et al. |
| 6,251,912 B1 | 6/2001 | Wissner et al. |
| 6,258,837 B1 | 7/2001 | Fukami et al. |
| 6,297,258 B1 | 10/2001 | Wissner et al. |
| 6,310,075 B1 | 10/2001 | DeNinno et al. |
| 6,313,298 B1 | 11/2001 | Gao et al. |
| 6,326,375 B1 | 12/2001 | Fukami et al. |
| 6,329,395 B1 | 12/2001 | Dugar et al. |
| 6,335,345 B1 | 1/2002 | Fukami et al. |
| 6,337,332 B1 | 1/2002 | Carpino |
| 6,340,683 B1 | 1/2002 | Marzabadi et al. |
| 6,358,951 B1 | 3/2002 | Carpino |
| 6,365,633 B1 | 4/2002 | Cheetham et al. |
| 6,369,067 B1 | 4/2002 | Gurram et al. |
| 6,384,051 B1 | 5/2002 | Frost et al. |
| 6,395,751 B1 | 5/2002 | DeNinno et al. |
| 6,451,822 B1 | 9/2002 | Bisagni et al. |
| 6,489,478 B1 | 12/2002 | DeNinno et al. |
| 6,586,448 B1 | 7/2003 | DeNinno et al. |
| 6,649,619 B1 | 11/2003 | Hickey et al. |
| 6,683,079 B2 | 1/2004 | Bisagni et al. |
| 6,706,742 B2 | 3/2004 | De Nanteuil et al. |
| 6,737,427 B2 | 5/2004 | Zhou et al. |
| 6,844,368 B1 | 1/2005 | Roberts et al. |
| 6,872,827 B2 | 3/2005 | Webb et al. |
| 6,900,232 B2 | 5/2005 | Khanna et al. |
| 6,906,082 B2 | 6/2005 | DeNinno et al. |
| 6,921,767 B2 | 7/2005 | Khanna et al. |
| 6,930,185 B2 | 8/2005 | Ishihara et al. |
| 6,949,578 B2 | 9/2005 | Khanna et al. |
| 6,962,914 B2 | 11/2005 | Gudmundsson et al. |
| 7,030,134 B2 | 4/2006 | Gudmundsson et al. |
| 7,034,030 B2 | 4/2006 | Alberti et al. |
| 7,034,039 B2 | 4/2006 | Oi et al. |
| 7,053,217 B2 | 5/2006 | Gurram et al. |
| 7,067,539 B2 | 6/2006 | Kozlowski et al. |
| 7,087,595 B2 | 8/2006 | Janssens et al. |
| 7,109,209 B2 | 9/2006 | Alberti et al. |
| 7,141,569 B2 | 11/2006 | Cheung et al. |
| 7,148,214 B1 | 12/2006 | Janssens et al. |
| 7,153,855 B2 | 12/2006 | Boyd et al. |
| 7,153,861 B2 | 12/2006 | Leach et al. |
| 7,157,581 B2 | 1/2007 | Gurram et al. |
| 7,166,293 B2 | 1/2007 | Teng et al. |
| 7,166,595 B2 | 1/2007 | Zhou et al. |
| 7,169,777 B2 | 1/2007 | Backer et al. |
| 7,183,287 B2 | 2/2007 | Durley |
| 7,235,690 B2 | 6/2007 | Brendel et al. |
| 7,332,514 B2 | 2/2008 | Maeda et al. |
| 7,332,608 B2 | 2/2008 | Brendel et al. |
| 7,345,051 B2 | 3/2008 | Zhou et al. |
| 7,348,334 B2 | 3/2008 | Igbal et al. |
| 7,361,665 B2 | 4/2008 | Ledeboer et al. |
| 7,432,377 B2 | 10/2008 | Chew et al. |
| 7,470,694 B2 | 12/2008 | Leach et al. |
| 7,482,343 B2 | 1/2009 | Zhou et al. |
| 7,504,401 B2 | 3/2009 | Kelly et al. |
| 7,504,409 B2 | 3/2009 | Zhou et al. |
| 7,507,767 B2 | 3/2009 | Kozlowski et al. |
| 7,560,552 B2 | 7/2009 | Michaelides et al. |
| 7,582,645 B2 | 9/2009 | Dixon et al. |
| 7,589,197 B2 | 9/2009 | Yen et al. |
| 7,615,643 B2 | 11/2009 | Kuntz et al. |
| 7,638,520 B2 | 12/2009 | Hickey et al. |
| 7,652,019 B2 | 1/2010 | Hickey et al. |
| 7,652,022 B2 | 1/2010 | Floersheimer et al. |
| 7,678,804 B2 | 3/2010 | Dixon et al. |
| 7,718,702 B2 | 5/2010 | Kozlowski et al. |
| 7,807,701 B2 | 10/2010 | Maeda et al. |
| 7,872,018 B2 | 1/2011 | Ibrahim et al. |
| 7,906,517 B2 | 3/2011 | Nakamura et al. |
| 7,973,060 B2 | 7/2011 | Kim et al. |
| 8,008,307 B2 | 8/2011 | Claiborne et al. |
| 8,076,364 B2 | 12/2011 | Nakamura et al. |
| 8,110,583 B2 | 2/2012 | Staehle et al. |

(56) References Cited

U.S. PATENT DOCUMENTS

| | | |
|---|---|---|
| 8,163,788 B2 | 4/2012 | Famulok et al. |
| 8,193,206 B2 | 6/2012 | Yen et al. |
| 8,207,345 B2 | 6/2012 | Schiemann et al. |
| 8,236,823 B2 | 8/2012 | Hodous et al. |
| 8,252,822 B2 | 8/2012 | An et al. |
| 8,268,849 B2 | 9/2012 | Kador et al. |
| 8,299,123 B2 | 10/2012 | Dey et al. |
| 8,309,550 B2 | 11/2012 | Luo et al. |
| 8,415,386 B2 | 4/2013 | Devasthale et al. |
| 8,461,161 B2 | 6/2013 | Burns et al. |
| 8,466,141 B2 | 6/2013 | Yoo et al. |
| 8,470,841 B2 | 6/2013 | Zoller et al. |
| 8,481,550 B2 | 7/2013 | Claiborne et al. |
| 8,497,265 B2 | 7/2013 | Allen et al. |
| 8,614,234 B2 | 12/2013 | Guo et al. |
| 8,633,182 B2 | 1/2014 | Hamprecht et al. |
| 8,642,660 B2 | 2/2014 | Goldfarb |
| 8,716,470 B2 | 5/2014 | Yoshihara et al. |
| 8,759,371 B2 | 6/2014 | Lucas |
| 8,765,757 B2 | 7/2014 | Chan et al. |
| 8,765,768 B2 | 7/2014 | Cushing et al. |
| 8,791,272 B2 | 7/2014 | Oost et al. |
| 8,871,775 B2 | 10/2014 | Hickey et al. |
| 8,884,020 B2 | 11/2014 | Talley et al. |
| 8,906,944 B2 | 12/2014 | Guo et al. |
| 8,946,230 B2 | 2/2015 | Allen et al. |
| 8,957,073 B2 | 2/2015 | Allen et al. |
| 9,029,386 B2 | 5/2015 | Bums et al. |
| 9,040,538 B2 | 5/2015 | Attardo et al. |
| 9,266,841 B2 | 2/2016 | Hickey et al. |
| 9,708,272 B2 | 7/2017 | Pellicciari et al. |
| 9,957,247 B2 | 5/2018 | Wang |
| 10,513,499 B2 | 12/2019 | Pellicciari et al. |
| 2002/0006964 A1 | 1/2002 | Young et al. |
| 2002/0022637 A1 | 2/2002 | Li et al. |
| 2002/0049196 A1 | 4/2002 | Carpino et al. |
| 2002/0103199 A1 | 8/2002 | Corbett et al. |
| 2003/0087821 A1 | 5/2003 | Beeley et al. |
| 2003/0158199 A1 | 8/2003 | Stieber et al. |
| 2003/0162762 A1 | 8/2003 | Lee et al. |
| 2003/0181468 A1 | 9/2003 | Michaelides et al. |
| 2003/0225273 A1 | 12/2003 | Michaelides et al. |
| 2005/0026933 A1 | 2/2005 | Greenberger et al. |
| 2005/0197327 A1 | 9/2005 | Bergnes et al. |
| 2005/0245570 A1 | 11/2005 | DeNinno et al. |
| 2006/0035893 A1 | 2/2006 | Jung et al. |
| 2006/0100226 A1 | 5/2006 | Sikorski et al. |
| 2006/0167026 A1 | 7/2006 | Nawa et al. |
| 2006/0235046 A1 | 10/2006 | Zacharchuk et al. |
| 2007/0060594 A1 | 3/2007 | Schwartz et al. |
| 2007/0208164 A1 | 9/2007 | Olszewski et al. |
| 2008/0004302 A1 | 1/2008 | Theoclitou et al. |
| 2008/0045534 A1 | 2/2008 | Vernier et al. |
| 2008/0280891 A1 | 11/2008 | Kelly et al. |
| 2008/0293711 A1 | 11/2008 | Clark et al. |
| 2009/0017036 A1 | 1/2009 | Jung et al. |
| 2009/0118503 A1 | 5/2009 | Sprott et al. |
| 2009/0143396 A1 | 6/2009 | Malecha et al. |
| 2009/0163545 A1 | 6/2009 | Goldfarb |
| 2009/0169558 A1 | 7/2009 | Heng et al. |
| 2009/0170877 A1 | 7/2009 | Hickey et al. |
| 2009/0181846 A1 | 7/2009 | Lim et al. |
| 2009/0306039 A1 | 12/2009 | Pan et al. |
| 2010/0048594 A1 | 2/2010 | Famulok et al. |
| 2010/0144765 A1 | 6/2010 | Hickey et al. |
| 2010/0152165 A1 | 6/2010 | Negoro et al. |
| 2010/0184809 A1 | 7/2010 | Kremoser et al. |
| 2010/0216827 A1 | 8/2010 | Ma et al. |
| 2010/0286131 A1 | 11/2010 | Beaulieu et al. |
| 2010/0311748 A1 | 12/2010 | Dakin et al. |
| 2011/0092490 A1 | 4/2011 | Wang et al. |
| 2011/0294836 A1 | 12/2011 | Song et al. |
| 2012/0184572 A1 | 7/2012 | Song et al. |
| 2012/0189670 A1 | 7/2012 | Kirkpatrick et al. |
| 2012/0220614 A1 | 8/2012 | Boyle et al. |
| 2012/0225061 A1 | 9/2012 | Burger et al. |
| 2012/0292565 A1 | 11/2012 | Delfort et al. |
| 2013/0029948 A1 | 1/2013 | Roppe et al. |
| 2013/0085131 A1 | 4/2013 | Bui et al. |
| 2013/0096134 A1 | 4/2013 | Duguette et al. |
| 2013/0137708 A1 | 5/2013 | Garske et al. |
| 2013/0190320 A1 | 7/2013 | Xu et al. |
| 2014/0070180 A1 | 3/2014 | Choi et al. |
| 2014/0073634 A1 | 3/2014 | Jones et al. |
| 2014/0100231 A1 | 4/2014 | Arrington et al. |
| 2014/0148484 A1 | 5/2014 | Schnapp et al. |
| 2014/0228363 A1 | 8/2014 | Burger et al. |
| 2014/0248378 A1 | 9/2014 | Cockcroft et al. |
| 2014/0249159 A1 | 9/2014 | Kurose et al. |
| 2014/0303163 A1 | 10/2014 | Luo |
| 2014/0350256 A1 | 11/2014 | McKenzie et al. |
| 2015/0141434 A1 | 5/2015 | Park et al. |
| 2015/0152077 A1 | 6/2015 | Wang et al. |
| 2015/0174132 A1 | 6/2015 | Foley et al. |
| 2015/0197513 A1 | 7/2015 | Wrasidlo et al. |
| 2016/0060226 A1 | 3/2016 | Pellicciari et al. |
| 2018/0134677 A1 | 5/2018 | Nan |

FOREIGN PATENT DOCUMENTS

| | | |
|---|---|---|
| CN | 104059082 | 9/2014 |
| DE | 102011088009 | 6/2013 |
| EP | 0 1010691 | 9/1983 |
| EP | 0 1044970 | 4/1984 |
| EP | 0 318 860 | 6/1989 |
| EP | 0 411 703 | 2/1991 |
| EP | 518435 | 12/1992 |
| EP | 687935 | 12/1995 |
| EP | 934934 | 8/1999 |
| EP | 1 258 476 | 11/2002 |
| FR | 2996129 | 4/2014 |
| GB | 2388596 | 11/2003 |
| JP | 01132581 A | 5/1989 |
| JP | H01216997 | 8/1989 |
| JP | H08327993 | 12/1996 |
| JP | H09124633 | 5/1997 |
| JP | H09274290 | 10/1997 |
| JP | H11209366 | 8/1999 |
| JP | 2000/256190 | 9/2000 |
| JP | 2002/114768 | 4/2002 |
| JP | 2004/250400 | 9/2004 |
| JP | 2005/015421 | 1/2005 |
| JP | 2005/060299 | 3/2005 |
| JP | 2005/104851 | 4/2005 |
| JP | 2005/194250 | 7/2005 |
| JP | 2007/317714 | 12/2007 |
| RU | 2135503 C1 | 8/1999 |
| WO | WO 94/09134 | 4/1994 |
| WO | WO 95/19358 | 7/1995 |
| WO | WO 96/14307 | 5/1996 |
| WO | WO 96/23513 | 8/1996 |
| WO | WO 96/23514 | 8/1996 |
| WO | WO 96/23515 | 8/1996 |
| WO | WO 96/23516 | 8/1996 |
| WO | WO 96/23517 | 8/1996 |
| WO | WO 96/23518 | 8/1996 |
| WO | WO 96/23519 | 8/1996 |
| WO | WO 96/23520 | 8/1996 |
| WO | WO 96/33159 | 10/1996 |
| WO | WO 97/19682 | 6/1997 |
| WO | WO 97/20820 | 6/1997 |
| WO | WO 97/20821 | 6/1997 |
| WO | WO 97/20822 | 6/1997 |
| WO | WO 97/20823 | 6/1997 |
| WO | WO 97/27847 | 8/1997 |
| WO | WO 97/27857 | 8/1997 |
| WO | WO 97/28115 | 8/1997 |
| WO | WO 97/28137 | 8/1997 |
| WO | WO 97/29079 | 8/1997 |
| WO | WO 98/22128 | 5/1998 |
| WO | WO 98/27063 | 6/1998 |
| WO | WO 98/31227 | 7/1998 |
| WO | WO 98/33765 | 8/1998 |
| WO | WO 98/37061 | 8/1998 |

(56) References Cited

FOREIGN PATENT DOCUMENTS

| | | |
|---|---|---|
| WO | WO 98/41519 | 9/1998 |
| WO | WO 98/43635 | 10/1998 |
| WO | WO 98/43636 | 10/1998 |
| WO | WO 99/00123 | 1/1999 |
| WO | WO 99/02499 | 1/1999 |
| WO | WO 99/08501 | 2/1999 |
| WO | WO 99/25728 | 5/1999 |
| WO | WO 99/041237 A1 | 8/1999 |
| WO | WO 99/43813 | 9/1999 |
| WO | WO 99/51600 | 10/1999 |
| WO | WO 99/64002 | 12/1999 |
| WO | WO 00/10967 | 3/2000 |
| WO | WO 00/10968 | 3/2000 |
| WO | WO 00/18573 | 4/2000 |
| WO | WO 00/21509 | 4/2000 |
| WO | WO 2000/018740 | 4/2000 |
| WO | WO 2000/058300 | 10/2000 |
| WO | WO 00/64880 | 11/2000 |
| WO | WO 00/68197 | 11/2000 |
| WO | WO 00/69849 | 11/2000 |
| WO | WO 00/74679 | 12/2000 |
| WO | WO 01/02379 | 1/2001 |
| WO | WO 01/07409 | 2/2001 |
| WO | WO 01/09120 | 2/2001 |
| WO | WO 01/14376 | 3/2001 |
| WO | WO 01/23387 | 4/2001 |
| WO | WO 01/23388 | 4/2001 |
| WO | WO 01/23389 | 4/2001 |
| WO | WO 01/27060 | 4/2001 |
| WO | WO 01/27068 | 4/2001 |
| WO | WO 01/44201 | 6/2001 |
| WO | WO 01/56592 | 8/2001 |
| WO | WO 01/58869 | 8/2001 |
| WO | WO 01/062341 | 8/2001 |
| WO | WO 01/62737 | 8/2001 |
| WO | WO 01/62738 | 8/2001 |
| WO | WO 2001/057018 | 8/2001 |
| WO | WO 01/64632 | 9/2001 |
| WO | WO 01/64633 | 9/2001 |
| WO | WO 01/64634 | 9/2001 |
| WO | WO 01/66548 | 9/2001 |
| WO | WO 01/68609 | 9/2001 |
| WO | WO 01/70337 | 9/2001 |
| WO | WO 01/70708 | 9/2001 |
| WO | WO 01/74782 | 10/2001 |
| WO | WO 01/74844 | 10/2001 |
| WO | WO 01/77094 | 10/2001 |
| WO | WO 01/82925 | 11/2001 |
| WO | WO 01/85098 | 11/2001 |
| WO | WO 01/85173 | 11/2001 |
| WO | WO 01/85690 | 11/2001 |
| WO | WO 01/85714 | 11/2001 |
| WO | WO 01/85730 | 11/2001 |
| WO | WO 01/87335 | 11/2001 |
| WO | WO 01/87834 | 11/2001 |
| WO | WO 01/89528 | 11/2001 |
| WO | WO 01/90090 | 11/2001 |
| WO | WO 01/90091 | 11/2001 |
| WO | WO 01/90092 | 11/2001 |
| WO | WO 01/91752 | 12/2001 |
| WO | WO 01/94299 A1 | 12/2001 |
| WO | WO 01/94300 | 12/2001 |
| WO | WO 01/96302 | 12/2001 |
| WO | WO 02/04433 | 1/2002 |
| WO | WO 02/06245 | 1/2002 |
| WO | WO 02/08250 | 1/2002 |
| WO | WO 02/059095 | 1/2002 |
| WO | WO 02/10169 | 2/2002 |
| WO | WO 02/011715 | 2/2002 |
| WO | WO 02/12166 | 2/2002 |
| WO | WO 02/12178 | 2/2002 |
| WO | WO 02/14291 | 2/2002 |
| WO | WO 02/15845 | 2/2002 |
| WO | WO 02/15905 | 2/2002 |
| WO | WO 02/15909 | 2/2002 |
| WO | WO 02/20488 | 3/2002 |
| WO | WO 02/20530 | 3/2002 |
| WO | WO 02/22592 | 3/2002 |
| WO | WO 02/26707 | 4/2002 |
| WO | WO 02/26743 | 4/2002 |
| WO | WO 02/32888 | 4/2002 |
| WO | WO 02/32897 | 4/2002 |
| WO | WO 02/36596 | 5/2002 |
| WO | WO 02/40456 | 5/2002 |
| WO | WO 02/40457 | 5/2002 |
| WO | WO 02/44152 | 6/2002 |
| WO | WO 02/48106 | 6/2002 |
| WO | WO 02/48124 | 6/2002 |
| WO | WO 02/48152 | 6/2002 |
| WO | WO 02/49648 | 6/2002 |
| WO | WO 02/051232 | 7/2002 |
| WO | WO 02/051809 | 7/2002 |
| WO | WO 02/051838 | 7/2002 |
| WO | WO 02/051844 | 7/2002 |
| WO | WO 02/059107 | 8/2002 |
| WO | WO 02/059108 | 8/2002 |
| WO | WO 02/059117 | 8/2002 |
| WO | WO 02/062764 | 8/2002 |
| WO | WO 2002/062750 | 8/2002 |
| WO | WO 02/067869 | 9/2002 |
| WO | WO 02/068387 | 9/2002 |
| WO | WO 02/068388 | 9/2002 |
| WO | WO 02/076949 | 10/2002 |
| WO | WO 02/083128 | 10/2002 |
| WO | WO 03/000180 | 1/2003 |
| WO | WO 03/000181 | 1/2003 |
| WO | WO 03/000250 | 1/2003 |
| WO | WO 03/002530 | 1/2003 |
| WO | WO 03/002531 | 1/2003 |
| WO | WO 03/002553 | 1/2003 |
| WO | WO 03/002593 | 1/2003 |
| WO | WO 03/004490 | 1/2003 |
| WO | WO 03/004496 | 1/2003 |
| WO | WO 03/007887 | 1/2003 |
| WO | WO 03/007949 | 1/2003 |
| WO | WO 03/009847 | 2/2003 |
| WO | WO 03/026591 | 4/2003 |
| WO | WO 03/027637 | 4/2003 |
| WO | WO 03/057235 | 7/2003 |
| WO | WO 2004/087677 | 10/2004 |
| WO | WO-2005/076854 A2 | 8/2005 |
| WO | WO 2005/085205 | 9/2005 |
| WO | WO 2005/092896 | 10/2005 |
| WO | WO 2006/032987 | 3/2006 |
| WO | WO 2006/033001 | 3/2006 |
| WO | WO 2006/040646 | 4/2006 |
| WO | WO 2006/128129 | 11/2006 |
| WO | WO 2008/016811 | 2/2008 |
| WO | WO 2009/013545 | 1/2009 |
| WO | WO 2010/085246 | 7/2010 |
| WO | WO 2010/132999 A1 | 11/2010 |
| WO | WO 2011/082098 | 7/2011 |
| WO | WO 2012/026495 | 3/2012 |
| WO | WO 2013/155262 | 10/2013 |
| WO | WO 2013/178816 | 12/2013 |
| WO | WO 2013/184755 A2 | 12/2013 |
| WO | WO 2014/062938 | 4/2014 |
| WO | WO 2014/133112 | 9/2014 |
| WO | WO 2014/175465 | 10/2014 |
| WO | WO 2014/181287 | 11/2014 |
| WO | WO 2015/017546 | 2/2015 |
| WO | WO 2015/058163 | 4/2015 |
| WO | WO 2015/061247 | 4/2015 |
| WO | WO 2015/069287 | 5/2015 |
| WO | WO 2016/030534 A1 | 3/2016 |

OTHER PUBLICATIONS

CAS Registry No. 1796824-13-9.
CAS Registry No. 1796760-16-1.
CAS Registry No. 1795977-02-4.
CAS Registry No. 1541953-22-3.
CAS Registry No. 1540342-74-2.
CAS Registry No. 1538939-71-7.

(56) References Cited

OTHER PUBLICATIONS

CAS Registry No. 1537362-15-4.
CAS Registry No. 1517005-29-6.
CAS Registry No. 1512922-48-3.
CAS Registry No. 1510462-97-1.
CAS Registry No. 1499720-82-9.
CAS Registry No. 1365966-55-7.
CAS Registry No. 1328182-44-0.
CAS Registry No. 1284728-65-9.
CAS Registry No. 1283157-34-5.
CAS Registry No. 1181228-22-7.
CAS Registry No. 1112390-80-3.
CAS Registry No. 1112336-45-4.
CAS Registry No. 1082595-46-7.
CAS Registry No. 1082595-42-3.
CAS Registry No. 1082595-27-4.
CAS Registry No. 1082541-27-2.
CAS Registry No. 1082541-05-6.
CAS Registry No. 1082540-82-6.
CAS Registry No. 1082540-60-0.
CAS Registry No. 1082520-96-4.
CAS Registry No. 1082474-13-2.
CAS Registry No. 1082473-86-6.
CAS Registry No. 1082473-70-8.
CAS Registry No. 1082450-40-5.
CAS Registry No. 1082450-18-7.
CAS Registry No. 1082450-16-5.
CAS Registry No. 1082449-98-6.
CAS Registry No. 1082449-94-2.
CAS Registry No. 1082449-76-0.
CAS Registry No. 1082370-83-9.
CAS Registry No. 1082370-48-6.
CAS Registry No. 1082155-84-7.
CAS Registry No. 1082131-05-2.
CAS Registry No. 1051114-63-6.
CAS Registry No. 1029777-12-5.
CAS Registry No. 1012013-94-3.
CAS Registry No. 1011967-29-5.
CAS Registry No. 1011966-19-0.
CAS Registry No. 1011966-08-7.
CAS Registry No. 1007701-71-4.
CAS Registry No. 954850-51-2.
CAS Registry No. 954330-96-2.
CAS Registry No. 941980-38-7.
CAS Registry No. 927968-94-3.
CAS Registry No. 927968-51-2.
CAS Registry No. 922829-35-4.
CAS Registry No. 922829-05-8.
CAS Registry No. 922653-24-5.
CAS Registry No. 900706-61-8.
CAS Registry No. 900706-59-4.
CAS Registry No. 900706-57-2.
CAS Registry No. 900706-55-0.
CAS Registry No. 892352-75-9.
CAS Registry No. 881298-30-2.
CAS Registry No. 881298-26-6.
CAS Registry No. 881298-18-6.
CAS Registry No. 881298-13-1.
CAS Registry No. 881298-10-8.
CAS Registry No. 881298-06-2.
CAS Registry No. 881297-78-5.
CAS Registry No. 881251-56-5.
CAS Registry No. 881246-64-6.
CAS Registry No. 881246-58-8.
CAS Registry No. 881246-52-2.
CAS Registry No. 881242-29-1.
CAS Registry No. 881242-24-6.
CAS Registry No. 552309-77-0.

Choi, W-K, et al. "Studies on the synthesis of new medicinal agent. III: Studies on the synthesis and antibacterial activities of new cephalosporin derivatives," J. Korean Chem. Soc. (1994), 38(8), 603-607.
Clift M. D. et al. "Synthesis and evaluation of novel aromatic substrates and competitive inhibitors of GABA aminotransferase," Bioorg. Med. Chem. Lett., 15;18(10):3122-3125, (2008).
Database Registry [Online] Chemical Abstracts Service, Columbus, Ohio, US; Dec. 9, 2008, XP002750878, retrieved from STN. Database accession No. 1082473-69-5.
Database Registry [Online] Chemical Abstracts Service, Columbus, Ohio, US; Dec. 9, 2008, XP002750879, retrieved from STN. Database accession No. 1082520-77-1.
Database Registry [Online] Chemical Abstracts Service, Columbus, Ohio, US; Dec. 10, 2008, XP002750880, retrieved from STN. Database accession No. 1082540-59-7.
Database Registry [Online] Chemical Abstracts Service, Columbus, Ohio, US; Feb. 19, 2006, XP002750881, retrieved from STN. Database accession No. 874606-82-3.
Database Registry [Online] Chemical Abstracts Service, Columbus, Ohio, US; Apr. 24, 2008 XP002750882, retrieved from STN. Database accession No. 1017053-26-7.
Database Registry [Online] Chemical Abstracts Service, Columbus, Ohio, US; Feb. 23, 2014 XP002750883, retrieved from STN Database accession No. 1552449-54-3.
Database Registry [Online] Chemical Abstracts Service, Columbus, Ohio, US; Oct. 30, 2007 XP002750884, Database accession No. 951908-78-4.
Database Registry [Online] Chemical Abstracts Service, Columbus, Ohio, US; Jun. 22, 2008 XP002750885, retrieved from STN Database accession No. 1029777-12-5.
Database Registry [Online] Chemical Abstracts Service, Columbus, Ohio, US; Feb. 26, 2009 XP002750886, retrieved from STN Database accession No. 1112336-45-4.
Database Registry [Online] Chemical Abstracts Service, Columbus, Ohio, US; Dec. 9, 2008 XP002750895, Database accession No. 1082369-53-6.
Database Registry [Online] Chemical Abstracts Service, Columbus, Ohio, US; Nov. 19, 2007 XP002750896, retrieved from STN Database accession No. 954850-51-2.
De Figueiredo, L. et al. "Pathway analysis of $NAD^{+\ metabolism}$," Biochem. J., vol. 439, 2011, p. 341-348.
Del Mar-Grasa, M. et al., Daily Oral Oleoyl-Estrone Gavage Induces a Dose-Dependent Loss of Fat in Wistar Rats, Obesity Research, 9:202-209 (2001).
Falch, E. et al: "Substituted Heteroaromatic Anthranlic Acids with Anti-inflammatory Activity", J. Med. Chem., vol. 11, No. 3, May 1, 1968, pp. 608-611.
Fukuwatari, T. et al. "Phthalate esters enhance quinolinate production by inhibiting alpha-amino-beta-carboxymuconate-epsilon-semialdehyde decarboxylase (ACMSD), a key enzyme of the tryptophan pathway", Toxicological Sciences, (2004), vol. 81, p. 302-308.
Fukuwatari, T. et al. "Identification of a toxic mechanism of the plasticizers, phtahlic acid esters, which are putative endocrine disrupters: time-dependent increase in quinolinic acid and its metabolites in rats fed di(2-ethylhexyl)phthalate," Biosci Biotechnol Biochem. (2002), vol. 66, No. 12, p. 2687-2691.
El-Reedy, A. M. et al., "Azolopyrimidines and pyrimidoquinazolines from 4-chloropyrimidines," J. Het. Chem., (1989), 26, 313-316.
Fukuwatari, T. et al., "Growth-promoting activity of pyrazinoic acid, a putative active compound of antituberculosis drug pyrazinamide, in niacin-deficient rats through the inhibition of ACMSD activity", Biosci. Biotechnol. Biochem., (2002), vol. 66, No. 7, p. 1435-1441.
Garavaglia, S. et al. "The crystal structure of human α-amino-β-carboxymuconate-ε-semialdehyde decarboxylase in complex with 1,3-dihydroxyacetonephosphate suggests a regulatory link between NAD synthesis and glycolysis", FEBS J., (2009), vol. 276, No. 22, p. 6615-6623.
Gätjens, J. et al. "Corroborative cobalt and zinc model compounds of alpha-amino-beta-carboxymuconic-epsilon-semialdehyde decarboxylase (ACMSD)", Dalton Transactions, (2009), vol. 1, p. 51-62.

(56) References Cited

OTHER PUBLICATIONS

Hirose, M, et al. "Design and synthesis of novel DFG-out RAF/vascular endothelial growth factor receptor 2 (VEGFR2) inhibitors: 3. Evaluation of 5-amino-linked thiazolo[5,4-d]pyrimidine and thiazolo[5,4-b]pyridine derivatives", Bioorg. Med. Chem., 15;20(18):5600-5615 (2012).

Iwahashi, M. et al., "Design and synthesis of new prostaglandin $D_2$ receptor antagonists," Bioorg. Med. Chem., 19(18):5361-5371, (2011).

Kiec-Kononowicz, K. et al., "Importance of the lipophilic group in carbamates having histamine H3-receptor antagonist activity", Pharmazie, 55:349-355 (2000).

Lazewska, D. et al., "Piperidine-containing histamine H3-receptor antagonists of the carbamate series: variation of the spacer length", Pharmazie, 56:927-932 (2001).

Le Floc'h, N et al., "Tryptophan metabolism, from nutrition to potential therapeutic applications", Amino Acids, (2011), 41(5), p. 1195-1205.

Li, T. et al. "Alpha-amino-beta-carboxymuconic-epsilon-semialdehyde decarboxylase (ACMSD) is a new member of the amidohydrolase superfamily", Biochemistry, (2006), vol. 45, No. 21, p. 6628-6634.

Martynowski D. et al. "Crystal structure of alpha-amino-beta-carboxymuconate-epsilon-semialdehyde decarboxylase: insight into the active site and catalytic mechanism of a novel decarboxylation reaction", Biochemistry, (2006), vol. 45, No. 35, p. 10412-10421.

Norman et al., "Structure-Activity Relationships of a Series of Pyrrolo [3,2-d]pyrimidine Derivatives and Related Compounds as Neuropeptide Y5 Receptor Antagonists", J. Med. Chem. 43:4288-4312 (2000).

Pucci, L. et al., "Tissue expression and biochemical characterization of human 2-amino 3-carboxymuconate 6-semialdehyde decarboxylase, a key enzyme in tryptophan catabolism", FEBS Journal, (2007), vol. 274, No. 3, p. 827-840.

Reidemeister, S. et al., "Substituted N-phenylcarbamates as histamine H3 receptor antagonists with improved in vivo potency", Pharmazie, 55:83-6 (2000).

Sasaki, N. et al. "Down-regulation of alpha-amino-beta-carboxymuconate-epsilon-semialdehyde decarboxylase by polyunsaturated fatty acids in hepatocytes is not mediated by PPARalpha", Eur. J. Nutr. (2008), vol. 47, No. 2, p. 80-86.

Sasse, A. et al., "New Histamine H3-Receptor Ligands of the Proxifan Series: Imoproxifan and Other Selective Antagonists with High Oral in Vivo Potency", J. Med. Chem. 43:3335-3343 (2000).

Sasse, A. et al. "Benzophenone Derivatives and Related Compounds as Potent Histamine H3-Receptor Antagonists and Potential PET/SPECT Ligands", Arch. Pharm., (Weinheim), 334:45-52 (2001).

Chaudhary et al. "Design, syntheses and evaluation of 4-oxo-4-cyano thiouracils as SecA inhibitors," Bioorg. Med. Chem. 23(1):105-117 (2015).

Tyynismaa, H. et al. "Mutant mitochondrial helicase Twinkle causes multiple mtDNA deletions and a late-onset mitochondrial disease in mice.", Proc. Natl. Acad. Sci. USA vol. 102: No. 49 17687-17692 (2005).

Wei, Q., et al. "Mouse model of ischemic acute kidney injury: technical notes and trick", Am. J. Physiol-Rena, (2012), 303(11), F1487-F1494.

CAS Registry Numbers (Indexed 2003).
CAS Registry Numbers (Indexed 2006).
B. Stanovinik et al.,91 Advances in Heterocyclic Chemistry, 1-134 (2006).
Mai et al., 18 Bioorganic & Medicinal Chemistry Letters, 2530-2535 (2008).
CAS Registry Nos. (2001).
CAS Registry Nos. (2003).
CAS Registry Nos. (2006).
CAS Registry Nos. (2007).
CAS Registry Nos. (2008).
CAS Registry Nos. (2009).
CAS Registry Nos. (2011).
CAS Registry Nos. (2012).
CAS Registry Nos. (2013).
CAS Registry Nos. (2014).
Chekanov, "Design, synthesis and biological evaluation of 2-aminopyrimidinones and their 6-aza-analogs as a new class of CK2 inhibitors," Journal of Enzyme Inhibition and Medicinal Chemistry, 639-646 (2014).
Montezano et al., Basic & Clinical Pharmacology & Toxicology, 87-94 (2011).
CAS Abstract WO 2001/94299 (2001), 2 pages.
Lin et al., "Nicotinamide adenine dinucleotide, a metabolic regulator of transcription, longevity and disease," 15 Current Opinion in Cell Biology, 241-246 (2003).
Wang et al., "Mathematical modeling in cancer drug discovery," Drug Discovery Today, 19(2):145-150 (2014).
Marelli et al., "Tumor Targeting via Intergrin Ligands," Frontiers in Oncology, 1-12 (2013).
Kahn et al., "Nicotinamide adenine dinucleotide metabolism as an attractive target for drug discovery," Expert Opinion on Therapeutic Targets, 695-705 (2007).
Shi et al., Advanced Oxidation Protein Products Promote Inflammation in Diabetic Kidney through Activation of Renal Nicotinamide Adenine Dinucleotide Phosphate Oxidase, Endocrinology, 1829-1839 (2008).
Sevastianova et al., "Nonalcoholic Fatty Liver Disease: Detection of Elevated Nicotinamide Adenine Dinucleotide Phosphate \Nith in Vivo 3.0-$T^{31}P$ MR Spectroscopy with Proton Decoupling," Radiology, 466-473 (2010).
Aoyama et al., "Nicotinamide Adenine Dinucleotide Phosphate Oxidase in Experimental Liver Fibrosis: GKT137831 as a Novel Potential Therapeutic Agent," 56 Hepatology, 2316-2327 (2012).
Fukuoka et al., "Identification and Expression of α Cdna Encoding Human 2-Amino-3-Carboxymuconate-6-Semialdehyde Decarboxylase (ACMSD): A Key Enzyme for the Tryptophan-Niacine Pathway and Quinolinate Hypothesis," 527 Advances in Experimental Medidne and Biology, 443-453 (2003).
Pellicciari et al., "α-Amino-β-carboxymuconate-e-semialdehyde Decarboxylase (ACMSD) Inhibitors as Novel Modulators of De Novo Nicotinamide Adenine Dinucleotide (NAD+) Biosynthesis," Journal of Medicinal Chemistry, 745-749 (2018).
CAS Abstract JP 01132581 (1989), 1 page.
Choi, et al., "Inhibition of Acetolactate Synthase by Pyrimidyl-oxybenzoate and Pyrimidyl-thio-benzenes," Korean Biochem J. 26(7):638-643 (1993).
Shoar et al., "Synthesis of Thio Analogues of Quinolone Antibacterials," Phosphorus, Sulfur, and Silicon 180:2563-2567 (2005).
CAS registration No. 1082595-47-8, dated Dec. 10, 2008, 1 page.
CAS registration No. 1558199-96-4, dated Feb. 28, 2014, 28 pages.

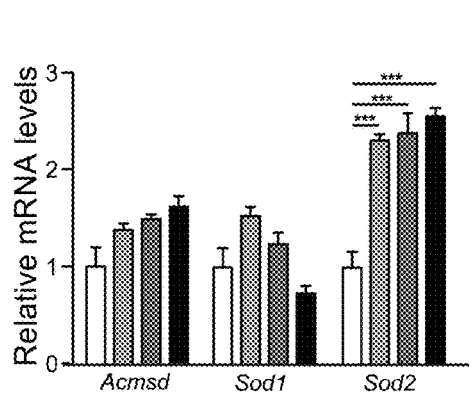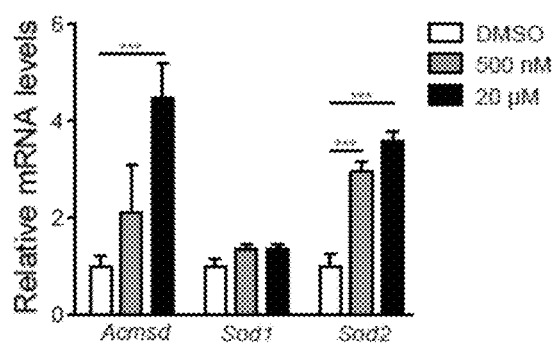
FIG. 4A
FIG. 4B
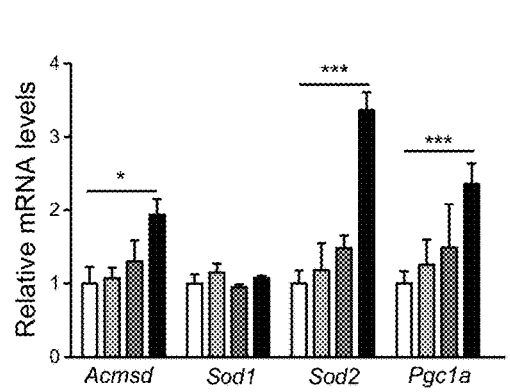
FIG. 4C

INHIBITORS OF ALPHA-AMINO-BETA-CARBOXYMUCONIC ACID SEMIALDEHYDE DECARBOXYLASE

RELATED APPLICATIONS

This application is a continuation of U.S. patent application Ser. No. 15/612,877, filed Jun. 2, 2017, which is a divisional of U.S. patent application Ser. No. 14/839,209, filed on Aug. 28, 2015, now U.S. Pat. No. 9,708,272, issued Jul. 18, 2017, which claims the benefit of and priority to U.S. Provisional Application No. 62/043,853, filed Aug. 29, 2014, the disclosures of which are incorporated herein by reference in their entirety.

FIELD OF THE DISCLOSURE

The present disclosure relates to compounds capable of modulating the activity of α-amino-β-carboxymuconic acid semialdehyde decarboxylase (ACMSD). The compounds of the disclosure may be used in methods for the prevention and/or the treatment of diseases and disorders associated with defects in $NAD^+$ biosynthesis, e.g., metabolic disorders, neurodegenerative diseases, chronic inflammatory diseases, kidney diseases, and diseases associated with ageing.

BACKGROUND OF THE DISCLOSURE

ACMSD is a critical enzyme for tryptophan metabolism, and regulates $NAD^+$ biosynthesis from tryptophan. ACMSD is a zinc-dependent amidohydrolase that participates in picolinic acid (PA), quinolinic acid (QA) and NAD homeostasis. ACMSD stands at a branch point of the $NAD^+$ biosynthetic pathway from tryptophan and determines the final fate of the amino acid, i.e., transformation into PA, complete oxidation through the citric acid cycle, or conversion into $NAD^+$ through QA synthesis.

ACMSD has been purified from liver, kidney, and brain human tissues. There are two isoforms ACMSD1 and ACMSD2 derived from a differential splicing of ACMSD gene transcription but only ACMSD1 is endowed with enzymatic activity. ACMSD1 directs ACMS (α-amino-ω-carboxymuconic acid semialdehyde) to the acetyl-CoA pathway, and when ACMSD1 is inhibited, ACMS is non-enzymatically converted to quinolinic acid (QA) leading to the formation of $NAD^+$ and an increase in the intracellular level of $NAD^+$.

Increased levels of $NAD^+$ have been shown to protect against neuronal degeneration, improve muscle function and oxidative metabolism in mice, and enhance lifespan in worms. Whilst reduced levels of $NAD^+$ have been associated with a range of pathophysiological states including type 2 diabetes (T2D), hyperlipidemia (elevated cholesterol and TAGs), mitochondrial diseases, neutropenia, cancers, and kidney disorders.

The inhibition of ACMSD thus represents a novel approach to increase $NAD^+$ levels and modify disease pathophysiologies associated with defects in $NAD^+$ biosynthesis.

SUMMARY OF THE DISCLOSURE

It is an object of embodiments of the disclosure to provide novel series of compounds capable of modulating the activity of α-amino-β-carboxymuconic acid semialdehyde decarboxylase (ACMSD), which compounds are useful for the prevention and/or the treatment of diseases and disorders associated with defects in $NAD^+$ biosynthesis, e.g., metabolic disorders, neurodegenerative diseases, chronic inflammatory diseases, kidney diseases, and diseases associated with ageing.

Compounds of Formula (I), as defined herein, may be used in the treatment of a disease or disorder in which ACMSD plays a role. The disclosure features methods of treating a disease or disorder associated with ACMSD dysfunction or with abnormalities in $NAD^+$ biosynthesis by administering to subjects suffering from or susceptible to developing a disease or disorder associated with ACMSD dysfunction a therapeutically effective amount of one or more compounds that increases intracellular $NAD^+$ by ACMSD1 inhibition, in an amount sufficient to activate sirtuins (SIRTs) and the downstream targets of SIRTs, such as PGC-1α, FoxO1 and/or superoxide dismutase (SOD). The methods of the present disclosure can be used in the treatment of ACMSD dependent diseases by inhibiting ACMSD. Inhibition of ACMSD may provide a novel approach to the prevention and treatment of metabolic disorders, neurodegenerative diseases, chronic inflammatory diseases, kidney diseases, diseases associated with ageing and other ACMSD dependent diseases, or diseases characterized by defective $NAD^+$ synthesis.

Accordingly, a first aspect of the present disclosure relates to a compound represented by Formula (I):

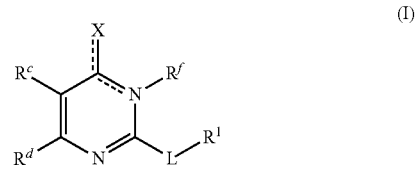

or a pharmaceutically acceptable salt or tautomer thereof, wherein:

X is O, OH, or Cl;

L is $-(CH_2)_mCH_2CH_2-$, $-(CH_2)_mY(CH_2)_p-$, $-(CH_2)_mC(O)(CH_2)_p-$, $-(CH_2)_mC(O)O(CH_2)_p-$, $-(CH_2)_mC(O)NR^2(CH_2)_p-$, or $-(CH_2)_mNR^2C(O)(CH_2)_p$;

Y is O, N or $S(O)_q$;

$R^1$ is $C_6$-$C_{10}$ aryl or heteroaryl, wherein the aryl and heteroaryl are substituted with $R^a$ and $R^b$, and optionally substituted with one or more $R^e$;

$R^2$ is H or $C_1$-$C_6$ alkyl;

one of $R^a$ and $R^b$ is hydrogen and the other is $-(CH_2)_rCO_2R^x$, $-OCH_2CO_2R^x$, $-(CH_2)_r$tetrazole, $-(CH_2)_r$oxadiazolone, $-(CH_2)_r$tetrazolone, $-(CH_2)_r$thiadiazolol, $-(CH_2)_r$ isoxazol-3-ol, $-(CH_2)_rP(O)(OH)OR^x$, $-(CH_2)_rS(O)_2OH$, $-(CH_2)_rC(O)NHCN$, or $-(CH_2)_rC(O)NHS(O)_2$alkyl;

$R^c$ is H, $C_1$-$C_6$ alkyl, $C_1$-$C_6$ haloalkyl, halogen, $-CN$, $-OR^x$, $-CO_2R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, $-OR^y$, $C_1$-$C_6$ haloalkyl, $-NHR^z$, $-OH$, or $-CN$;

$R^f$ is H or absent;

each $R^y$ and $R^z$ is independently hydrogen, $C_1$-$C_6$ alkyl, or $C_1$-$C_6$ haloalkyl;

each m and p independently is 0, 1 or 2, wherein m+p<3;
q is 0, 1, or 2;
r is 0 or 1; and
the dotted line is an optional double bond;
with the proviso that $R^c$ is not hydrogen or —CN when X is O, L is —SCH$_2$— and $R^d$ is optionally substituted phenyl, $R^c$ is not C$_1$-C$_6$ alkyl when X is O, L is —SCH$_2$— and $R^d$ is methyl, and that $R^c$ is not —CN when X is O, L is —SCH$_2$— and $R^d$ is 2-furyl.

A second aspect of the present disclosure relates to pharmaceutical compositions comprising a compound of Formula (I), or a pharmaceutically acceptable salt thereof, and at least one of a pharmaceutically acceptable carrier, diluent, or excipient.

A third aspect of the disclosure relates to a method of treating a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I).

A fourth aspect of the disclosure relates to a method of preventing a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I).

A fifth aspect of the disclosure relates to a method of reducing the risk of a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I).

A sixth aspect of the disclosure relates to a method of treating a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I).

A seventh aspect of the disclosure relates to a method of preventing a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I).

An eighth aspect of the disclosure relates to a method of reducing the risk of a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I).

An ninth aspect of the disclosure relates to a method of treating a disorder associated with mitochondrial dysfunction comprising administering to the subject suffering from or susceptible to developing a metabolic disorder a therapeutically effective amount of one or more compounds of Formula (I) that increases intracellular nicotinamide adenine dinucleotide (NAD$^+$).

A tenth aspect of the disclosure relates to a method of promoting oxidative metabolism comprising administering to the subject suffering from or susceptible to developing a metabolic disorder a therapeutically effective amount of one or more compounds of Formula (I) that increases intracellular nicotinamide adenine dinucleotide (NAD$^+$).

An eleventh aspect of the disclosure relates to a method for the manufacture of a medicament for treating a disease or condition mediated by ACMSD, wherein the medicament comprises a compound of Formula (I), or a pharmaceutically acceptable salt thereof.

A twelfth aspect of the disclosure relates to a pharmaceutical composition for use in a method for treating a disease or condition mediated by ACMSD, wherein the medicament comprises a compound of Formula (I), or a pharmaceutically acceptable salt thereof.

A thirteenth aspect of the disclosure relates to a method of treating a disease or disorder associated with α-amino-β-carboxymuconate-ε-semialdehyde decarboxylase (ACMSD) dysfunction, comprising administering to a subject in need thereof, a therapeutically effective amount of compound having one of the following Formulae:

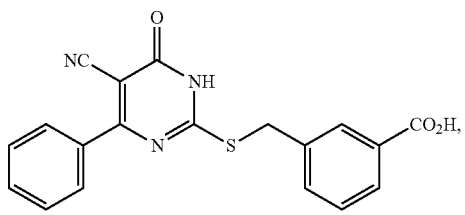

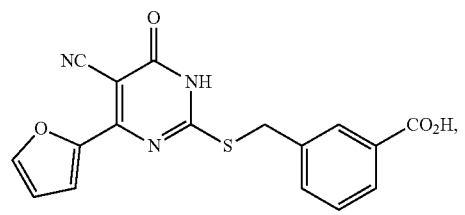

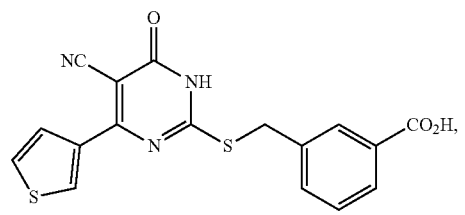

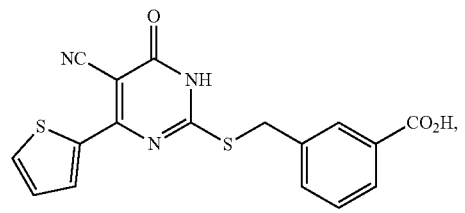

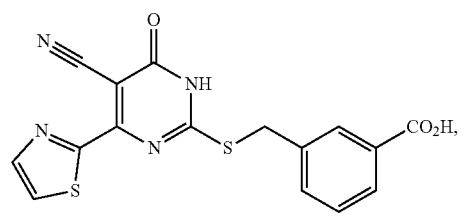

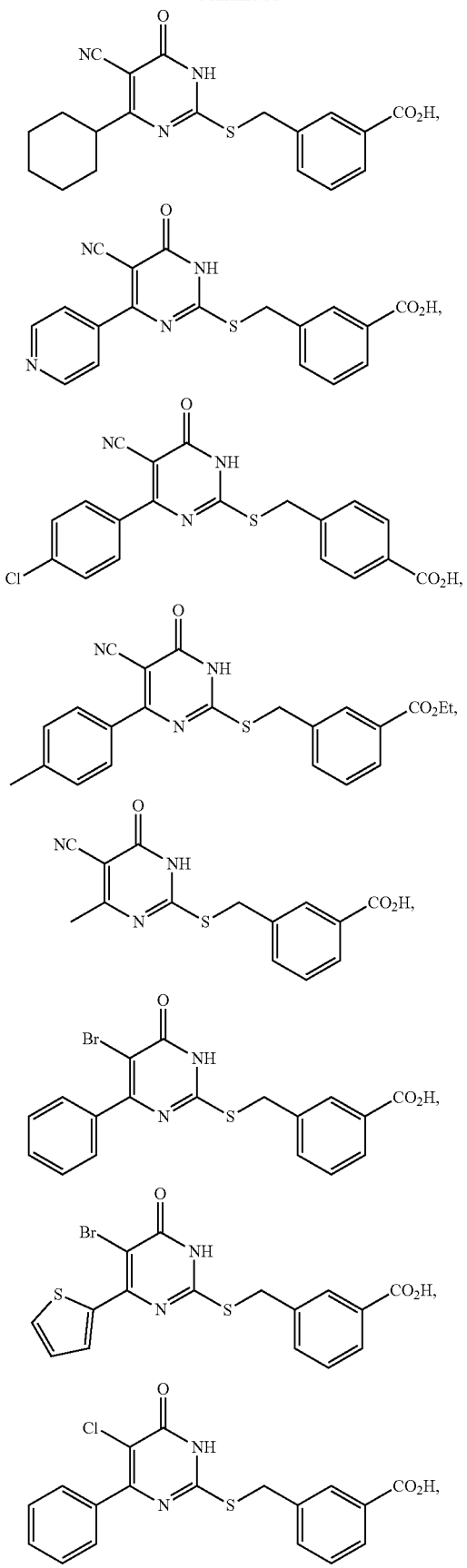
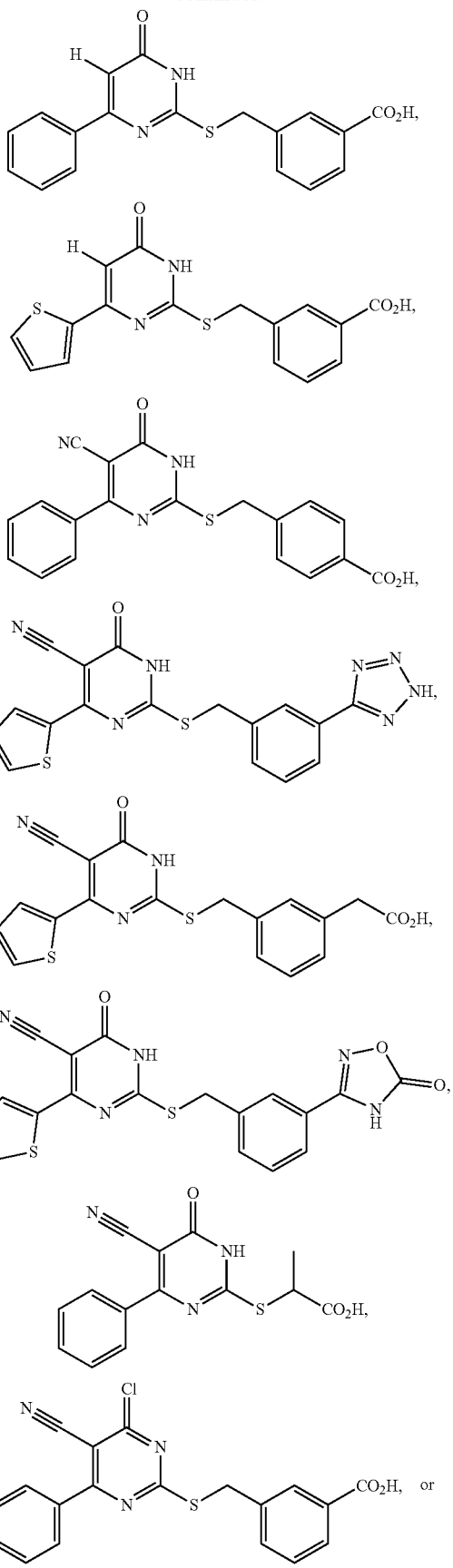

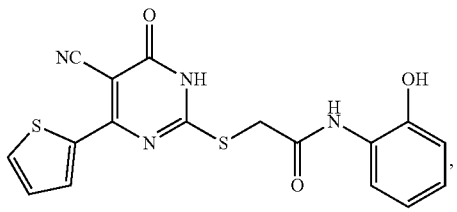

or a pharmaceutically acceptable salt thereof.

A fourteenth aspect of the disclosure relates to the use of a compound of Formula (I), or a pharmaceutically acceptable salt thereof in the manufacture of a medicament for treating, preventing or reducing the risk of a disease or disorder associated with α-amino-β-carboxymuconate-ε-semialdehyde decarboxylase (ACMSD) dysfunction.

A fifteenth aspect of the disclosure relates to the use of a compound of Formula (I), or a pharmaceutically acceptable salt thereof in the manufacture of a medicament for treating, preventing or reducing the risk of a disease or disorder associated with reduced nicotinamide adenine dinucleotide (NAD$^+$) levels.

A sixteenth aspect of the disclosure relates to the use of a compound of Formula (I), or a pharmaceutically acceptable salt thereof in the manufacture of a medicament for treating, preventing or reducing the risk of a disorder associated with mitochondrial dysfunction.

A seventeenth aspect of the disclosure relates to the use of a compound of Formula (I), or a pharmaceutically acceptable salt thereof in the manufacture of a medicament for promoting oxidative metabolism.

A eighteenth aspect of the disclosure relates to the use of a compound of Formula (I), a pharmaceutically acceptable salt thereof in the manufacture of a medicament for treating, preventing or reducing the risk of a disease or disorder associated with α-amino-β-carboxymuconate-ε-semialdehyde decarboxylase (ACMSD) dysfunction.

A nineteenth aspect of the disclosure relates to a compound of Formula (I), or a pharmaceutically acceptable salt thereof for use as a medicament for treating, preventing or reducing the risk of a disease or disorder associated with reduced nicotinamide adenine dinucleotide (NAD$^+$) levels.

A twentieth aspect of the disclosure relates to a compound of Formula (I), or a pharmaceutically acceptable salt thereof for use as a medicament for treating, preventing or reducing the risk of a disorder associated with mitochondrial dysfunction.

A twenty first aspect of the disclosure relates to a compound of Formula (I), or a pharmaceutically acceptable salt thereof for use in treating, preventing or reducing the risk of a disease or disorder associated with reduced nicotinamide adenine dinucleotide (NAD$^+$) levels.

A twenty second aspect of the disclosure relates to a compound of Formula (I), or a pharmaceutically acceptable salt thereof for use in for treating, preventing or reducing the risk of a disorder associated with mitochondrial dysfunction.

A twenty third aspect of the disclosure relates to a compound of Formula (I), or a pharmaceutically acceptable salt thereof for use in promoting oxidative metabolism.

A twenty fourth aspect of the disclosure relates to a compound having the one of the following Formula:

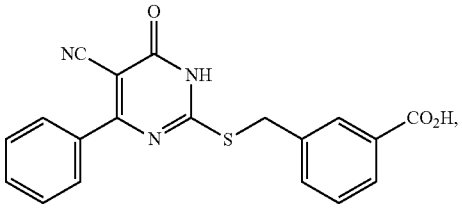

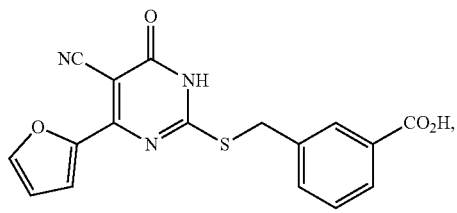

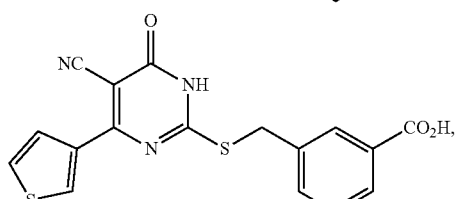

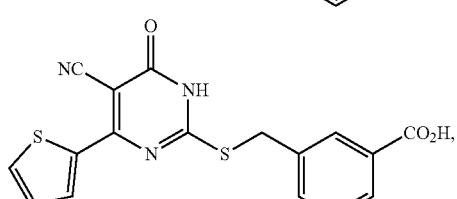

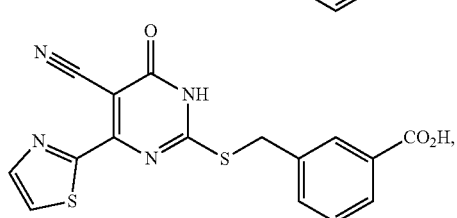

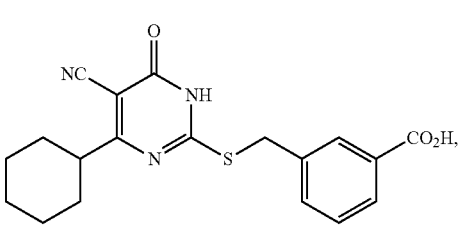

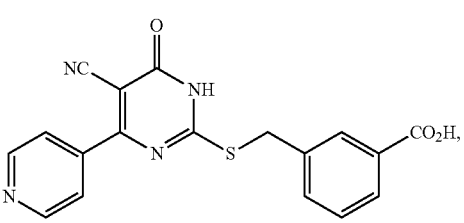

-continued
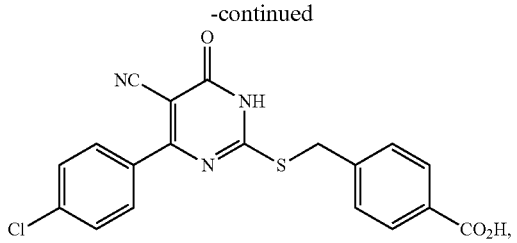
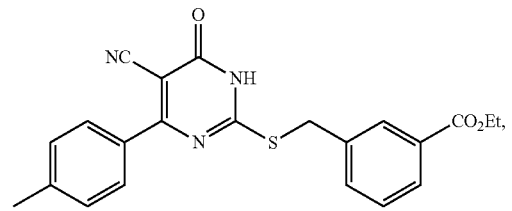
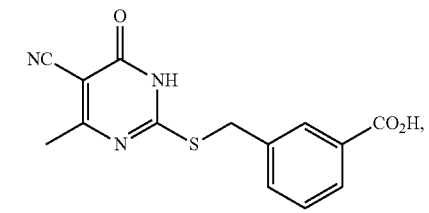
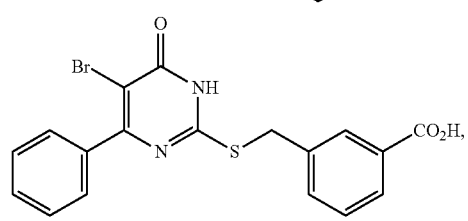
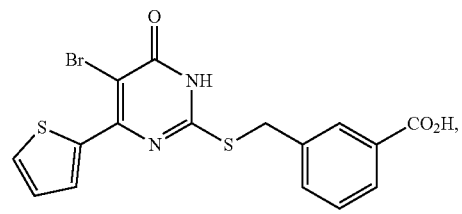
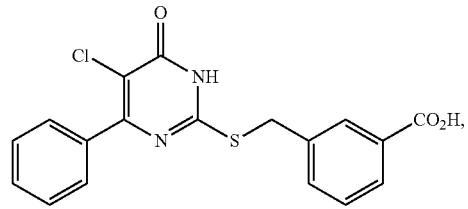
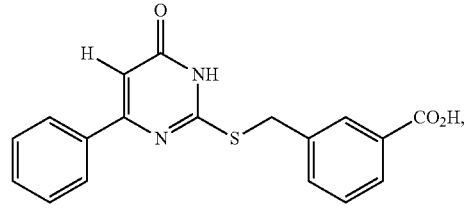
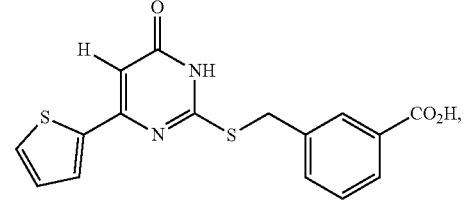
-continued
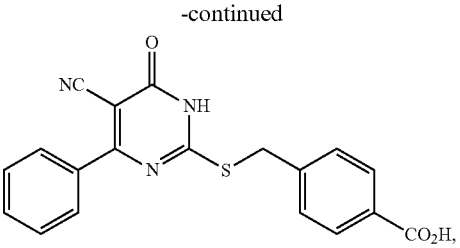
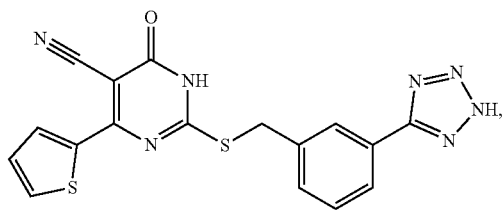
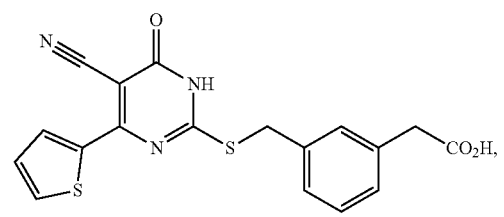
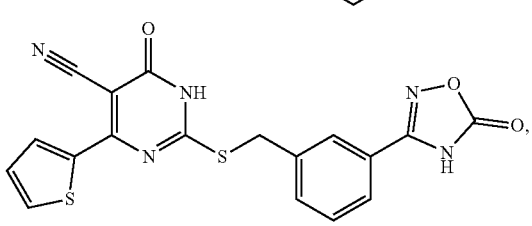
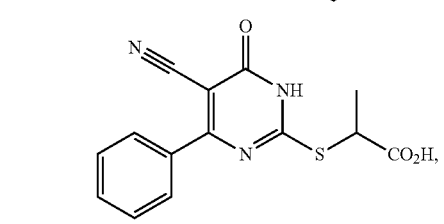
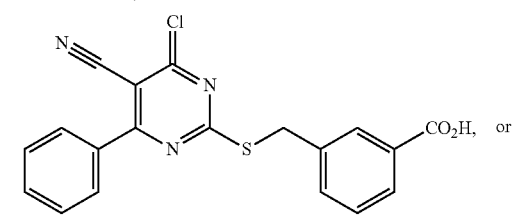
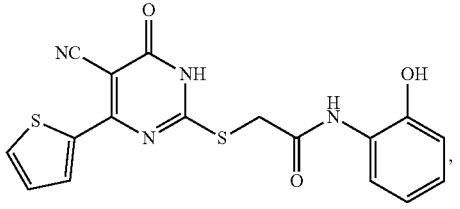
or a pharmaceutically acceptable salt thereof
in the manufacture of a medicament for treating a disease or disorder associated with α-amino-β-carboxymuconate-ε-semialdehyde decarboxylase (ACMSD) dysfunction.

A twenty fifth aspect of the disclosure relates to a compound having the one of the following Formula:
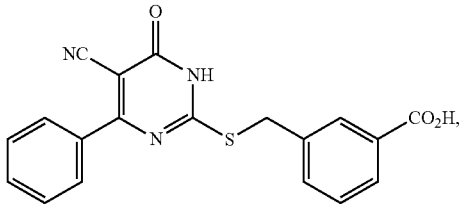
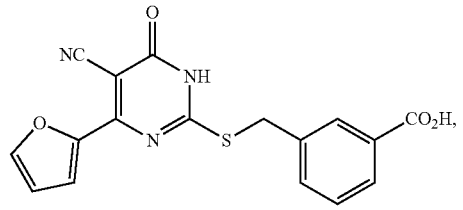
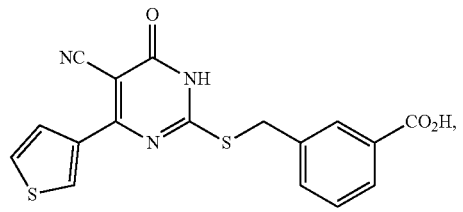
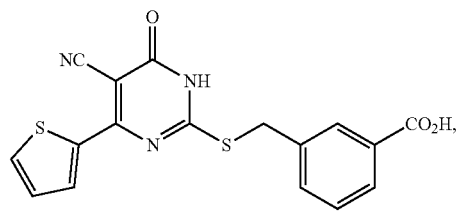
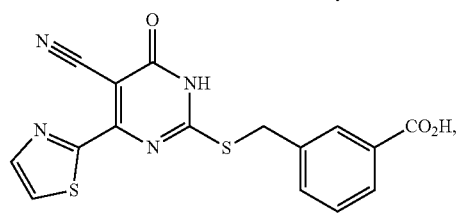
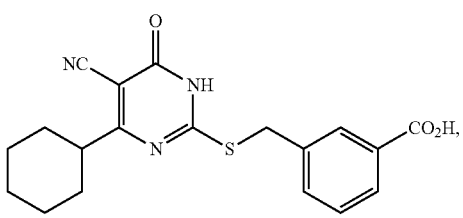
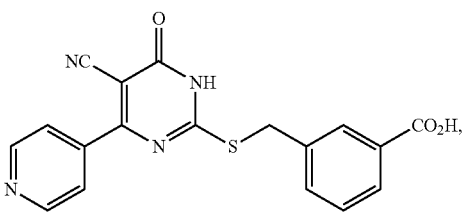
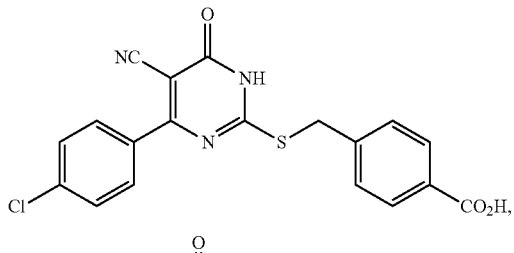
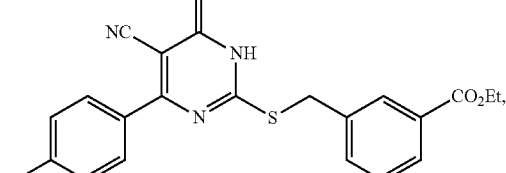
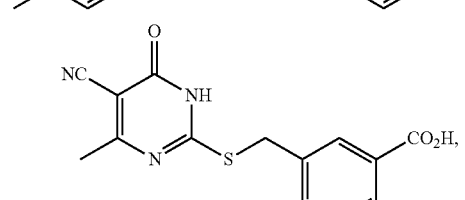
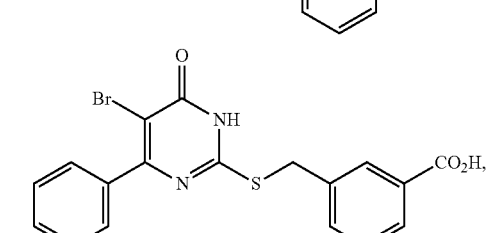
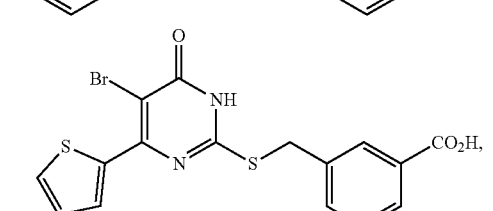
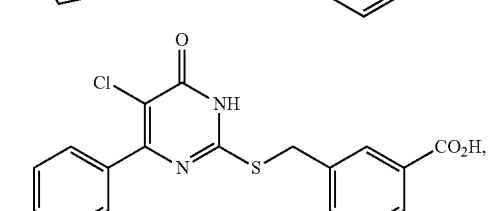
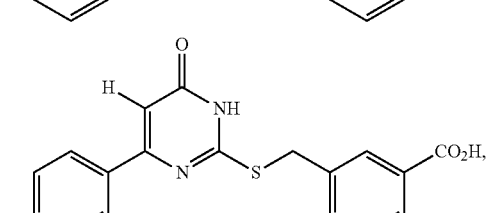
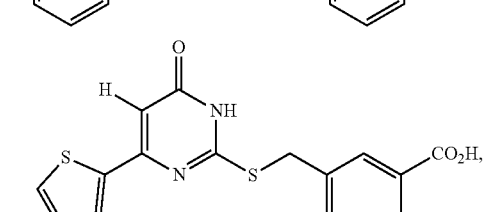

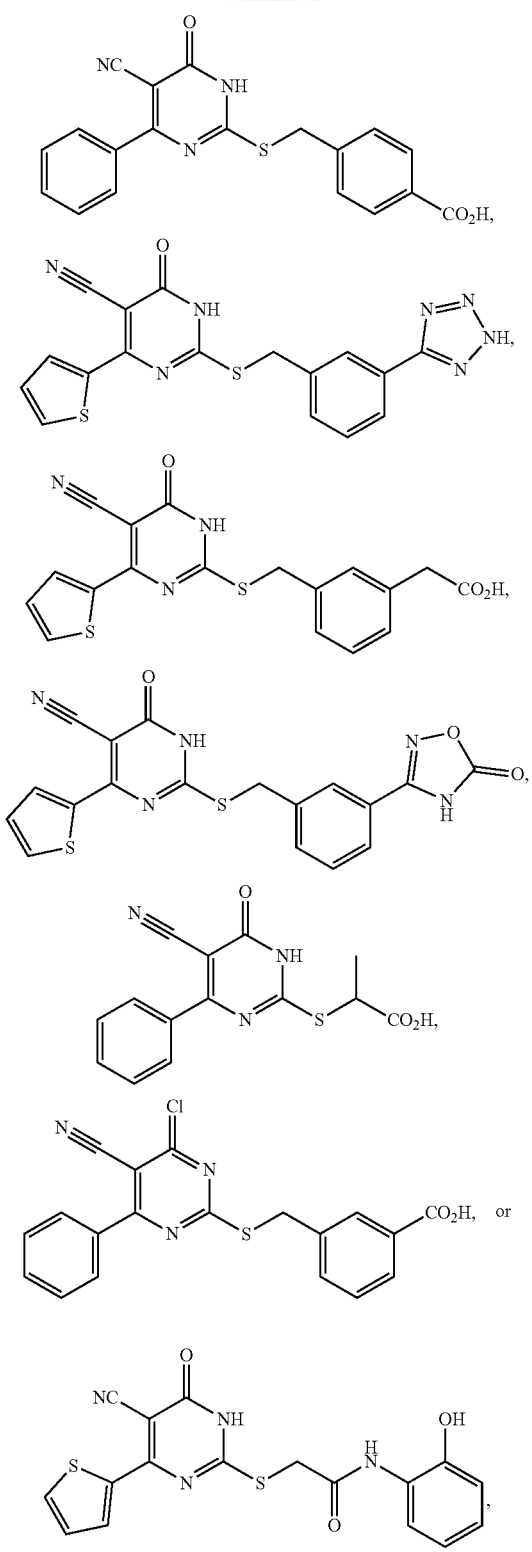
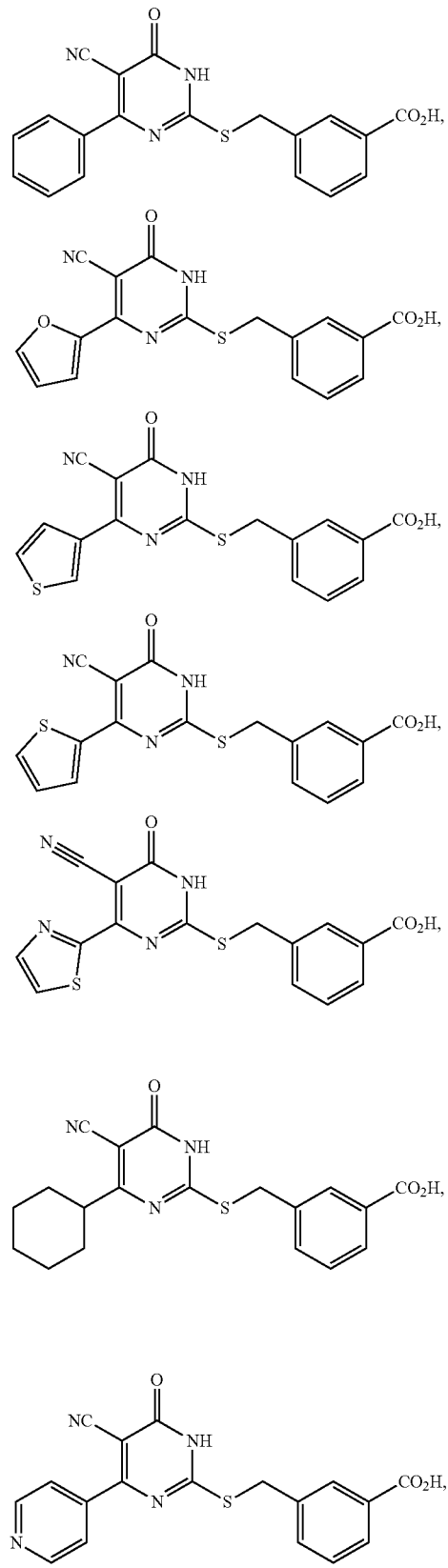
A twenty sixth aspect of the disclosure relates to a compound having the one of the following Formula:
or a pharmaceutically acceptable salt thereof for use as a medicament for treating a disease or disorder associated with α-amino-β-carboxymuconate-ε-semialdehyde decarboxylase (ACMSD) dysfunction.

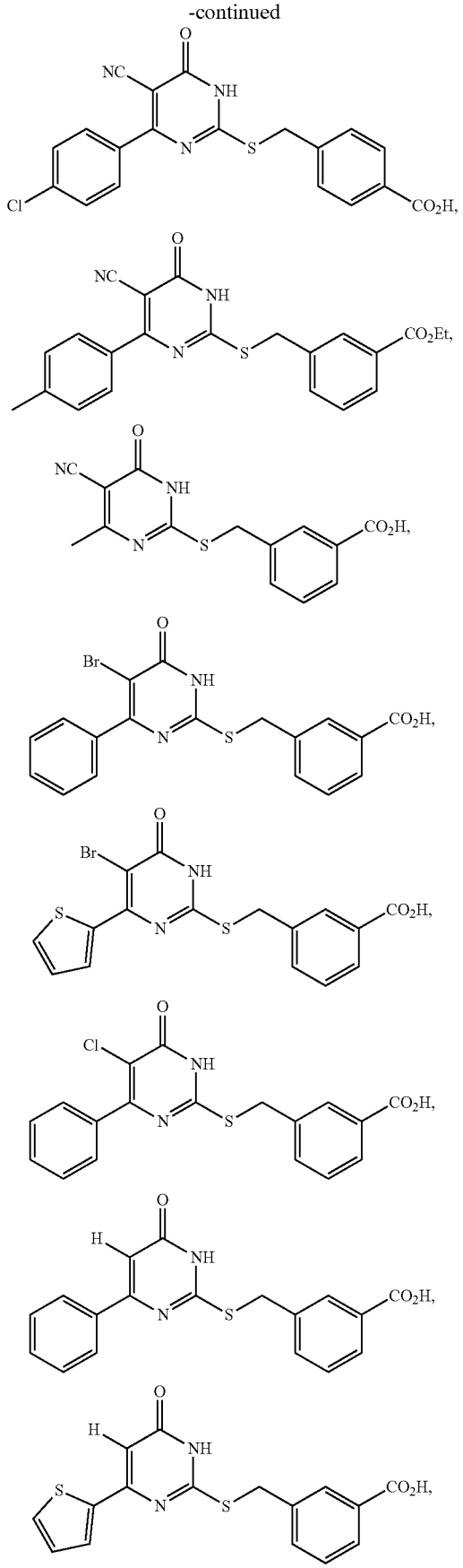
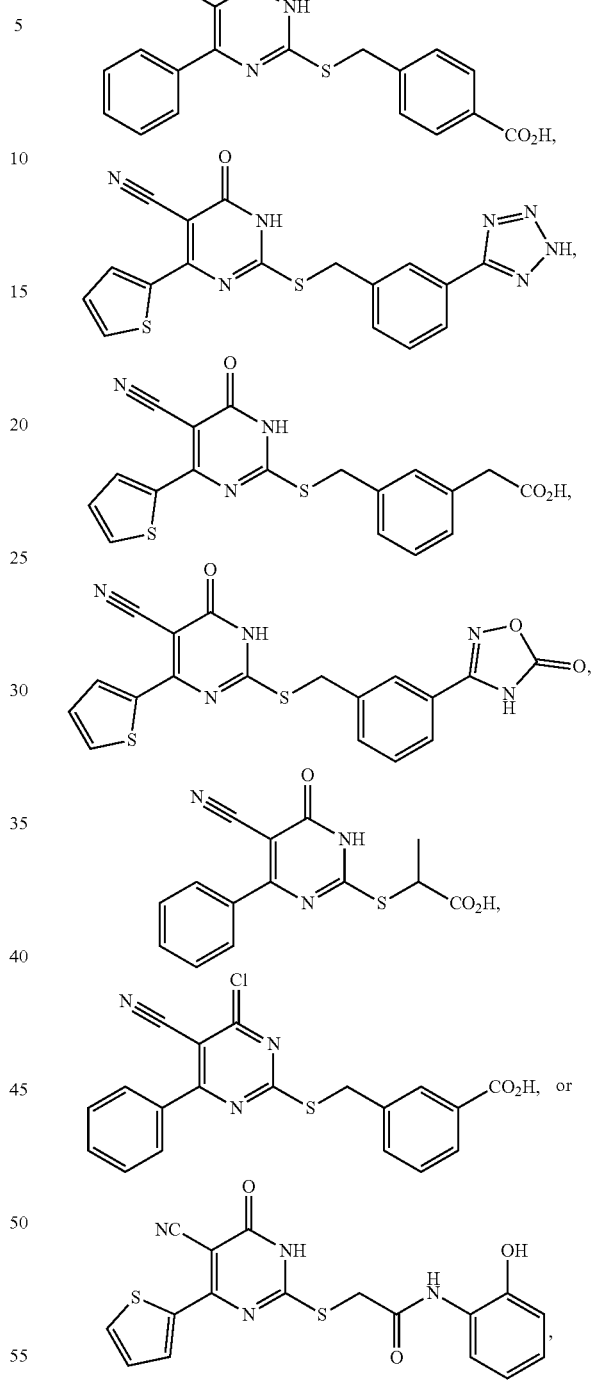

or a pharmaceutically acceptable salt thereof for use in treating a disease or disorder associated with α-amino-β-carboxymuconate-ε-semialdehyde decarboxylase (ACMSD) dysfunction.

In certain aspects, the ACMSD modulating compounds may be administered alone or in combination with other compounds, including other ACMSD modulating compounds, or other therapeutic agents.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar to or equivalent to those described herein can be used in the practice and testing of the disclosure, suitable methods and materials are described below. All publications, patent applications, patents, and other references mentioned herein are incorporated by reference. The references cited herein are not admitted to be prior art to the claimed disclosure. In the case of conflict, the present specification, including definitions, will control. In addition, the materials, methods, and examples are illustrative only and not intended to be limiting.

Other features and advantages of the disclosure will be apparent from the following detailed description and claims.

BRIEF DESCRIPTION OF THE DRAWINGS

FIG. 4A is a graph of gene expression of Acmsd, Sod-1, and Sod-2 as determined by RT-qPCR in AML-12 cells treated with Compound 1 for 24 hours. FIG. 4B is a graph of gene expression of Sod-1 and Sod-2 as determined by RT-qPCR in Hepa-1.6 cells treated with Compound 1 for 24 hours. FIG. 4C is a graph of gene expression of Acmsd, Sod-1, Sod-2, and Pgc1a as determined by RT-qPCR in primary mouse hepatocytes treated with Compound 17 for 24 hours. Bar graphs represent mean±SEM, ***p≤0.005

FIG. 7C shows that downregulation of acmsd-1 improves the survival of worms in a SIR-2.1 and DAF-16 dependent manner. FIG. 7F illustrates that the improvement of the survival of worms under paraquat conditions is independent of the developmental stage at which the worms were exposed to the acmsd-1 RNAi. FIG. 7G shows that the improved survival of worms with downregulated acmsd-1 is daf-16 dependent under paraquat-induced oxidative stress conditions.

DETAILED DESCRIPTION OF THE DISCLOSURE

Compounds of Formula (I)

Figure 1:
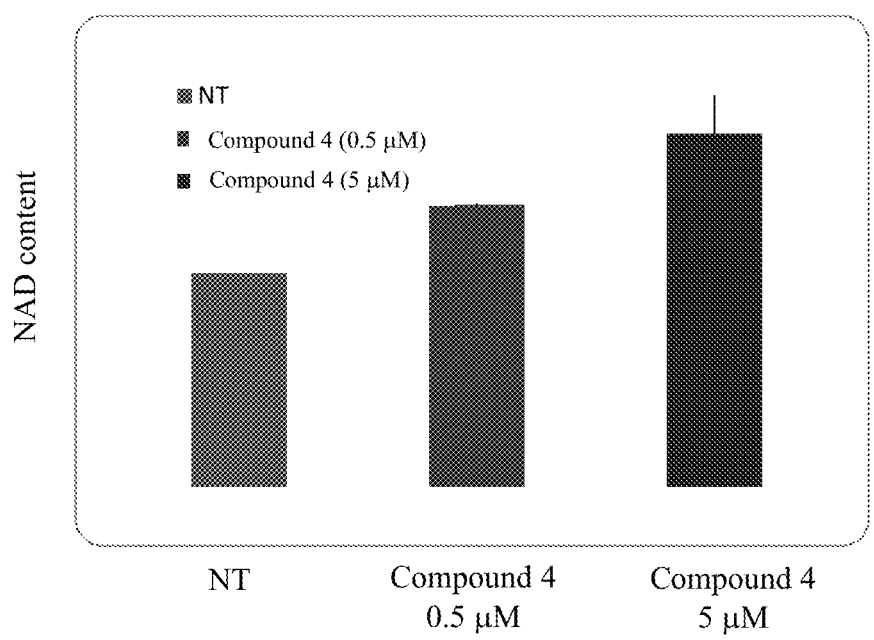
FIG. 1 is a graph of the measured $NAD^+$ levels in human primary hepatocytes treated with Compound 4, detected by LC-MS/MS.

The present disclosure relates to compounds of Formula (I):

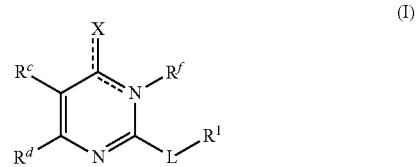

or a pharmaceutically acceptable salt or tautomer thereof, wherein:

X is O, OH, or Cl;

L is —$(CH_2)_m CH_2 CH_2$—, —$(CH_2)_m Y(CH_2)_p$—, —$(CH_2)_m C(O)(CH_2)_p$—, —$(CH_2)_m C(O)O(CH_2)_p$—, —$(CH_2)_m C(O)NR^2(CH_2)_p$—, or —$(CH_2)_m NR^2 C(O)(CH_2)_p$;

Y is O, N or $S(O)_q$;

$R^1$ is $C_6$-$C_{10}$ aryl or heteroaryl, wherein the aryl and heteroaryl are substituted with $R^a$ and $R^b$, and optionally substituted with one or more $R^e$;

$R^2$ is H or $C_1$-$C_6$ alkyl;

one of $R^a$ and $R^b$ is hydrogen and the other is —$(CH_2)_r CO_2 R^x$, —$OCH_2 CO_2 R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_r P(O)(OH)OR^x$, —$(CH_2)_r S(O)_2 OH$, —$(CH_2)_r C(O)NHCN$, or —$(CH_2)_r C(O)NHS(O)_2 alkyl$;

$R^c$ is H, $C_1$-$C_6$ alkyl, $C_1$-$C_6$ haloalkyl, halogen, —CN, —$OR^x$, —$CO_2 R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

$R^f$ is H or absent;

each $R^y$ and $R^z$ is independently hydrogen, $C_1$-$C_6$ alkyl, or $C_1$-$C_6$ haloalkyl;

each m and p independently is 0, 1 or 2, wherein m+p<3;

q is 0, 1, or 2;

r is 0 or 1; and the dotted line is an optional double bond;

with the proviso that $R^c$ is not hydrogen or —CN when X is O, L is —$SCH_2$— and $R^d$ is optionally substituted phenyl, $R^c$ is not $C_1$-$C_6$ alkyl when X is O, L is —$SCH_2$— and $R^d$ is methyl, and that $R^c$ is not —CN when L is —$SCH_2$— and $R^d$ is 2-furyl.

In some embodiments of Formula (I), X is O, OH, or Cl. In other embodiments, X is O. In other embodiments, X is OH. In other embodiments, X is Cl.

In some embodiments of Formula (I), L is —$(CH_2)_mCH_2CH_2$—, —$(CH_2)_mY(CH_2)_p$—, —$(CH_2)_mC(O)(CH_2)_p$—, —$(CH_2)_mC(O)O(CH_2)_p$—, —$(CH_2)_mC(O)NR^2(CH_2)_p$—, or —$(CH_2)_mNR^2C(O)(CH_2)_p$—. In other embodiments, L is —$CH_2CH_2$—, —$CH_2CH_2CH_2$—, —$SCH_2$—, —$SCH_2CH_2$—, —$CH_2S$—, —$CH_2SCH_2$—, —$CH_2CH_2S$—, —$S(O)CH_2$—, —$S(O)CH_2CH_2$—, —$CH_2S(O)$—, —$CH_2S(O)CH_2$—, —$CH_2CH_2S(O)$—, —$S(O)_2CH_2$—, —$S(O)_2CH_2CH_2$—, —$CH_2S(O)_2$—, —$CH_2S(O)_2CH_2$—, —$CH_2CH_2S(O)_2$—, —$OCH_2$—, —$OCH_2CH_2$—, —$CH_2O$—, —$CH_2OCH_2$—, —$CH_2CH_2O$—, —$NR^2CH_2$—, —$CH_2NR^2$—, —$CH_2NR^2CH_2$—, —$CH_2CH_2NR^2$—, —$NR^2CH_2CH_2$—, —$C(O)CH_2$—, —$C(O)CH_2CH_2$—, —$C(O)O$—, —$C(O)OCH_2$—, —$CH_2C(O)O$—, —$C(O)NR^2$—, —$C(O)NR^2CH_2$—, —$NR^2C(O)$, —$NR^2C(O)CH_2$, or —$CH_2NR^2C(O)$. In other embodiments, L is —$CH_2CH_2$—, —$CH_2CH_2CH_2$—, —$SCH_2$—, —$SCH_2CH_2$—, —$S(O)CH_2$—, —$S(O)CH_2CH_2$—, —$S(O)_2CH_2$—, —$S(O)_2CH_2CH_2$—, —$OCH_2$—, —$OCH_2CH_2$—, —$NR^2CH_2$—, —$NR^2CH_2CH_2$—, —$C(O)CH_2$—, —$C(O)CH_2CH_2$—, —$C(O)O$—, —$C(O)OCH_2$—, —$CH_2C(O)O$—, —$C(O)NR^2$—, —$C(O)NR^2CH_2$—, —$NR^2C(O)$, or —$NR^2C(O)CH_2$. In other embodiments, L is —$CH_2CH_2$—, —$CH_2C(O)$—, —$C(O)CH_2$—, —$NR^2CH_2$—, —$CH_2NR^2$—, —$OCH_2$—, —$CH_2O$—, —$SCH_2$—, —$CH_2S$—, —$S(O)CH_2$—, —$CH_2S(O)$—, —$CH_2S(O)_2$—, or —$S(O)_2CH_2$—.

In some embodiments of Formula (I), $R^1$ is $C_6$-$C_{10}$ aryl or heteroaryl, wherein the aryl and heteroaryl are substituted with $R^a$ and $R^b$, and optionally substituted with one or more $R^e$. In other embodiments, $R^1$ is $C_6$-$C_{10}$ aryl substituted with $R^a$ and $R^b$, and optionally substituted with one or more $R^e$. In other embodiments, $R^1$ is heteroaryl substituted with $R^a$ and $R^b$, and optionally substituted with one or more $R^e$. In further embodiments, $R^1$ is phenyl substituted with $R^a$ and $R^b$, and optionally substituted with one or more $R^e$.

In some embodiments of Formula (I), $R^a$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^a$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^a$ is hydrogen, $CO_2R^x$, $CH_2CO_2R^x$, tetrazole, or oxadiazolone. In further embodiments, $R^a$ is hydrogen, $CO_2H$, $CH_2CO_2H$, tetrazole, or 1,2,4-oxadiazol-5(4H)-one.

In some embodiments of Formula (I), $R^b$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^b$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^b$ is hydrogen, $CO_2R^x$, $CH_2CO_2R^x$, tetrazole, or oxadiazolone. In further embodiments, $R^b$ is hydrogen, $CO_2H$, $CH_2CO_2H$, tetrazole, or 1,2,4-oxadiazol-5(4H)-one. In further embodiments, $R^b$ is hydrogen.

In some embodiments of Formula (I), $R^c$ is H, $C_1$-$C_6$ alkyl, $C_1$-$C_6$ haloalkyl, halogen, —CN, —$OR^x$, —$CO_2R^x$, or $NO_2$. In other embodiments, $R^c$ is $C_1$-$C_6$ alkyl, $C_1$-$C_6$ haloalkyl, halogen, —CN, —$OR^x$, —$CO_2R^x$, or $NO_2$. In other embodiments, $R^c$ is halogen, —CN, —$OR^x$, or $C_1$-$C_6$ alkyl. In other embodiments, $R^c$ is halogen, —CN, —$OR^x$, or $C_1$-$C_3$ alkyl. In other embodiments, $R^c$ is H, —CN, or halogen. In other embodiments, $R^c$ is —CN or halogen.

In some embodiments of Formula (I), $R^d$ is methyl, optionally substituted 5- to 10-membered aryl, optionally substituted 5- or 6-membered heteroaryl, or optionally substituted 5- or 6-membered carbocycle. In other embodiments, $R^d$ is methyl, optionally cyclohexyl, optionally substituted pyridinyl, optionally substituted thiazolyl, optionally substituted phenyl, or optionally substituted thienyl. In other embodiments, $R^d$ is methyl, cyclohexyl, pyridinyl, thiazolyl, phenyl, or thienyl. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, $C_1$-$C_6$ haloalkoxy, —OH, CN, and amino. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, and $C_1$-$C_6$ haloalkoxy. In other embodiments, $R^d$ is cyclohexyl, pyridinyl, thiazolyl, phenyl, or thienyl, wherein each is optionally substituted with one or more halogen. In yet other embodiments, $R^d$ is cyclohexyl, pyridinyl, thiazolyl, phenyl, or thienyl. In other embodiments, $R^d$ is cyclohexyl, pyridinyl, thiazolyl, phenyl, 4-chlorophenyl, 4-methylphenyl, or thienyl.

In some embodiments of Formula (I), each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN. In other embodiments, $C_1$-$C_4$ alkyl, $C_2$-$C_4$ alkenyl, $C_2$-$C_4$ alkynyl, halogen, —$OR^y$, $C_1$-$C_4$ haloalkyl, —$NHR^z$, —OH, or —CN.

In some embodiments of Formula (I), $R^f$ is H or absent. In other embodiments, $R^f$ is H. In other embodiments, $R^f$ is absent, when N to which it is attached participates in a double bond.

In some embodiments of Formula (I), $R^x$ is hydrogen or $C_1$-$C_6$ alkyl. In other embodiments, $R^x$ is hydrogen or $C_1$-$C_3$ alkyl. In further embodiments, $R^x$ is hydrogen, methyl, ethyl, n-propyl, or iso-propyl.

In some embodiments of Formula (I), $R^y$ is independently hydrogen, $C_1$-$C_6$ alkyl, or $C_1$-$C_6$ haloalkyl. In other embodiments, $R^y$ is hydrogen, $C_1$-$C_3$ alkyl, or $C_1$-$C_3$ haloalkyl.

In some embodiments of Formula (I), each $R^z$ is independently hydrogen, $C_1$-$C_6$ alkyl, or $C_1$-$C_6$ haloalkyl. In other embodiments, $R^z$ is hydrogen, $C_1$-$C_3$ alkyl, or $C_1$-$C_3$ haloalkyl.

In some embodiments of Formula (I), m is 0, 1 or 2. In other embodiments, m is 0. In other embodiments, m is 1. In yet other embodiments, m is 2.

In some embodiments of Formula (I), p is 0, 1 or 2. In other embodiments, p is 0. In other embodiments, p is 1. In yet other embodiments, p is 2.

In some embodiments of Formula (I), m+p<3;

In some embodiments of Formula (I), q is 0, 1, or 2. In other embodiments, q is 0. In other embodiments, q is 1. In other embodiments, q is 2.

In some embodiments of Formula (I), r is 0 or 1. In other embodiments, r is 0. In other embodiments, r is 1.

In some embodiments of Formula (I), the dotted line is a single bond. In other embodiments, the dotted line is a double bond.

In some embodiments of Formula (I), one of $R^a$ and $R^b$ is hydrogen and the other is $CO_2R^x$, $CH_2CO_2R^x$, tetrazole, or oxadiazolone. In other embodiments, $R^b$ is hydrogen and $R^a$ is $CH_2CO_2H$, tetrazole, or (1,2,4-oxadiazol-5(4H)-one).

In some embodiments of Formula (I), $R^b$ is hydrogen, $R^c$ is —CN, $R^d$ is thienyl, and $R^a$ is $CH_2CO_2H$, tetrazole, or (1,2,4-oxadiazol-5(4H)-one).

In some embodiments of Formula (I), $R^c$ is halogen, $R^a$ is —$CO_2H$, and $R^b$ is H. In other embodiments, $R^c$ is —Br, $R^a$ is —$CO_2H$, and $R^b$ is H. In further embodiments, $R^c$ is —Cl, $R^a$ is —$CO_2H$, and $R^b$ is H.

In some embodiments of Formula (I), $R^c$ is halogen, $R^a$ is tetrazole, and $R^b$ is H. In other embodiments, $R^c$ is —Br, $R^a$ is tetrazole, and $R^b$ is H. In further embodiments, $R^c$ is —Cl, $R^a$ is tetrazole, and $R^b$ is H.

In some embodiments of Formula (I), $R^c$ is halogen, $R^a$ is —$CH_2CO_2H$, and $R^b$ is H. In other embodiments, $R^c$ is —Br, $R^a$ is —$CH_2CO_2H$, and $R^b$ is H. In further embodiments, $R^c$ is —Cl, $R^a$ is —$CH_2CO_2H$, and $R^b$ is H.

In some embodiments of Formula (I), $R^c$ is halogen, $R^a$ is (1,2,4-oxadiazol-5(4H)-one), and $R^b$ is H. In other embodiments, $R^c$ is —Br, $R^a$ is (1,2,4-oxadiazol-5(4H)-one), and $R^b$ is H. In other embodiments, $R^c$ is —Cl, $R^a$ is (1,2,4-oxadiazol-5(4H)-one), and $R^b$ is H.

In some embodiments of Formula (I), $R^c$ is —CN, $R^a$ is —$CO_2H$, and $R^b$ is H. In other embodiments, $R^c$ is —CN, $R^a$ is —$CH_2CO_2H$, and $R^b$ is H. In other embodiments, $R^c$ is —CN, $R^a$ is tetrazole, and $R^b$ is H. In yet other embodiments, $R^c$ is —CN, $R^a$ is (1,2,4-oxadiazol-5(4H)-one), and $R^b$ is H.

In some embodiments of Formula (I), $R^c$ is not hydrogen or —CN and X is O, L is —$SCH_2$— and $R^d$ is optionally substituted phenyl. In other embodiments, $R^c$ is not $C_1$-$C_6$ alkyl and X is O, L is —$SCH_2$— and $R^d$ is methyl. In other embodiments, $R^c$ is not —CN and X is O, L is —$SCH_2$— and $R^d$ is 2-furyl.

In some embodiments of Formula (I), $R^c$ is not hydrogen or —CN when X is O, L is —$SCH_2$— and $R^d$ is optionally substituted phenyl.

In some embodiments of Formula (I), $R^c$ is not $C_1$-$C_6$ alkyl when X is O, L is —$SCH_2$— and $R^d$ is methyl.

In some embodiments of Formula (I), $R^c$ is not —CN when X is O, L is —$SCH_2$— and $R^d$ is 2-furyl.

In one embodiment, the compound of Formula (I) is represented by Formula (Ia):

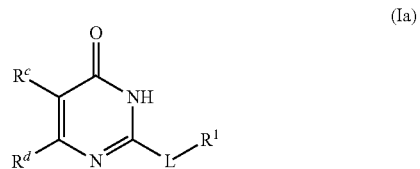

or a pharmaceutically acceptable salt, or tautomer thereof, wherein:

L is —$(CH_2)_mCH_2CH_2$—, —$(CH_2)_mY(CH_2)_p$—, —$(CH_2)_mC(O)(CH_2)_p$—, —$(CH_2)_mC(O)O(CH_2)_p$—, —$(CH_2)_mC(O)NR^2(CH_2)_p$—, or —$(CH_2)_mNR^2C(O)(CH_2)_p$;

Y is O, N or $S(O)_q$;

$R^1$ is $C_6$-$C_{10}$ aryl or heteroaryl, wherein the aryl and heteroaryl are substituted with $R^a$ and $R^b$, and optionally substituted with one or more $R^e$;

$R^2$ is H or $C_1$-$C_6$ alkyl;

one of $R^a$ and $R^b$ is hydrogen and the other is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl;

$R^c$ is H, $C_1$-$C_6$ alkyl, $C_1$-$C_6$ haloalkyl, halogen, —CN, —$OR^x$, —$CO_2R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

each $R^y$ and $R^z$ is independently hydrogen, $C_1$-$C_6$ alkyl, or $C_1$-$C_6$ haloalkyl;

each m and p independently is 0, 1 or 2, wherein m+p<3;

q is 0, 1, or 2; and r is 0 or 1;

with the proviso that $R^c$ is not hydrogen or —CN when L is —$SCH_2$— and $R^d$ is optionally substituted phenyl, $R^c$ is not $C_1$-$C_6$ alkyl when L is —$SCH_2$— and $R^d$ is methyl, and that $R^c$ is not —CN when L is —$SCH_2$— and $R^d$ is 2-furyl.

In some embodiments of Formula (Ia),

L is —$CH_2CH_2$—, —$CH_2C(O)$—, —$C(O)CH_2$—, —$NR^2CH_2$—, —$CH_2NR^2$—, —$OCH_2$—, —$CH_2O$—, —$SCH_2$—, —$CH_2S$—, —$S(O)CH_2$—, —$CH_2S(O)$—, —$CH_2S(O)_2$—, or —$S(O)_2CH_2$—;

Y is O, N or $S(O)_q$;

$R^1$ is $C_6$-$C_{10}$ aryl or heteroaryl, wherein the aryl and heteroaryl are substituted with $R^a$ and $R^b$, and optionally substituted with one or more $R^e$;

$R^2$ is H or $C_1$-$C_6$ alkyl;

one of $R^a$ and $R^b$ is hydrogen and the other is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl;

$R^c$ is $C_1$-$C_6$ alkyl, $C_1$-$C_6$ haloalkyl, halogen, —CN, —$OR^x$, —$CO_2R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

each $R^y$ and $R^z$ is independently hydrogen, $C_1$-$C_6$ alkyl, or $C_1$-$C_6$ haloalkyl;

each m and p independently is 0, 1 or 2, wherein m+p<3;

q is 0, 1, or 2; and r is 0 or 1;

with the proviso that $R^c$ is not —CN when L is —$SCH_2$— and $R^d$ is optionally substituted phenyl, $R^c$ is not $C_1$-$C_6$ alkyl when L is —$SCH_2$— and $R^d$ is methyl, and that $R^c$ is not —CN when L is —$SCH_2$— and $R^d$ is 2-furyl.

In some embodiments of Formula (Ia), L is —$(CH_2)_mCH_2CH_2$—, —$(CH_2)_mY(CH_2)_p$—, —$(CH_2)_mC(O)(CH_2)_p$—, —$(CH_2)_mC(O)O(CH_2)_p$—, —$(CH_2)_mC(O)NR^2(CH_2)_p$—, or —$(CH_2)_mNR^2C(O)(CH_2)_p$. In other embodiments, L is —$CH_2CH_2$—, —$CH_2CH_2CH_2$—, —$SCH_2$—, —$SCH_2CH_2$—, —$CH_2S$—, —$CH_2SCH_2$—, —$CH_2CH_2S$—, —$S(O)CH_2$—, —$S(O)CH_2CH_2$—, —$CH_2S(O)$—, —$CH_2S(O)CH_2$—, —$CH_2CH_2S(O)$—, —$S(O)_2CH_2$—, —$S(O)_2CH_2CH_2$—, —$CH_2S(O)_2$—, —$CH_2S(O)_2CH_2$—, —$CH_2CH_2S(O)_2$—, —$OCH_2$—, —$OCH_2CH_2$—, —$CH_2O$—, —$CH_2OCH_2$—, —$CH_2CH_2O$—, —$NR^2CH_2$—, —$CH_2NR^2$—, —$CH_2NR^2CH_2$—, —$CH_2CH_2NR^2$—, —$NR^2CH_2CH_2$—, —$C(O)CH_2$—, —$C(O)CH_2CH_2$—, —$C(O)O$—, —$C(O)OCH_2$—, —$CH_2C(O)O$—, —$C(O)NR^2$—, —$C(O)NR^2CH_2$—, —$NR^2C(O)$, —$NR^2C(O)CH_2$, or —$CH_2NR_2C(O)$. In other embodiments, L is —$CH_2CH_2$—, —$CH_2CH_2CH_2$—, —$SCH_2$—, —$SCH_2CH_2$—, —$S(O)CH_2$—, —$S(O)CH_2CH_2$—, —$S(O)_2CH_2$—, —$S(O)_2CH_2CH_2$—, —$OCH_2$—, —$OCH_2CH_2$—, —$NR^2CH_2$—, —$NR^2CH_2CH_2$—, —$C(O)CH_2$—, —$C(O)CH_2CH_2$—, —$C(O)O$—, —$C(O)OCH_2$—, —$CH_2C(O)O$—, —$C(O)NR^2$—, —$C(O)NR^2CH_2$—, —$NR^2C(O)$, or —$NR^2C(O)CH_2$. In other embodiments, L is —$CH_2CH_2$—, —$CH_2C(O)$—, —$C(O)CH_2$—, —$NR^2CH_2$—, —$CH_2NR^2$—, —$OCH_2$—, —$CH_2O$—, —$SCH_2$—, —$CH_2S$—, —$S(O)CH_2$—, —$CH_2S(O)$—, —$CH_2S(O)_2$—, or —$S(O)_2CH_2$—.

In some embodiments of Formula (Ia), $R^1$ is $C_6$-$C_{10}$ aryl or heteroaryl, wherein the aryl and heteroaryl are substituted with $R^a$ and $R^b$, and optionally substituted with one or more $R^e$. In other embodiments, $R^1$ is $C_6$-$C_{10}$ aryl substituted with $R^a$ and $R^b$, and optionally substituted with one or more $R^e$. In other embodiments, $R^1$ is heteroaryl substituted with $R^a$ and $R^b$, and optionally substituted with one or more $R^e$. In further embodiments, $R^1$ is phenyl substituted with $R^a$ and $R^b$, and optionally substituted with one or more $R^e$.

In some embodiments of Formula (Ia), $R^a$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^a$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^a$ is hydrogen, $CO_2R^x$, $CH_2CO_2R^x$, tetrazole, or oxadiazolone. In further embodiments, $R^a$ is hydrogen, $CO_2H$, $CH_2CO_2H$, tetrazole, or 1,2,4-oxadiazol-5(4H)-one.

In some embodiments of Formula (Ia), $R^b$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^b$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^b$ is hydrogen, $CO_2R^x$, $CH_2CO_2R^x$, tetrazole, or oxadiazolone. In further embodiments, $R^b$ is hydrogen, $CO_2H$, $CH_2CO_2H$, tetrazole, or 1,2,4-oxadiazol-5(4H)-one. In further embodiments, $R^b$ is hydrogen.

In some embodiments of Formula (Ia), $R^c$ is H, $C_1$-$C_6$ alkyl, $C_1$-$C_6$ haloalkyl, halogen, —CN, —$OR^x$, —$CO_2R^x$, or $NO_2$. In other embodiments, $R^c$ is $C_1$-$C_6$ alkyl, $C_1$-$C_6$ haloalkyl, halogen, —CN, —$OR^x$, —$CO_2R^x$, or $NO_2$. In other embodiments, $R^c$ is halogen, —CN, —$OR^x$, or $C_1$-$C_6$ alkyl. In other embodiments, $R^c$ is halogen, —CN, —$OR^x$, or $C_1$-$C_3$ alkyl. In other embodiments, $R^c$ is H, —CN, or halogen. In other embodiments, $R^c$ is —CN or halogen.

In some embodiments of Formula (Ia), $R^d$ is methyl, optionally substituted 5- to 10-membered aryl, optionally substituted 5- or 6-membered heteroaryl, or optionally substituted 5- or 6-membered carbocycle. In other embodiments, $R^d$ is methyl, optionally cyclohexyl, optionally substituted pyridinyl, optionally substituted thiazolyl, optionally substituted phenyl, or optionally substituted thienyl. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, $C_1$-$C_6$ haloalkoxy, —OH, CN, and amino. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, and $C_1$-$C_6$ haloalkoxy. In other embodiments, $R^d$ is cyclohexyl, pyridinyl, thiazolyl, phenyl, or thienyl, wherein each is optionally substituted with one or more halogen. In other embodiments, $R^d$ is methyl, cyclohexyl, pyridinyl, thiazolyl, phenyl, or thienyl. In yet other embodiments, $R^d$ is cyclohexyl, pyridinyl, thiazolyl, phenyl, or thienyl. In other embodiments, $R^d$ is cyclohexyl, pyridinyl, thiazolyl, phenyl, 4-chlorophenyl, 4-methylphenyl, or thienyl.

In some embodiments of Formula (Ia), each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN. In other embodiments, $C_1$-$C_4$ alkyl, $C_2$-$C_4$ alkenyl, $C_2$-$C_4$ alkynyl, halogen, —$OR^y$, $C_1$-$C_4$ haloalkyl, —$NHR^z$, —OH, or —CN.

In some embodiments of Formula (Ia), $R^x$ is hydrogen or $C_1$-$C_6$ alkyl. In other embodiments, $R^x$ is hydrogen or $C_1$-$C_3$ alkyl. In further embodiments, $R^x$ is hydrogen, methyl, ethyl, n-propyl, or iso-propyl.

In some embodiments of Formula (Ia), $R^y$ is independently hydrogen, $C_1$-$C_6$ alkyl, or $C_1$-$C_6$ haloalkyl. In other embodiments, $R^y$ is hydrogen, $C_1$-$C_3$ alkyl, or $C_1$-$C_3$ haloalkyl.

In some embodiments of Formula (Ia), each $R^z$ is independently hydrogen, $C_1$-$C_6$ alkyl, or $C_1$-$C_6$ haloalkyl. In other embodiments, $R^z$ is hydrogen, $C_1$-$C_3$ alkyl, or $C_1$-$C_3$ haloalkyl.

In some embodiments of Formula (Ia), m is 0, 1 or 2. In other embodiments, m is 0. In other embodiments, m is 1. In yet other embodiments, m is 2.

In some embodiments of Formula (Ia), p is 0, 1 or 2. In other embodiments, p is 0. In other embodiments, p is 1. In yet other embodiments, p is 2.

In some embodiments of Formula (Ia), q is 0, 1, or 2. In other embodiments, q is 0. In other embodiments, q is 1. In other embodiments, q is 2.

In some embodiments of Formula (Ia), r is 0 or 1. In other embodiments, r is 0. In other embodiments, r is 1.

In some embodiments of Formula (Ia), one of $R^a$ and $R^b$ is hydrogen and the other is $CO_2R^x$, $CH_2CO_2R^x$, tetrazole, or oxadiazolone. In other embodiments, $R^b$ is hydrogen and $R^a$ is $CH_2CO_2H$, tetrazole, or (1,2,4-oxadiazol-5(4H)-one).

In some embodiments of Formula (Ia), $R^b$ is hydrogen, $R^c$ is —CN, $R^d$ is thienyl, and $R^a$ is $CH_2CO_2H$, tetrazole, or (1,2,4-oxadiazol-5(4H)-one).

In some embodiments of Formula (Ia), $R^c$ is halogen, $R^a$ is —$CO_2H$, and $R^b$ is H. In other embodiments, $R^c$ is —Br, $R^a$ is —$CO_2H$, and $R^b$ is H. In further embodiments, $R^c$ is —Cl, $R^a$ is —$CO_2H$, and $R^b$ is H.

In some embodiments of Formula (Ia), $R^c$ is halogen, $R^a$ is tetrazole, and $R^b$ is H. In other embodiments, $R^c$ is —Br, $R^a$ is tetrazole, and $R^b$ is H. In further embodiments, $R^c$ is —Cl, $R^a$ is tetrazole, and $R^b$ is H.

In some embodiments of Formula (Ia), $R^c$ is halogen, $R^a$ is —$CH_2CO_2H$, and $R^b$ is H. In other embodiments, $R^c$ is —Br, $R^a$ is —$CH_2CO_2H$, and $R^b$ is H. In further embodiments, $R^c$ is —Cl, $R^a$ is —$CH_2CO_2H$, and $R^b$ is H.

In some embodiments of Formula (Ia), $R^c$ is halogen, $R^a$ is (1,2,4-oxadiazol-5(4H)-one), and $R^b$ is H. In other embodiments, $R^c$ is —Br, $R^a$ is (1,2,4-oxadiazol-5(4H)-one), and $R^b$ is H. In other embodiments, $R^c$ is —Cl, $R^a$ is (1,2,4-oxadiazol-5(4H)-one), and $R^b$ is H.

In some embodiments of Formula (Ia), $R^c$ is —CN, $R^a$ is —$CO_2H$, and $R^b$ is H. In other embodiments, $R^c$ is —CN, $R^a$ is —$CH_2CO_2H$, and $R^b$ is H. In other embodiments, $R^c$ is —CN, $R^a$ is tetrazole, and $R^b$ is H. In yet other embodiments, $R^c$ is —CN, $R^a$ is (1,2,4-oxadiazol-5(4H)-one), and $R^b$ is H.

In some embodiments of Formula (Ia), $R^c$ is not hydrogen or —CN and L is —$SCH_2$— and $R^d$ is optionally substituted phenyl. In other embodiments, $R^c$ is not $C_1$-$C_6$ alkyl and L is —$SCH_2$— and $R^d$ is methyl. In other embodiments, $R^c$ is not —CN and L is —$SCH_2$— and $R^d$ is 2-furyl.

In some embodiments of Formula (Ia), $R^c$ is not hydrogen or —CN when L is —$SCH_2$— and $R^d$ is optionally substituted phenyl.

In some embodiments of Formula (Ia), $R^c$ is not $C_1$-$C_6$ alkyl when L is —$SCH_2$— and $R^d$ is methyl.

In some embodiments of Formula (Ia), $R^c$ is not —CN when L is —$SCH_2$— and $R^d$ is 2-furyl.

In another embodiment, the compound of Formula (I) is represented by Formula (Ib):

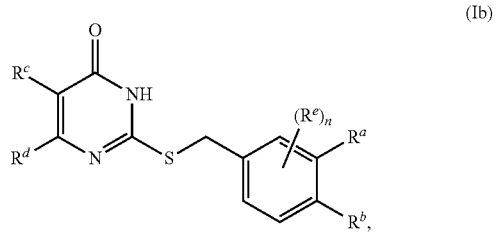

(Ib)

or a pharmaceutically acceptable salt thereof wherein:

$R^a$ and $R^b$ is hydrogen and the other is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2alkyl$;

$R^c$ is H, $C_1$-$C_6$ alkyl, $C_1$-$C_6$ haloalkyl, halogen, —CN, —$OR^x$, —$CO_2R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

each $R^y$ and $R^z$ is independently hydrogen, $C_1$-$C_6$ alkyl, or $C_1$-$C_6$ haloalkyl; and n is 0, 1, 2, or 3;

with the proviso that $R^c$ is not hydrogen or —CN when and $R^d$ is optionally substituted phenyl, $R^c$ is not $C_1$-$C_6$ alkyl when $R^d$ is methyl, and that $R^c$ is not —CN when $R^d$ is 2-furyl.

In some embodiments of Formula (Ib), one of $R^a$ and $R^b$ is hydrogen and the other is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2alkyl$;

$R^c$ is $C_1$-$C_6$ alkyl, $C_1$-$C_6$ haloalkyl, halogen, —CN, —$OR^x$, —$CO_2R^x$, or $NO_2$;

$R^d$ is methyl, optionally substituted 5- to 10-membered aryl, optionally substituted 5- or 6-membered heteroaryl, or optionally substituted 5- or 6-membered carbocycle;

each $R^x$ is independently at each occurrence hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

with the proviso that $R^c$ is not hydrogen or —CN when $R^d$ is optionally substituted phenyl, $R^c$ is not $C_1$-$C_6$ alkyl when $R^d$ is methyl, and that $R^c$ is not —CN when $R^d$ is 2-furyl.

In some embodiments of formula (Ib), one of $R^a$ and $R^b$ is hydrogen and the other is $CO_2R^x$, $CH_2CO_2R^x$, tetrazole, or oxadiazolone;

$R^c$ is halogen, —CN, —$OR^x$, or $C_1$-$C_6$ alkyl;

$R^d$ is methyl, optionally substituted 5- to 10-membered aryl, optionally substituted 5- or 6-membered heteroaryl, or optionally substituted 5- or 6-membered carbocycle; and $R^x$ is hydrogen or $C_1$-$C_6$ alkyl;

each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN;

each $R^y$ and $R^z$ is independently hydrogen, $C_1$-$C_6$ alkyl, or $C_1$-$C_6$ haloalkyl; and n is 0, 1, 2, or 3;

with the proviso that $R^c$ is not —CN when $R^d$ is optionally substituted phenyl, $R^c$ is not $C_1$-$C_6$ alkyl when $R^d$ is methyl, and that $R^c$ is not —CN when $R^d$ is 2-furyl.

In some embodiments of Formula (Ib), $R^a$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^a$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^a$ is hydrogen, $CO_2R^x$, $CH_2CO_2R^x$, tetrazole, or oxadiazolone. In further embodiments, $R^a$ is hydrogen, $CO_2H$, $CH_2CO_2H$, tetrazole, or 1,2,4-oxadiazol-5(4H)-one.

In some embodiments of Formula (Ib), $R^b$ is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl. In other embodiments, $R^b$ is —$(CH_2)_rCO_2R^x$, —$OCH_2CO_2R^x$, tetrazole, —$(CH_2)$tetrazole, oxadiazolone, —$(CH_2)$oxadiazolone, tetrazolone, —$(CH_2)$tetrazolone, thiadiazolol, —$(CH_2)$thiadiazolol, isoxazol-3-ol, —$(CH_2)$ isoxazol-3-ol, —$P(O)(OH)OR^x$, —$(CH_2)P(O)(OH)OR^x$, —$S(O)_2OH$, —$(CH_2)S(O)_2OH$, —$C(O)NHCN$ —$(CH_2)C(O)NHCN$, —$C(O)NHS(O)_2$alkyl, or —$(CH_2)C(O)NHS(O)_2$alkyl. In other embodiments, $R^b$ is hydrogen, $CO_2R^x$, $CH_2CO_2R^x$, tetrazole, or oxadiazolone. In further embodiments, $R^b$ is hydrogen, $CO_2H$, $CH_2CO_2H$, tetrazole, or 1,2,4-oxadiazol-5(4H)-one. In further embodiments, $R^b$ is hydrogen.

In some embodiments of Formula (Ib), $R^c$ is H, $C_1$-$C_6$ alkyl, $C_1$-$C_6$ haloalkyl, halogen, —CN, —$OR^x$, —$CO_2R^x$, or $NO_2$. In other embodiments, $R^c$ is $C_1$-$C_6$ alkyl, $C_1$-$C_6$ haloalkyl, halogen, —CN, —$OR^x$, —$CO_2R^x$, or $NO_2$. In other embodiments, $R^c$ is halogen, —CN, —$OR^x$, or $C_1$-$C_6$ alkyl. In other embodiments, $R^c$ is halogen, —CN, —$OR^x$, or $C_1$-$C_3$ alkyl. In other embodiments, $R^c$ is H, —CN, or halogen. In other embodiments, $R^c$ is —CN or halogen.

In some embodiments of Formula (Ib), $R^d$ is methyl, optionally substituted 5- to 10-membered aryl, optionally substituted 5- or 6-membered heteroaryl, or optionally substituted 5- or 6-membered carbocycle. In other embodiments, $R^d$ is methyl, optionally cyclohexyl, optionally substituted pyridinyl, optionally substituted thiazolyl, optionally substituted phenyl, or optionally substituted thienyl. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, $C_1$-$C_6$ haloalkoxy, —OH, CN, and amino. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, and $C_1$-$C_6$ haloalkoxy. In other embodiments, $R^d$ is cyclohexyl, pyridinyl, thiazolyl, phenyl, or thienyl, wherein each is optionally substituted with one or more halogen. In other embodiments, $R^d$ is methyl, cyclohexyl, pyridinyl, thiazolyl, phenyl, or thienyl. In yet other embodiments, $R^d$ is cyclohexyl, pyridinyl, thiazolyl, phenyl, or thienyl. In other embodiments, $R^d$ is cyclohexyl, pyridinyl, thiazolyl, phenyl, 4-chlorophenyl, 4-methylphenyl, or thienyl.

In some embodiments of Formula (Ib), each $R^e$ is independently $C_1$-$C_6$ alkyl, $C_2$-$C_6$ alkenyl, $C_2$-$C_6$ alkynyl, halogen, —$OR^y$, $C_1$-$C_6$ haloalkyl, —$NHR^z$, —OH, or —CN. In other embodiments, $C_1$-$C_4$ alkyl, $C_2$-$C_4$ alkenyl, $C_2$-$C_4$ alkynyl, halogen, —$OR^y$, $C_1$-$C_4$ haloalkyl, —$NHR^z$, —OH, or —CN.

In some embodiments of Formula (Ib), $R^x$ is hydrogen or $C_1$-$C_6$ alkyl. In other embodiments, $R^x$ is hydrogen or $C_1$-$C_3$ alkyl. In further embodiments, $R^x$ is hydrogen, methyl, ethyl, n-propyl, or iso-propyl.

In some embodiments of Formula (Ib), $R^y$ is independently hydrogen, $C_1$-$C_6$ alkyl, or $C_1$-$C_6$ haloalkyl. In other embodiments, $R^y$ is hydrogen, $C_1$-$C_3$ alkyl, or $C_1$-$C_3$ haloalkyl.

In some embodiments of Formula (Ib), each $R^z$ is independently hydrogen, $C_1$-$C_6$ alkyl, or $C_1$-$C_6$ haloalkyl. In other embodiments, $R^z$ is hydrogen, $C_1$-$C_3$ alkyl, or $C_1$-$C_3$ haloalkyl.

In some embodiments of Formula (Ib), n is 0, 1, 2, or 3. In other embodiments, n is 0 or 1. In further embodiments, n is 0.

In some embodiments of Formula (Ib), one of $R^a$ and $R^b$ is hydrogen and the other is $CO_2R^x$, $CH_2CO_2R^x$, tetrazole, or oxadiazolone. In other embodiments, $R^b$ is hydrogen and $R^a$ is $CH_2CO_2H$, tetrazole, or (1,2,4-oxadiazol-5(4H)-one).

In some embodiments of Formula (Ib), $R^b$ is hydrogen, $R^c$ is —CN, $R^d$ is thienyl, and $R^a$ is $CH_2CO_2H$, tetrazole, or (1,2,4-oxadiazol-5(4H)-one).

In some embodiments of Formula (Ib), $R^c$ is halogen, $R^a$ is —$CO_2H$, and $R^b$ is H. In other embodiments, $R^c$ is —Br, $R^a$ is —$CO_2H$, and $R^b$ is H. In further embodiments, $R^c$ is —Cl, $R^a$ is —$CO_2H$, and $R^b$ is H.

In some embodiments of Formula (Ib), $R^c$ is halogen, $R^a$ is tetrazole, and $R^b$ is H. In other embodiments, $R^c$ is —Br, $R^a$ is tetrazole, and $R^b$ is H. In further embodiments, $R^c$ is —Cl, $R^a$ is tetrazole, and $R^b$ is H.

In some embodiments of Formula (Ib), $R^c$ is halogen, $R^a$ is —$CH_2CO_2H$, and $R^b$ is H. In other embodiments, $R^c$ is —Br, $R^a$ is —$CH_2CO_2H$, and $R^b$ is H. In further embodiments, $R^c$ is —Cl, $R^a$ is —$CH_2CO_2H$, and $R^b$ is H.

In some embodiments of Formula (Ib), $R^c$ is halogen, $R^a$ is (1,2,4-oxadiazol-5(4H)-one), and $R^b$ is H. In other embodiments, $R^c$ is —Br, $R^a$ is (1,2,4-oxadiazol-5(4H)-one), and $R^b$ is H. In other embodiments, $R^c$ is —Cl, $R^a$ is (1,2,4-oxadiazol-5(4H)-one), and $R^b$ is H.

In some embodiments of Formula (Ib), $R^c$ is —CN, $R^a$ is —$CO_2H$, and $R^b$ is H. In other embodiments, $R^c$ is —CN, $R^a$ is —$CH_2CO_2H$, and $R^b$ is H. In other embodiments, $R^c$ is —CN, $R^a$ is tetrazole, and $R^b$ is H. In yet other embodiments, $R^c$ is —CN, $R^a$ is (1,2,4-oxadiazol-5(4H)-one), and $R^b$ is H.

In some embodiments of Formula (Ib), $R^c$ is not hydrogen or —CN and $R^d$ is optionally substituted phenyl. In other embodiments, $R^c$ is not $C_1$-$C_6$ alkyl and $R^d$ is methyl. In other embodiments, $R^c$ is not —CN and $R^d$ is 2-furyl.

In some embodiments of Formula (Ib), $R^c$ is not hydrogen or —CN when and $R^d$ is optionally substituted phenyl.

In some embodiments of Formula (Ib), $R^c$ is not $C_1$-$C_6$ alkyl when $R^d$ is methyl.

In some embodiments of Formula (Ib), $R^c$ is not —CN when $R^d$ is 2-furyl.

In another embodiment, the compound of Formula (I) is represented by Formula (II):

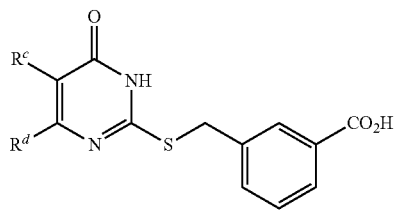

(II)

or a pharmaceutically acceptable salt thereof,
wherein:
$R^c$ is halogen, —CN, —OR$^x$, or $C_1$-$C_6$ alkyl;
$R^d$ is methyl, optionally substituted 5- to 10-membered aryl, optionally substituted 5- or 6-membered heteroaryl, or optionally substituted 5- or 6-membered carbocycle; and
$R^x$ is hydrogen or $C_1$-$C_6$ alkyl
with the proviso that $R^c$ is not —CN when and $R^d$ is optionally substituted phenyl, $R^c$ is not $C_1$-$C_6$ alkyl when $R^d$ is methyl, and that $R^c$ is not —CN when $R^d$ is 2-furyl.

In some embodiments of Formula (II), $R^c$ is halogen, —CN, —OR$^x$, or $C_1$-$C_6$ alkyl; $R^d$ is methyl, optionally substituted 5- to 10-membered aryl, optionally substituted 5- or 6-membered heteroaryl, or optionally substituted 5- or 6-membered carbocycle; and $R^x$ is hydrogen or $C_1$-$C_6$ alkyl with the proviso that $R^c$ is not $C_1$-$C_6$ alkyl when $R^d$ is methyl, and that $R^c$ is not —CN when $R^d$ is 2-furyl.

In some embodiments of Formula (II), $R^c$ is halogen, —CN, —OR$^x$, or $C_1$-$C_6$ alkyl. In other embodiments, $R^c$ is halogen, —CN, —OR$^x$, or $C_1$-$C_3$ alkyl. In further embodiments, $R^c$ is —CN or halogen.

In some embodiments of Formula (II), $R^d$ is methyl, optionally substituted 5- to 10-membered aryl, optionally substituted 5- or 6-membered heteroaryl, or optionally substituted 5- or 6-membered carbocycle. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, $C_1$-$C_6$ haloalkoxy, —OH, CN, and amino. In other embodiments, $R^d$ is cyclohexyl, pyridinyl, thiazolyl, phenyl, or thienyl, wherein each is optionally substituted with one or more substituents independently selected from halogen, $C_1$-$C_6$ alkyl, $C_1$-$C_6$ hydroxyalkyl, $C_1$-$C_6$ alkoxy, $C_1$-$C_6$ haloalkyl, and $C_1$-$C_6$ haloalkoxy. In other embodiments, $R^d$ is cyclohexyl, pyridinyl, thiazolyl, phenyl, or thienyl, wherein each is optionally substituted with one or more halogen. In further embodiments, $R^d$ is methyl, cyclohexyl, pyridinyl, thiazolyl, phenyl, or thienyl.

In some embodiments of Formula (II), $R^b$ is hydrogen, $CO_2R^x$, $CH_2CO_2R^x$, tetrazole, or oxadiazolone. In other embodiments, $R^b$ is hydrogen, $CO_2H$, $CH_2CO_2H$, tetrazole, or 1,2,4-oxadiazol-5(4H)-one. In further embodiments, $R^b$ is hydrogen.

In some embodiments of Formula (II), $R^a$ is hydrogen, $CO_2R^x$, $CH_2CO_2R^x$, tetrazole, or oxadiazolone. In further embodiments, $R^a$ is hydrogen, $CO_2H$, $CH_2CO_2H$, tetrazole, or 1,2,4-oxadiazol-5(4H)-one.

In some embodiments of Formula (II), each $R^e$ is independently $C_1$-$C_6$ alkyl, $C_2$-$C_6$ alkenyl, $C_2$-$C_6$ alkynyl, halogen, —OR$^y$, $C_1$-$C_6$ haloalkyl, —NHR$^z$, —OH, or —CN.

In some embodiments of Formula (II), each $R^y$ is independently hydrogen, $C_1$-$C_6$ alkyl, or $C_1$-$C_6$ haloalkyl.

In some embodiments of Formula (II), each $R^z$ is independently hydrogen, $C_1$-$C_6$ alkyl, or $C_1$-$C_6$ haloalkyl.

In some embodiments of Formula (II), n is 0, 1, 2, or 3. In other embodiments, n is 0 or 1. In further embodiments, n is 0.

In some embodiments of Formula (II), one of $R^a$ and $R^b$ is hydrogen and the other is $CO_2R^x$, $CH_2CO_2R^x$, tetrazole, or oxadiazolone. In other embodiments, $R^b$ is hydrogen and $R^a$ is $CH_2CO_2H$, tetrazole, or (1,2,4-oxadiazol-5(4H)-one).

In some embodiments of Formula (II), $R^b$ is hydrogen, $R^c$ is —CN, $R^d$ is thienyl, and $R^a$ is $CH_2CO_2H$, tetrazole, or (1,2,4-oxadiazol-5(4H)-one).

In some embodiments of Formula (II), $R^c$ is halogen, $R^a$ is —$CO_2H$, and $R^b$ is H. In other embodiments, $R^c$ is —Br, $R^a$ is —$CO_2H$, and $R^b$ is H. In further embodiments, $R^c$ is —Cl, $R^a$ is —$CO_2H$, and $R^b$ is H.

In some embodiments of Formula (II), $R^c$ is halogen, $R^a$ is tetrazole, and $R^b$ is H. In other embodiments, $R^c$ is —Br, $R^a$ is tetrazole, and $R^b$ is H. In further embodiments, $R^c$ is —Cl, $R^a$ is tetrazole, and $R^b$ is H.

In some embodiments of Formula (II), $R^c$ is halogen, $R^a$ is —$CH_2CO_2H$, and $R^b$ is H. In other embodiments, $R^c$ is —Br, $R^a$ is —$CH_2CO_2H$, and $R^b$ is H. In further embodiments, $R^c$ is —Cl, $R^a$ is —$CH_2CO_2H$, and $R^b$ is H.

In some embodiments of Formula (II), $R^c$ is halogen, $R^a$ is (1,2,4-oxadiazol-5(4H)-one), and $R^b$ is H. In other embodiments, $R^c$ is —Br, $R^a$ is (1,2,4-oxadiazol-5(4H)-one), and $R^b$ is H. In other embodiments, $R^c$ is —Cl, $R^a$ is (1,2,4-oxadiazol-5(4H)-one), and $R^b$ is H.

In some embodiments of Formula (II), $R^c$ is —CN, $R^a$ is —$CO_2H$, and $R^b$ is H. In other embodiments, $R^c$ is —CN, $R^a$ is —$CH_2CO_2H$, and $R^b$ is H. In other embodiments, $R^c$ is —CN, $R^a$ is tetrazole, and $R^b$ is H. In yet other embodiments, $R^c$ is —CN, $R^a$ is (1,2,4-oxadiazol-5(4H)-one), and $R^b$ is H.

In another embodiment, the compound of Formula (I) is represented by Formula (III):

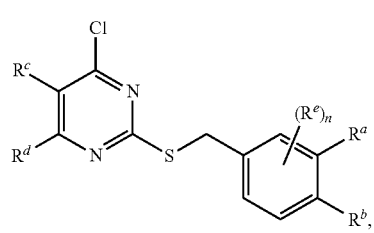

(III)

or a pharmaceutically acceptable salt thereof
wherein:
$R^a$ and $R^b$ is hydrogen and the other is —$(CH_2)_rCO_2R^x$, —$OCH_2CO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$isoxazol-3-ol, —(CH$_2$)$_r$P(O)(OH)OR$^x$, —(CH$_2$)$_r$S(O)$_2$OH, —(CH$_2$)$_r$C(O)NHCN, or —(CH$_2$)$_r$C(O)NHS(O)$_2$alkyl;

R$^c$ is H, C$_1$-C$_6$ alkyl, C$_1$-C$_6$ haloalkyl, halogen, —CN, —OR$^x$, —CO$_2$R$^x$, or NO$_2$;

R$^d$ is methyl, optionally substituted 5- to 10-membered aryl, optionally substituted 5- or 6-membered heteroaryl, or optionally substituted 5- or 6-membered carbocycle;

each R$^x$ is independently at each occurrence hydrogen or C$_1$-C$_6$ alkyl;

each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN;

each R$^y$ and R$^z$ is independently hydrogen, C$_1$-C$_6$ alkyl, or C$_1$-C$_6$ haloalkyl; and n is 0, 1, 2, or 3.

In some embodiments of Formula (III), one of R$^a$ and R$^b$ is hydrogen and the other is —(CH$_2$)$_r$CO$_2$R$^x$, —OCH$_2$CO$_2$R$^x$, —(CH$_2$)$_r$tetrazole, —(CH$_2$)$_r$oxadiazolone, —(CH$_2$)$_r$tetrazolone, —(CH$_2$)$_r$thiadiazolol, —(CH$_2$)$_r$ isoxazol-3-ol, —(CH$_2$)$_r$P(O)(OH)OR$^x$, —(CH$_2$)$_r$S(O)$_2$OH, —(CH$_2$)$_r$C(O)NHCN, or —(CH$_2$)$_r$C(O)NHS(O)$_2$alkyl;

R$^c$ is C$_1$-C$_6$ alkyl, C$_1$-C$_6$ haloalkyl, halogen, —CN, —OR$^x$, —CO$_2$R$^x$, or NO$_2$;

R$^d$ is methyl, optionally substituted 5- to 10-membered aryl, optionally substituted 5- or 6-membered heteroaryl, or optionally substituted 5- or 6-membered carbocycle;

each R$^x$ is independently at each occurrence hydrogen or C$_1$-C$_6$ alkyl;

each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN.

In some embodiments of formula (III), one of R$^a$ and R$^b$ is hydrogen and the other is CO$_2$R$^x$, CH$_2$CO$_2$R$^x$, tetrazole, or oxadiazolone;

R$^c$ is halogen, —CN, —OR$^x$, or C$_1$-C$_6$ alkyl;

R$^d$ is methyl, optionally substituted 5- to 10-membered aryl, optionally substituted 5- or 6-membered heteroaryl, or optionally substituted 5- or 6-membered carbocycle; and R$^x$ is hydrogen or C$_1$-C$_6$ alkyl;

each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN;

each R$^y$ and R$^z$ is independently hydrogen, C$_1$-C$_6$ alkyl, or C$_1$-C$_6$ haloalkyl; and n is 0, 1, 2, or 3;

with the proviso that R$^c$ is not hydrogen or —CN when R$^d$ is optionally substituted phenyl and that R$^c$ is not —CN when R$^d$ is 2-furyl.

In some embodiments of Formula (III), R$^a$ is —(CH$_2$)$_r$CO$_2$R$^x$, —OCH$_2$CO$_2$R$^x$, —(CH$_2$)$_r$tetrazole, —(CH$_2$)$_r$oxadiazolone, —(CH$_2$)$_r$tetrazolone, —(CH$_2$)$_r$thiadiazolol, —(CH$_2$)$_r$ isoxazol-3-ol, —(CH$_2$)$_r$P(O)(OH)OR$^x$, —(CH$_2$)$_r$S(O)$_2$OH, —(CH$_2$)$_r$C(O)NHCN, or —(CH$_2$)$_r$C(O)NHS(O)$_2$alkyl. In other embodiments, R$^a$ is —(CH$_2$)$_r$CO$_2$R$^x$, —OCH$_2$CO$_2$R$^x$, tetrazole, —(CH$_2$)tetrazole, oxadiazolone, —(CH$_2$)oxadiazolone, tetrazolone, —(CH$_2$)tetrazolone, thiadiazolol, —(CH$_2$)thiadiazolol, isoxazol-3-ol, —(CH$_2$) isoxazol-3-ol, —P(O)(OH)OR$^x$, —(CH$_2$)P(O)(OH)OR$^x$, —S(O)$_2$OH, —(CH$_2$)S(O)$_2$OH, —C(O)NHCN —(CH$_2$)C(O)NHCN, —C(O)NHS(O)$_2$alkyl, or —(CH$_2$)C(O)NHS(O)$_2$alkyl. In other embodiments, R$^a$ is hydrogen, CO$_2$R$^x$, CH$_2$CO$_2$R$^x$, tetrazole, or oxadiazolone. In further embodiments, R$^a$ is hydrogen, CO$_2$H, CH$_2$CO$_2$H, tetrazole, or 1,2,4-oxadiazol-5(4H)-one.

In some embodiments of Formula (III), R$^b$ is —(CH$_2$)$_r$CO$_2$R$^x$, —OCH$_2$CO$_2$R$^x$, —(CH$_2$)$_r$tetrazole, —(CH$_2$)$_r$oxadiazolone, —(CH$_2$)$_r$tetrazolone, —(CH$_2$)$_r$thiadiazolol, —(CH$_2$)$_r$ isoxazol-3-ol, —(CH$_2$)$_r$P(O)(OH)OR$^x$, —(CH$_2$)$_r$S(O)$_2$OH, —(CH$_2$)$_r$C(O)NHCN, or —(CH$_2$)$_r$C(O)NHS(O)$_2$alkyl. In other embodiments, R$^b$ is —(CH$_2$)$_r$CO$_2$R$^x$, —OCH$_2$CO$_2$R$^x$, tetrazole, —(CH$_2$)tetrazole, oxadiazolone, —(CH$_2$)oxadiazolone, tetrazolone, —(CH$_2$)tetrazolone, thiadiazolol, —(CH$_2$)thiadiazolol, isoxazol-3-ol, —(CH$_2$) isoxazol-3-ol, —P(O)(OH)OR$^x$, —(CH$_2$)P(O)(OH)OR$^x$, —S(O)$_2$OH, —(CH$_2$)S(O)$_2$OH, —C(O)NHCN —(CH$_2$)C(O)NHCN, —C(O)NHS(O)$_2$alkyl, or —(CH$_2$)C(O)NHS(O)$_2$alkyl. In other embodiments, R$^b$ is hydrogen, CO$_2$R$^x$, CH$_2$CO$_2$R$^x$, tetrazole, or oxadiazolone. In further embodiments, R$^b$ is hydrogen, CO$_2$H, CH$_2$CO$_2$H, tetrazole, or 1,2,4-oxadiazol-5(4H)-one. In further embodiments, R$^b$ is hydrogen.

In some embodiments of Formula (III), R$^c$ is H, C$_1$-C$_6$ alkyl, C$_1$-C$_6$ haloalkyl, halogen, —CN, —OR$^x$, —CO$_2$R$^x$, or NO$_2$. In other embodiments, R$^c$ is C$_1$-C$_6$ alkyl, C$_1$-C$_6$ haloalkyl, halogen, —CN, —OR$^x$, —CO$_2$R$^x$, or NO$_2$. In other embodiments, R$^c$ is halogen, —CN, —OR$^x$, or C$_1$-C$_6$ alkyl. In other embodiments, R$^c$ is halogen, —CN, —OR$^x$, or C$_1$-C$_3$ alkyl. In other embodiments, R$^c$ is H, —CN, or halogen. In other embodiments, R$^c$ is —CN or halogen.

In some embodiments of Formula (III), R$^d$ is methyl, optionally substituted 5- to 10-membered aryl, optionally substituted 5- or 6-membered heteroaryl, or optionally substituted 5- or 6-membered carbocycle. In other embodiments, R$^d$ is methyl, optionally cyclohexyl, optionally substituted pyridinyl, optionally substituted thiazolyl, optionally substituted phenyl, or optionally substituted thienyl. In other embodiments, R$^d$ is cyclohexyl, pyridinyl, thiazolyl, phenyl, or thienyl, wherein each is optionally substituted with one or more substituents independently selected from halogen, C$_1$-C$_6$ alkyl, C$_1$-C$_6$ hydroxyalkyl, C$_1$-C$_6$ alkoxy, C$_1$-C$_6$ haloalkyl, C$_1$-C$_6$ haloalkoxy, —OH, CN, and amino. In other embodiments, R$^d$ is cyclohexyl, pyridinyl, thiazolyl, phenyl, or thienyl, wherein each is optionally substituted with one or more substituents independently selected from halogen, C$_1$-C$_6$ alkyl, C$_1$-C$_6$ hydroxyalkyl, C$_1$-C$_6$ alkoxy, C$_1$-C$_6$ haloalkyl, and C$_1$-C$_6$ haloalkoxy. In other embodiments, R$^d$ is cyclohexyl, pyridinyl, thiazolyl, phenyl, or thienyl, wherein each is optionally substituted with one or more halogen. In other embodiments, R$^d$ is methyl, cyclohexyl, pyridinyl, thiazolyl, phenyl, or thienyl. In yet other embodiments, R$^d$ is cyclohexyl, pyridinyl, thiazolyl, phenyl, or thienyl. In other embodiments, R$^d$ is cyclohexyl, pyridinyl, thiazolyl, phenyl, 4-chlorophenyl, 4-methylphenyl, or thienyl.

In some embodiments of Formula (III), each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN. In other embodiments, C$_1$-C$_4$ alkyl, C$_2$-C$_4$ alkenyl, C$_2$-C$_4$ alkynyl, halogen, —OR$^y$, C$_1$-C$_4$ haloalkyl, —NHR$^z$, —OH, or —CN.

In some embodiments of Formula (III), R$^x$ is hydrogen or C$_1$-C$_6$ alkyl. In other embodiments, R$^x$ is hydrogen or C$_1$-C$_3$ alkyl. In further embodiments, R$^x$ is hydrogen, methyl, ethyl, n-propyl, or iso-propyl.

In some embodiments of Formula (III), R$^y$ is independently hydrogen, C$_1$-C$_6$ alkyl, or C$_1$-C$_6$ haloalkyl. In other embodiments, R$^y$ is hydrogen, C$_1$-C$_3$ alkyl, or C$_1$-C$_3$ haloalkyl.

In some embodiments of Formula (III), each R$^z$ is independently hydrogen, C$_1$-C$_6$ alkyl, or C$_1$-C$_6$ haloalkyl. In other embodiments, R$^z$ is hydrogen, C$_1$-C$_3$ alkyl, or C$_1$-C$_3$ haloalkyl.

In some embodiments of Formula (III), n is 0, 1, 2, or 3. In other embodiments, n is 0 or 1. In further embodiments, n is 0.

In some embodiments of Formula (III), one of $R^a$ and $R^b$ is hydrogen and the other is $CO_2R^x$, $CH_2CO_2R^x$, tetrazole, or oxadiazolone. In other embodiments, $R^b$ is hydrogen and $R^a$ is $CH_2CO_2H$, tetrazole, or (1,2,4-oxadiazol-5(4H)-one).

In some embodiments of Formula (III), $R^b$ is hydrogen, $R^c$ is —CN, $R^d$ is thienyl, and $R^a$ is $CH_2CO_2H$, tetrazole, or (1,2,4-oxadiazol-5(4H)-one).

In some embodiments of Formula (III), $R^c$ is halogen, $R^a$ is —$CO_2H$, and $R^b$ is H. In other embodiments, $R^c$ is —Br, $R^a$ is —$CO_2H$, and $R^b$ is H. In further embodiments, $R^c$ is —Cl, $R^a$ is —$CO_2H$, and $R^b$ is H.

In some embodiments of Formula (III), $R^c$ is halogen, $R^a$ is tetrazole, and $R^b$ is H. In other embodiments, $R^c$ is —Br, $R^a$ is tetrazole, and $R^b$ is H. In further embodiments, $R^c$ is —Cl, $R^a$ is tetrazole, and $R^b$ is H.

In some embodiments of Formula (III), $R^c$ is halogen, $R^a$ is —$CH_2CO_2H$, and $R^b$ is H. In other embodiments, $R^c$ is —Br, $R^a$ is —$CH_2CO_2H$, and $R^b$ is H. In further embodiments, $R^c$ is —Cl, $R^a$ is —$CH_2CO_2H$, and $R^b$ is H.

In some embodiments of Formula (III), $R^c$ is halogen, $R^a$ is (1,2,4-oxadiazol-5(4H)-one), and $R^b$ is H. In other embodiments, $R^c$ is —Br, $R^a$ is (1,2,4-oxadiazol-5(4H)-one), and $R^b$ is H. In other embodiments, $R^c$ is —Cl, $R^a$ is (1,2,4-oxadiazol-5(4H)-one), and $R^b$ is H.

In some embodiments of Formula (III), $R^c$ is —CN, $R^a$ is —$CO_2H$, and $R^b$ is H. In other embodiments, $R^c$ is —CN, $R^a$ is —$CH_2CO_2H$, and $R^b$ is H. In other embodiments, $R^c$ is —CN, $R^a$ is tetrazole, and $R^b$ is H. In yet other embodiments, $R^c$ is —CN, $R^a$ is (1,2,4-oxadiazol-5(4H)-one), and $R^b$ is H.

In some embodiments of Formula (III), $R^c$ is not hydrogen or —CN when $R^d$ is optionally substituted phenyl, $R^c$ is not $C_1$-$C_6$ alkyl when $R^d$ is methyl, and that $R^c$ is not —CN when $R^d$ is 2-furyl.

In some embodiments of Formula (I), (Ia), (Ib), (II) and (III), one of $R^a$ or $R^b$ is a carboxylic acid or a carboxylic acid bioisostere.

In some embodiments of Formula (I), (Ia), (Ib), (II) and (III), $R^a$ is —$CO_2H$, —$(CH_2)CO_2H$, or —$OCH_2CO_2H$. In other embodiments, $R^a$ is —$CO_2CH_3$, —$CO_2CH_2CH_3$, —$CO_2CH_2CH_2CH_3$, —$CO_2CH(CH_3)_2$, —$(CH_2)CO_2CH_3$, —$(CH_2)CO_2CH_2CH_3$, —$(CH_2)CO_2CH_2CH_2CH_3$, or —$(CH_2)CO_2CH(CH_3)_2$.

In some embodiments of Formula (I), (Ia), (Ib), (II) and (III), $R^a$ is —$P(O)(OH)OH$, —$(CH_2)P(O)(OH)OH$, —$P(O)(OH)OCH_3$, —$P(O)(OH)OCH_2CH_3$, —$P(O)(OH)OCH_2CH_2CH_3$, —$P(O)(OH)OCH(CH_3)_2$, —$(CH_2)P(O)(OH)OCH_3$, —$(CH_2)P(O)(OH)OCH_2CH_3$, —$(CH_2)P(O)(OH)OCH_2CH_2CH_3$, or —$(CH_2)P(O)(OH)OCH(CH_3)_2$.

In some embodiments of Formula (I), (Ia), (Ib), (II) and (III), $R^a$ is —$S(O)_2OH$, —$(CH_2)S(O)_2OH$, —$C(O)NHCN$, or —$(CH_2)C(O)NHCN$.

In some embodiments of Formula (I), (Ia), (Ib), (II) and (III), $R^a$ is —$C(O)NHS(O)_2CH_3$, —$C(O)NHS(O)_2CH_2CH_3$, —$C(O)NHS(O)_2CH_2CH_2CH_3$, —$C(O)NHS(O)_2CH(CH_3)_2$, —$(CH_2)C(O)NHS(O)_2CH_3$, —$(CH_2)C(O)NHS(O)_2CH_2CH_3$, —$(CH_2)C(O)NHS(O)_2CH_2CH_2CH_3$, or —$(CH_2)C(O)NHS(O)_2CH(CH_3)_2$.

In some embodiments of Formula (I), (Ia), (Ib), (II) and (III), $R^a$ is

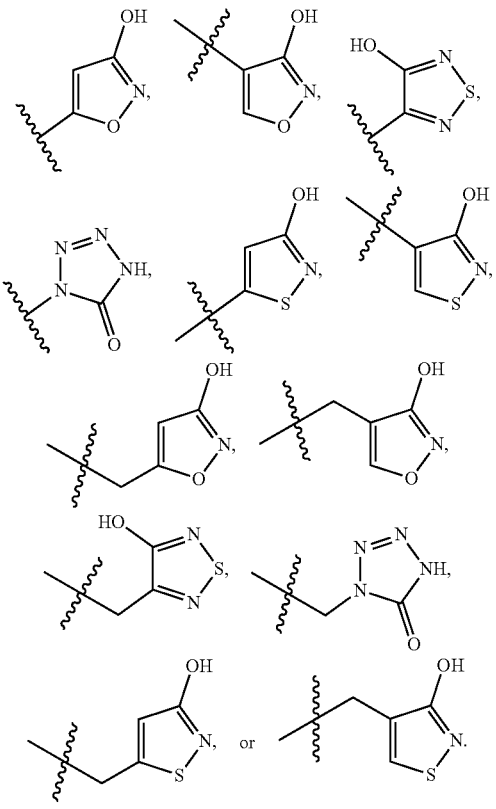

In some embodiments of Formula (I), (Ia), (Ib), (II), and (III), $R^a$ is

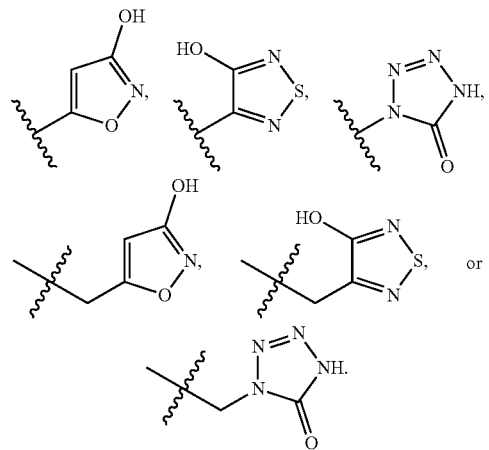

In some embodiments of Formula (I), (Ia), (Ib), (II) and (III), $R^b$ is —$CO_2H$, —$(CH_2)CO_2H$, or —$OCH_2CO_2H$. In other embodiments, $R^b$ is —$CO_2CH_3$, —$CO_2CH_2CH_3$, —$CO_2CH_2CH_2CH_3$, —$CO_2CH(CH_3)_2$, —$(CH_2)CO_2CH_3$, —$(CH_2)CO_2CH_2CH_3$, —$(CH_2)CO_2CH_2CH_2CH_3$, or —$(CH_2)CO_2CH(CH_3)_2$.

In some embodiments of Formula (I), (Ia), (Ib), (II) and (III), $R^b$ is —$P(O)(OH)OH$, —$(CH_2)P(O)(OH)OH$, —$P(O)(OH)OCH_3$, —$P(O)(OH)OCH_2CH_3$, —$P(O)(OH)$ OCH$_2$CH$_2$CH$_3$, —P(O)(OH)OCH(CH$_3$)$_2$, —(CH$_2$) P(O)(OH)OCH$_3$, —(CH$_2$)P(O)(OH)OCH$_2$CH$_3$, —(CH$_2$)P(O)(OH)OCH$_2$CH$_2$CH$_3$, or —(CH$_2$)P(O)(OH)OCH(CH$_3$)$_2$.

In some embodiments of Formula (I), (Ia), (Ib), (II) and (III), R$^b$ is —S(O)$_2$OH, —(CH$_2$)S(O)$_2$OH, —C(O)NHCN, or —(CH$_2$)C(O)NHCN.

In some embodiments of Formula (I), (Ia), (Ib), (II) and (III), R$^b$ is —C(O)NHS(O)$_2$CH$_3$, —C(O)NHS(O)$_2$CH$_2$CH$_3$, —C(O)NHS(O)$_2$CH$_2$CH$_2$CH$_3$, —C(O)NHS(O)$_2$CH(CH$_3$)$_2$, —(CH$_2$)C(O)NHS(O)$_2$CH$_3$, —(CH$_2$)C(O)NHS(O)$_2$CH$_2$CH$_3$, —(CH$_2$)C(O)NHS(O)$_2$CH$_2$CH$_2$CH$_3$, or —(CH$_2$)C(O)NHS(O)$_2$CH(CH$_3$)$_2$.

In some embodiments of Formula (I), (Ia), (Ib), (II) and (III), R$^b$ is

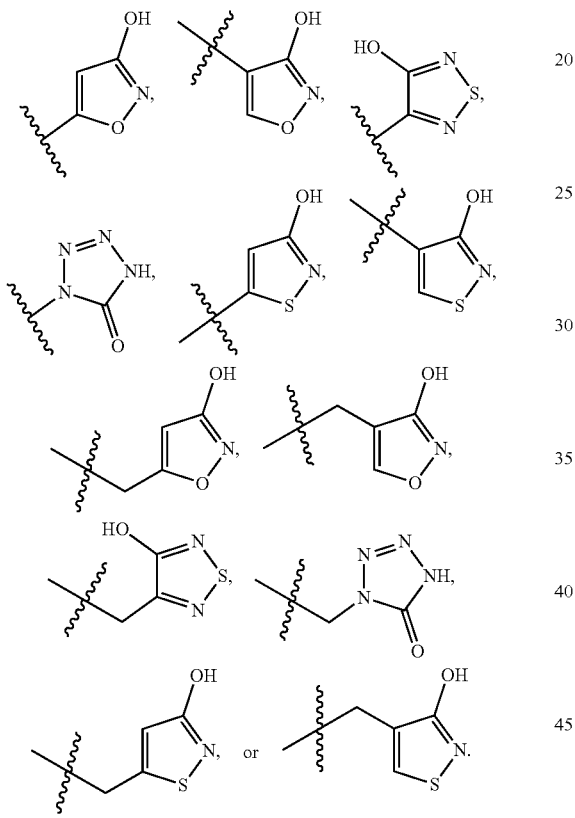

In some embodiments of Formula (I), (Ia), (Ib), (II) and (III), R$^b$ is

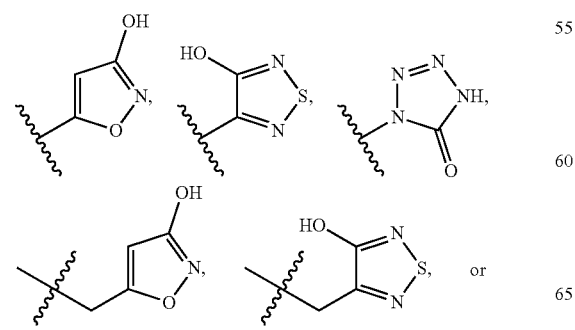

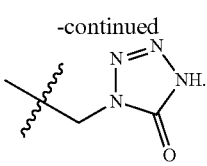

In some embodiments, the compound of Formula (I) is a compound having any one of the following Formulae:

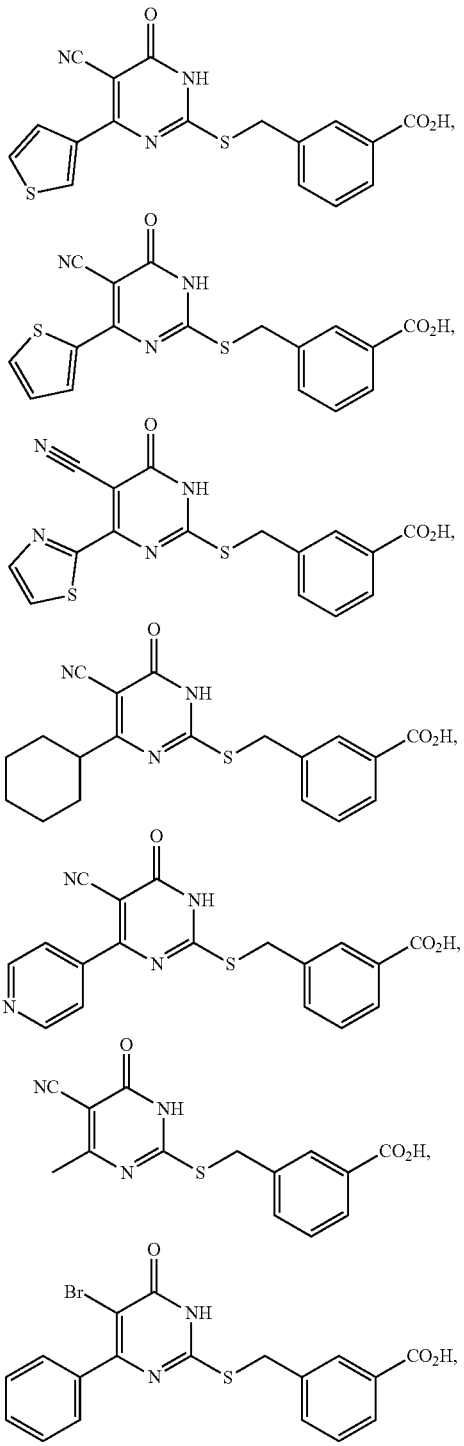

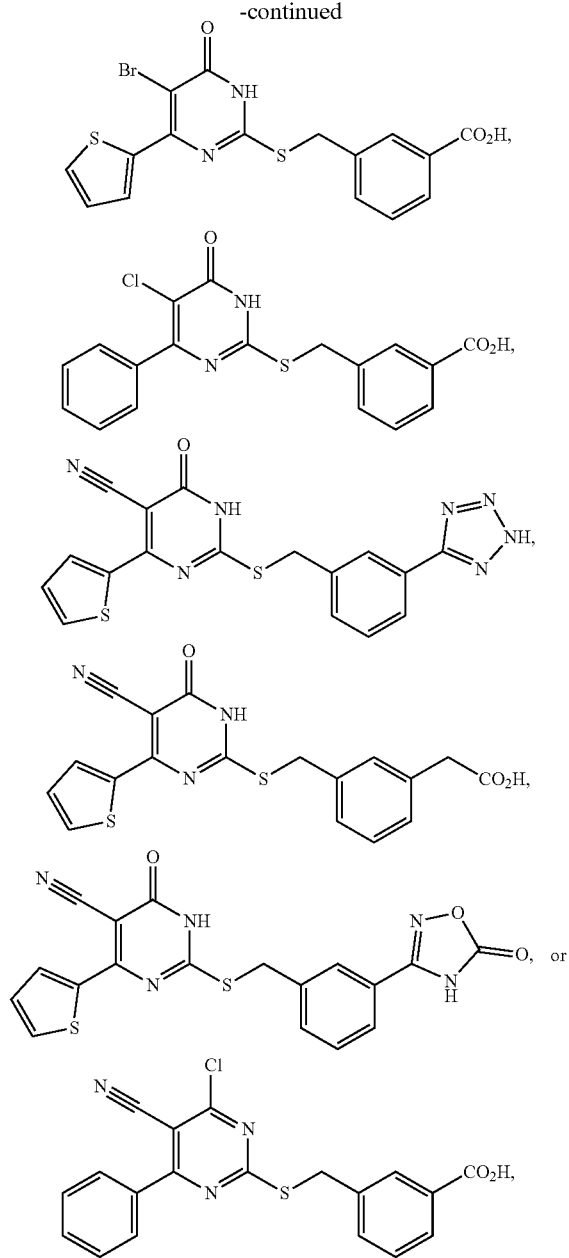

or a pharmaceutically acceptable salt thereof

The above definition of the compounds of Formula (I) is referred to herein by the expressions "compound of Formula (I)" as defined herein, or simply "compounds of Formula (I)", etc. The above definition of the compounds of Formula (Ia) is referred to herein by the expressions "compound of Formula (Ia)" as defined herein, or simply "compounds of Formula (Ia)", etc. The above definition of the compounds of Formula (Ib) is referred to herein by the expressions "compound of Formula (Ib)" as defined herein, or simply "compounds of Formula (Ib)", etc. The above definition of the compounds of Formula (II) is referred to herein by the expressions "compound of Formula (II)" as defined herein, or simply "compounds of Formula (II)", etc. The above definition of the compounds of Formula (III) is referred to herein by the expressions "compound of Formula (III)" as defined herein, or simply "compounds of Formula (III)", etc.

It should be understood, that such references are intended to encompass not only the above general formula, but also each and every of the embodiments, etc. discussed in the following. It should also be understood, that unless stated to the opposite, such references also encompass isomers, mixtures of isomers, pharmaceutically acceptable salts, solvates and prodrugs of the compounds of Formula (I), Formula (Ia), Formula (Ib), Formula (II), and Formula (III).

Definitions

The term "alkyl" as used herein refers to a saturated, straight or branched hydrocarbon chain. The hydrocarbon chain preferably contains from one to eight carbon atoms ($C_{1-8}$-alkyl), more preferred from one to six carbon atoms ($C_{1-6}$-alkyl), in particular from one to four carbon atoms ($C_{1-4}$-alkyl), including methyl, ethyl, propyl, isopropyl, butyl, isobutyl, secondary butyl, tertiary butyl, pentyl, isopentyl, neopentyl, tertiary pentyl, hexyl, isohexyl, heptyl and octyl. In a preferred embodiment "alkyl" represents a $C_{1-4}$-alkyl group, which may in particular include methyl, ethyl, propyl, isopropyl, butyl, isobutyl, secondary butyl, and tertiary butyl. Correspondingly, the term "alkylene" means the corresponding biradical (-alkyl-).

The term "cycloalkyl" or "carbocycle" as used herein refers to a cyclic alkyl group, preferably containing from three to ten carbon atoms ($C_{3-10}$-cycloalkyl or $C_{3-10}$-carbocycle), such as from three to eight carbon atoms ($C_{3-8}$-cycloalkyl or $C_{3-10}$-carbocycle), preferably from three to six carbon atoms ($C_{3-6}$-cycloalkyl or $C_{3-10}$-carbocycle), including cyclopropyl, cyclobutyl, cyclopentyl, cyclohexyl, cycloheptyl and cyclooctyl. Furthermore, the term "cycloalkyl" as used herein may also include polycyclic groups such as for example bicyclo[2.2.2]octyl, bicyclo[2.2.1]heptanyl, decalinyl and adamantyl. Correspondingly, the term "cycloalkylene" means the corresponding biradical (-cycloalkyl-). Alkyl and cycloalkyl groups may be optionally substituted with 1-4 substituents. Examples of substituents on alkyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The term "alkenyl" as used herein refers to a straight or branched hydrocarbon chain or cyclic hydrocarbons containing one or more double bonds, including di-enes, tri-enes and poly-enes. Typically, the alkenyl group comprises from two to eight carbon atoms ($C_{2-8}$-alkenyl), such as from two to six carbon atoms ($C_{2-6}$-alkenyl), in particular from two to four carbon atoms ($C_{2-4}$-alkenyl), including at least one double bond. Examples of alkenyl groups include ethenyl; 1- or 2-propenyl; 1-, 2- or 3-butenyl, or 1,3-but-dienyl; 1-, 2-, 3-, 4- or 5-hexenyl, or 1,3-hex-dienyl, or 1,3,5-hextrienyl; 1-, 2-, 3-, 4-, 5-, 6-, or 7-octenyl, or 1,3-octadienyl, or 1,3,5-octatrienyl, or 1,3,5,7-octatetraenyl, or cyclohexenyl. Correspondingly, the term "alkenylene" means the corresponding biradical (-alkenyl-). Alkenyl groups may be optionally substituted with 1-4 substituents. Examples of substituents on alkenyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The term "alkynyl" as used herein refers to a straight or branched hydrocarbon chain containing one or more triple bonds, including di-ynes, tri-ynes and poly-ynes. Typically, the alkynyl group comprises of from two to eight carbon atoms ($C_{2-8}$-alkynyl), such as from two to six carbon atoms ($C_{2-6}$-alkynyl), in particular from two to four carbon atoms ($C_{2-4}$-alkynyl), including at least one triple bond. Examples of preferred alkynyl groups include ethynyl; 1- or 2-propynyl; 1-, 2- or 3-butynyl, or 1,3-but-diynyl; 1-, 2-, 3-, 4- or 5-hexynyl, or 1,3-hex-diynyl, or 1,3,5-hex-triynyl; 1-, 2-, 3-, 4-, 5-, 6-, or 7-octynyl, or 1,3-oct-diynyl, or 1,3,5-oct-triynyl, or 1,3,5,7-oct-tetraynyl. Correspondingly, the term "alkynylene" means the corresponding biradical (-alkynyl-). Alkynyl groups may be optionally substituted with 1-4 substituents. Examples of substituents on alkynyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The terms "halo" and "halogen" as used herein refer to fluoro, chloro, bromo or iodo. Thus a trihalomethyl group represents, e.g., a trifluoromethyl group, or a trichloromethyl group. Preferably, the terms "halo" and "halogen" designate fluoro or chloro.

The term "haloalkyl" as used herein refers to an alkyl group, as defined herein, which is substituted one or more times with one or more halogen. Examples of haloalkyl groups include, but are not limited to, trifluoromethyl, difluoromethyl, pentafluoroethyl, trichloromethyl, etc.

The term "alkoxy" as used herein refers to an "alkyl-O—" group, wherein alkyl is as defined above.

The term "hydroxyalkyl" as used herein refers to an alkyl group (as defined hereinabove), which alkyl group is substituted one or more times with hydroxy. Examples of hydroxyalkyl groups include HO—$CH_2$—, HO—$CH_2$—$CH_2$— and $CH_3$—CH(OH)—.

The term "oxy" as used herein refers to an "—O—" group.

The term "oxo" as used herein refers to an "=O" group.

The term "amine" as used herein refers to primary (R—$NH_2$, R≠H), secondary ((R)$_2$—NH, (R)$_2$≠H) and tertiary ((R)$_3$—N, R≠H) amines. A substituted amine is intended to mean an amine where at least one of the hydrogen atoms has been replaced by the substituent.

The term "carbamoyl" as used herein refers to a "$H_2$N(C=O)—" group.

The term "aryl", as used herein, unless otherwise indicated, includes carbocyclic aromatic ring systems derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, biphenyl, indenyl, naphthyl, anthracenyl, phenanthrenyl, pentalenyl, azulenyl, and biphenylenyl. Preferred "aryl" is phenyl, naphthyl or indanyl, in particular phenyl, unless otherwise stated. Any aryl used may be optionally substituted. Correspondingly, the term "arylene" means the corresponding biradical (-aryl-). Aryl groups may be optionally substituted with 1-4 substituents. Examples of substituents on aryl groups include, but are not limited to, alkyl, alkenyl, alkynyl, halogen, haloalkyl, alkoxy, heteroaryl, aryl, carbocyclyl, hydroxyl, and —CN.

The term "heteroaryl", as used herein, refers to aromatic groups containing one or more heteroatoms selected from O, S, and N, preferably from one to four heteroatoms, and more preferably from one to three heteroatoms. Heteroaryl furthermore includes bi-, tri- and polycyclic groups, wherein at least one ring of the group is aromatic, and at least one of the rings contains a heteroatom selected from O, S, and N. Heteroaryl also include ring systems substituted with one or more oxo moieties. Examples of preferred heteroaryl moieties include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, phteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, azaindolyl, pyrazolinyl, 1,2,4-oxadiazol-5(4H)-one, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-). Heteroaryl groups may be optionally substituted with 1-4 substituents. Examples of substituents on heteroaryl groups include, but are not limited to, alkyl, alkenyl, alkynyl, halogen, haloalkyl, alkoxy, heteroaryl, aryl, carbocyclyl, hydroxyl, and —CN.

The term "heterocyclyl" as used herein, refers to cyclic non-aromatic groups containing one or more heteroatoms selected from O, S, and N, preferably from one to four heteroatoms, and more preferably from one to three heteroatoms. Heterocyclyl furthermore includes bi-, tri- and polycyclic non-aromatic groups, and at least one of the rings contains a heteroatom selected from O, S, and N. Heterocyclyl also include ring systems substituted with one or more oxo moieties. Examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholinyl, thiomorpholinyl, 1,4-oxathianyl, benzofuranyl, isobenzofuranyl, indazolyl, benzimidazolyl, quinolinyl, isoquinolinyl, chromayl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocyclylene" means the corresponding biradical (-heterocyclyl-). Heterocyclyl groups may be optionally substituted with 1-4 substituents. Examples of substituents on heterocyclyl groups include, but are not limited, to alkyl, alkenyl, alkynyl, halogen, haloalkyl, alkoxy, heteroaryl, aryl, carbocyclyl, hydroxyl, and —CN.

The term "N-heterocyclic ring" as used herein, refers to a heterocyclyl or a heteroaryl, as defined hereinabove, having at least one nitrogen atom, and being bound via a nitrogen atom. Examples of such N-heterocyclic rings are pyrrolidinyl, pyrrolyl, 3H-pyrrolyl, pyrazolyl, pyrazolidinyl, imidazolyl, imidazolidinyl, 3H-pyrazolyl, 1,2-oxazolyl, 1,2-thiazolyl, 1,3-thiazolyl, piperidinyl, pyridinyl, pyridazinyl, pyrazinyl, piperazinyl, morpholinyl, pyridinyl, pyridazinyl, pyrimidinyl, pyrazolyl, pyrazinyl, tetrazolyl, etc.

Isomers

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. Accordingly, it should be understood that the definition of compounds of Formulae (I), (Ia), (Ib), (II) and (III) include each and every individual isomer corresponding to the Formula: Formulae (I), (Ia), (Ib), (II) and (III), including cis-trans isomers, stereoisomers and tautomers, as well as racemic mixtures of these and pharmaceutically acceptable salts thereof. Hence, the definition of compounds of Formulae (I), (Ia), (Ib), (II) and (III) are also intended to encompass all R- and S-isomers of a chemical structure in any ratio, e.g., with enrichment (i.e., enantiomeric excess or diastereomeric excess) of one of the possible isomers and corresponding smaller ratios of other isomers. In addition, a crystal polymorphism may be present for the compounds represented by Formulae (I), (Ia), (Ib), (II) and (III). It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J Chem. Educ. 1964, 41, 116).

Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula (I), (Ia), (Ib), (II) or (III) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formulae (I), (Ia), (Ib), (II) and (III) can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Method of Treatment

In another aspect, the present disclosure relates to a method of treating a disease or disorder in which α-amino-β-carboxymuconate-ε-semialdehyde decarboxylase (ACMSD) plays a role comprising administering to the subject in need thereof a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of treating a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I), Formula (Ia), Formula (Ib), Formula (II), or Formula (III), or a pharmaceutically acceptable salt thereof.

In another aspect, the present disclosure relates to a method of preventing a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I), Formula (Ia), Formula (Ib), Formula (II), or Formula (III), or a pharmaceutically acceptable salt thereof.

In yet another aspect, the present disclosure relates to a method of reducing the risk of a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of ameliorating the risk of a disease or disorder associated with α-amino-β-carboxymuconate-ε-semialdehyde decarboxylase (ACMSD) dysfunction comprising administering to the subject suffering from or susceptible to developing a disease or disorder associated with ACMSD dysfunction a therapeutically effective amount of one or more compounds of Formula (I), Formula (Ia), Formula (Ib), Formula (II), or Formula (III), or a pharmaceutically acceptable salt thereof.

In another aspect, the present disclosure relates to a method of treating a disease or disorder in which nicotinamide adenine dinucleotide (NAD$^+$) modulation plays a role comprising administering to the subject in need thereof a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of preventing a disease or disorder in which nicotinamide adenine dinucleotide (NAD$^+$) modulation plays a role comprising administering to the subject in need thereof a therapeutically effective amount of one or more compounds of Formula (I), Formula (Ia), Formula (Ib), Formula (II), or Formula (III), or a pharmaceutically acceptable salt thereof.

In another aspect, the present disclosure relates to a method of reducing the risk of a disease or disorder in which nicotinamide adenine dinucleotide (NAD$^+$) modulation plays a role comprising administering to the subject in need thereof a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of ameliorating a disease or disorder in which nicotinamide adenine dinucleotide (NAD$^+$) modulation plays a role comprising administering to the subject in need thereof a therapeutically effective amount of one or more compounds of Formula (I), Formula (Ia), Formula (Ib), Formula (II), or Formula (III), or a pharmaceutically acceptable salt thereof.

In another aspect, the present disclosure relates to a method of treating a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I), Formula (Ia), Formula (Ib), Formula (II), or Formula (III), or a pharmaceutically acceptable salt thereof.

The present disclosure also relates to a method of preventing a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of reducing the risk of a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I), Formula (Ia), Formula (Ib), Formula (II), or Formula (III), or a pharmaceutically acceptable salt thereof.

In another aspect, the present disclosure relates to a method of ameliorating a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of Formula (I), Formula (Ia), Formula (Ib), Formula (II), or Formula (III), or a pharmaceutically acceptable salt thereof.

Another aspect of the present disclosure relates to a method of treating a disorder associated with mitochondrial dysfunction comprising administering to the subject suffering from or susceptible to developing a metabolic disorder a therapeutically effective amount of one or more compounds of Formula (I), Formula (Ia), Formula (Ib), Formula (II), or Formula (III), or a pharmaceutically acceptable salt thereof. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

In another aspect, the present disclosure relates to a method of preventing a disorder associated with mitochondrial dysfunction comprising administering to the subject suffering from or susceptible to developing a metabolic disorder a therapeutically effective amount of one or more compounds of Formula (I), Formula (Ia), Formula (Ib), Formula (II), or Formula (III), or a pharmaceutically acceptable salt thereof. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

Another aspect of the present disclosure relates to a method of reducing the risk of a disorder associated with mitochondrial dysfunction comprising administering to the subject suffering from or susceptible to developing a metabolic disorder a therapeutically effective amount of one or more compounds of Formula (I), Formula (Ia), Formula (Ib), Formula (II), or Formula (III), or a pharmaceutically acceptable salt thereof. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

Another aspect of the present disclosure relates to a method of ameliorating a disorder associated with mitochondrial dysfunction comprising administering to the subject suffering from or susceptible to developing a metabolic disorder a therapeutically effective amount of one or more compounds of Formula (I), Formula (Ia), Formula (Ib), Formula (II), or Formula (III), or a pharmaceutically acceptable salt thereof. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

In another aspect, the present disclosure relates to a method of promoting oxidative metabolism comprising administering to the subject suffering from or susceptible to developing a metabolic disorder a therapeutically effective amount of one or more compounds of Formula (I), Formula (Ia), Formula (Ib), Formula (II), or Formula (III), or a pharmaceutically acceptable salt thereof, that increases intracellular nicotinamide adenine dinucleotide (NAD$^+$).

In yet another aspect, the present disclosure relates to a method for the manufacture of a medicament for treating a disease or condition mediated by ACMSD, wherein the medicament comprises a compound of Formula (I), Formula (Ia), Formula (Ib), Formula (II), or Formula (III), or a pharmaceutically acceptable salt thereof.

Another aspect of the present disclosure relates to a method for the manufacture of a medicament for preventing a disease or condition mediated by ACMSD, wherein the medicament comprises a compound of Formula (I), Formula (Ia), Formula (Ib), Formula (II), or Formula (III), or a pharmaceutically acceptable salt thereof.

In another aspect, the present disclosure relates to a method for the manufacture of a medicament for reducing the risk of a disease or condition mediated by ACMSD, wherein the medicament comprises a compound of Formula (I), Formula (Ia), Formula (Ib), Formula (II), or Formula (III), or a pharmaceutically acceptable salt thereof.

In yet another aspect, the present disclosure relates to a method for the manufacture of a medicament for ameliorating a disease or condition mediated by ACMSD, wherein the medicament comprises a compound of Formula (I), Formula (Ia), Formula (Ib), Formula (II), or Formula (III), or a pharmaceutically acceptable salt thereof.

In another aspect, the present disclosure relates to a pharmaceutical composition for use in a method for treating a disease or condition mediated by ACMSD, wherein the medicament comprises a compound of Formula (I), Formula (Ia), Formula (Ib), Formula (II), or Formula (III), or a pharmaceutically acceptable salt thereof.

In another aspect, the present disclosure relates to a pharmaceutical composition for use in a method for preventing a disease or condition mediated by ACMSD, wherein the medicament comprises a compound of Formula (I), Formula (Ia), Formula (Ib), Formula (II), or Formula (III), or a pharmaceutically acceptable salt thereof.

In another aspect, the present disclosure relates to a pharmaceutical composition for use in a method for reducing the risk of a disease or condition mediated by ACMSD, wherein the medicament comprises a compound of Formula (I), Formula (Ia), Formula (Ib), Formula (II), or Formula (III), or a pharmaceutically acceptable salt thereof.

Another aspect of the present disclosure relates to a pharmaceutical composition for use in a method for ameliorating a disease or condition mediated by ACMSD, wherein the medicament comprises a compound of Formula (I), Formula (Ia), Formula (Ib), Formula (II), or Formula (III), or a pharmaceutically acceptable salt thereof.

In yet another aspect, the present disclosure relates to a compound for use in a method for treating a disease or condition mediated by ACMSD, wherein the compound comprises a compound of Formula (I), Formula (Ia), Formula (Ib), Formula (II), or Formula (III), or a pharmaceutically acceptable salt thereof.

Another aspect of the present disclosure relates to a compound for use in a method for preventing a disease or condition mediated by ACMSD, wherein the compound comprises a compound of Formula (I), Formula (Ia), Formula (Ib), Formula (II), or Formula (III), or a pharmaceutically acceptable salt thereof.

In another aspect, the present disclosure relates to a compound for use in a method for reducing the risk of a disease or condition mediated by ACMSD, wherein the compound comprises a compound of Formula (I), Formula (Ia), Formula (Ib), Formula (II), or Formula (III), or a pharmaceutically acceptable salt thereof.

Another aspect of the present disclosure relates to a compound for use in a method for ameliorating a disease or condition mediated by ACMSD, wherein the compound comprises a compound of Formula (I), Formula (Ia), Formula (Ib), Formula (II), or Formula (III), or a pharmaceutically acceptable salt thereof.

Another aspect of the present disclosure relates to the use of a compound of Formula (I), Formula (Ia), Formula (Ib), Formula (II), or Formula (III), or a pharmaceutically acceptable salt thereof in the manufacture of a medicament for treating, preventing or reducing the risk of a disease or disorder associated with α-amino-β-carboxymuconate-ε-semialdehyde decarboxylase (ACMSD) dysfunction.

In another aspect, the present disclosure relates to the use of a compound of Formula (I), Formula (Ia), Formula (Ib), Formula (II), or Formula (III), or a pharmaceutically acceptable salt thereof in the manufacture of a medicament for treating the risk of a disease or disorder associated with α-amino-β-carboxymuconate-ε-semialdehyde decarboxylase (ACMSD) dysfunction.

Another aspect of the present disclosure relates to the use of a compound of Formula (I), Formula (Ia), Formula (Ib), Formula (II), or Formula (III), or a pharmaceutically acceptable salt thereof in the manufacture of a medicament for preventing a disease or disorder associated with α-amino-β-carboxymuconate-ε-semialdehyde decarboxylase (ACMSD) dysfunction.

In another aspect, the present disclosure relates to the use of a compound of Formula (I), Formula (Ia), Formula (Ib), Formula (II), or Formula (III), or a pharmaceutically acceptable salt thereof in the manufacture of a medicament for reducing the risk of a disease or disorder associated with α-amino-β-carboxymuconate-ε-semialdehyde decarboxylase (ACMSD) dysfunction.

Another aspect of the present disclosure relates to the use of a compound of Formula (I), Formula (Ia), Formula (Ib), Formula (II), or Formula (III), or a pharmaceutically acceptable salt thereof in the manufacture of a medicament for ameliorating a disease or disorder associated with α-amino-β-carboxymuconate-ε-semialdehyde decarboxylase (ACMSD) dysfunction.

In another aspect, the present disclosure relates to the use of a compound of a compound of Formula (I), Formula (Ia), Formula (Ib), Formula (II), or Formula (III), or a pharmaceutically acceptable salt thereof in the manufacture of a medicament for treating, preventing or reducing the risk of a disease or disorder associated with reduced nicotinamide adenine dinucleotide (NAD$^+$) levels.

Another aspect of the present disclosure relates to the use of a compound of a compound of Formula (I), Formula (Ia), Formula (Ib), Formula (II), or Formula (III), or a pharmaceutically acceptable salt thereof in the manufacture of a medicament for treating a disease or disorder associated with reduced nicotinamide adenine dinucleotide (NAD$^+$) levels.

In another aspect, the present disclosure relates to the use of a compound of a compound of Formula (I), Formula (Ia), Formula (Ib), Formula (II), or Formula (III), or a pharmaceutically acceptable salt thereof in the manufacture of a medicament for preventing a disease or disorder associated with reduced nicotinamide adenine dinucleotide (NAD$^+$) levels.

Another aspect of the present disclosure relates to the use of a compound of a compound of Formula (I), Formula (Ia), Formula (Ib), Formula (II), or Formula (III), or a pharmaceutically acceptable salt thereof in the manufacture of a medicament reducing the risk of a disease or disorder associated with reduced nicotinamide adenine dinucleotide (NAD$^+$) levels.

In another aspect, the present disclosure relates to the use of a compound of a compound of Formula (I), Formula (Ia), Formula (Ib), Formula (II), or Formula (III), or a pharmaceutically acceptable salt thereof in the manufacture of a medicament for ameliorating a disease or disorder associated with reduced nicotinamide adenine dinucleotide (NAD$^+$) levels.

Another aspect of the present disclosure relates to the use of a compound of Formula (I), Formula (Ia), Formula (Ib), Formula (II), or Formula (III), or a pharmaceutically acceptable salt thereof in the manufacture of a medicament for treating, preventing or reducing the risk of a disorder associated with mitochondrial dysfunction.

In another aspect, the present disclosure relates to the use of a compound of Formula (I), Formula (Ia), Formula (Ib), Formula (II), or Formula (III), or a pharmaceutically acceptable salt thereof in the manufacture of a medicament for treating a disorder associated with mitochondrial dysfunction.

Another aspect of the present disclosure relates to the use of a compound of Formula (I), Formula (Ia), Formula (Ib), Formula (II), or Formula (III), or a pharmaceutically acceptable salt thereof in the manufacture of a medicament for preventing a disorder associated with mitochondrial dysfunction.

In another aspect, the present disclosure relates to the use of a compound of Formula (I), Formula (Ia), Formula (Ib), Formula (II), or Formula (III), or a pharmaceutically acceptable salt thereof in the manufacture of a medicament for reducing the risk of a disorder associated with mitochondrial dysfunction.

Another aspect of the present disclosure relates to the use of a compound of Formula (I), Formula (Ia), Formula (Ib), Formula (II), or Formula (III), or a pharmaceutically acceptable salt thereof in the manufacture of a medicament for ameliorating a disorder associated with mitochondrial dysfunction.

In another aspect, the present disclosure relates to the use of a compound of a compound of Formula (I), Formula (Ia), Formula (Ib), Formula (II), or Formula (III), or a pharmaceutically acceptable salt thereof in the manufacture of a medicament for promoting oxidative metabolism.

Another aspect of the present disclosure relates to a compound of Formula (I), Formula (Ia), Formula (Ib), Formula (II), or Formula (III), or a pharmaceutically acceptable salt thereof for use in the manufacture of a medicament for treating, preventing or reducing the risk of a disease or disorder associated with α-amino-β-carboxymuconate-ε-semialdehyde decarboxylase (ACMSD) dysfunction.

In another aspect, the present disclosure relates to a compound of Formula (I), Formula (Ia), Formula (Ib), Formula (II), or Formula (III), or a pharmaceutically acceptable salt thereof for use in the manufacture of a medicament for treating a disease or disorder associated with α-amino-β-carboxymuconate-ε-semialdehyde decarboxylase (ACMSD) dysfunction.

Another aspect of the present disclosure relates to a compound of Formula (I), Formula (Ia), Formula (Ib), Formula (II), or Formula (III), or a pharmaceutically acceptable salt thereof for use in the manufacture of a medicament for preventing a disease or disorder associated with α-amino-β-carboxymuconate-ε-semialdehyde decarboxylase (ACMSD) dysfunction.

In another aspect, the present disclosure relates to a compound of Formula (I), Formula (Ia), Formula (Ib), Formula (II), or Formula (III), or a pharmaceutically acceptable salt thereof for use in the manufacture of a medicament for reducing the risk of a disease or disorder associated with α-amino-β-carboxymuconate-ε-semialdehyde decarboxylase (ACMSD) dysfunction.

Another aspect of the present disclosure relates to a compound of Formula (I), Formula (Ia), Formula (Ib), Formula (II), or Formula (III), or a pharmaceutically acceptable salt thereof for use in the manufacture of a medicament for ameliorating a disease or disorder associated with α-amino-β-carboxymuconate-ε-semialdehyde decarboxylase (ACMSD) dysfunction.

In another aspect, the present disclosure relates to a compound of Formula (I), Formula (Ia), Formula (Ib), Formula (II), or Formula (III), or a pharmaceutically acceptable salt thereof for use as a medicament for treating, preventing or reducing the risk of a disease or disorder associated with reduced nicotinamide adenine dinucleotide (NAD$^+$) levels.

Another aspect of the present disclosure relates to a compound of Formula (I), Formula (Ia), Formula (Ib), Formula (II), or Formula (III), or a pharmaceutically acceptable salt thereof for use as a medicament for treating a disease or disorder associated with reduced nicotinamide adenine dinucleotide (NAD$^+$) levels.

In another aspect, the present disclosure relates to a compound of Formula (I), Formula (Ia), Formula (Ib), Formula (II), or Formula (III), or a pharmaceutically acceptable salt thereof for use as a medicament for preventing a disease or disorder associated with reduced nicotinamide adenine dinucleotide (NAD$^+$) levels.

Another aspect of the present disclosure relates to a compound of Formula (I), Formula (Ia), Formula (Ib), Formula (II), or Formula (III), or a pharmaceutically acceptable salt thereof for use as a medicament for reducing the risk of a disease or disorder associated with reduced nicotinamide adenine dinucleotide (NAD$^+$) levels.

In another aspect, the present disclosure relates to a compound of Formula (I), Formula (Ia), Formula (Ib), Formula (II), or Formula (III), or a pharmaceutically acceptable salt thereof for use as a medicament for ameliorating a disease or disorder associated with reduced nicotinamide adenine dinucleotide (NAD$^+$) levels.

Another aspect of the present disclosure relates to a compound of Formula (I), Formula (Ia), Formula (Ib), Formula (II), or Formula (III), or a pharmaceutically acceptable salt thereof for use as a medicament for treating, preventing or reducing the risk of a disorder associated with mitochondrial dysfunction.

In another aspect, the present disclosure relates to a compound of Formula (I), Formula (Ia), Formula (Ib), Formula (II), or Formula (III), or a pharmaceutically acceptable salt thereof for use as a medicament for treating a disorder associated with mitochondrial dysfunction.

Another aspect of the present disclosure relates to a compound of Formula (I), Formula (Ia), Formula (Ib), Formula (II), or Formula (III), or a pharmaceutically acceptable salt thereof for use as a medicament for preventing a disorder associated with mitochondrial dysfunction.

In another aspect, the present disclosure relates to a compound of Formula (I), Formula (Ia), Formula (Ib), Formula (II), or Formula (III), or a pharmaceutically acceptable salt thereof for use as a medicament for reducing the risk of a disorder associated with mitochondrial dysfunction.

Another aspect of the present disclosure relates to a compound of Formula (I), Formula (Ia), Formula (Ib), Formula (II), or Formula (III), or a pharmaceutically acceptable salt thereof for use as a medicament for ameliorating a disorder associated with mitochondrial dysfunction.

In another aspect, the present disclosure relates to a compound of Formula (I), Formula (Ia), Formula (Ib), Formula (II), or Formula (III), or a pharmaceutically acceptable salt thereof for use as a medicament for promoting oxidative metabolism.

Another aspect of the present disclosure relates to a compound of Formula (I), Formula (Ia), Formula (Ib), Formula (II), or Formula (III), or a pharmaceutically acceptable salt thereof for use in treating, preventing or reducing the risk of a disease or disorder associated with reduced nicotinamide adenine dinucleotide (NAD$^+$) levels.

In another aspect, the present disclosure relates to a compound of Formula (I), Formula (Ia), Formula (Ib), Formula (II), or Formula (III), or a pharmaceutically acceptable salt thereof for use in treating a disease or disorder associated with reduced nicotinamide adenine dinucleotide (NAD$^+$) levels.

Another aspect of the present disclosure relates to a compound of Formula (I), Formula (Ia), Formula (Ib), Formula (II), or Formula (III), or a pharmaceutically acceptable salt thereof for use in preventing a disease or disorder associated with reduced nicotinamide adenine dinucleotide (NAD$^+$) levels.

In another aspect, the present disclosure relates to a compound of Formula (I), Formula (Ia), Formula (Ib), Formula (II), or Formula (III), or a pharmaceutically acceptable salt thereof for use in reducing the risk of a disease or disorder associated with reduced nicotinamide adenine dinucleotide (NAD$^+$) levels.

Another aspect of the present disclosure relates to a compound of Formula (I), Formula (Ia), Formula (Ib), Formula (II), or Formula (III), or a pharmaceutically acceptable salt thereof for use in ameliorating a disease or disorder associated with reduced nicotinamide adenine dinucleotide (NAD$^+$) levels.

In another aspect, the present disclosure relates to a compound of Formula (I), Formula (Ia), Formula (Ib), Formula (II), or Formula (III), or a pharmaceutically acceptable salt thereof for use in for treating, preventing or reducing the risk of a disorder associated with mitochondrial dysfunction.

Another aspect of the present disclosure relates to a compound of Formula (I), Formula (Ia), Formula (Ib), Formula (II), or Formula (III), or a pharmaceutically acceptable salt thereof for use in for treating a disorder associated with mitochondrial dysfunction.

In another aspect, the present disclosure relates to a compound of Formula (I), Formula (Ia), Formula (Ib), Formula (II), or Formula (III), or a pharmaceutically acceptable salt thereof for use in for preventing a disorder associated with mitochondrial dysfunction.

Another aspect of the present disclosure relates to a compound of Formula (I), Formula (Ia), Formula (Ib), Formula (II), or Formula (III), or a pharmaceutically acceptable salt thereof for use in for reducing the risk of a disorder associated with mitochondrial dysfunction.

In another aspect, the present disclosure relates to a compound of Formula (I), Formula (Ia), Formula (Ib), Formula (II), or Formula (III), or a pharmaceutically acceptable salt thereof for use in for ameliorating a disorder associated with mitochondrial dysfunction.

Another aspect of the present disclosure relates to a compound of Formula (I), Formula (Ia), Formula (Ib), Formula (II), or Formula (III), or a pharmaceutically acceptable salt thereof for use in promoting oxidative metabolism.

In another aspect, the present disclosure relates to a method of treating, preventing, ameliorating or reducing the risk of a disease or disorder associated with α-amino-β-carboxymuconate-ε-semialdehyde decarboxylase (ACMSD) dysfunction, comprising administering to a subject in need thereof, a therapeutically effective amount of compound having the following Formulae:

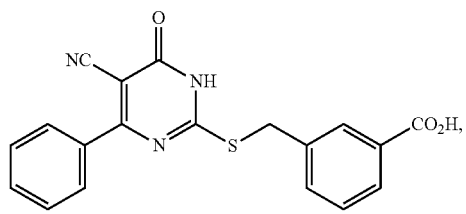

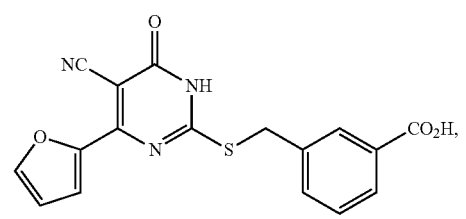

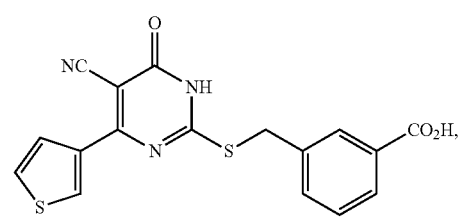

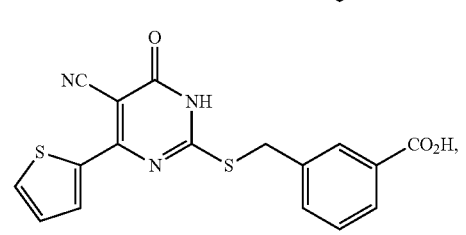

-continued

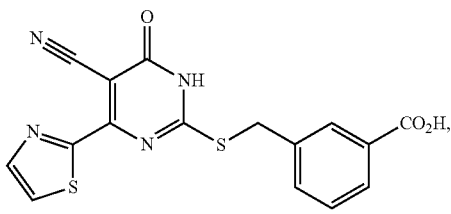

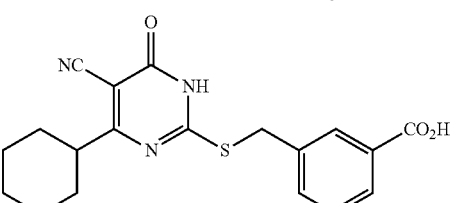

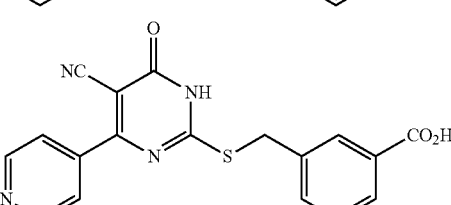

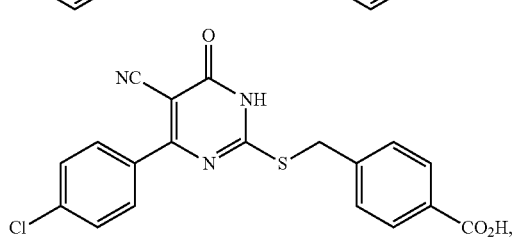

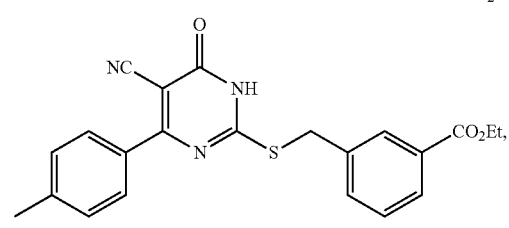

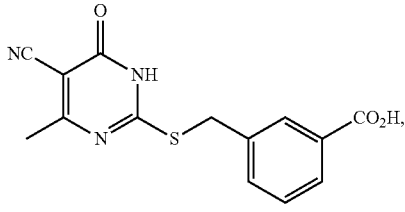

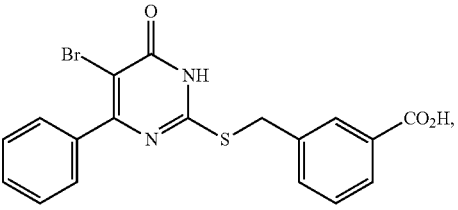

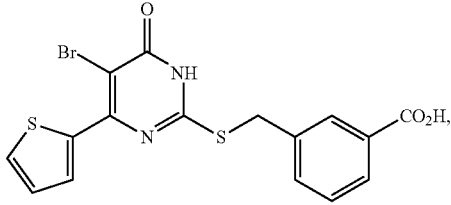

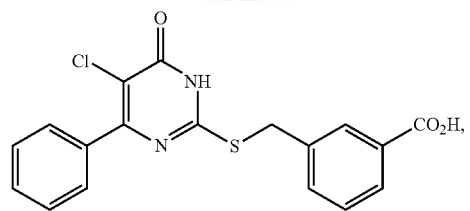
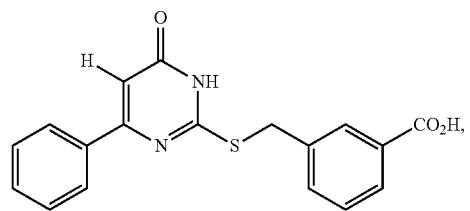
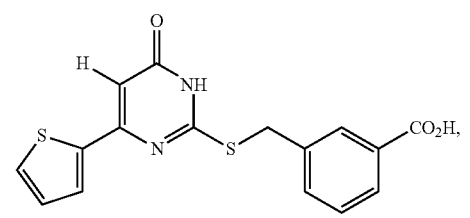
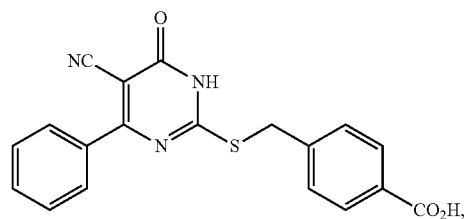
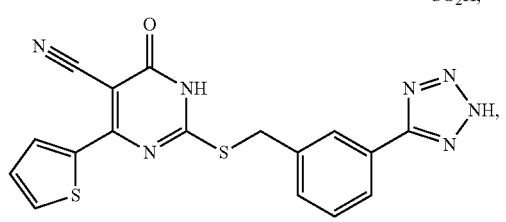
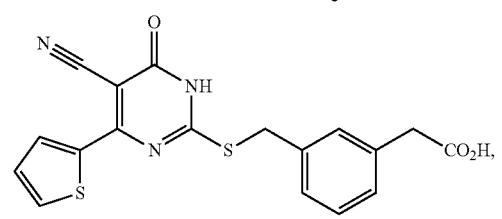
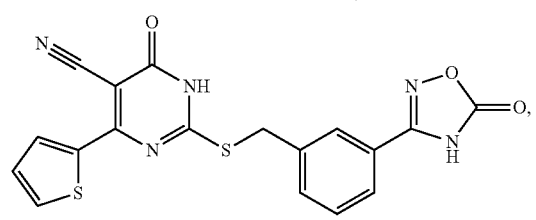
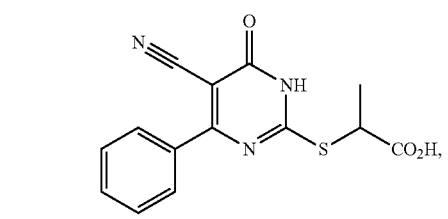
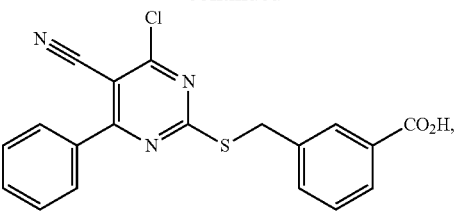
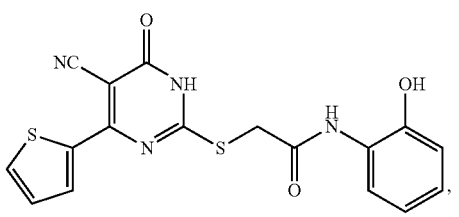
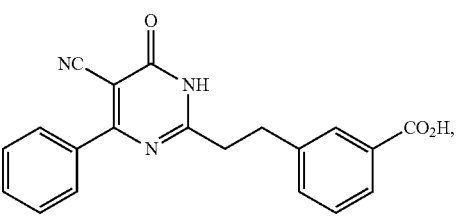
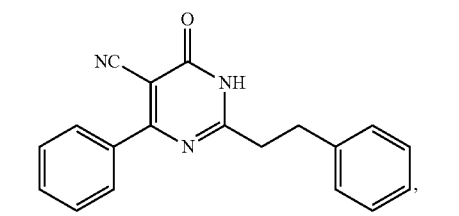
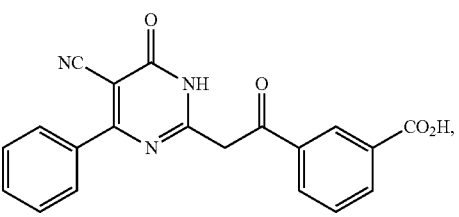
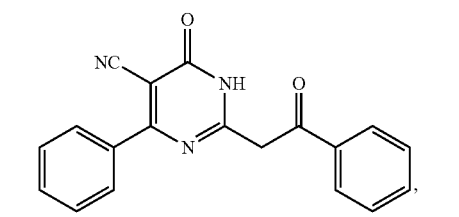
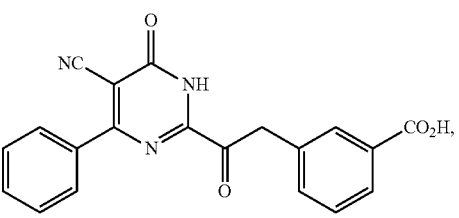
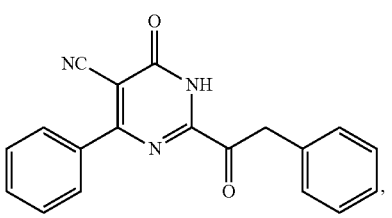

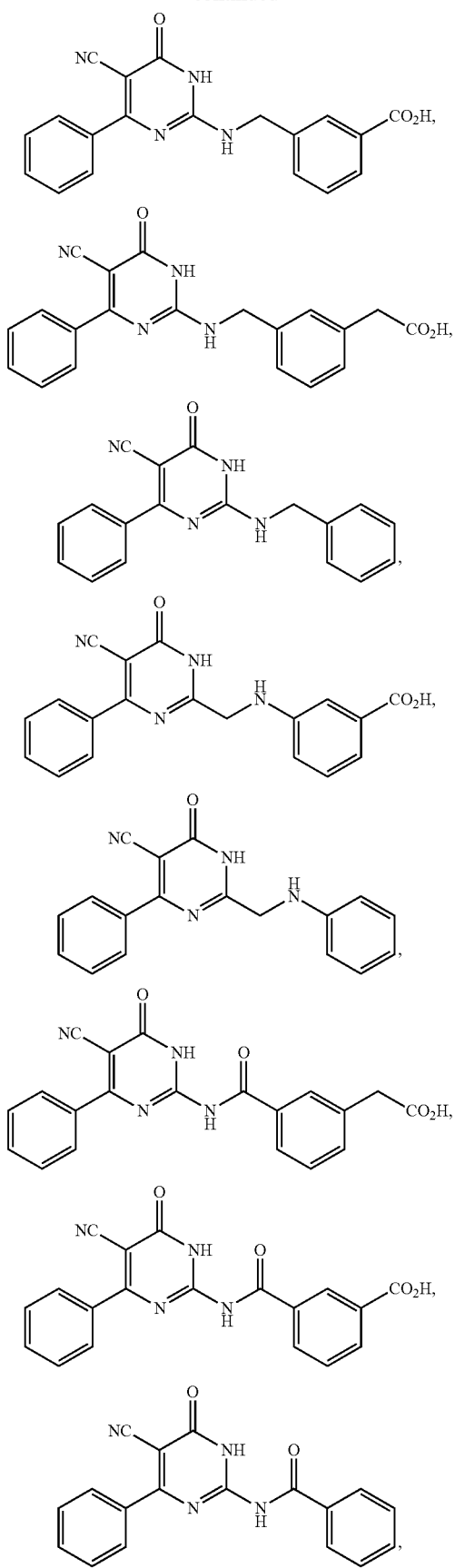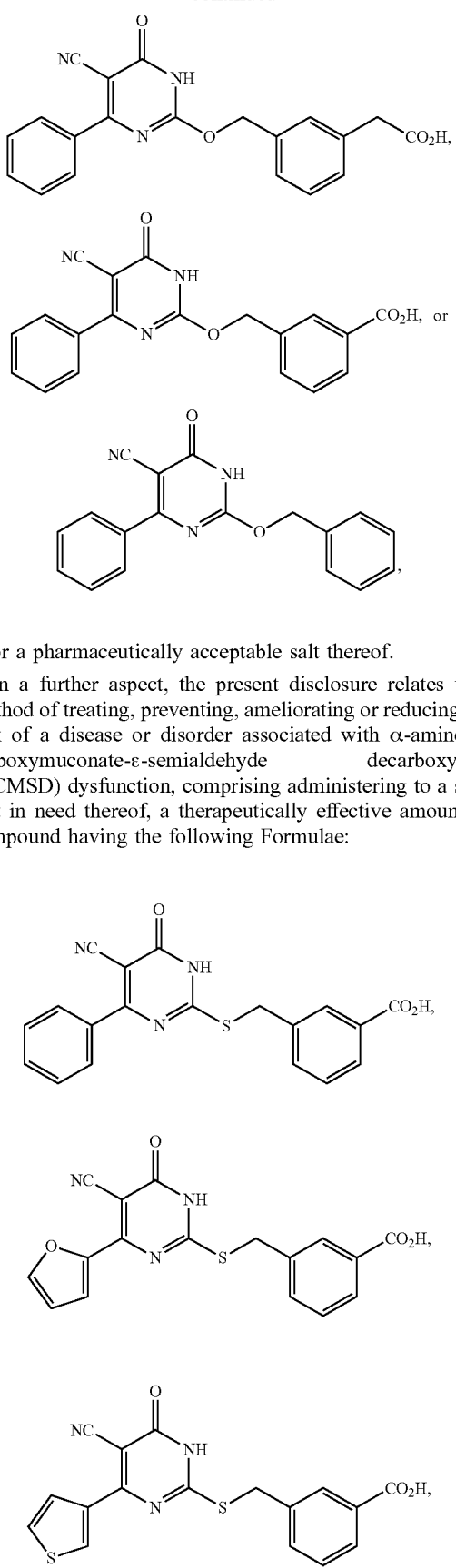

or a pharmaceutically acceptable salt thereof.

In a further aspect, the present disclosure relates to a method of treating, preventing, ameliorating or reducing the risk of a disease or disorder associated with α-amino-β-carboxymuconate-ε-semialdehyde decarboxylase (ACMSD) dysfunction, comprising administering to a subject in need thereof, a therapeutically effective amount of compound having the following Formulae:

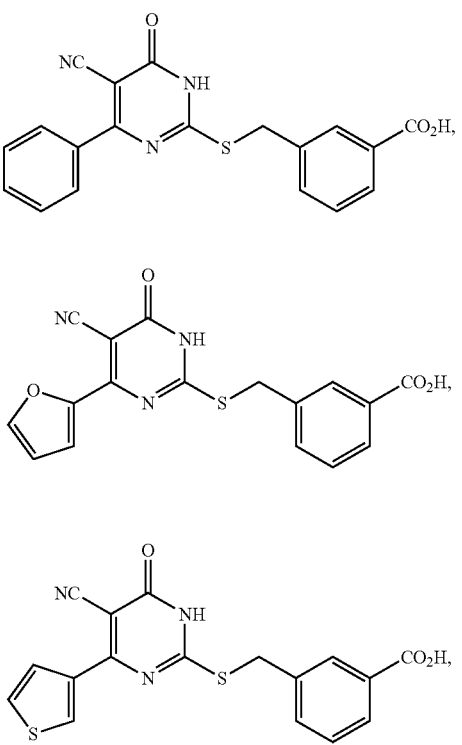

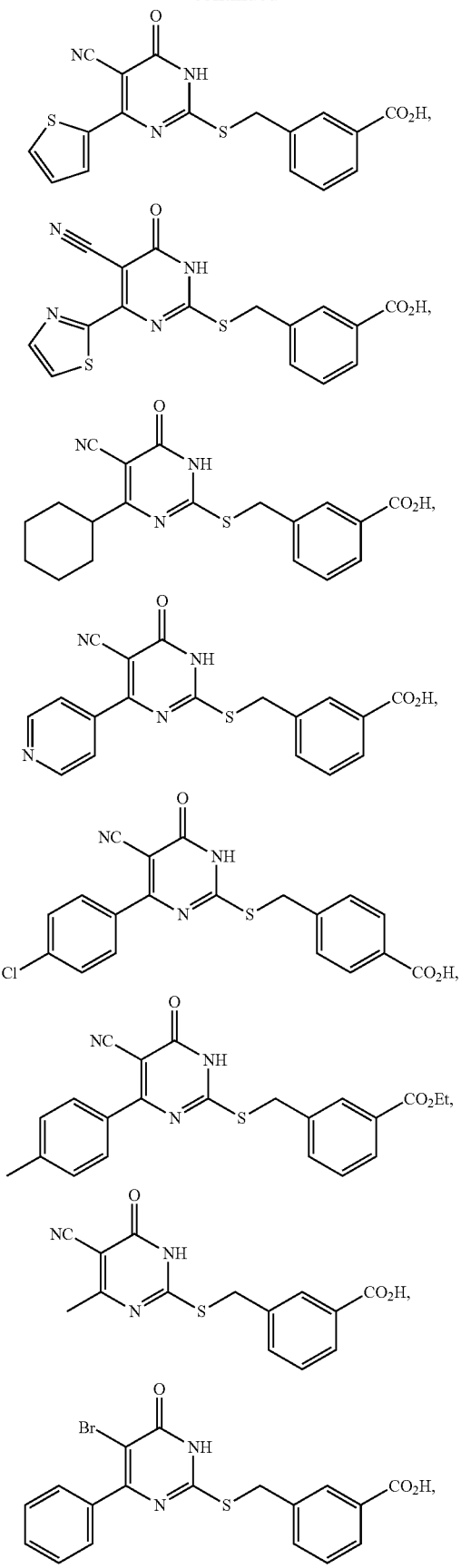
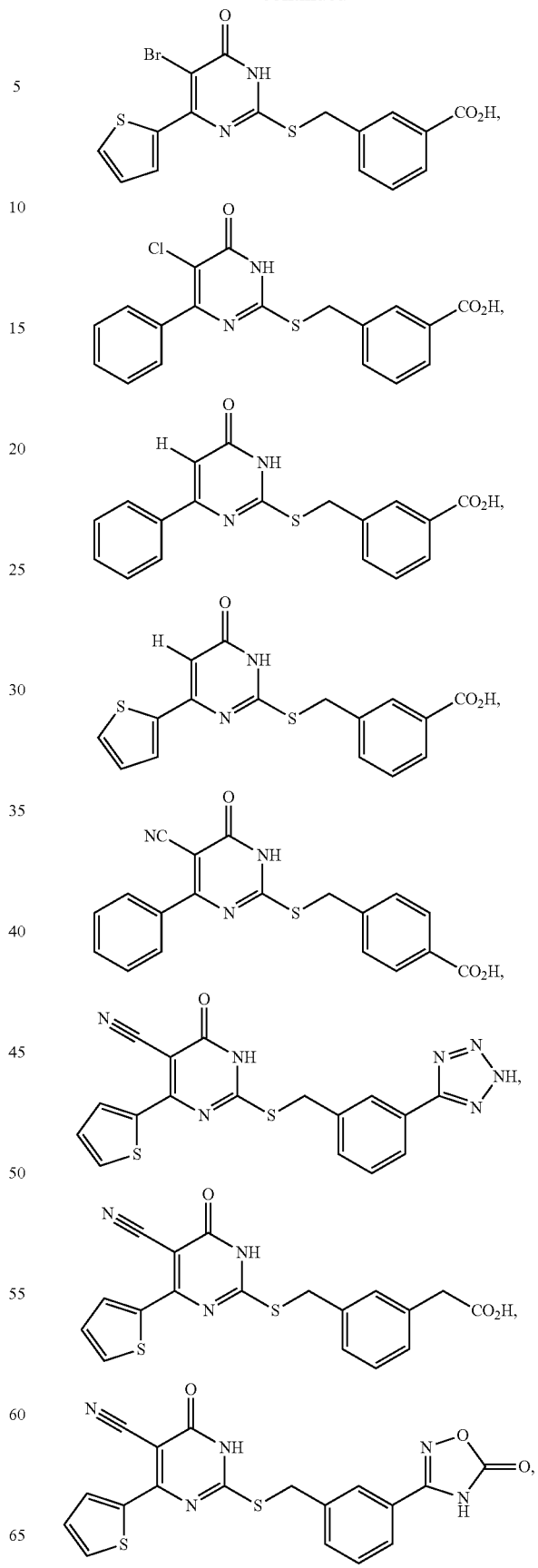

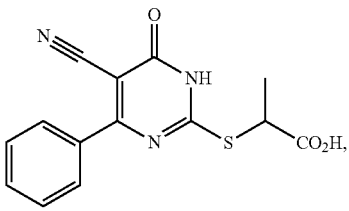
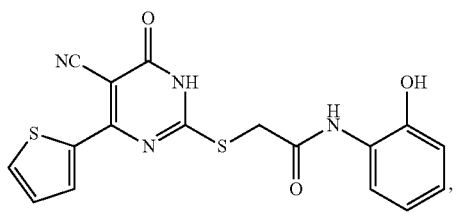 [SMILES: N#Cc1c(-c2cccs2)nc(SCC(=O)Nc2ccccc2O)[nH]c1=O]
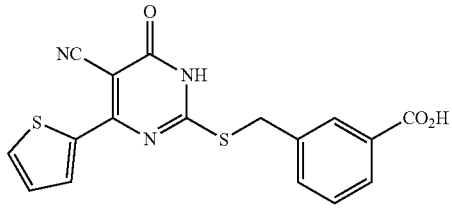
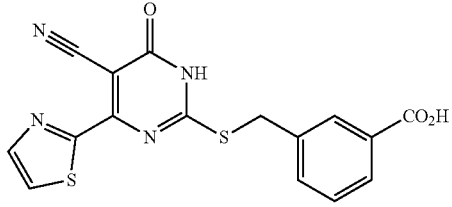
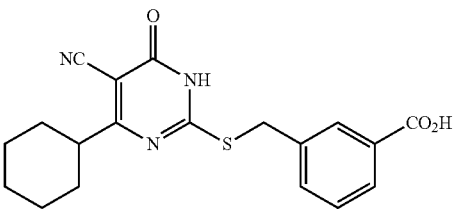 [SMILES: N#Cc1c(C2CCCCC2)nc(SCc2cccc(C(=O)O)c2)[nH]c1=O]
or a pharmaceutically acceptable salt thereof.
Hence, the disclosure also relates to a compound of Formula (I), Formula (Ia), Formula (Ib), Formula (II), or Formula (III), or a pharmaceutically acceptable salt thereof, as defined herein, for use as a medicament.
Another aspect of the present disclosure relates to the use of a compound having the one of the following Formula:
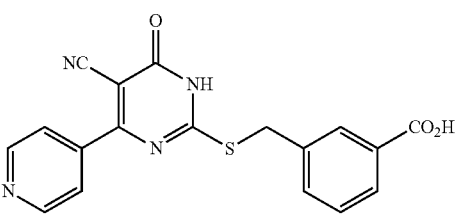 [SMILES: N#Cc1c(-c2ccncc2)nc(SCc2cccc(C(=O)O)c2)[nH]c1=O]
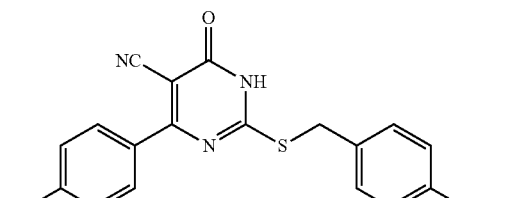
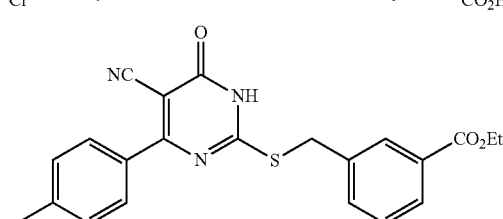
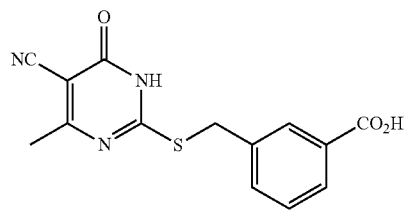
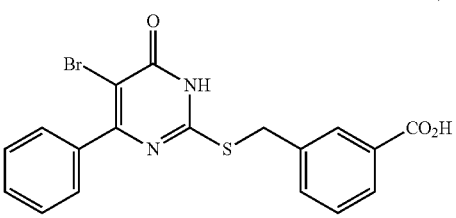

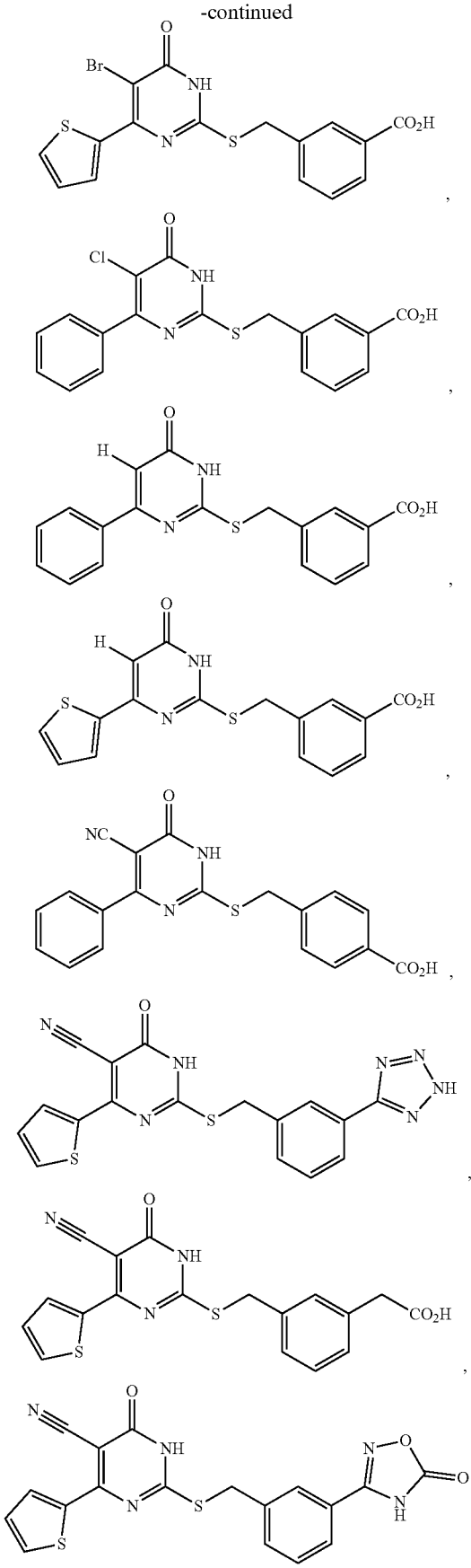
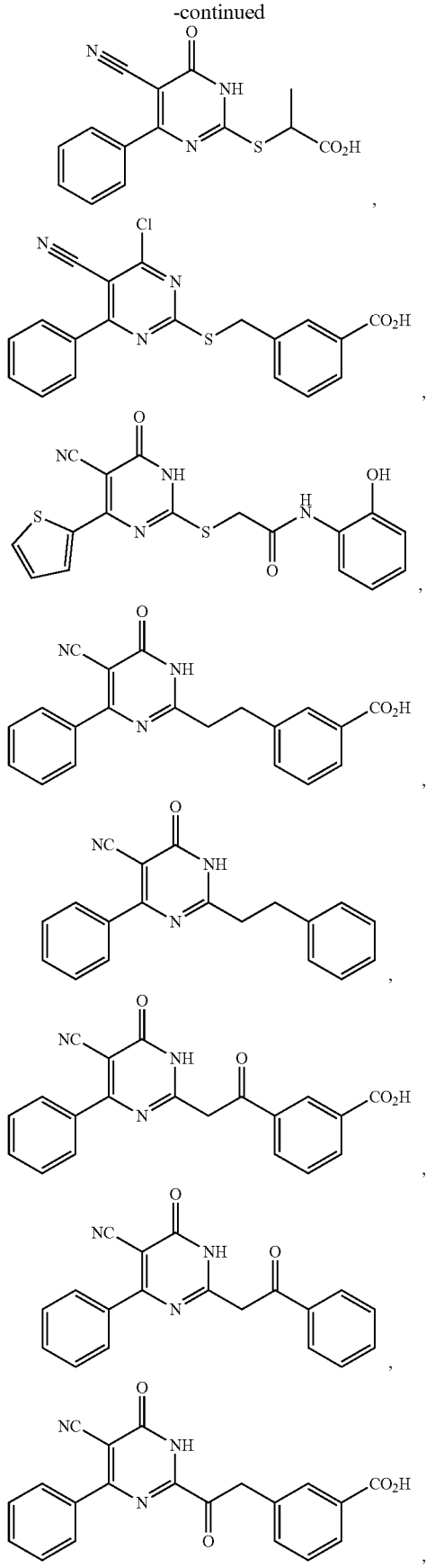

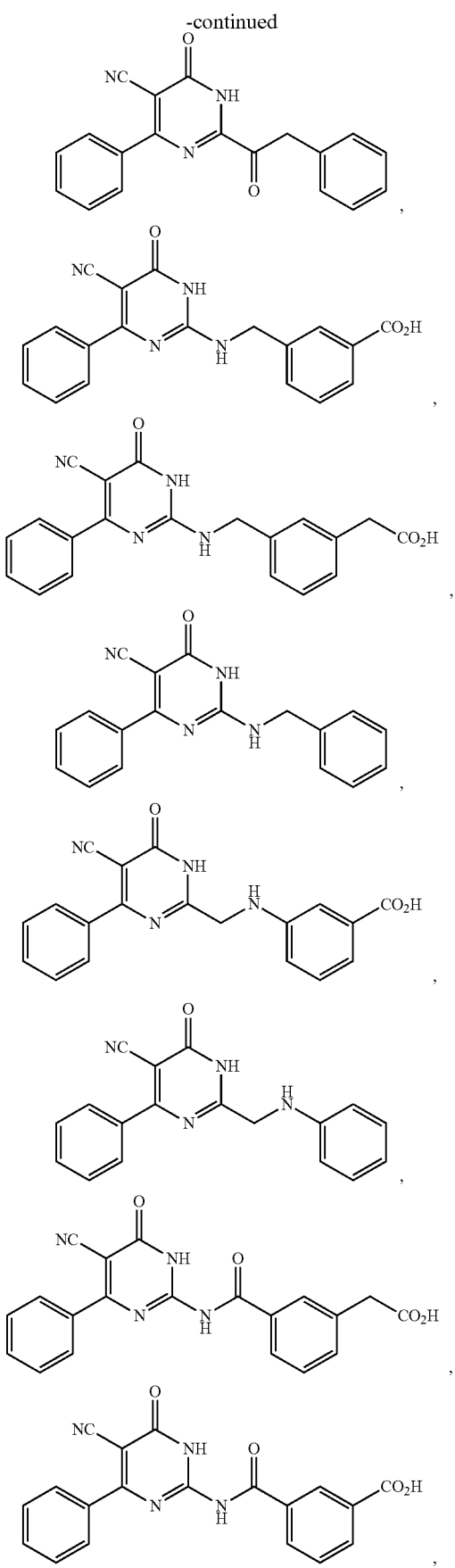

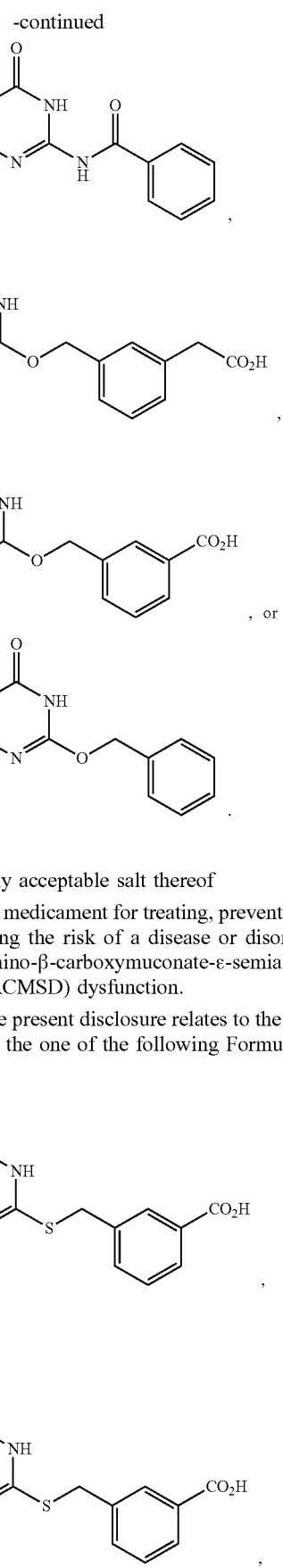

or a pharmaceutically acceptable salt thereof in the manufacture of a medicament for treating, preventing, ameliorating or reducing the risk of a disease or disorder associated with oct-amino-β-carboxymuconate-ε-semialdehyde decarboxylase (ACMSD) dysfunction.

Another aspect of the present disclosure relates to the use of a compound having the one of the following Formula:

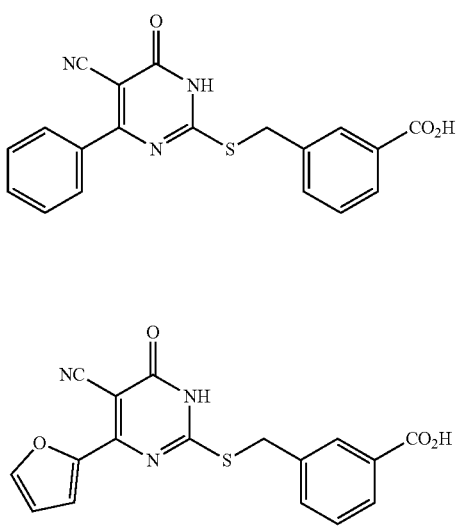

-continued
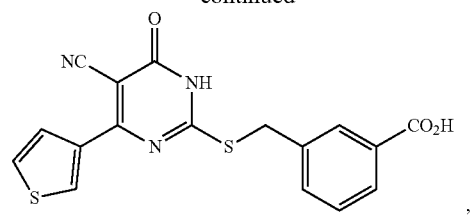
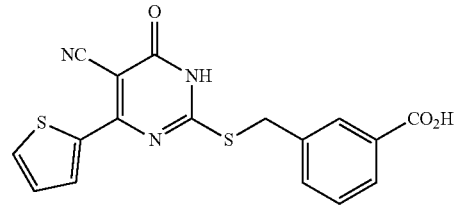
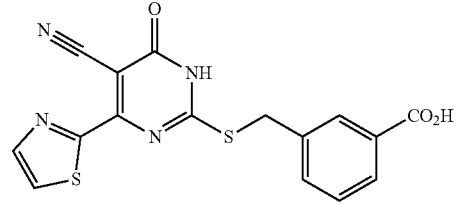
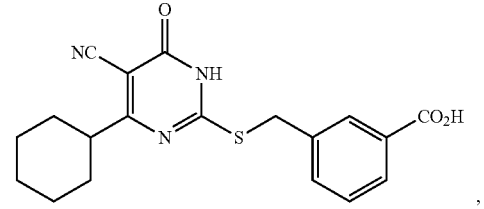
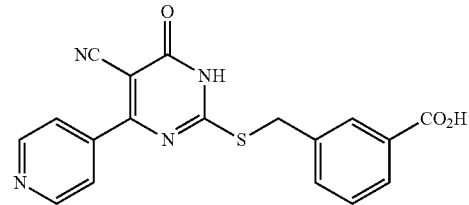
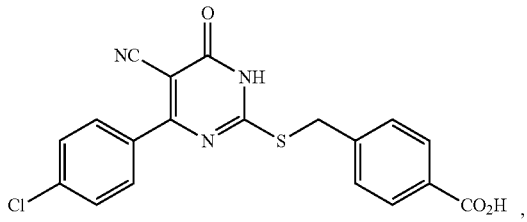
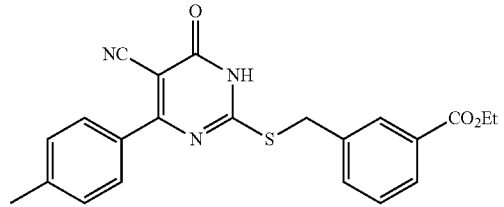 [SMILES: CCOC(=O)c1cccc(CSc2nc(-c3ccc(C)cc3)c(C#N)c(=O)[nH]2)c1]
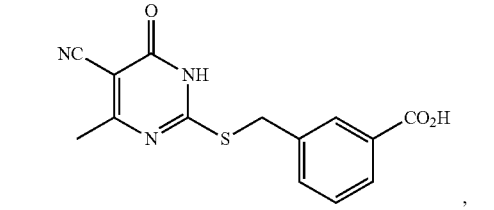
-continued
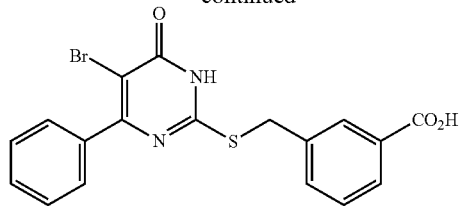
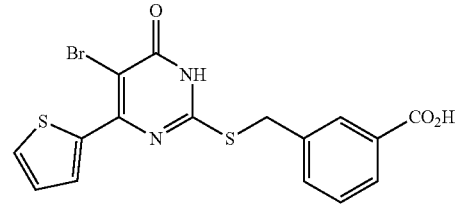
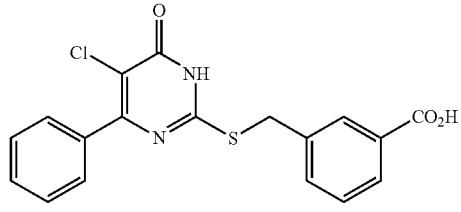 [SMILES: O=C(O)c1cccc(CSc2nc(-c3ccccc3)c(Cl)c(=O)[nH]2)c1]
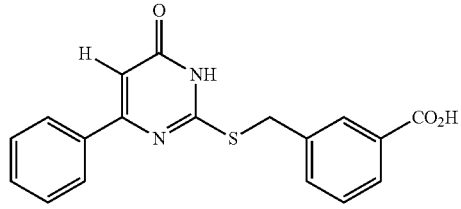 [SMILES: O=C(O)c1cccc(CSc2nc(-c3ccccc3)cc(=O)[nH]2)c1]
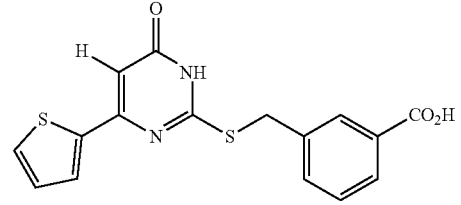
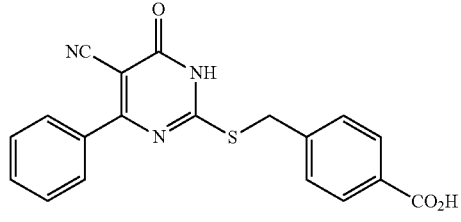 [SMILES: N#Cc1c(-c2ccccc2)nc(SCc2ccc(C(=O)O)cc2)[nH]c1=O]
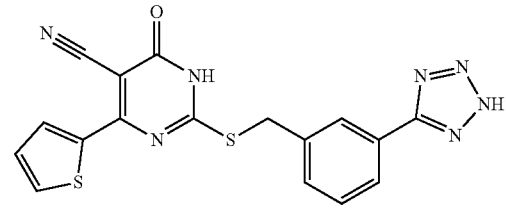
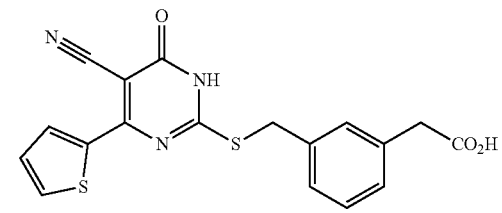

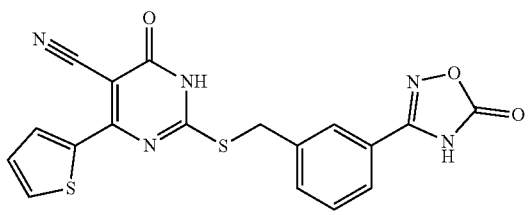

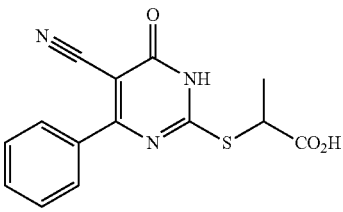

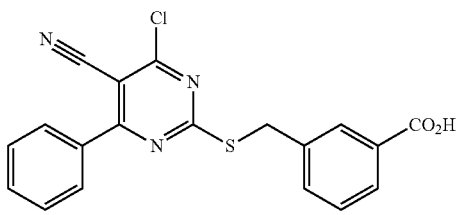

, or

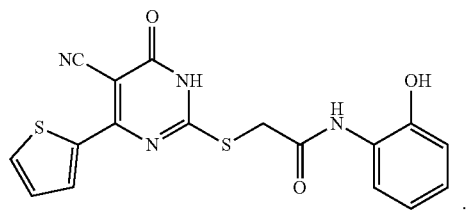

or a pharmaceutically acceptable salt thereof
in the manufacture of a medicament for treating, preventing, ameliorating or reducing the risk of a disease or disorder associated with α-amino-β-carboxymuconate-ε-semialdehyde decarboxylase (ACMSD) dysfunction.

In another aspect, the present disclosure relates to a compound having the one of the following Formula:

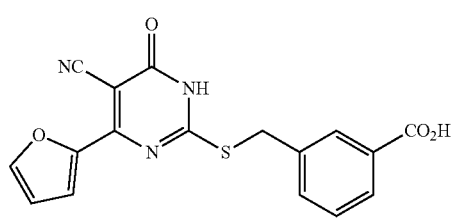

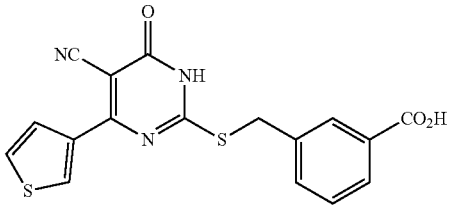

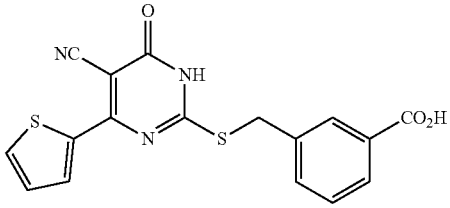

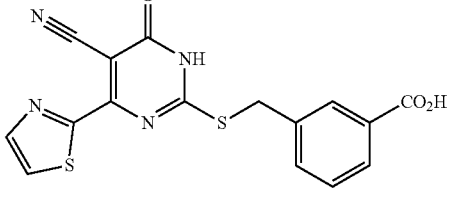

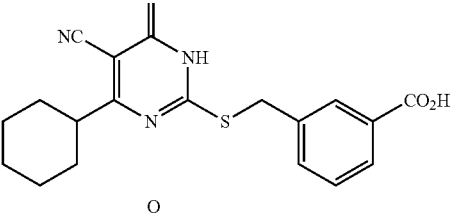

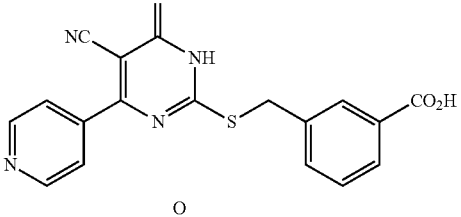

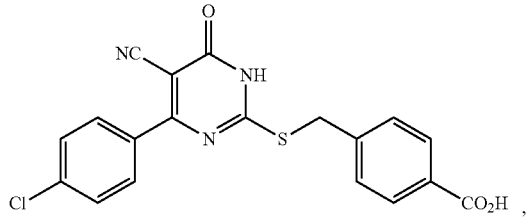

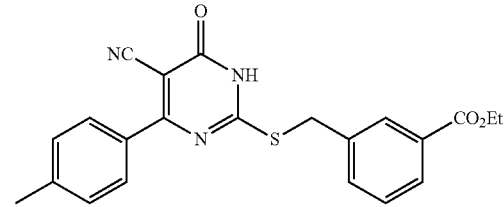

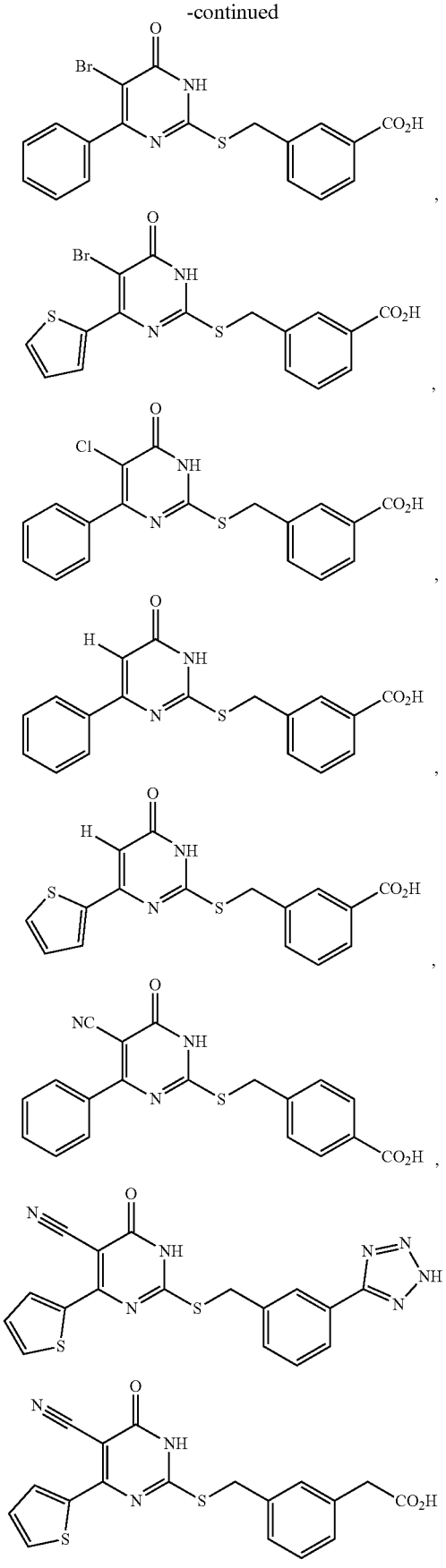
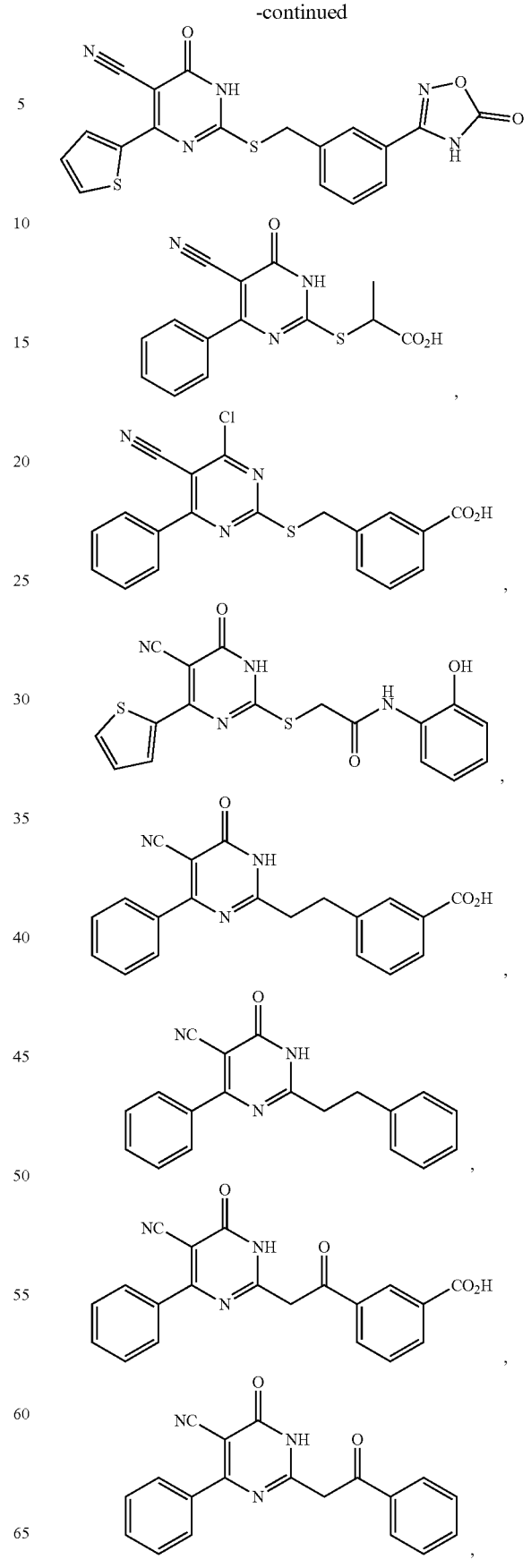

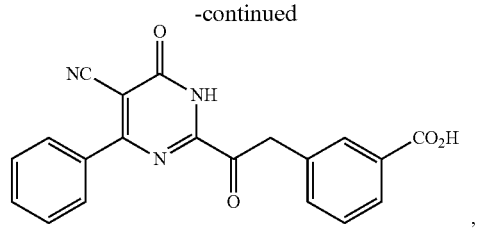
,
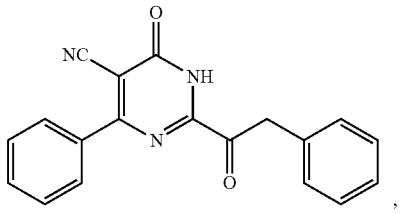
,
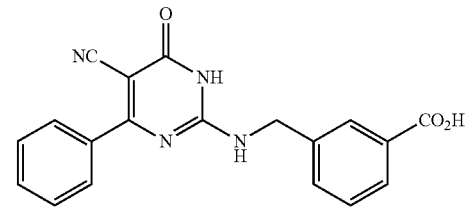
,
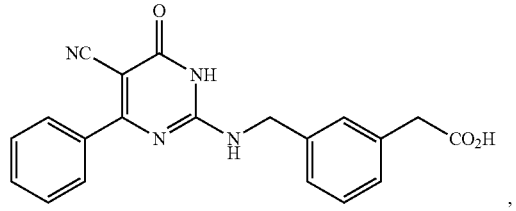
,
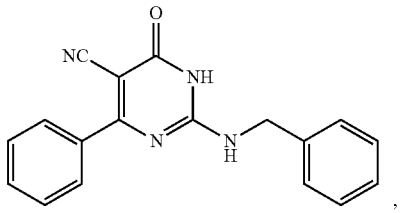
,
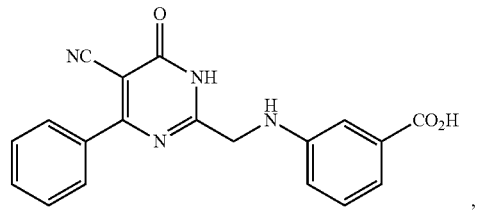
,
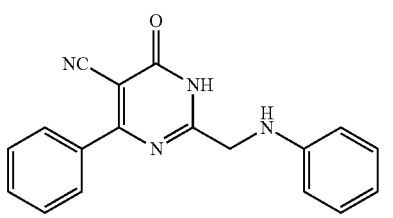
,
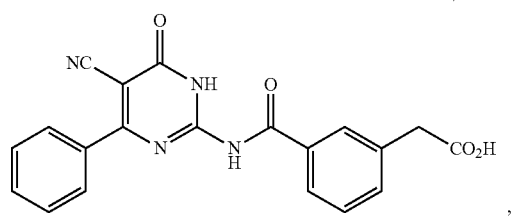
,
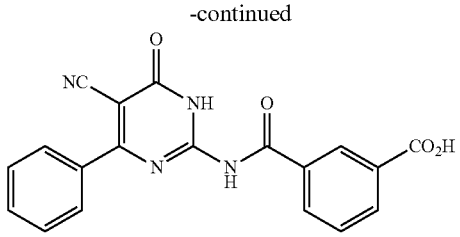
,
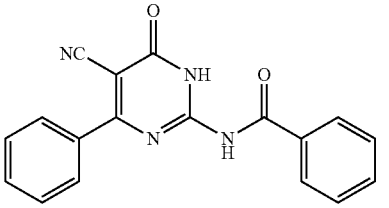
,
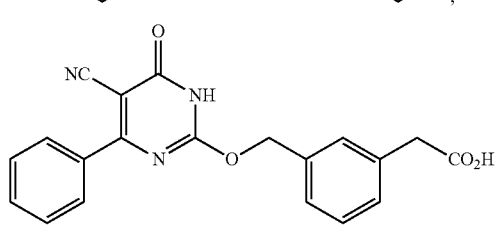
,
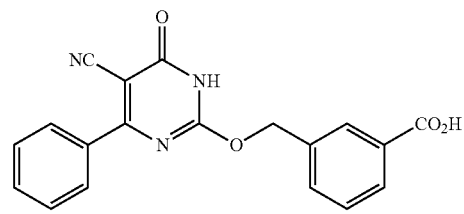
, or
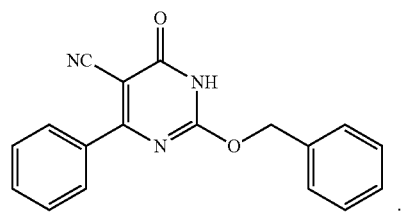
.
or a pharmaceutically acceptable salt thereof, for use as a medicament for treating, preventing, ameliorating or reducing the risk of a disease or disorder associated with α-amino-β-carboxymuconate-ε-semialdehyde decarboxylase (ACMSD) dysfunction.
In another aspect, the present disclosure relates to a compound having the one of the following Formula:
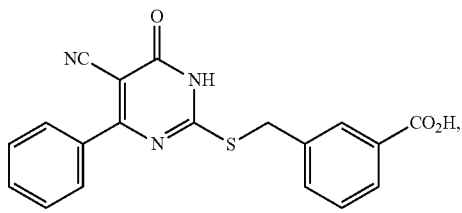

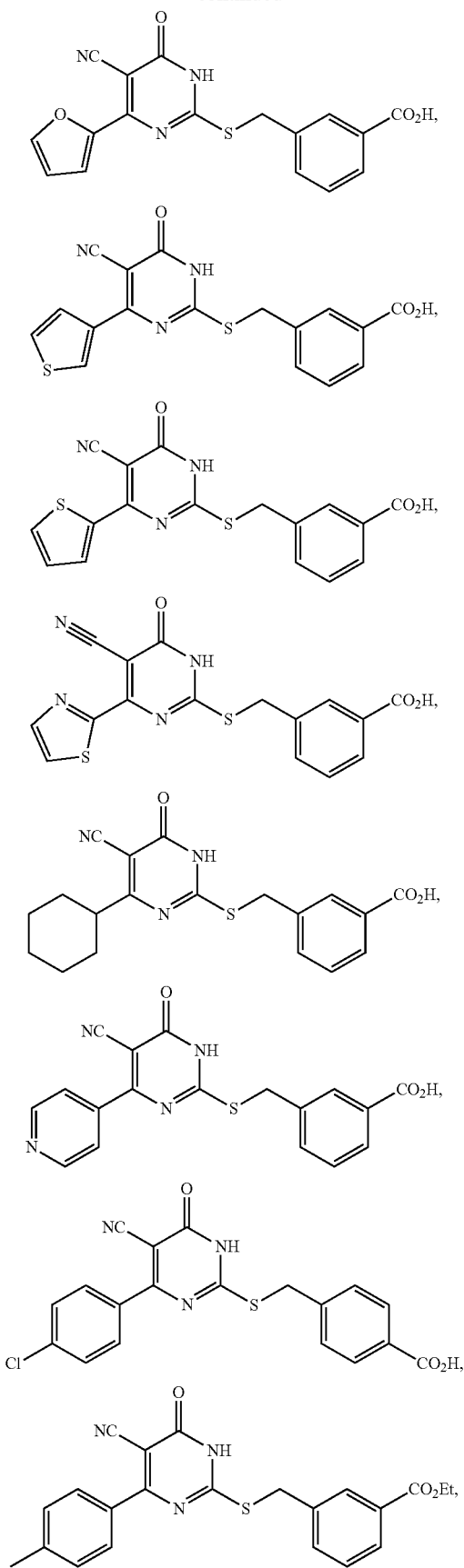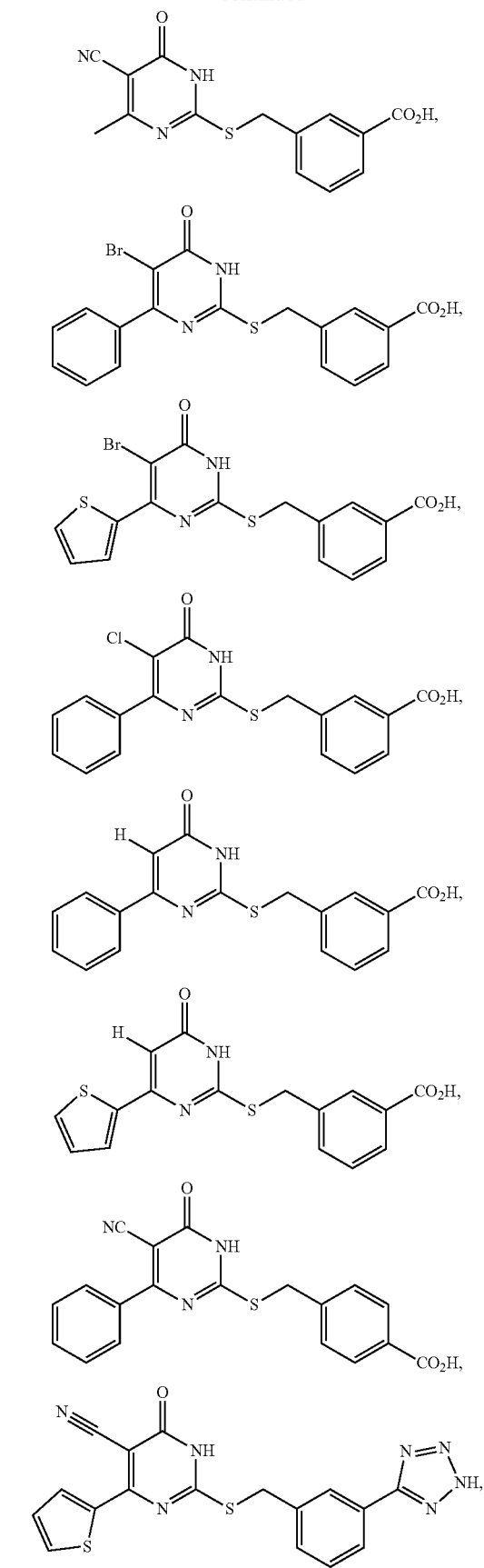

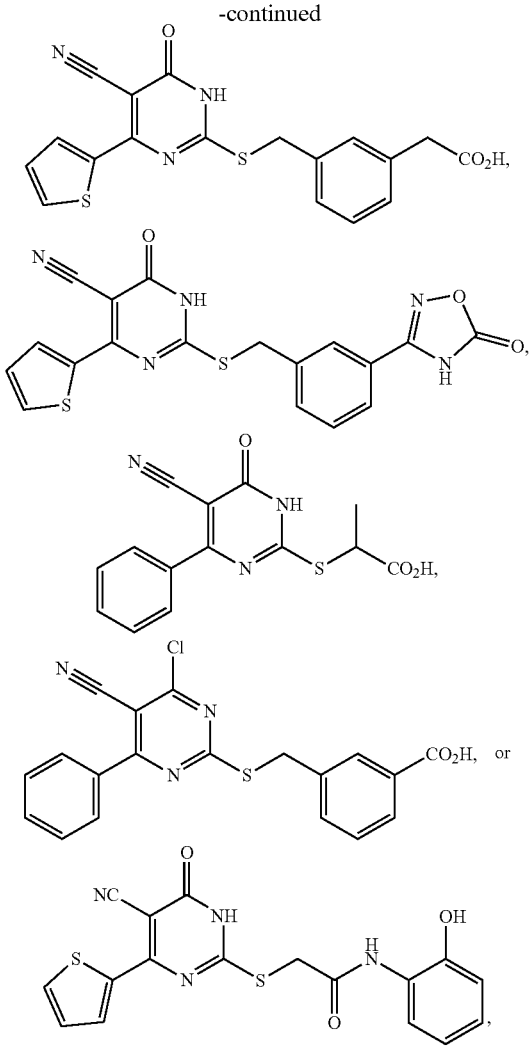
or a pharmaceutically acceptable salt thereof, for use as a medicament for treating, preventing, ameliorating or reducing the risk of a disease or disorder associated with α-amino-β-carboxymuconate-ε-semialdehyde decarboxylase (ACMSD) dysfunction.
Another aspect of the present disclosure relates to a compound having the one of the following Formula:
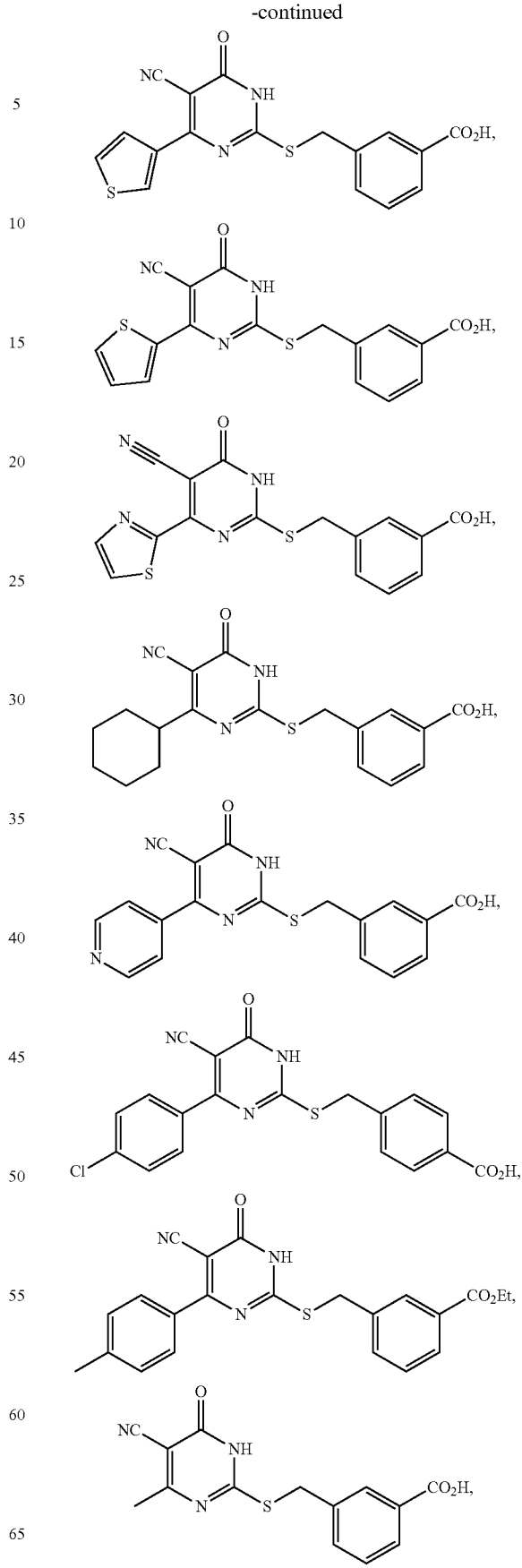

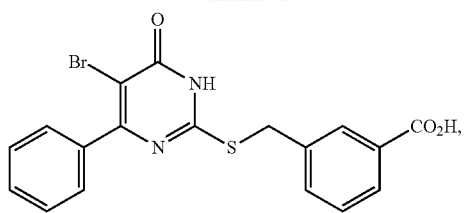
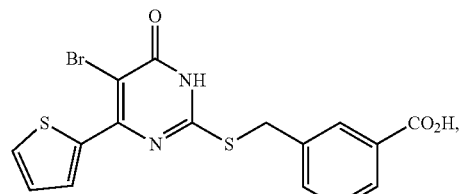
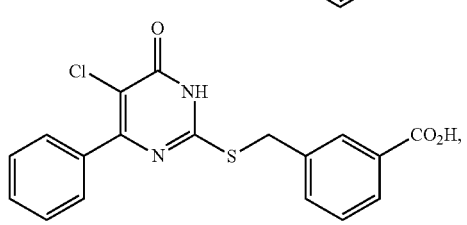
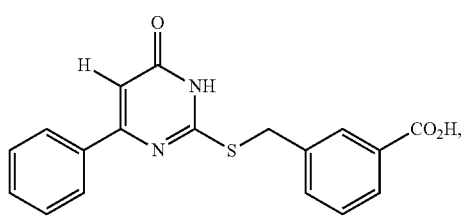
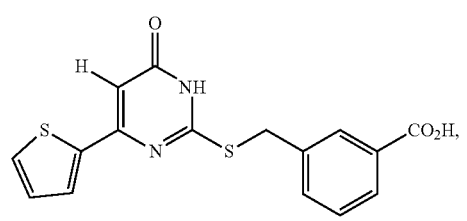
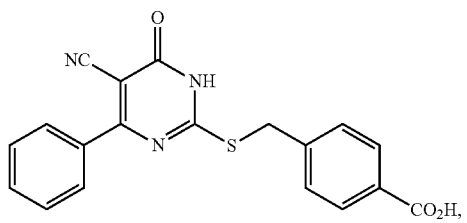
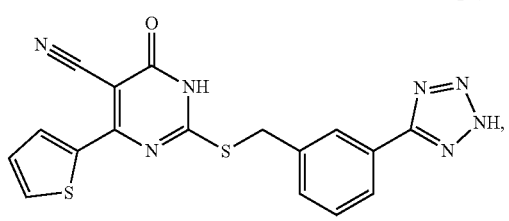
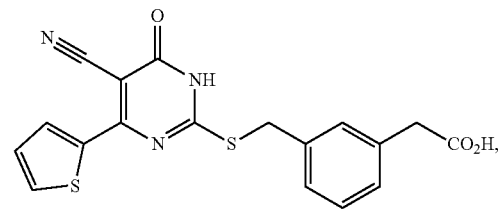
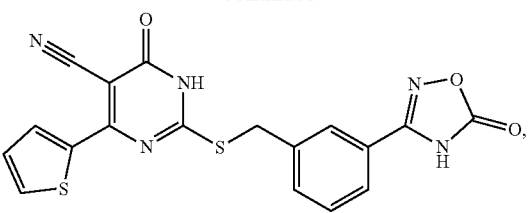
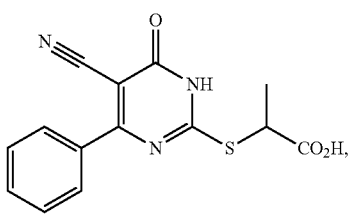
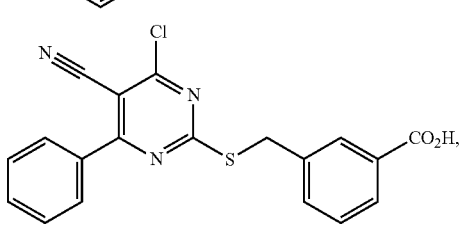
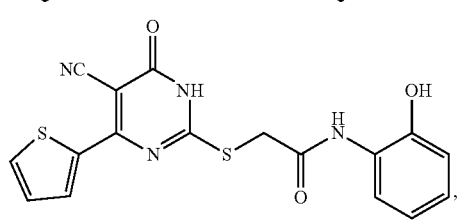
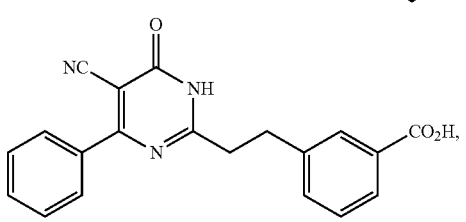
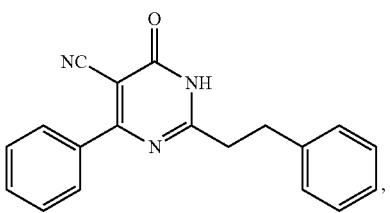
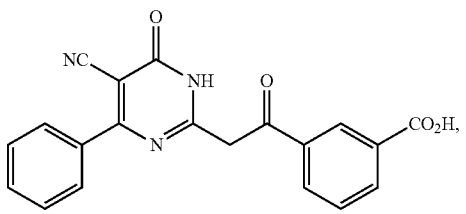
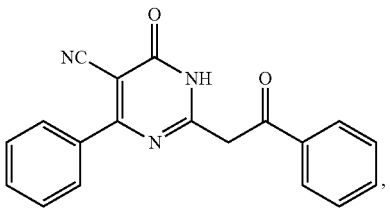

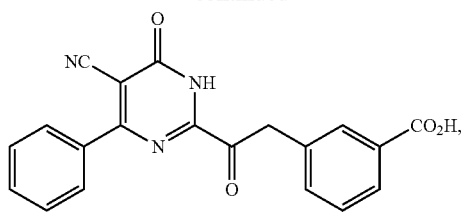
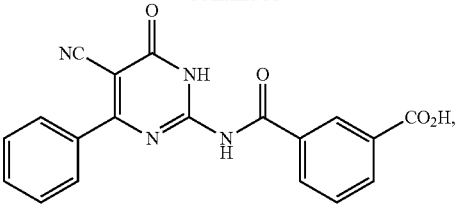
or a pharmaceutically acceptable salt thereof for use in treating, preventing, ameliorating or reducing the risk of a disease or disorder associated with α-amino-β-carboxymuconate-ε-semialdehyde decarboxylase (ACMSD) dysfunction.
In another aspect, the present disclosure relates to a compound having the one of the following Formula:
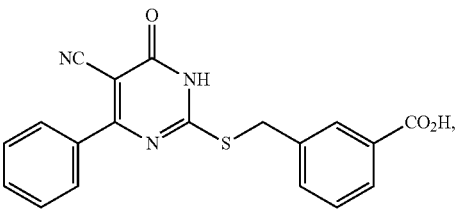
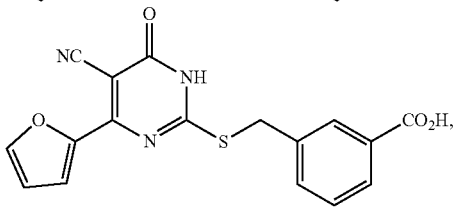

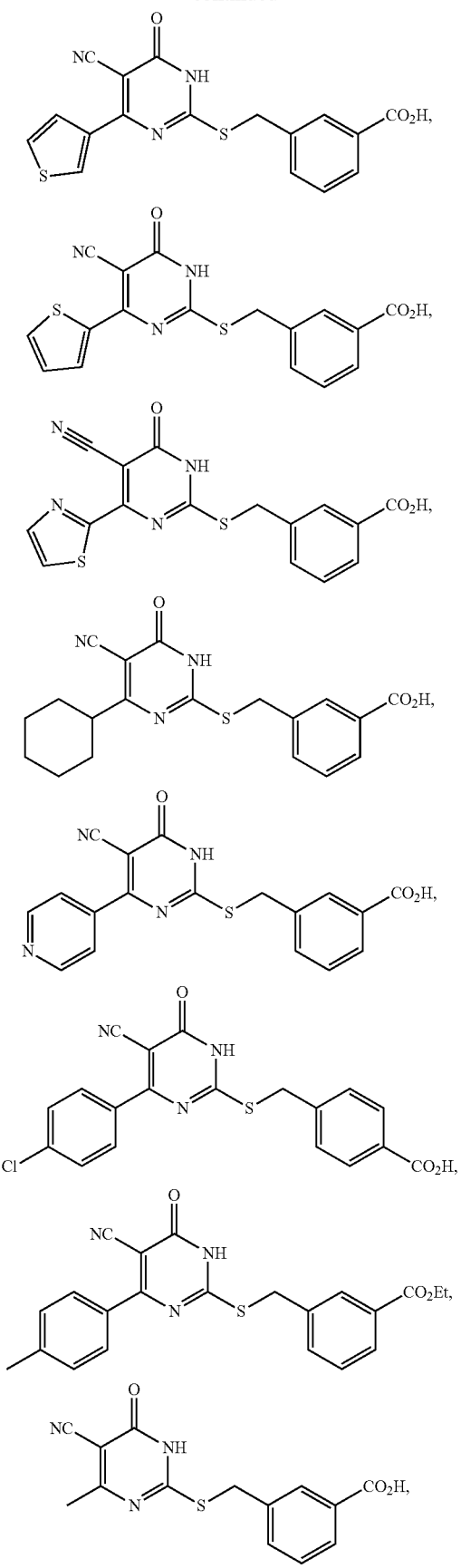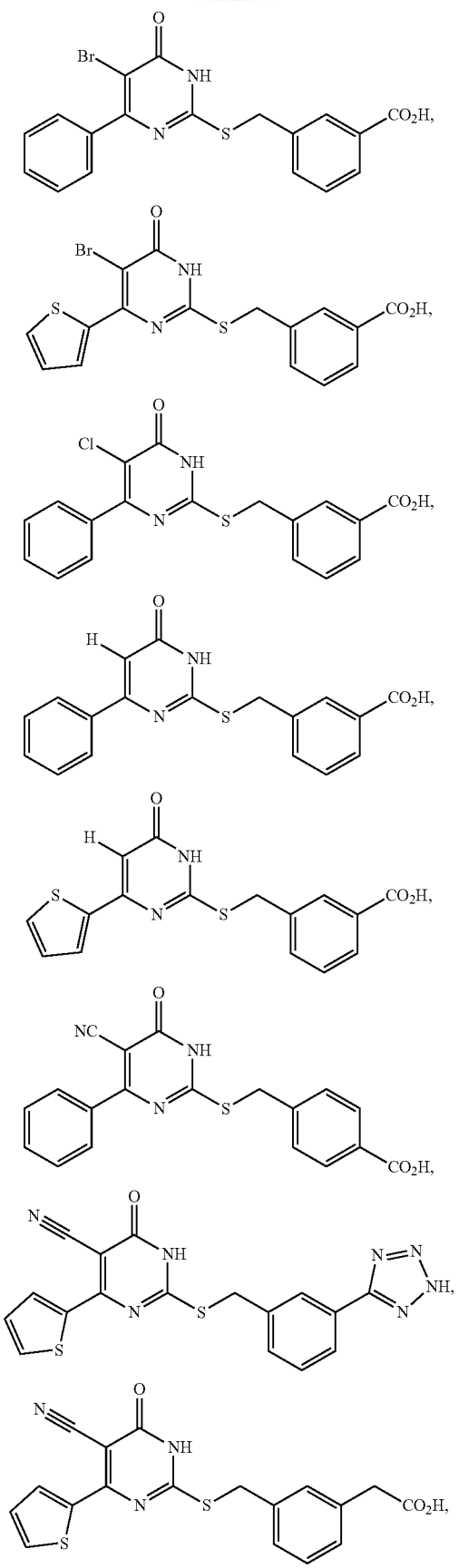

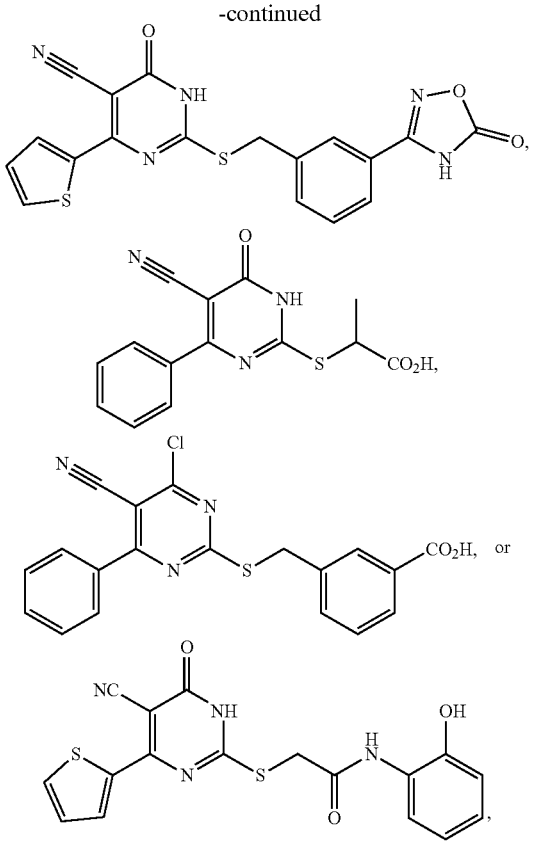

or a pharmaceutically acceptable salt thereof
for use in treating, preventing, ameliorating or reducing the risk of a disease or disorder associated with α-amino-β-carboxymuconate-ε-semialdehyde decarboxylase (ACMSD) dysfunction.

As used herein, "treating" or "treat" describes the management and care of a patient for the purpose of reversing, inhibiting, or combating a disease, condition, or disorder and includes the administration of a compound of the present disclosure (i.e., a compound of Formula (I), Formula (Ia), Formula (Ib), Formula (II), or Formula (III)), or a pharmaceutically acceptable salt, prodrug, metabolite, polymorph or solvate thereof, to reverse the disease, condition, or disorder, eliminate the disease, condition, or disorder, or inhibit the process of the disease, condition, or disorder.

A compound of the present disclosure (i.e., a compound of Formula (I), Formula (Ia), Formula (Ib), Formula (II), or Formula (III)), or a pharmaceutically acceptable salt, prodrug, metabolite, polymorph or solvate thereof, can also be used to prevent a disease, condition, or disorder or one or more symptoms of such disease, condition, or disorder. As used herein, "preventing" or "prevent" describes reducing or eliminating the onset of the symptoms or complications of the disease, condition, or disorder.

A compound of the present disclosure (i.e., a compound of Formula (I), Formula (Ia), Formula (Ib), Formula (II), or Formula (III)), or a pharmaceutically acceptable salt, prodrug, metabolite, polymorph or solvate thereof, can also be used to alleviate one or more symptoms of such disease, condition, or disorder. As used herein, the term "alleviate" is meant to describe a process by which the severity of a sign or symptom of a disorder is decreased. Importantly, a sign or symptom can be alleviated without being eliminated. Preferably treatment is curative or ameliorating.

Methods for the Preparation of Compounds of Formulae (I), (Ia), (Ib), (II) and (III)

The compounds of the present disclosure (e.g., compounds of Formula (I), Formula (Ia), Formula (Ib), Formula (II), and Formula (II)) can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below. The final products of the reactions described herein may be isolated by conventional techniques, e.g., by extraction, crystallisation, distillation, chromatography, etc.

Compounds of the present disclosure can be synthesized by following the steps outlined in General Scheme A to E which comprise different sequences of assembling intermediates Ia-Ih and Ij-Io. Starting materials are either commercially available or made by known procedures in the reported literature or as illustrated. Useful steps that may be used in the preparation steps of the compounds will be known to the skilled person. The method below is given as a non-limiting example on how the compounds may be prepared.

General Scheme A

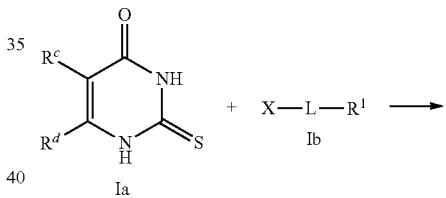

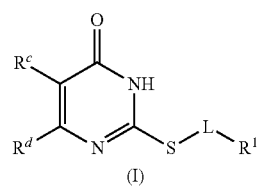

wherein $R^1$, $R^c$, $R^d$, and L are defined as in Formula (I).

The general way of preparing compounds of Formula (I) by using intermediates Ia, and Ib is outlined in General Scheme A. Coupling of Ia with Ib using a base, i.e., potassium carbonate ($K_2CO_3$), in a solvent, i.e., acetonitrile ($CH_3CN$), optionally at elevated temperature provides the desired produce of Formula (I). Bases that can be used include, but are not limited to, sodium carbonate ($Na_2CO_3$), potassium carbonate ($K_2CO_3$), N,N-diisopropylethylamine (DIPEA) and triethylamine. Solvents used in the coupling reaction can be polar or non-polar solvents. For example, the solvent can be acetonitrile ($CH_3CN$), acetone, or dimethylsulfoxide (DMSO).

General Scheme B

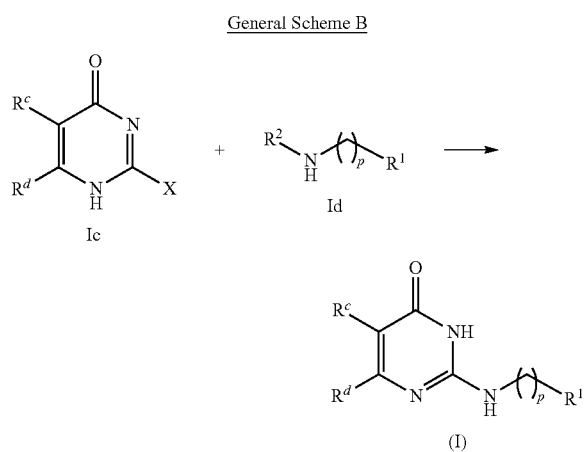

wherein X is a good leaving group, i.e., Cl, Br, —SCH$_3$, or S(O)$_2$CH$_3$, and R$^1$, R$^2$, R$^c$, R$^d$, and p are defined as in Formula (I).

Alternatively, compounds of Formula (I) can be prepared using intermediates Ic and Id as outlined in General Scheme B. Amination of Intermediate Ic with Ie using a base, i.e., sodium hydroxide (NaOH), potassium hydroxide (KOH), etc., in a solvent, i.e., methanol (MeOH), ethanol (EtOH), water (H$_2$O), etc., provides compounds of Formula (I).

General Scheme C

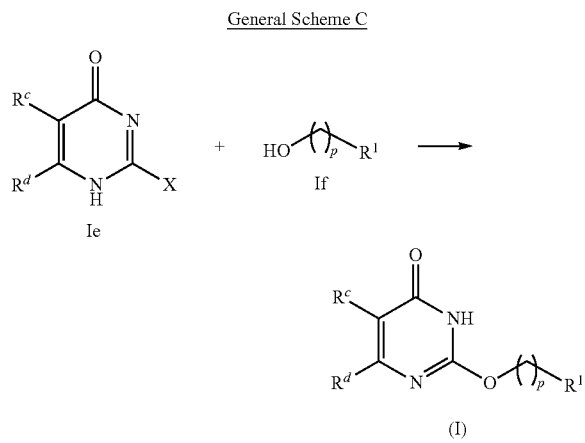

wherein X is a good leaving group, i.e., Cl, Br, —SCH$_3$, or S(O)$_2$CH$_3$, and R$^1$, R$^2$, R$^c$, R$^d$, and p are defined as in Formula (I).

Compounds of Formula (I) can also be prepared using intermediates Ie and If as outlined in General Scheme C. Amination of Intermediate Ie with If using a base, i.e., sodium hydroxide (NaOH), potassium hydroxide (KOH), etc., in a solvent, i.e., methanol (MeOH), ethanol (EtOH), water (H$_2$O), etc., provides compounds of Formula (I).

General Scheme D

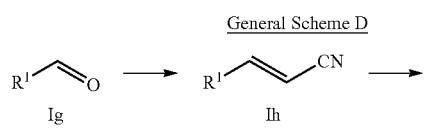

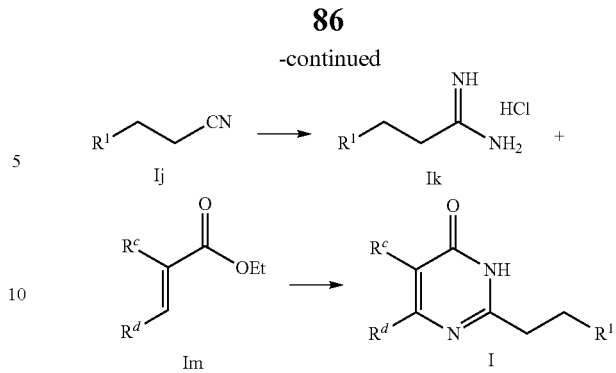

wherein and R$^1$, R$^c$, and R$^d$ are defined as in Formula (I).

Alternatively, compounds of Formula (I) can also be prepared using intermediates Ig, Ih, Ij, Ik, and Im as outlined in General Scheme D. Olefination of intermediate Ig using a base i.e., potassium carbonate (K$_2$CO$_3$) and diethyl (cyanomethyl)phosphonate in a solvent, i.e., tetrahydrofuran (THF), water (H$_2$O), optionally at an elevated temperature provides Intermediate Ih. Hydrogenation of Ih using a metal catalyst, i.e., palladium on carbon (Pd/C), platinum dioxide (PtO$_2$), etc., and hydrogen (H$_2$) gas in a solvent, i.e., ethanol (EtOH) and/or tetrahydrofuran (THF), provides Intermediate Ij. Intermediate Ik is obtained by treating Intermediate Ij with an acid, i.e., hydrochloric acid (HCl) in a solvent, i.e., ethanol (EtOH), dichloromethane (CH$_2$Cl$_2$), etc., and then subsequent treatment with a base, i.e., ammonia (NH$_3$). Cyclization of Intermediate Ik and Im using a base, i.e., sodium hydroxide (NaOH), potassium hydroxide (KOH), etc., in a solvent, i.e., dimethylacetamide (DMA), optionally at elevated temperature provides compounds of Formula (I).

General Scheme E

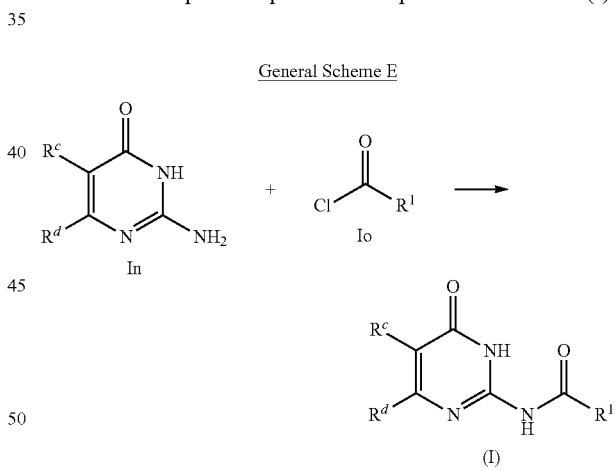

wherein and R$^1$, R$^c$, and R$^d$ are defined as in Formula (I).

Alternatively, compounds of Formula (I) can be prepared using intermediates In and Io as outlined in General Scheme D. Acylation of Intermediate In with Io using a base, i.e., sodium hydroxide (NaOH), potassium hydroxide (KOH), etc., in a solvent, i.e., methanol (MeOH), ethanol (EtOH), water (H$_2$O), etc., provides compounds of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups R$^1$, R$^2$, X, L, Y, R$^a$, $R^b$, $R^c$, $R^d$, $R^e$, $R^f$, $R^x$, $R^y$, $R^z$, m, n, p, q, r and other variables are as defined herein above, except where otherwise indicated. Furthermore, for synthetic purposes, the compounds of General Schemes A-E are mere representative with elected radicals to illustrate the general synthetic methodology of the compounds of Formula (I) as defined herein.

Biological Assays and Animals Studies

Method of Screening ACMSD1 Inhibition

The activity of compounds as inhibitors of ACMSD1 is determined in a spectrophotometrical in vitro assay. The pre-assay mixture is incubated and a compound of Formula (I), Formula (Ia), Formula (Ib), Formula (II), or Formula (III), or a pharmaceutically acceptable salt thereof, and ACMSD1 solution is then added. The effect of ACMS concentration on the enzyme activity is investigated by varying 3-hydroxyanthranilic acid (3OH-HA) concentration in the pre-assay mixture. Kinetic parameters are calculated from the initial velocity data using a Lineweaver-Burk plot.

Cellular Assay Methods

The mouse hepatocytes cell lines are grown and plated. The cells are maintained in culture at 37° C. and once the cells are attached, different concentrations of a compound of Formula (I), Formula (Ia), Formula (Ib), Formula (II), or Formula (III), or a pharmaceutically acceptable salt thereof, or DMSO are added. Primary hepatocytes are harvested about 24 hrs later.

Determination of ACMSD-1 Modulation in HEK293T Cells.

HEK293T cells are seeded and transfected to transiently express ACMSD. The cells are then stimulated with different concentrations of Compound 1, and then lysed to measure the ACMSD activity in a spectrophotometrical in vitro assay. The amount of the whole protein content in cell lysates is detected by Bradford analysis and used to get the specificity activity of the enzyme normalized in all samples.

Determination of $NAD^+$ Content in Human Primary Hepatocytes

Primary hepatocytes are treated with different concentrations of a compound of Formula (I), Formula (Ia), Formula (Ib), Formula (II), or Formula (III), or a pharmaceutically acceptable salt thereof, or MEHP (control) after seeding. The compound is replaced every 24 hours, and then cells are directly harvested and lysed to detect $NAD^+$ content through LC MS/MS (liquid chromatography mass spectrometry/mass spectroscopy).

Modulation of SOD2 Activity in AML12 Cells and Murine Primary Hepatocytes

Primary hepatocytes or AML-12 cells are lysed and total protein concentration is determined using the Bradford assay. SOD2 activity is determined at indicated times after treatment with a compound of Formula (I), Formula (Ia), Formula (Ib), Formula (II), or Formula (III), or a pharmaceutically acceptable salt thereof, using a SOD Assay Kit. Absorbance is determined and results are expressed in U/ml/mg of protein according to the standard curve and measured protein concentration.

Determination of $NAD^+$ Content in Murine Primary Hepatocytes $NAD^+$ is extracted using acidic extraction method and samples are collected and homogenized. After insoluble protein parts are pelleted, the samples are separated by high-performance liquid chromatography (HPLC) and analyzed by mass-spectrometry. The proteins in the pellet are quantified by Bradford assay and are used for normalization.

RNA Preparation and RT-qPCR Analysis of ACMSD and SIRT1-Regulated Genes in Cells, Cells (AML-12, Hepa-1.6, HEK-293, primary human and murine hepatocytes) are treated with different concentrations of a compound of Formula (I), Formula (Ia), Formula (Ib), Formula (II), or Formula (III), or a pharmaceutically acceptable salt thereof and the gene expression of ACMSD, Pgc1a, Sod1, and Sod2 (MnSOD) is determined using RT-qPCR. Total RNA is extracted from cells and the extracted RNA is treated with DNase and used for reverse transcription (RT).

Modulation of Caspase 3/7 Activity in MDCK Cells

MDCK cells are cultured in base medium to a final concentration of 10%. Cells are plated into 96 wells and 24 hours after cell plating the medium is changed with fresh medium supplemented with 1% FBS. Cisplatin is then used to induce cell injury. Different concentrations of Formula (I), Formula (Ia), Formula (Ib), Formula (II), or Formula (III), or a pharmaceutically acceptable salt thereof (in DMSO) are added in combination with cisplatin or prior to adding cisplatin. Caspase 3/7 activity (Promega) is determined according to standard procedures using a luminescent signal readout on a plate reader. Each experiment/condition is performed in triplicate. Caspase activity is analyzed as percentage effect normalized to the cisplatin alone and vehicle treated cells.

Cytotoxicity and hERG Screening

HePG2 and AML-12 cells are seeded and a dose-response of the compound is performed at various concentrations. Cells are stimulated and the supernatant is used to perform LDH release as a measure of necrosis while the cells are lysed to detect ATP levels for determining cell viability.

The Predictor hERG assay kit is stably transfected with hERG potassium channel and a high-affinity red fluorescent hERG channel ligand and is used for the determination of hERG channel affinity binding of compounds of Formula (I), Formula (Ia), Formula (Ib), Formula (II), or Formula (III), or a pharmaceutically acceptable salt thereof. Compounds that bind to the hERG channel protein (competitors) are identified by their ability to displace the tracer which results in a lower fluorescence polarization.

*C. elegans* Experiments—ACMSD1 Silencing, Lifespan Assays, Mobility Assessment and GFP Quantification ACMSD1 silencing: Bacterial feeding RNAi experiments to determine the effects of downregulation or silencing of acmsd-1 on gene expression and survival are carried out in the nematode *Caenorhabditis elegans* (*C. elegans*). The clones used for the bacterial feeding experiments are acmsd-1, SIR-2.1 and DAF-16. Total RNA is extracted from cells and the extracted RNA is treated with DNase, and used for reverse transcription (RT).

Worms are grown on NGM agar plates additionally containing Carbenicillin and IPTG and seeded with bacterial cultures. After RNAi treatment, worms are transferred to plates containing paraquat and seeded with RNAi bacteria. Control animals are grown on RNAi bacteria containing an empty vector (control) and then transferred to plates containing paraquat and seeded with RNAi bacteria. Quantification of gene expression of sod-3 at mRNA levels and protein levels using RT-qPCR and survival analyses are performed. The movement of worms is recorded at days 1, 3, and 5 of adulthood.

Anti-Diabetic Effects Studies in C57BL/6J and KK-Ay Mice

Mice are fed with regular chow or a high fat diet (HFD). A compound of Formula (I), Formula (Ia), Formula (Ib), Formula (II), or Formula (III), or a pharmaceutically acceptable salt thereof, is dosed daily and blood and tissues are harvested for RNA isolation, lipid measurements and histology. Oxygen consumption is measured and histological analysis and transmission electron microscopy are performed. An oral glucose tolerance test and an intraperitoneal insulin tolerance test are also performed to quantify glucose and to measure plasma insulin concentrations.

Anti-Diabetic and Anti-Obesity Studies in db/db Mice with LepR Mutation

Animals are fed a high-fat diet (HFD). For subchronic intervention, the animals are treated once/day with a compound of Formula (I), Formula (Ia), Formula (Ib), Formula (II), or Formula (III), or a pharmaceutically acceptable salt thereof, for 14 days. Blood samples are collected and glucose concentrations of each blood sample are determined. For acute intervention, initial blood samples are collected and then compounds of Formula (I), Formula (Ia), Formula (Ib), Formula (II), or Formula (III), or a pharmaceutically acceptable salt thereof, are administered. Diet-access is then restricted, and a second blood sample is collected. The mice are subjected to an oral glucose tolerance test and blood glucose concentrations are determined.

For the euglycemic-hyperinsulinemic clamps assay, the animals receive a primed-continuous [3-$^3$H]glucose infusion and a blood sample is then collected to determine plasma insulin, glucose and [3-$^3$H]glucose concentrations and to calculate basal endogenous glucose appearance rates. The mice then receive vehicle or a compound of Formula (I), Formula (Ia), Formula (Ib), Formula (II), or Formula (III), or a pharmaceutically acceptable salt thereof, via gavage. Subsequently, the animals receive a [3-$^3$H]glucose infusion containing insulin causing a moderate net-increase in plasma insulin concentrations. Blood glucose concentrations are measured and target glycemia is established by adjusting the rate of glucose infusion. 2-deoxy-D-[1-$^{14}$C] glucose is then given intravenously and blood samples are collected. The mice are then sacrificed. Gastrocnemius muscle and epididymal adipose tissue are collected and plasma [$^3$H]- and [$^{14}$C]-radioactivity is determined in deproteinized plasma.

Body weights are assessed and brown adipose tissue (BAT) and gonadal white adipose tissue (WAT) are dissected and weighed. Volume oxygen (VO$_2$) and volume carbon dioxide production (VCO$_2$) are measured and are reported as average VO$_2$ per hour normalized to body weight (mL/h/kg). Activity counts by infrared beam interruptions and food intake are simultaneously measured.

Non-Alcoholic Fatty Liver Disease (NAFLD) and Non-Alcoholic Steatohepatitis (NASH) Studies in Male C57BL/6J Mice Mice are fed a 'Western' HF-HSD (high fat-high sucrose diet) or normal chow diet (NCD) as control. The animals are then treated with a compound of Formula (I), Formula (Ia), Formula (Ib), Formula (II), or Formula (III), or a pharmaceutically acceptable salt thereof, for 4, 12 or 20 weeks, and then sacrificed. Body weight and food intake are monitored weekly and total fat mass is analysed. An intraperitoneal glucose tolerance test (IPGTT) is also performed and tail vein glucose levels are measured after glucose administration. Insulin resistance is calculated using the Homeostasis Model of Insulin Resistance. The mice are then sacrificed by blood sampling via cardiac puncture. Plasma is obtained and tissues were collected together with the plasma for further biochemical and molecular analyses or for histological analysis.

Non-Alcoholic Fatty Liver Disease (NAFLD) and Non-Alcoholic Steatohepatitis (NASH) Studies in in Methionine and Choline Deficient Mice Mice weighing 25 g are either fed a methionine- and choline-deficient diet (MCD to induce NASH) or chow diet (as a control). Animal experiments and evaluation of NAFLD and NASH are conducted as described above in for C57BL/6J mice fed the high fat and high sucrose diet.

Atherosclerosis Studies in High Cholesterol Fed LDL-R Knockout Mice

LDL-R knockout (KO) mice are sacrificed about 12 weeks after the initiation of the atherogenic diet, after which the heart and aorta are perfused with PBS and subsequently fixed. Atherosclerosis and biochemistry parameters are measured with the appropriate commercially available kits. For the in vivo lipopolysaccharide (LPS) study, mice are intraperitoneally injected with LPS, and blood is taken from the tail vein. TNFα levels are quantified with a Mouse TNFα ELISA assay. Blood cell counts are determined.

Inherited Mitochondrial Disease Studies in Sco2$^{KO/KI}$ Mice

Compounds of Formula (I), Formula (Ia), Formula (Ib), Formula (II), or Formula (III) are dissolved in water and added to a standard powder diet at the appropriate concentration. The diet supply is changed every three days and administered ad libitum for one month. Tissues are collected for histological analysis. For the muscle quadriceps samples, the spectrophotometric activity of cI, cII, cII, and cIV, as well as CS, is measured. NAD$^+$ is extracted from tissues using acidic and alkaline extraction methods, respectively, and analysed with mass spectrometry.

Inherited Mitochondrial Disease Studies in Deletor mice

Deletor and WT male mice are administered either chow diet (CD) or a compound of Formula (I), Formula (Ia), Formula (Ib), Formula (II), or Formula (III) admixed with the CD. The mice are regularly monitored for weight, food consumption, and physical endurance and their exercise capability is measured. Oxygen consumption and carbon dioxide production, as well as spontaneous moving and feeding activities, are recorded. Tissue sections are collected and prepared from the quadriceps, liver, and BAT. Frozen sections from quadriceps are assayed for in situ histochemical COX and succinate dehydrogenase (SDH) activities, crista content in both BAT and muscle is determined from electron micrographs and skeletal muscle samples are analysed for citrate synthase activity.

Kidney Disease Studies

C57BL/6J WT mice are fed a standard commercial diet and divided into four groups: control; cisplatin; a compound of Formula (I), Formula (Ia), Formula (Ib), Formula (II), or Formula (III), or a pharmaceutically acceptable salt thereof, and cisplatin; and a compound of Formula (I), Formula (Ia), Formula (Ib), Formula (II), or Formula (III), or a pharmaceutically acceptable salt thereof, alone. The mice are sacrificed and tissue samples and serum are collected. Serum creatinine and BUN levels are measured and the proinflammatory cytokines TNF-α, IL-1b, and IL-6 from serum or homogenates from kidney tissue are quantified. Mouse kidneys are collected and stained for analysis. Tubular damage is examined and scored based on the percentage of cortical tubular necrosis. Neutrophil infiltration is quantitatively assessed on stained tissue by counting the number of neutrophils per high-power field.

Alternatively, C57BL/6J WT mice are numbered and kept in acclimatization for a period and then randomized into different treatment groups based on their body weight. Different groups are maintained on a specified diet for a period of time. Body weight measurements are taken and food consumption is evaluated. Blood is collected by retro-orbital puncture under mild anesthesia and used for analysis of basal blood urea nitrogen levels (BUN).

Mice are anesthetized and placed on a surgical platform. Both kidneys are exposed through incisions and renal pedicles are occluded using vascular clamps. The clamp is then removed and the surgical site is sutured. The sham-operated group is subjected to similar surgical procedures, except that the occluding clamp is not applied. Animals are monitored until recovery from anesthesia and returned to their home cage. Animals are observed every day for general clinical signs and symptoms and mortality.

One day prior to termination, animals are individually housed in metabolic cages and urine is collected for estimation of urea, creatinine, sodium and potassium. Blood is also collected by retro orbital puncture under mild anesthesia and plasma is used for analysis of blood urea nitrogen levels (BUN) and serum creatinine. Animals are then euthanized and organs are collected. One kidney is fixed and the other is flash frozen and used for the estimation of lipid peroxidation, GSH, MPO and SOD levels.

Ischemia/Reperfusion-Induced Acute Kidney Injury Studies

CD-1 (ICR) mice are treated with a compound of Formula (I), Formula (Ia), Formula (Ib), Formula (II), or Formula (III), or a pharmaceutically acceptable salt thereof, by oral gavage once per day. CD-1 mice are divided into four groups: (1) young mice with sham injury; (2) young mice with ischemic/reperfusion (I/R) injury; (3) adult mice with sham injury; and (4) adult mice with I/R injury. An additional 27 adult mice are randomized into two groups: mice receiving a compound of Formula (I), Formula (Ia), Formula (Ib), Formula (II), or Formula (III), or a pharmaceutically acceptable salt thereof, and mice receiving the vehicle as a control. The serum creatinine level is measured and BUN measurements are recorded. Renal tissue is then evaluated and tubular injury is scored.

Determination of the Effects on FoxO1 Phosphorylation Levels

AML-12 cells are treated with different concentrations of a compound of Formula (I), Formula (Ia), Formula (Ib), Formula (II), or Formula (III), or a pharmaceutically acceptable salt thereof. Cells are then lysed, and analyzed by SDS-PAGE/western blot. Blocking and antibody incubations are then done and each protein present is detected with its specific antibody.

Inhibitory Effect

The present disclosure also relates to a compound of Formula (I), Formula (Ia), Formula (Ib), Formula (II), or Formula (III), or a pharmaceutically acceptable salt thereof, as defined herein, in a method for inhibiting the activity of ACMSD. The method includes contacting a cell with a compound of Formula (I), Formula (Ia), Formula (Ib), Formula (II), or Formula (III), or a pharmaceutically acceptable salt thereof. In a related embodiment, the method further provides that the compound is present in an amount effective to produce a concentration sufficient to selectively inhibit ACMSD in the cell.

Thus, preferably in an assay for ACMSD inhibition (i.e., an ACMSD assay described herein, e.g., Example 29, or an ACMSD assays known in the literature), the preferred compounds of Formula (I), Formula (Ia), Formula (Ib), Formula (II), or Formula (III), or a pharmaceutically acceptable salt thereof, are compounds capable of reducing or preferably inhibiting ACMSD and increasing NAD$^+$ levels and/or activating SIRTs and the downstream targets of SIRTs, such as PGC-1α, FoxO1 and/or SOD. Preferably, said inhibition is determined as the $IC_{50}$ of said compound of Formula (I), Formula (Ia), Formula (Ib), Formula (II), or Formula (III) with respect to said ACMSD inhibition assay. Preferred compounds of Formula (I), Formula (Ia), Formula (Ib), Formula (II), or Formula (III), or a pharmaceutically acceptable salt thereof, have an $IC_{50}$ at or below 1 μM, more preferably less than 300 nM, for example less than 100 nM, such as less than 50 nM with respect to inhibition of ACMSD.

Pharmaceutically Acceptable Salts

The compound of Formula (I), Formula (Ia), Formula (Ib), Formula (II), or Formula (III) may be provided in any form suitable for the intended administration, in particular including pharmaceutically acceptable salts, solvates and prodrugs of the compound of Formula (I), Formula (Ia), Formula (Ib), Formula (II), or Formula (III).

Pharmaceutically acceptable salts refer to salts of the compounds of Formula (I), Formula (Ia), Formula (Ib), Formula (II), or Formula (III) which are considered to be acceptable for clinical and/or veterinary use. Typical pharmaceutically acceptable salts include those salts prepared by reaction of the compounds of Formula (I), Formula (Ia), Formula (Ib), Formula (II), or Formula (III) and a mineral or organic acid or an organic or inorganic base. Such salts are known as acid addition salts and base addition salts, respectively. It will be recognized that the particular counter-ion forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology.

Examples of pharmaceutically acceptable addition salts include acid addition salts formed with inorganic acids, e.g., hydrochloric, hydrobromic, sulfuric, nitric, hydroiodic, metaphosphoric, or phosphoric acid; and organic acids e.g., succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. It should be understood that all references to pharmaceutically acceptable salts include solvent addition forms (solvates) or crystal forms (polymorphs) as defined herein, of the same salt.

The compound of Formula (I), Formula (Ia), Formula (Ib), Formula (II), or Formula (III), or a pharmaceutically acceptable salt thereof, may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like.

The compound of Formula (I), Formula (Ia), Formula (Ib), Formula (II), or Formula (III), or a pharmaceutically acceptable salt thereof, may be provided as a prodrug. The term "prodrug" used herein is intended to mean a compound which—upon exposure to certain physiological conditions—will liberate the compound of Formula (I), Formula (Ia), Formula (Ib), Formula (II), or Formula (III), or a pharmaceutically acceptable salt thereof, which then will be able to exhibit the desired biological action. A typical example is a labile carbamate of an amine.

Since prodrugs are known to enhance numerous desirable qualities of pharmaceuticals (e.g., solubility, bioavailability, manufacturing, etc.), the compounds of the present disclosure can be delivered in prodrug form. Thus, the present disclosure is intended to cover prodrugs of the presently claimed compounds, methods of delivering the same and compositions containing the same. "Prodrugs" are intended to include any covalently bonded carriers that release an active parent drug of the present disclosure in vivo when such prodrug is administered to a subject. Prodrugs in the present disclosure are prepared by modifying functional groups present in the compound in such a way that the modifications are cleaved, either in routine manipulation or in vivo, to the parent compound. Prodrugs include compounds of the present disclosure wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., $C_{1-6}$ alkyl esters, e.g., methyl esters, ethyl esters, 2-propyl esters, phenyl esters, 2-aminoethyl esters, morpholinoethanol esters, etc.) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like. See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one aspect of this disclosure, there is provided a pharmaceutical composition comprising at, as an active ingredient, at least one compound of Formula (I), Formula (Ia), Formula (Ib), Formula (II), or Formula (III), or a pharmaceutically acceptable salt thereof, as defined herein, and optionally one or more pharmaceutically acceptable excipients, diluents and/or carriers. The compounds of Formula (I), Formula (Ia), Formula (Ib), Formula (II), or Formula (III), or a pharmaceutically acceptable salt thereof, may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

A "pharmaceutical composition" is a formulation containing the compounds of the present disclosure in a form suitable for administration to a subject. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The pharmaceutical compositions formed by combining a compound of Formula (I), Formula (Ia), Formula (Ib), Formula (II), or Formula (III), or a pharmaceutically acceptable salt thereof, as defined herein, with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders, and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of Formula (I), Formula (Ia), Formula (Ib), Formula (II), or Formula (III), or a pharmaceutically acceptable salt thereof, as defined herein, may suitably be combined with an oral, non-toxic, pharmaceutically acceptable carrier such as ethanol, glycerol, water, or the like. Furthermore, suitable binders, lubricants, disintegrating agents, flavouring agents, and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes, or the like. Lubricants include, e.g., sodium oleate, sodium stearate, magnesium stearate, sodium benzoate, sodium acetate, sodium chloride, or the like. Disintegrating agents include, e.g., starch, methyl cellulose, agar, bentonite, xanthan gum, sodium starch glycolate, crospovidone, croscarmellose sodium, or the like. Additional excipients for capsules include macrogels or lipids.

For the preparation of solid compositions such as tablets, the active compound of Formula (I), Formula (Ia), Formula (Ib), Formula (II), or Formula (III), or a pharmaceutically acceptable salt thereof, is mixed with one or more excipients, such as the ones described above, and other pharmaceutical diluents such as water to make a solid pre-formulation composition containing a homogeneous mixture of a compound of Formula (I), Formula (Ia), Formula (Ib), Formula (II), or Formula (III), or a pharmaceutically acceptable salt thereof. The term "homogenous" is understood to mean that the compound of Formula (I), Formula (Ia), Formula (Ib), Formula (II), or Formula (III), or a pharmaceutically acceptable salt thereof, is dispersed evenly throughout the composition so that the composition may readily be subdivided into equally effective unit dosage forms such as tablets or capsules.

Liquid compositions for either oral or parenteral administration of the compound of Formula (I), Formula (Ia), Formula (Ib), Formula (II), or Formula (III), or a pharmaceutically acceptable salt thereof, include, e.g., aqueous solutions, syrups, elixirs, aqueous or oil suspensions and emulsion with edible oils such as cottonseed oil, sesame oil, coconut oil, or peanut oil. Suitable dispersing or suspending agents for aqueous suspensions include synthetic or natural gums such as tragacanth, alginate, acacia, dextran, sodium carboxymethylcellulose, gelatin, methylcellulose, or polyvinylpyrrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

The preparation of all these solutions under sterile conditions is readily accomplished by standard pharmaceutical techniques well known to those skilled in the art.

For example, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Depot injectable compositions are also contemplated as being within the scope of the present disclosure.

For parenteral administration, solutions containing a compound of Formula (I), Formula (Ia), Formula (Ib), Formula (II), or Formula (III), or a pharmaceutically acceptable salt thereof, in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

In addition to the aforementioned ingredients, the compositions of a compound of Formula (I), Formula (Ia), Formula (Ib), Formula (II), or Formula (III), or a pharmaceutically acceptable salt thereof, may include one or more additional ingredients such as diluents, buffers, flavouring agents, colourant, surface active agents, thickeners, preservatives, e.g., methyl hydroxybenzoate (including anti-oxidants), emulsifying agents and the like.

The term "therapeutically effective amount", as used herein, refers to an amount of a pharmaceutical agent to treat, ameliorate, or prevent an identified disease, disorder, or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or disorder to be treated is a disease or disorder associated with α-amino-β-carboxymuconate-ε-semialdehyde decarboxylase (ACMSD) dysfunction.

For any compound, the therapeutically effective amount can be estimated initially either in cell culture assays, e.g., in cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

A suitable dosage of the compound of Formula (I), Formula (Ia), Formula (Ib), Formula (II), or Formula (III), or a pharmaceutically acceptable salt thereof, will depend on the age and condition of the patient, the severity of the disease to be treated and other factors well known to the practicing physician. The compound may be administered for example either orally, parenterally or topically according to different dosing schedules, e.g., daily or with intervals, such as weekly intervals. In general a single dose will be in the range from 0.01 to 500 mg/kg body weight, preferably from about 0.05 to 100 mg/kg body weight, more preferably between 0.1 to 50 mg/kg body weight, and most preferably between 0.1 to 25 mg/kg body weight. The compound may be administered as a bolus (i.e., the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

As used herein, a "subject" or "subject in need thereof" is a subject having a disease or disorder associated with α-amino-β-carboxymuconate-ε-semialdehyde decarboxylase (ACMSD) dysfunction. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The compounds of Formula (I), Formula (Ia), Formula (Ib), Formula (II), or Formula (III), or a pharmaceutically acceptable salt thereof, may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances, or preferably an active substance as described in the section "combination treatment" herein below.

Clinical Conditions and Other Uses of Compounds

The compounds according to Formula (I), Formula (Ia), Formula (Ib), Formula (II), or Formula (III), or a pharmaceutically acceptable form thereof, compositions, medicaments, and compounds for use, as defined herein, are useful for treatment of a disease or disorder in which α-amino-β-carboxymuconate-ε-semialdehyde decarboxylase (ACMSD) modulation plays a role. The compounds may be used either in human or in veterinary medicine and the patient may be any mammal, but especially a human. The treatment may include administering to any mammal, but especially a human, suffering from a disease or disorder in which α-amino-β-carboxymuconate-ε-semialdehyde decarboxylase (ACMSD) modulation plays a role, a therapeutically effective amount of a compound according to Formula (I), Formula (Ia), Formula (Ib), Formula (II), or Formula (III), or a pharmaceutically acceptable salt thereof, as defined herein.

The present disclosure also relates to a compound of Formula (I), Formula (Ia), Formula (Ib), Formula (II), or Formula (III), or a pharmaceutically acceptable salt thereof, as defined herein, for use in a disease or disorder associated with α-amino-β-carboxymuconate-ε-semialdehyde decarboxylase (ACMSD) dysfunction, such as obesity, type II diabetes and its complications (e.g., diabetic retinopathy and nephropathy), non-alcoholic fatty liver disease (NAFLD), non-alcoholic steatohepatitis (NASH), or chronic kidney disease.

By the term "disease or disorder associated with α-amino-β-carboxymuconate-ε-semialdehyde decarboxylase (ACMSD) dysfunction" is meant any disease characterized by reduced nicotinamide adenine dinucleotide ($NAD^+$) expression and/or activity in at least in some instances of the disease, or a disease which is ameliorated by elevation of the levels of $NAD^+$.

The methods, medicaments and compounds for use of the present disclosure are useful to treat, alleviate the symptoms of, or delay the onset of a disorder associated with aberrant mitochondrial function. Disorders associated with aberrant mitochondrial function include, for example, metabolic disorders, neurodegenerative disorders, aging related disorders, and chronic inflammatory disorders. Mitochondrial disorders also include diseases with inherited and/or acquired mitochondrial dysfunction (i.e., Charcot-Marie-Tooth disease, Type 2A2, Mitochondrial Encephalopathy Lactic Acidosis and Stroke (MELAS), Leigh syndrome, Barth syndrome, and Leber's optic neuropathy), fatty acid oxidation disorders, inherited forms of deafness and blindness, and metabolic abnormalities induced by exposure to toxic chemicals and/or drugs (e.g., cisplatin induced deafness).

Metabolic disorders include, for example, type II diabetes, obesity, hyperglycemia, glucose intolerance, insulin resistance (i.e., hyperinsulinemia, metabolic syndrome, syndrome X), hypercholesterolemia, hypertension, hyperlipoproteinemia, hyperlipidemia (e.g., dyslipidemia), hypertriglylceridemia, cardiovascular disease, atherosclerosis, peripheral vascular disease, kidney disease, ketoacidosis, thrombotic disorders, nephropathy, diabetic neuropathy, diabetic retinopathy, sexual dysfunction, dermatopathy, dyspepsia, hypoglycemia, cancer, and edema.

Neurodegenerative disorders include diseases such as photoreceptor degeneration (i.e., retinitis pigmentosa), Dementia, Alzheimer's disease, Parkinson's disease, and Huntington's disease.

Chronic inflammatory diseases include diseases such as celiac disease, vasculitis, lupus, chronic obstructive pulmonary disease (COPD), irritable bowel disease, atherosclerosis, arthritis, and psoriasis.

Aging related disorders include diseases such as cancer, dementia, cardiovascular disease (i.e., arteriosclerosis), hypertension, diabetes mellitus (type I or type II), arthritis, cataracts, Alzheimer's disease, macular degeneration, and osteoporosis.

The subject can be suffering from or susceptible to developing a metabolic disorder. Subjects suffering from or at risk of developing a metabolic disorder are identified by methods known in the art. For example, diabetes can be diagnosed by measuring fasting blood glucose levels or insulin or by glucose tolerance test. Normal adult glucose levels are between about 60-126 mg/dl. Normal insulin levels are about 7 mU/mL±3 mU. Hypertension can be diagnosed by a blood pressure reading consistently at or above about 140/90. Cardiovascular disease can be diagnosed by measuring cholesterol levels. For example, LDL cholesterol above about 137 or total cholesterol above about 200 is indicative of cardiovascular disease. Hyperglycemia can be diagnosed by a blood glucose level higher than about 10 mmol/l (180 mg/dl). Glucose intolerance can be diagnosed by glucose levels of 140 to 199 mg per dL (7.8 to 11.0 mmol) after conducting a 75 g oral two-hour glucose tolerance test. Insulin resistance can be diagnosed by a fasting serum insulin level of greater than approximately 60 pmol/L. Hypoglycemia can be diagnosed by a blood glucose level lower than about 2.8 to 3.0 mmol/L (50 to 54 mg/dl). Obesity can be diagnosed, for example, by body mass index. Body mass index (BMI) is measured in $kg/m^2$ (or $lb/in^2\times 704.5$). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e., fat mass impedes current), estimates % fat) can be measured. The parameters for normal, overweight, or obese individuals are as follows: Underweight: BMI <18.5; Normal: BMI about 18.5 to about 24.9; Overweight: BMI=about 25 to about 29.9. Overweight individuals are characterized as having a waist circumference of >94 cm for men or >80 cm for women and waist to hip ratios of ≥0.95 in men and ≥0.80 in women. Obese individuals are characterized as having a BMI of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of ≥35.

The methods described herein may lead to a reduction in the severity or the alleviation of one or more symptoms of a metabolic disorder. For example, symptoms of diabetes include elevated fasting blood glucose levels, blood pressure at or above 140/90 mm/Hg; abnormal blood fat levels, such as high-density lipoproteins (HDL) less than or equal to 35 mg/dL, or triglycerides greater than or equal to 250 mg/dL (mg/dL=milligrams of glucose per deciliter of blood). Efficacy of treatment is determined in association with any known method for diagnosing the metabolic disorder. Alleviation of one or more symptoms of the metabolic disorder indicates that the compound confers a clinical benefit.

The methods of the present disclosure are useful to treat, alleviate the symptoms of, or delay the onset of a kidney disorder. Kidney disorders include acute kidney injury (AKI) and chronic kidney disease (CKD).

The subject can be suffering from or susceptible to developing acute kidney injury (AKI). The acute kidney injury can be characterized by one or more clinical criteria or conditions (i.e., an abrupt decrease in the ability of the kidneys to excrete nitrogenous waste products from the blood, resulting in azotemia). Subjects suffering from or at risk of developing acute kidney injury (AKI) are identified by methods known in the art. For example, the acute kidney injury can be characterized by an increase in serum creatinine by at least 50% over baseline, an absolute increase in serum creatinine of at least 0.3 mg/dL over baseline, a reduction in glomerular filtration rate of at least 25% compared to baseline, a decrease in urine output to 0.5 ml per kilogram of body weight or less per hour persisting for at least 6 hours, or any combination thereof. An acute kidney injury may be caused by ischemia, drugs or toxic agents (i.e., radiocontrast media, a non-steroidal anti-inflammatory drug (NSAID), alcohol, or a chemotherapy agent), viruses, and obstruction.

The subject can be suffering from or susceptible to developing chronic kidney disease (CKD). Chronic kidney disease (CKD) is defined as either (1) having kidney damage as defined by structural or functional abnormalities of the kidney for 3 months or longer with or without a decreased glomerular filtration rate (GFR) or (2) having a GFR of less than 60 mL/min/1.73 $m^2$ for 3 months or longer with or without kidney damage. Subjects suffering from or at risk of developing a chronic kidney disease (CKD) are identified by methods known in the art. Structural or functional abnormalities are manifested by symptoms such as either pathologic abnormalities or markers of kidney damage, including abnormalities identified in imaging studies or the composition of blood or urine.

For example, CKD can be diagnosed by testing for specific marker. For example, markers of kidney damage include a plasma creatinine concentration of above about 1.6 mg/dL and a blood urea nitrogen (BUN) concentration of above about 20 mg/dL. Typically, both of these markers are elevated in individuals with CKD. Additional markers of kidney damage can include hematuria (i.e., any detectable amount of blood in the urine), proteinuria (i.e., protein concentrations in urine above about 100 mg/dL), albuminuria (i.e., albumin concentrations in urine above about 100 mg/dL), an intact parathyroid hormone (PTH) concentration in the blood above about 150 pg/mL, or blood phosphate levels of above about 4.5 mg/dL. One specific marker of kidney disease is a GFR rate above normal (i.e., a GFR above about 90 mL/min/1.73 $m^2$), however a below normal GFR also indicates CKD.

The methods of the present disclosure are useful to treat, alleviate the symptoms of, or delay the onset of non-alcoholic fatty liver disease (NAFLD) and/or non-alcoholic steatohepatitis (NASH). The subject can be suffering from or susceptible to developing non-alcoholic fatty liver disease (NAFLD) and/or non-alcoholic steatohepatitis (NASH). Subjects suffering from or at risk of developing a non-alcoholic fatty liver disease (NAFLD) and/or non-alcoholic steatohepatitis (NASH) are identified by methods known in the art. For example, NAFLD and/or NASH can be diagnosed by liver biopsy.

Non-alcoholic fatty liver disease (NAFLD), as defined herein, is a disease with fat deposition in the liver, which occurs in patients whose alcohol ingestion history is not long enough to cause liver injury. Non-alcoholic fatty liver disease (NAFLD) can be further classified into simple fatty liver, steatohepatitis and cirrhosis. Nonalcoholic steatohepatitis (NASH) refers to a pathology associated with inflammation, liver cell necrosis, ballooning and fibrosis. The onset of nonalcoholic simple fatty liver is induced by fat deposition in liver cells, and this fat accumulation is defined by the balance between increasing factors (influx and synthesis of fats in liver cells) and decreasing factors (catabolism of fats and their release from liver cells). Once damage of liver cells occurs, in addition to this fat deposition, nonalcoholic simple fatty liver will progress to nonalcoholic steatohepatitis. Nonalcoholic steatohepatitis is progressive and may finally progress to cirrhosis and hepatocellular carcinoma.

Combination Treatment

A compound, compositions, medicaments and compounds for use of Formula (I), Formula (Ia), Formula (Ib), Formula (II), or Formula (III), or a pharmaceutically acceptable salt thereof, may also be used to advantage in combination with one or more other therapeutic agents. Such therapeutic agents include, but are not limited to other ACMSD inhibitors; anti-diabetic agents such as PPARy agonists, PPARα/γ dual agonists, PPARδ agonists, biguanides, protein tyrosine phosphatase-1B (PTP-1B), dipeptidyl peptidase IV (DPP-IV) inhibitors, sulfonylureas, meglitinides, alpha glucoside hydrolase inhibitors, alpha-amylase inhibitors, insulin secreatagogues, A2 antagonists, insulin or insulin mimetics, glycogen phosphorylase inhibitors, GLP-1 agonists, non-thiazolidinediones, glycokinase, and 11 β HSD-1 inhibitor; anti-obesity agents such as uncoupling Protein (UCP-1, UCP-2, and UCP-3) activators, β3 adrenergic receptor (β3), thyroid hormone β agonists, fatty acid synthase (PAS) inhibitors, phosphodieterase (PDE) inhibitors, lipase inhibitors, serotonin reuptake inhibitors, monoamine reuptake inhibitors, Mc4r agonists, 5HT2c agonists, growth hormone secretagogue (GHS) agonists, CNTF derivatives, ciliary neurotrophic factors (CNTh), cholecystokinin-A (CCK-A) agonists, opioid antagonists, orexin antagonists, acyl-estrogens, leptin, NPY 5 antagonists, neuropeptide Y5 (NPY5) antagonists, neuropeptide Y2 (NPY2) agonists, melanin-concentrating hormone receptor (MCHLR) antagonists and melanin-concentrating hormone 2 receptor (MCH2R), MCH1R antagonists, neuropeptide Y1, ghrelin antagonists, cannabinoid receptor 1 (CB-1), serotonin (5HT) transport inhibitors, CCK-A agonists and histamine 3 (H3) antagonist/inverse agonists; cholesterol lower agents such as 3-hydroxy-3-methylglutaryl-coenzyme A (HMG CoA) reductase inhibitors, HMG-CoA synthase inhibitors, squalene epoxidase inhibitors, fibric acids, bile acid-binding resins probucol and niacin (nicotinic acid); compounds that boost NAD levels such as NAD+ precursors (i.e., nicotinamide ribose (NA), nicotinamide mononucleotide (NMN), nicotinic acid (NA) and nicotinamide); and compounds that inhibit NAD+ consumption such as PARP inhibitors and CD38 inhibitors.

PPARy agonists useful in the present disclosure include, but are not limited to, glitazones (e.g., balaglitazone, ciglitazone, darglitazone, englitazone, isaglitazone (MCC-555), pioglitazone, rosiglitazone, troglitazone, CLX-0921, 5-BTZD, and the like); GW-0207, LG-100641, LY-300512, LY-519818, R483 (Roche), T131 (Tularik), and compounds disclosed in WO97/27857, 97/28115, 97/28137 and 97/27847; and pharmaceutically acceptable salts or esters thereof. PPARα/γ dual agonists useful in the present disclosure, include, but are not limited to, CLX-0940, GW-1536, GW1929, GW-2433, KRP-297, L-796449, LR-90, MK-0767, SB 219994, and muraglitazar, and pharmaceutically acceptable salts or esters thereof. KRP-297 is 5-[(2,4-Dioxo-5-thiazolidinyl)methyl]-2-methoxy-N-[[4-(trifluoromethyl) phenyl] methyl]benzamide, and pharmaceutically acceptable salts or esters thereof. PPARδ agonists useful in the present disclosure include, but are not limited to, GW 501516, GW 590735, and compounds disclosed in JP 10237049, and WO 02/14291; and pharmaceutically acceptable salts or esters thereof.

Biguanides useful in the present disclosure include, but are not limited to, buformin, metformin, and phenformin, and pharmaceutically acceptable salts or esters thereof. Metformin (Glucophage®) is indicated for patients with non-insulin dependent diabetes mellitus, particularly those with refractory obesity. Physician's Desk Reference® page 1080-1086, (56th ed. 2002).

Protein tyrosine phosphatase-1B (PTP-1B) inhibitors useful in the present disclosure include, but are not limited to, A-401,674, KR 61639, OC-060062, OC-83839, OC-297962, MC52445, MC52453, and the compounds disclosed in WO 02/26707, WO 02/26743, JP 2002114768, and pharmaceutically acceptable salts or esters thereof.

Dipeptidyl peptidase IV (DPP-IV) inhibitors, such as isoleucine thiazolidide; NVP-DPP728; P32/98; and LAP 237, P 3298, TSL 225, valine pyrrolidide, TMC-2A/2B/2C, CD-26 inhibitors, FE 999011, P9310/K364, VIP 0177, DPP4, SDZ 274A444; and the compounds disclosed in WO 03/00449; WO 03/004496; EP 1 258 476; WO 02/083128; WO 021062764; WO 03/000250; WO 03/002530; WO 03/002531; WO 03/002553; WO 03/002593; WO 03/000180; and WO 03/000181.

Sulfonylureas useful in the present disclosure include, but are not limited to, acetohexamide, chlorpropamide, diabinese, glibenclamide, glipizide, glyburide, glimepiride, gliclazide, glipentide, gliquidone, glisolamide, tolazamide, and tolbutamide, pharmaceutically acceptable salts or esters thereof. Meglitinides useful in the present disclosure include, but are not limited to, repaglinide and nateglinide, and pharmaceutically acceptable salts or esters thereof.

Alpha glucoside hydrolase inhibitors (or glucoside inhibitors) useful in the present disclosure include, but are not limited to, acarbose, adiposine, camiglibose, emiglitate, miglitol, voglibose, pradimicin-Q, salbostatin, CKD-711, MDL-25,637, MDL-73,945, and MOR 14, and pharmaceutically acceptable salts or esters thereof, and the compounds disclosed in U.S. Pat. Nos. 4,062,950, 4,174,439, 4,254,256, 4,701,559, 4,639,436, 5,192,772, 4,634,765, 5,157,116, 5,504,078, 5,091,418, 5,217,877, and 5,091,524. Alpha-amylase inhibitors useful in the present disclosure include, but are not limited to, tendamistat, trestatin, and A1-3688, and pharmaceutically acceptable salts and esters thereof, and the compounds disclosed in U.S. Pat. Nos. 4,451,455, 4,623, 714, and 4,273,765.

Insulin secreatagogues useful in the present disclosure include, but are not limited to, linogliride and A-4166, and pharmaceutically acceptable salts and esters thereof.

Fatty acid oxidation inhibitors useful in the present disclosure include, but are not limited to, clomoxir, and etomoxir, and pharmaceutically acceptable salts and esters thereof. A2 antagonists useful in the present disclosure include, but are not 'limited to, midaglizole, isaglidole, deriglidole, idazoxan, earoxan, fluparoxan, and pharmaceutically acceptable salts and esters thereof. Insulin or insulin mimetics useful in the present disclosure include, but are not limited to, biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH2), and pharmaceutically acceptable salts or esters thereof.

Glycogen phosphorylase inhibitors useful in the present disclosure include, but are not limited to, CP-368, 296, CP-316,819, BAYR3401, and compounds disclosed in WO 01/94300, and WO 02/20530, and pharmaceutically acceptable salts or esters thereof. GLP-1 agonists useful in the present disclosure include, but are not limited to, exendin-3 and exendin-4, and compounds disclosed in US 2003087821 and NZ 504256, and pharmaceutically acceptable salts or esters thereof.

Non-thiazolidinediones useful in the present disclosure include, but are not limited to, JT-501, and farglitazar (GW-2570/GI-262579), and pharmaceutically acceptable salts or esters thereof. Glycokinase activators useful in this disclosure, include, but are not limited to, fused heteroaromatic compounds such as those disclosed in US 2002103199, and isoindolin-1-one-substituted propionamide compounds such as those disclosed in WO 02/48106.

Serotonin (5HT) transport inhibitors useful in this disclosure include, but are not limited to, paroxetine, fluoxetine, fenfluramine, fluvoxamine, sertraline, and imipramine. Norepinephrine (NE) transport inhibitors useful in this disclosure include, but are not limited to, GW 320659, despiramine, talsupram, and nomifensine. Cannabinoid receptor 1 (CB-1) antagonist/inverse agonists useful in the present disclosure include: U.S. Pat. Nos. 5,532,237, 4,973,587, 5,013,837, 5,081,122, 5,112,820, 5,292,736, 5,624,941 and 6,028,084, and PCT Application Nos. WO 96/33159, WO 98/33765, WO98/43636, WO98/43635, WO 01/09120, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 01/64634, and WO 03/007887, and EPO Application No. EP-658546. Specific CB-1 antagonists/inverse agonists useful in the present disclosure include, but are not limited to, rimonabant (Sanofi Synthelabo), SR-147778 (Sanofi Synthelabo), BAY 65-2520 (Bayer), and SLY 319 (Solvay). CCK-A agonists useful in the present disclosure include GI 181771, and SR 146,131. Ghrelin antagonists useful in the present disclosure, include: PCT Application Nos. WO 01/87335, and WO 02/08250. Histamine 3 (H3) antagonist/inverse agonists useful in the present disclosure include: PCT Application No. WO 02/15905, and O-[3-(1H-imidazol4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al. Arch. Pharm. (Weinheim) 334:45-52 (2001)), substituted N-phenyl carbamates (Reidemeister, S. et al., Pharmazie, 55:83-6 (2000)), and proxifan derivatives (Sasse, A. et al., J. Med. Chem. 43:3335-43 (2000)). Specific H3 antagonists/inverse agonists useful in the present disclosure include, but are not limited to, thioperamide, 3-(1H-imidazol4-yl)propyl N-4-pentenyl)carbamate, clobenpropit, iodophenpropit, imoproxifan, GT2394 (Gliatech), and A331440.

Melanin-concentrating hormone receptor (MCHLR) antagonists and melanin-concentrating hormone 2 receptor (MCH2R) agonist/antagonists useful in the present disclosure include PCT Patent Application Nos. WO 01/82925, WO 01/87834, WO 02/06245, WO 02/04433, and WO 02/51809, and Japanese Patent Application No. JP 13226269. Specific MCH1R antagonists useful in the present disclosure include, but are not limited to, T-226296 (Takeda), SB 568849, and SNAP 7941. Neuropeptide Y1 (NPY1) antagonists useful in the present disclosure, include: U.S. Pat. No. 6,001,836, and PCT Application Nos. WO 96/14307, WO 01/23387, WO 99/51600, WO 01/85690, WO 01/85098, WO 01/85173, and WO 01/89528. Specific examples of NPY1 antagonists useful in the present disclosure include, but are not limited to, BIBP3226, J-115814, BIBO 3304, LY-357897, CP-671906, and GI-264879A. Neuropeptide Y2 (NPY2) agonists useful in the present disclosure, include, but are not limited to, peptide YY (PYY), and PYY3_36, peptide YY analogs, PYY agonists, and the compounds disclosed in WO 03/026591, WO 03/057235, and WO 03/027637. Neuropeptide Y5 (NPY5) antagonists useful in the present disclosure, include, but are not limited to, the compounds described in: U.S. Pat. Nos. 6,140,354, 6,191,160, 6,258,837, 6,313,298, 6,337,332, 6,329,395, and 6,340,683, 6,326,375, 6,329,395, 6,337,332, 6,335,345, European Patent Nos. EP-01010691, and EP 01044970, and PCT-International Patent Publication Nos. WO 97/19682, WO 97/20820, WO 97/20821, WO 97/20822, WO 97/20823, WO 98/27063, WO 00/107409, WO00/185714, WO 00/185730, WO 00/64880, WO 00/68197, WO 00/69849, wo 01/09120, wo 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, and WO 01/14376. Specific NPY5 antagonists useful in the combinations of the present disclosure, include, but are not limited to GW-569180A, GW-594884A, GW-587081X, GW-548118X, FR 235,208, FR226928, FR 240662, FR252384, 1229U91, GI-264879A, CGP71683A, LY-377897, LY366377, PD-160170, SR-120562A, SR-120819A, JCF-104, and H409/22. Additional specific NPY5 antagonists useful in the combinations of the present disclosure, include, but are not limited to the compounds described in Norman et al., J. Med. Chem. 43:42884312 (2000). Leptin includes, but is not limited to, recombinant human leptin (PEG-OB, Hoffman La Roche) and recombinant methionyl human leptin (Amgen). Leptin derivatives (e.g., truncated forms ofleptin) useful in the present disclosure include: U.S. Pat. Nos. 5,552,524, 5,552,523, 5,552, 522, 5,521,283, and PCT International Publication Nos. WO 96/23513, WO 96/23514, WO 96/23515, WO 96/23516, WO 96/23517, WO 96/23518, WO 96/23519, and WO 96/23520.

Opioid antagonists useful in the present disclosure include: PCT Application No. WO 00/21509. Specific opioid antagonists useful in the present disclosure include, but are not limited to, nalmefene (Revex®), 3-methoxynaltrexone, naloxone, and naltrexone. Orexin antagonists useful in the present disclosure include: PCT Patent Application Nos. WO 01/96302, WO 01/68609, WO 02/51232, WO 02/51838, and WO 03/023561. Specific orexin antagonists useful in the present disclosure include, but are not limited to, SB-334867-A. Acyl-estrogens useful in the present disclosure include oleoyl-estrone (del Mar-Grasa, M. et al., Obesity Research, 9:202-9 (2001)). Cholecystokinin-A (CCK-A) agonists useful in the present disclosure include U.S. Pat. No. 5,739,106. Specific CCK-A agonists include, but are not limited to, AR-R 15849, GI181771, JMv-180, A-71378, A-71623 and SR146131. Specific ciliary neurotrophic factors (CNTh) useful in the present disclosure include, but are not limited to, GI-181771 (GlaxoSmithKline), SR146131 (Sanofi Synthelabo), butabindide, PD170,292, PD 149164 (Pfizer). CNTF derivatives useful in the present disclosure include, but are not limited to, axokine (Regeneron), and PCT Application Nos. WO 94/09134, WO 98/22128, and WO 99/43813. Growth hormone secretagogue (GHS) agonists useful in the present disclosure include: U.S. Pat. No. 6,358,951, and U.S. Patent Application Nos. 2002/049196 and 2002/022637, and PCT Application Nos. WO 01/56592, and WO 02/32888. Specific GHS agonists include, but are not limited to, NN703, hexarelin, MK-0677, SM-130686, CP424 391, L-692,429 and L-163, 255.

5HT2c agonists useful in the present disclosure include: U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457. Specific 5HT2c agonists useful in this disclosure include, but are not limited to, BVT933, DPCA37215, 1K264, PNU 22394, WAY161503, R-1065, and YM 348.

Mc4r agonists useful in the present disclosure include: PCT Application Nos. WO 99/64002, WO 00/74679, WO 01/991752, WO 01/74844, WO 01/70708, WO 01/70337, WO 01/91752, WO 02/059095, WO 02/059107, WO 02/059108, WO 02/059117, wo 02/12166, WO 02111715, WO 02/12178, WO 02/15909, WO 02/068387, WO 02/068388, WO 02/067869, WO 03/007949, and WO 03/009847. Specific Mc4r agonists useful in the present disclosure include CIR86036 (Chiron), ME-10142, and ME-10145 (Melacure).

Monoamine reuptake inhibitors useful in the present disclosure include: PCT Application Nos. WO 01/27068, and WO 01/62341. Specific monoamine reuptake inhibitors useful in the present disclosure include, but are not limited to, sibutramine (Meridia O/Reductil®) disclosed in U.S. Pat. Nos. 4,746,680, 4,806,570, and 5,436,272, and U.S. Patent Publication No. 2002/0006964.

Serotonin reuptake inhibitors, and releasers, useful in the present disclosure include: dexfenfluramine, fluoxetine, and other serotonin reuptake inhibitors, including, but not limited to, those in U.S. Pat. No. 6,365,633, and PCT Patent Application Nos. WO 01/27060, and WO 01/162341.

11 β HSD-1 inhibitor useful in the present disclosure include, but are not limited to, BVT 3498, BVT 2733, and those compounds disclosed in WO 01/90091, WO 01/90090, WO 01/90092. Uncoupling Protein (UCP-1, UCP-2, and UCP-3) activators useful in the present disclosure include: PCT Patent Application No. WO 99/00123. Specific uncoupling protein (UCP-1, UCP-2, and UCP-3) activators useful in the present disclosure include, but are not limited to, phytanic acid, 4-[(E)-2-(5,6, 7,8-tetrahydro-5,5,8,8-tetramethyl-2-napthalenyl)-1-propenyl]benzoic acid (TTNPB), and retinoic acid.

β3 adrenergic receptor (β3) agonists useful in the present disclosure include: U.S. Pat. Nos. 5,705,515 and 5,451,677 and PCT Patent Application Nos. WO 01/74782, and WO 02/32897. Specific β agonists useful in the present disclosure include, but are not limited to, AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A.

Thyroid hormone β agonists useful in the present disclosure include: PCT Application No. WO 02/15845 and Japanese Patent Application No. JP 2000256190. Specific thyroid hormone β agonists useful in the present disclosure include, but are not limited to, KB-2611 (KaroBioBMS). Specific fatty acid synthase (PAS) inhibitors useful in the present disclosure, include, but are not limited to, Cerulenin and C75. Specific phosphodieterase (PDE) inhibitors useful in the present disclosure, include, but are not limited to, theophylline, pentoxifYlline, zaprinast, sildenafil, amrinone, milrinone, cilostamide, rolipram, and cilomilast.

Lipase inhibitors useful in the present disclosure include, but are not limited to, those disclosed in PCT Application No. WO 01/77094, and U.S. Pat. Nos. 4,598,089, 4,452,813, 5,512,565, 5,391,571, 5,602,151, 4,405,644, 4,189,438, and 4,242,453. Specific lipase inhibitors useful in the present disclosure include, but are not limited to, tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267.

Examples of HMG-CoA reductase inhibitors include, but are not limited to, lovastatin, simvastatin, pravastatin and fluvastatin. Examples of HMG-CoA synthase inhibitors are the beta-lactone derivatives disclosed in U.S. Pat. Nos. 4,806,564, 4,816,477, 4,847,271, and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Examples of squalene epoxidase inhibitors are disclosed in European Patent Publication EP 0 318 860 and in Japanese Patent Publication J02 169-571A. Examples of LDL-receptor gene inducer molecules are disclosed in U.S. Pat. No. 5,182,298 filed Mar. 18, 1991. Other cholesterol lowering agents that may be administered include niacin, probucol, fibric acids (i.e., clofibrate and gemfibrozil), and LDL-receptor gene inducers.

Examples of PARP inhibitors include, but are not limited to, iodonitocoumarin, 5-iodo-6-nitrocoumarin, 3,4-dihydro-5-methyl-isoquinolinone, 4-amino-1,8-naphthalimide, 3-methoxybenzamide, 8-hydroxy-2-methyl-3-hydro-quinazolin-4-one, 2-{3-[4-(4-fluorophenyl)-3,6-dihydro-1(2h)-pyridinyl]propyl}-8-methyl-4(3h)-quinazolinone, 5-fluoro-1-[4-(4-phenyl-3,6-dihydropyridin-1(butyl]quinazoline-2,4 (1h,3h)-dione, 3-(4-chlorophenyl) quinoxaline-5-carboxamide, 2-(3'-methoxyphenyl)benzimidazole-4-carboxam, benzamide, 3-aminobenzamide, 3-aminophtalhydrazide, and 1,5-dihydroxyisoquinoline.

The above-mentioned compounds, which can be used in combination with a compound of Formula (I), Formula (Ia), Formula (Ib), Formula (II), or Formula (III), or a pharmaceutically acceptable salt thereof, can be prepared and administered as described in the art such as in the documents cited above.

The above compounds are only illustrative of the ACMSD inhibitors, anti-diabetic agents, anti-obesity agents, cholesterol lower agent, compounds that boost $NAD^+$ levels, compounds that inhibit $NAD^+$ consumption that can be used in the compositions of the present disclosure. As this listing of compounds is not meant to be comprehensive, the methods of the present disclosure may employ any anti-obesity agent and any anti-diabetic agent, and are not limited to any particular structural class of compounds.

As used herein, "combination therapy" includes the administration of a compound of the present disclosure, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, a cooperative, e.g., synergistic, effect and/or a pharmacokinetic or pharmacodynamic co-action, or any combination thereof, resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present disclosure.

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

All percentages and ratios used herein, unless otherwise indicated, are by weight. Other features and advantages of the present disclosure will become apparent from the different examples. The provided examples illustrate different components and methodology useful in practicing the present disclosure. Generally speaking, the disclosure extends to any novel one, or any novel combination, of the features disclosed in this specification (including the accompanying claims and drawings). The examples do not limit the claimed disclosure. Thus, features, integers, characteristics, compounds or chemical moieties described in conjunction with a particular aspect, embodiment or example of the disclosure are to be understood to be applicable to any other aspect, embodiment or example described herein, unless incompatible therewith. Based on the present disclosure the skilled artisan can identify and employ other components and methodology useful for practicing the present disclosure. Moreover, unless stated otherwise, any feature disclosed herein may be replaced by an alternative feature serving the same or a similar purpose.

The Disclosure will now be described by way of example only with reference to the Examples below:

EXEMPLIFICATION

I. Compound Preparation
General Methods and Materials

All chemicals were purchased from Sigma-Aldrich, Alfa Aesar. $^1$H NMR spectra were recorded at 200 and 400 MHz and $^{13}$C NMR spectra were recorded at 100.6 and 50.3 MHz by using deuterated solvents indicated below. TLC were performed on aluminium backed silica plates (silica gel 60 F254). All the reactions were performed under nitrogen atmosphere using distilled solvents. All tested compounds were found to have >95% purity determined by HPLC analysis. HPLC-grade water was obtained from a tandem Milli-Ro/Milli-Q apparatus. The analytical HPLC measurements were made on a Shimadzu LC-20APprominence equipped with a CBM-20A communication bus module, two LC-20AD dual piston pumps, a SPD-M20A photodiode array detector and a Rheodyne 7725i injector with a 20 μL stainless steel loop.

Scheme 1: Preparation of Intermediate 1.4

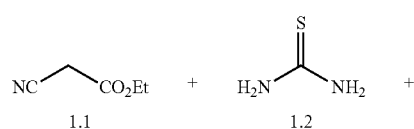

-continued

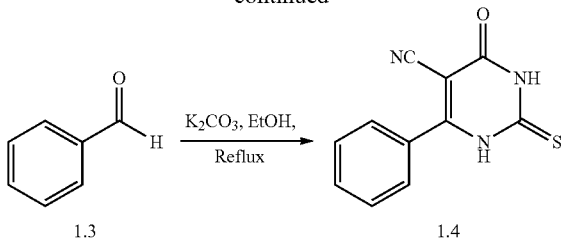

Example 1: Preparation of Intermediate 1.4

To a stirred solution of compound 1.1 (0.52 ml, 4.9 mmol), 1.2 (372 mg, 4.9 mmol) and 1.3 (0.5 mL, 0.83 mL, 4.9 mmol) in ethanol (25 mL) was added K$_2$CO$_3$ (812 mg, 5.88 mmol). Stirring was continued at reflux overnight. The pale yellow solid was collected after cooling, taken up with boiling water and filtered again. The aqueous phase was acidified to pH 5 with AcOH (15 drops), the precipitate was filtered and dried under vacuum. The title compound 1.4 was obtained as pale yellow solid (500 g, 2.18 mmol). Yield 44%.

Scheme 2: Preparation of Intermediate 2.2

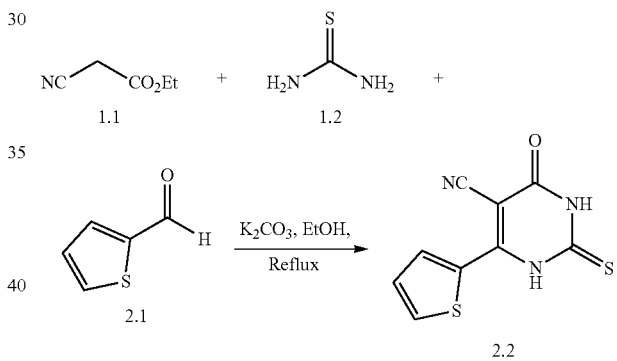

Example 2: Preparation of Intermediate 2.2

To a stirred solution of compound 1.1 (0.96 g, 8.8 mmol), 1.2 (672 mg, 8.8 mmol) and 2.1 (1 g, 0.83 mL) in ethanol (55 mL) was added K$_2$CO$_3$ (1.57 g, 11.44 mmol). Stirring was continued at reflux overnight. The yellowish solid was collected after cooling, taken up with hot water and filtered again. The aqueous phase was acidified to pH 1, the precipitate was filtered and dried under vacuum. The title compound 2.2 was obtained as yellowish solid (1 g, 4.25 mmol). Yield 49%. $^1$H NMR (200 MHz, DMSO) δ 7.22 (m, 1H), 7.68 (m, 1H), 7.85 (d, J=4.8 Hz, 1H), 8.05 (s, 1H).

Scheme 3: Preparation of Intermediate 3.2

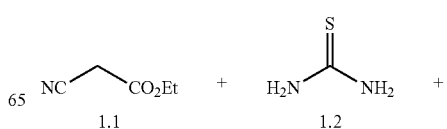

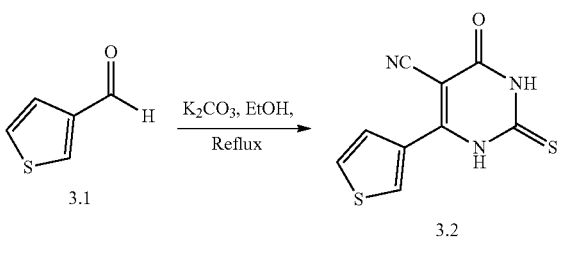

Example 3: Preparation of Intermediate 3.2

To a stirred solution of compound 1.1 (0.96 mL, 8.8 mmol), 1.2 (672 mg, 8.8 mmol) and 3.1 (1 g, 1.29 mL) in ethanol (55 mL) was added $K_2CO_3$ (1.57 g, 11.44 mmol). Stirring was continued at reflux overnight. The yellowish solid was collected after cooling, taken up with hot water and filtered again. The aqueous phase was acidified to pH 1, the precipitate was filtered and dried under vacuum. The title compound 3.2 was obtained as yellowish solid (1 g, 4.25 mmol). Yield 49%.

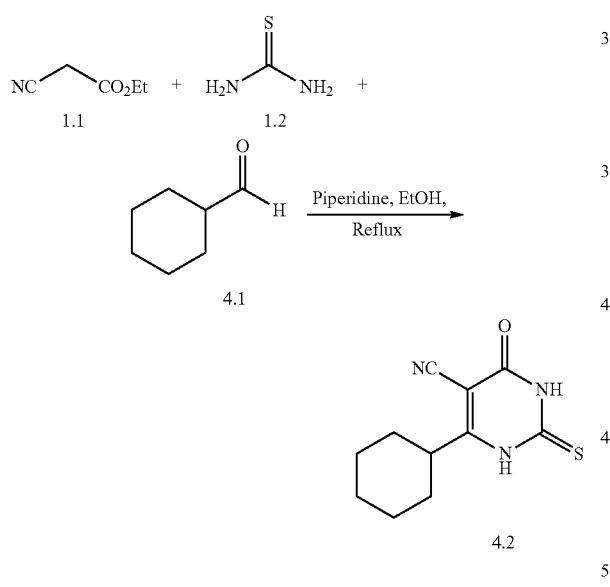

Example 4: Preparation of Intermediate 4.2

To a stirred solution of compound 1.1 (1.42 mL, 13.37 mmol), 1.2 (1.01 g, 13.3 mmol) and 4.1 (1.62 mL, 13.3 mL) in ethanol (50 mL) was added piperidine (2.64 mL, 26.7 mmol). Stirring was continued at reflux overnight. The solid was collected after cooling, taken up with hot water and filtered again. The aqueous phase was acidified to pH1 and extracted with EtOAc (3×25 mL). The organic phase was washed with brine and dried over $Na_2SO_4$. The crude of reaction was purified by flash chromatography ($CHCl_3$/MeOH as gradient, from 0 to 2% for product), affording the title compound 4.2 (930 mg, 3.95 mmol) as white solid. Yield 30%.

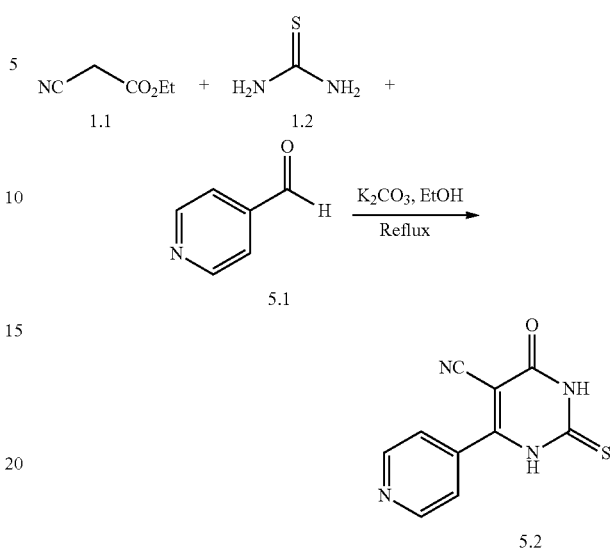

Example 5: Preparation of Intermediate 5.2

To a stirred solution of compound 1.1 (0.49 mL, 4.67 mmol), 1.2 (355 mg, 4.67 mmol) and 5.1 (0.44 mL, 4.67 mmol) in ethanol (25 mL) was added $K_2CO_3$ (773 mg, 5.6 mmol). Stirring was continued at reflux overnight. The white solid was collected after cooling, dried under vacuum and used for the next step without further purification. The title compound 5.2 was obtained as white solid (300 mg, 1.3 mmol). Yield 29%. $^1$H NMR (400 MHz, DMSO) δ 7.64 (d, J=4.7 Hz, 2H), 8.78 (d, J=4.7 Hz, 2H), 12.98 (s, 1H).

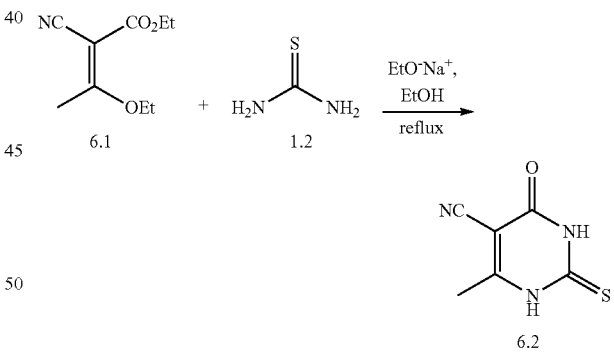

Example 6: Preparation of Intermediate 6.2

To a stirred solution NaOEt (1.02 mL, 2.73 mmol) in EtOH abs (20 mL) was added compound 6.1 (500 mg, 2.73 mmol) and 1.2 (207 mg, 2.73 mmol). Stirring was continued at reflux 4 h. The volatiles were removed under vacuum. The crude of reaction was taken up with water and acidified with AcOH. The precipitate was collected dissolved in water, washed with a mixture of $CHCl_3$ and MeOH. The aqueous phase was extracted with EtOAc (3×20 mL). The collected organic phase was washed with brine, dried over $Na_2SO_4$. The title compound 6.2 was obtained as white solid (250 mg, 1.49 mmol). Yield 55%.

Scheme 7: Preparation of Intermediate 7.3

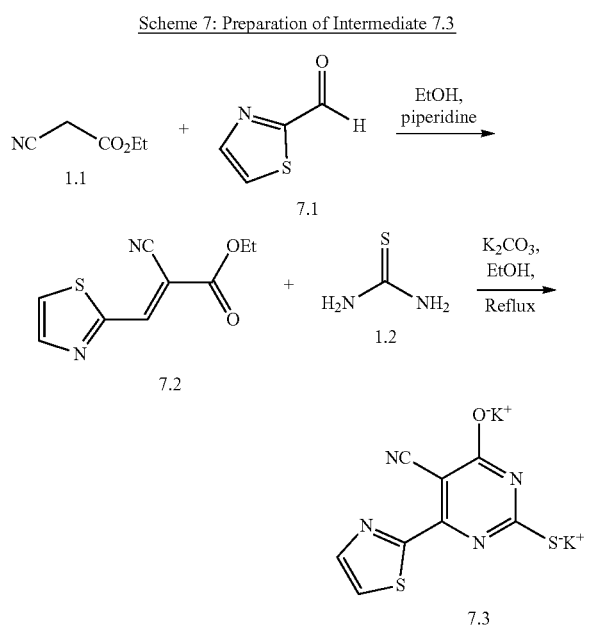

Example 7a: Preparation of Intermediate 7.2

To a stirred solution of compound 1.1 (0.14 mL, 1.3 mmol) and 7.1 (150 mg, 1.3 mmol) in EtOH (5 mL) was added piperidine (1 drop). Stirring was continued at room temperature overnight. The solvent was removed under vacuum. The crude of reaction was purified by flash chromatography affording the title compound 7.2 (160 mg, 0.77 mmol) as yellowish solid. Yield 58%.

Example 7b: Preparation of Intermediate 7.3

To a stirred suspension of compound 7.2 (150 mg, 0.72 mmol) and compound 1.2 (55 mg, 0.72 mmol) in EtOH (5 mL) was added $K_2CO_3$ (99 mg, 0.72 mmol). Stirring was continued at reflux overnight. The white precipitate was collected and used as well for the next step without further purification. The title compound 7.3 (150 mg, 0.48 mmol) was obtained as yellowish solid as di-potassium salt. Yield 67%.

Scheme 8: Preparation of Intermediate 8.5

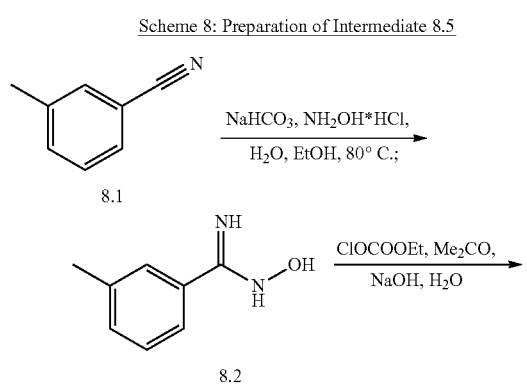

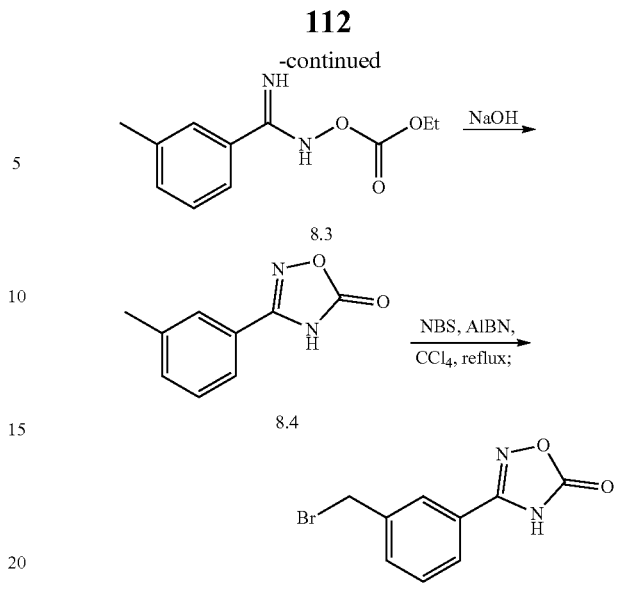

Example 8a: Preparation of Intermediate 8.2

To a stirred solution of $NH_2OH*HCl$ and $NaHCO_3$ in water (7 mL) was gradually added a solution of m-tolunitrile (8.1) (2 mL, 17.0 mmol) in EtOH (13.3 mL). Stirring was continued at 80° C. for 4 h. The volatiles were removed under vacuum. The crude of reaction was taken up with water, extracted with EtOAc (3×25 mL). The organic phase were collected, washed with brine and dried over $Na_2SO_4$ affording the title compound 8.2 (1.5 g, 9 mmol) as white solid. Yield 59%.

Example 8b: Preparation of Intermediate 8.3

To a solution of compound 8.2 (1 g, 6 mmol) in dry acetone (5 mL), was added dropwise at 0° C. EtOCOCl (0.63 mL, 6.6 mmol). Stirring was continued at this temperature for 1 h. Then a 5% NaOH solution was added to the mixture. Stirring was continued for additional 1 h. The solvent was removed under vacuum. The crude of reaction was poured in water, extracted with EtOAc (3×50 mL). The collected organic phase was washed with brine, dried over $Na_2SO_4$. The title compound 8.3 (600 mg, 2.7 mmol) was obtained as white solid. Yield 45%.

Example 8c: Preparation of Intermediate 8.4

To a solution of compound 8.3 (300 mg, 1.35 mmol) in EtOH abs (5 mL) was added sodium (50 mg) portion wise. Stirring was continued at room temperature for additional 4 h. The reaction was quenched by the addition of MeOH. The solvent was removed under reduced pressure and the crude was purified by flash chromatography. The title compound 8.4 (150 mg, 0.85 mmol) was obtained as white solid. Yield 63%.

Example 8d: Preparation of Intermediate 8.5

To a suspension of compound 8.4 (326 mg, 1.85 mmol) in $CCl_4$ (10 mL) was added AIBN (60.7 mg, 0.37 mmol) and NBS (493 mg, 2.77 mmol). Stirring was continued at reflux overnight. The solvent was removed under reduced pressure. The reaction was taken up with water, extracted with EtOAc (3×20 mL) washed with brine and dried over Na$_2$SO$_4$. The crude was purified by flash chromatography, eluting with Petroleum ether (Pet. Ether)/EtOAc (30% for product) affording the title compound 8.5 (280 mg, 1.09 mmol) was obtained as white solid. Yield 59%.

Scheme 9: Preparation of Intermediate 9.2

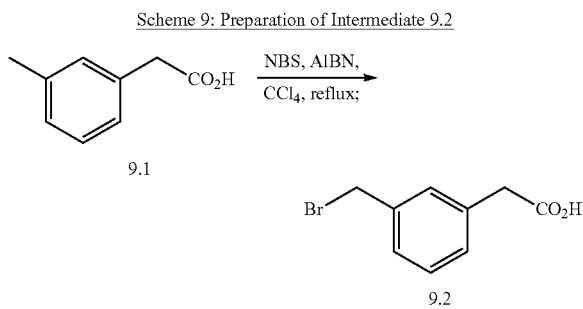

Example 9: Preparation of Intermediate 9.2

To a suspension of compound 9.1 (750 mg, 5 mmol) in CCl$_4$ (15 mL) was added AIBN (41 mg, 0.25 mmol) and NBS (933.7 mg, 5.24 mmol). Stirring was continued at reflux overnight. The solvent was removed under reduced pressure. The reaction was taken up with water, extracted with EtOAc (3×20 mL) washed with brine and dried over Na$_2$SO$_4$. The crude was purified by flash chromatography, eluting with CH$_2$Cl$_2$/MeOH (3% for product) affording the title compound 9.2 (800 mg, 3.49 mmol) as white solid. Yield 70%.

Scheme 10: Preparation of Intermediate 10.

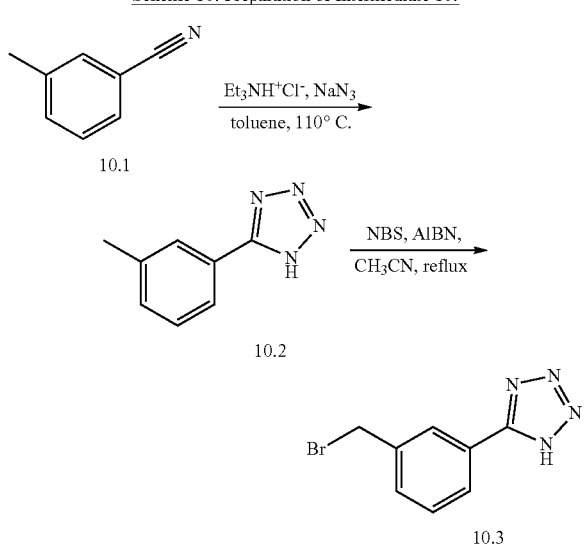

Example 10a: Preparation of Intermediate 10.2

A mixture of compound 10.1 (1.02 mL, 8.54 mmol), NaN$_3$ (832 mg, 12.8 mmol) and Et$_3$N*HCl (1.76 g, 12.8 mmol) was heated at reflux 4 h. The solvent was removed under vacuum. The crude was poured in water, acidified to pH 1 with 3N HCl and extracted with EtOAc (3×20 mL). The organic phase was washed with brine, dried over Na$_2$SO$_4$ and concentrated under reduced pressure. The title compound 10.2 (1.22 g, 7.6 mmol) was obtained as white solid. Yield 89%.

Example 10b: Preparation of Intermediate 10.3

To a suspension of compound 10.2 (300 mg, 1.87 mmol) in CH$_3$CN (15 mL) was added AIBN (31 mg, 0.18 mmol) and NBS (333 mg, 1.87 mmol). Stirring was continued at reflux overnight. The solvent was removed under reduced pressure. The reaction was taken up with water, extracted with EtOAc (3×20 mL) washed with brine and dried over Na$_2$SO$_4$. The crude was purified by flash chromatography, eluting with CH$_2$Cl$_2$/MeOH (7% for product) affording the title compound 10.3 (150 mg, 0.62 mmol) as light yellow solid. Yield 34%.

Scheme 11: Preparation of Intermediate 11.3

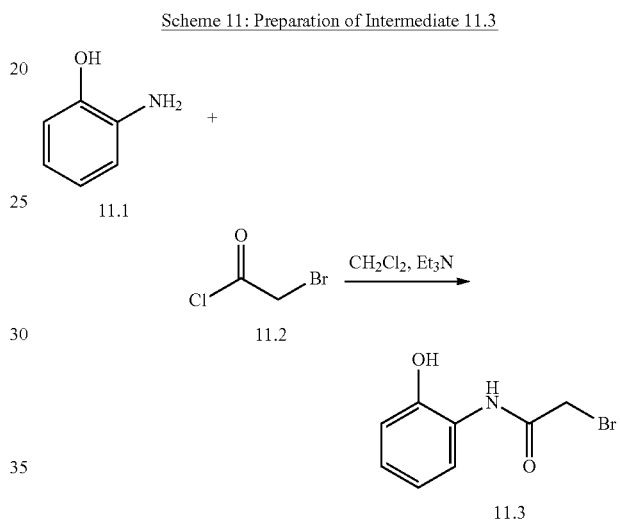

Example 11: Preparation of Intermediate 11.3

To a solution of compound 11.1 (2.5 g, 23 mmol) in CH$_2$Cl$_2$ (25 mL) was added pyridine (1.63 mL, 20.3 mmol) and compound 11.2 (1.68 mL, 20.3 mmol). Stirring was continued at room temperature overnight. The solvent was removed under reduced pressure. The reaction was taken up with water, extracted with CH$_2$Cl$_2$ (3×30 mL) washed with brine and dried over Na$_2$SO$_4$. The crude was purified by flash chromatography, eluting with Pet. Ether/EtOAc (25% for product) affording the title compound 11.3 (735 mg, 3.19 mmol) as brownish solid. Yield 14%.

Scheme 12: Preparation of Intermediate 12.2

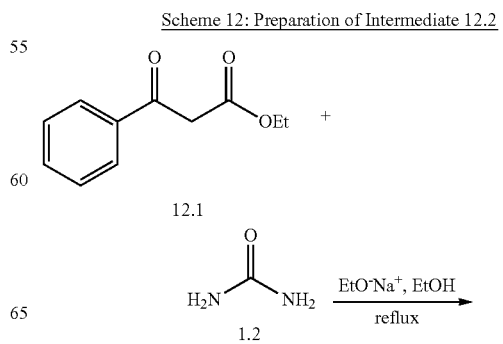

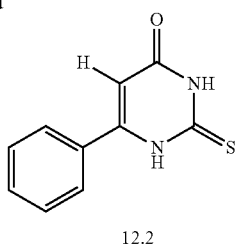

12.2

Example 12: Preparation of Intermediate 12.2

To a solution of compound 12.1 (2 g, 10.41 mmol) in EtOH (15 mL) was added EtONa (7 mL, 18.7 mmol) and compound 1.2 (1.18 g, 15.61 mmol). Stirring was continued at reflux overnight. The solvent was removed under reduced pressure. The reaction was taken up with water, acidified to pH 3, extracted with EtOAc (3×20 mL) washed with brine and dried over $Na_2SO_4$. The crude was purified by flash chromatography, eluting with $CH_2Cl_2$/MeOH (2.5% for product) affording the title compound 12.2 (500 mg, 2.44 mmol) as white solid. Yield 24%.

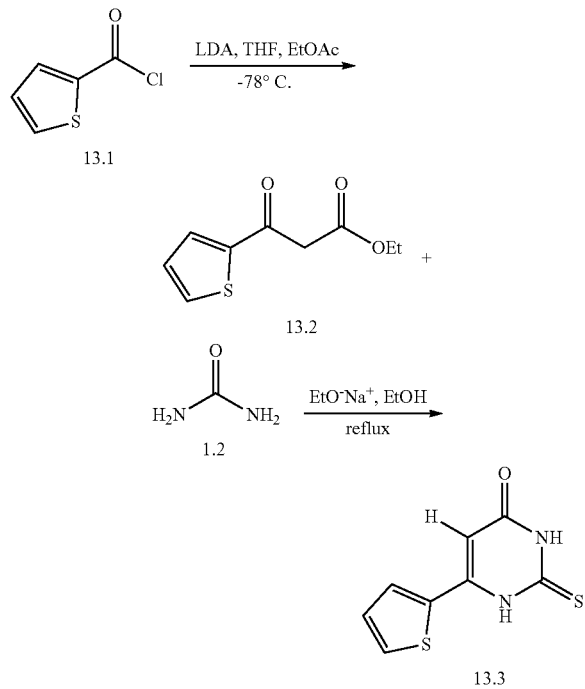

Example 13a: Preparation of Intermediate 13.2

To a stirred solution of DIPA (7.6 mL, 54 mmol) in THF (53 mL) was added n-BuLi (21.6 mL) at 0° C. Stirring was continued at this temperature 10 minutes. The mixture was then cooled to −78° C. and EtOAc (2.4 mL, 27 mmol) was added dropwise. Stirring was continued at this temperature 30 minutes. After that, a solution of compound 13.1 (3 mL, 27 mmol) in THF (20 mL) was added dropwise. The reaction was allowed to warm to room temperature and was stirred overnight. The crude of reaction was poured in water and extracted with EtOAc (3×30 mL). The collected organic phase were washed with brine, dried over $Na_2SO_4$ and concentrated under vacuum. The title compound 13.2 was obtained as brownish oil (4.8 g, 24.3 mmol). Yield 90%.

Example 13b: Preparation of Intermediate 13.3

To a solution of intermediate 13.2 (2 g, 10 mmol) in EtOH (15 mL) was added EtONa (21% wt/wt in EtOH) (7.5 mL, 20 mmol) and compound 1.2 (1.15 g, 15.1 mmol). Stirring was continued at reflux overnight. The solvent was removed under reduced pressure. The reaction was taken up with water. At pH 10 was recovered unreacted starting material. The mixture was then acidified to pH 5, extracted with EtOAc (3×20 mL) washed with brine and dried over $Na_2SO_4$. The crude was purified by flash chromatography, eluting with $CH_2Cl_2$/MeOH (7% for product) affording the title compound 13.3 (435 mg, 2.06 mmol) as yellowish solid. Yield 21%.

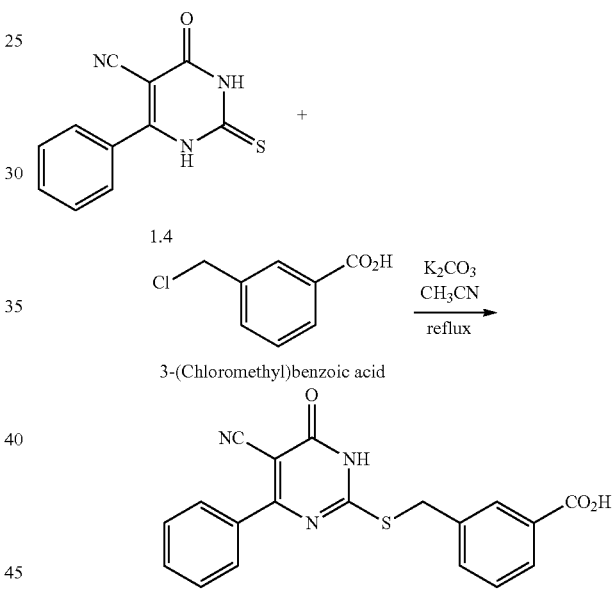

Example 14: Preparation of Compound 1

To a stirred suspension of intermediate 1.4 (1.6 g, 6.98 mmol) and $K_2CO_3$ (2.88 g, 20.9 mmol) in $CH_3CN$ (80 mL) was added 3-(chloromethyl)benzoic acid (1.19 g, 6.98 mmol). Stirring was continued overnight at reflux. The volatiles were removed under vacuo. The crude was taken up with water, acidified to pH 5 and washed with EtOAc to remove impurities. Then the pH was adjusted to 3/4 and the mixture was extracted with EtOAc (3×50 mL). Titration with hot acetone afforded compound 1 (936 mg, 2.78 mmol) as yellowish solid. Yield 40%. $^1$H NMR (400 MHz, DMSO) δ 4.58 (s, 2H), 7.44 (t, J=7.5 Hz, 1H), 7.54-7.61 (m, 3H), 7.67 (d, J=7.1 Hz, 1H), 7.83 (d, J=7.5 Hz, 1H), 7.91 (d, J=7.27 Hz, 2H), 8.04 (s, 1H), 13 (s, 1H); $^{13}$C NMR (100 MHz, DMSO) δ 33.5, 93.2, 115.6, 128.2, 128.4, 128.4, 128.5, 128.5, 128.6, 129.7, 130.8, 131.5, 133.3, 135.1, 137.4, 165.4, 166.8, 167.3. HPLC: 96.3%

Scheme 15: Preparation of Compound 4

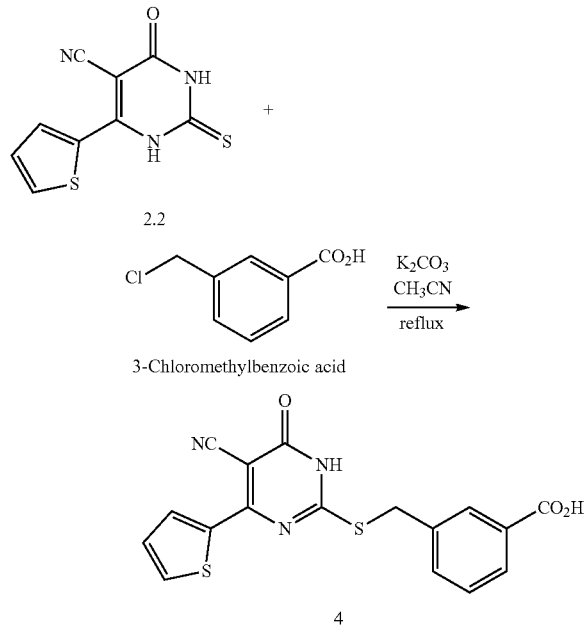

Example 15: Preparation of Compound 4

To a stirred suspension of intermediate 2.2 (250 mg, 1.06 mmol) and $K_2CO_3$ (440 mg, 3.18 mmol) in $CH_3CN$ (15 mL) was added 3-(chloromethyl)benzoic acid (180 mg, 1.06 mmol). Stirring was continued overnight at reflux. The volatiles were removed under vacuo. The crude was taken up with water, washed with EtOAc, acidified to pH 1 and extracted with EtOAc (3×50 mL). Titration with hot acetone afforded compound 4 (45 mg, 0.12 mmol) as yellowish solid. Yield 12%. $^1$H NMR (400 MHz, DMSO) δ 4.62 (s, 2H), 7.33 (t, J=4.3 Hz, 1H), 7.44 (t, J=7.6 Hz, 1H), 7.72 (d, J=7.5 Hz, 1H), 7.82 (d, J=7.5 Hz, 1H), 8.05 (m, 2H), 8.26 (d, J=3.8 Hz, 1H), 12.99 (s, 1H); $^{13}$C NMR (100 MHz, DMSO) δ 33.9, 88.7, 116.5, 128.8, 129.3, 129.9, 130.2, 131.5, 132.1, 133.7, 135.4, 137.9, 139.7, 159.0, 161.2, 165.3, 167.4. HPLC: 97.2%

Scheme 16: Preparation of Compound 3

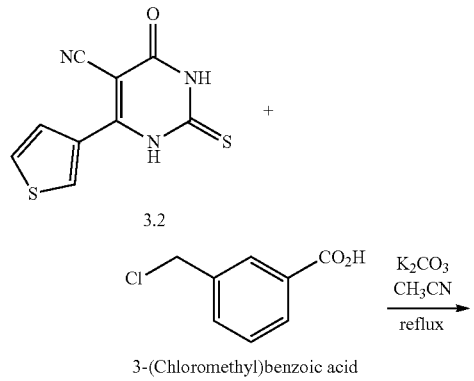

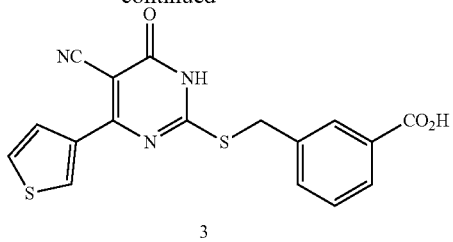

Example 16: Preparation of Compound 3

To a stirred suspension of intermediate 3.2 (250 mg, 1.06 mmol) and $K_2CO_3$ (440 mg, 3.18 mmol) in $CH_3CN$ (15 mL) was added 3-(chloromethyl)benzoic acid (180 mg, 1.06 mmol). Stirring was continued overnight at reflux. The volatiles were removed under vacuo. The crude was taken up with water, washed with EtOAc, acidified to pH 1 and extracted with EtOAc (3×50 mL). Titration with a mixture of $Et_2O$/acetone afforded compound 3 (260 mg, 0.7 mmol) as yellowish solid. Yield 70%. $^1$H NMR (400 MHz, DMSO) δ 4.63 (s, 2H), 7.44 (t, J=7.6 Hz, 1H), 7.69 (d, J=7.7 Hz, 1H), 7.74 (dd, J=5 Hz, J=2.9 Hz, 1H), 7.84 (m, 2H), 8.05 (s, 1H), 8.58 (m, 1H), 13.0 (s, 1H); $^{13}$C NMR (100 MHz, DMSO) δ 35.3, 90.1, 118.0, 130.2, 130.7, 131.3, 131.6, 132.9, 133.5, 135.1, 136.8, 139.3, 141.1, 160.4, 162.7, 166.7, 168.8. HPLC: 95.0%

Scheme 17: Preparation of Compound 6

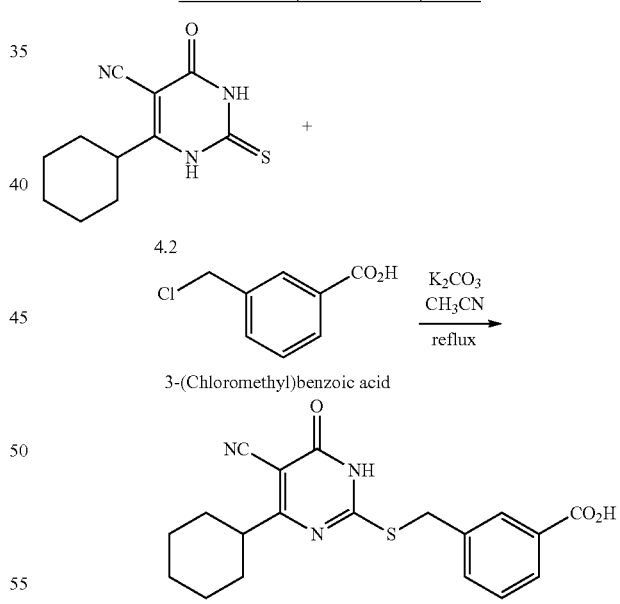

Example 17: Preparation of Compound 6

To a stirred suspension of intermediate 4.2 (250 mg, 1.18 mmol) and $K_2CO_3$ (495 mg, 3.56 mmol) in $CH_3CN$ (15 mL) was added 3-(chloromethyl)benzoic acid (202 mg, 1.18 mmol). Stirring was continued overnight at reflux. The volatiles were removed under vacuo. The crude was taken up with water, washed with EtOAc, acidified to pH 1 and extracted with EtOAc (3×50 mL). Titration with Et$_2$O afforded compound 6 (90 mg, 0.24 mmol) as white solid. Yield 21%. $^1$H NMR (400 MHz, DMSO) δ 1.24 (m, 3H), 1.60 (m, 7H), 2.74 (m, 1H), 4.52 (s, 2H), 7.45 (t, J=7.18 Hz, 1H), 7.67 (d, J=6.83 Hz, 1H), 7.82 (d, J=7.17 Hz, 1H), 8.04 (s, 1H), 13.0 (s, 1H). $^{13}$C NMR (100 MHz, DMSO) δ 25.4, 25.7, 25.7, 30.3, 30.3, 33.8, 44.9, 94.1, 115.3, 128.6, 129.2, 130.1, 131.3, 133.6, 138.5, 161.1, 166.2, 167.4, 177.9. HPLC: 98.1%

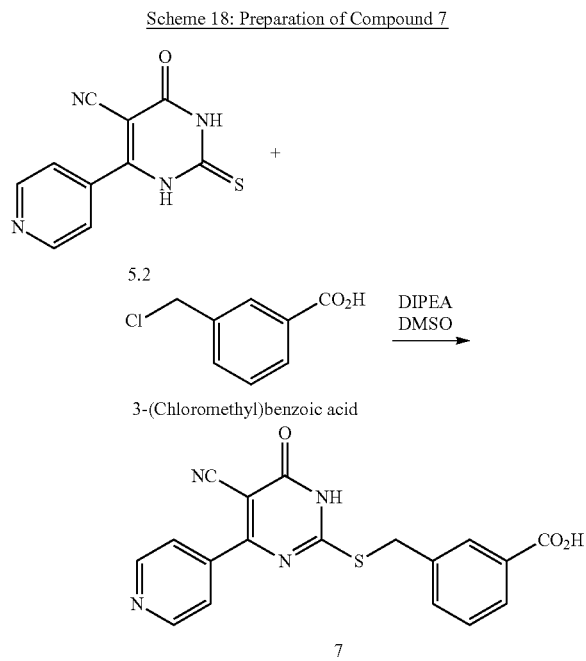

Scheme 18: Preparation of Compound 7

Example 18: Preparation of Compound 7

To a stirred suspension of intermediate 5.2 (220 mg, 0.95 mmol) and DIPEA (0.18 mL, 1.05 mmol) in DMSO (5 mL) was added 3-(chloromethyl)benzoic acid (178 mg, 1.05 mmol). Stirring was continued overnight at room temperature. The light yellow solid was collected, washed with crushed ice and water, and dried under vacuum. Trituration with hot EtOAc afforded compound 7 (180 mg, 0.49 mmol) as light yellow solid. Yield 53%. $^1$H NMR (400 MHz, DMSO) δ 4.55 (s, 2H), 7.44 (m, 1H), 7.66 (d, J=6 Hz, 1H), 7.81 (m, 3H), 8.02 (s, 1H), 8.80 (s, 2H), 13.1 (s, 1H); $^{13}$C NMR (100 MHz, DMSO) δ 34.1, 94.8, 115.8, 122.8, 122.8, 128.7, 129.2, 130.4, 131.3, 133.9, 138.1, 143.1, 150.5, 150.5, 161.8, 165.7, 167.4, 167.4. HPLC: 95.1%

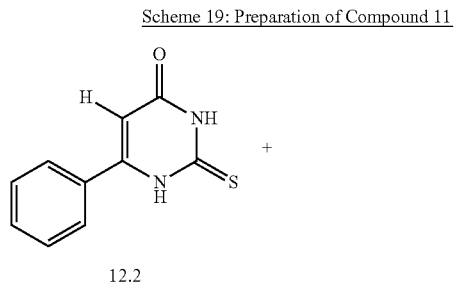

Scheme 19: Preparation of Compound 11

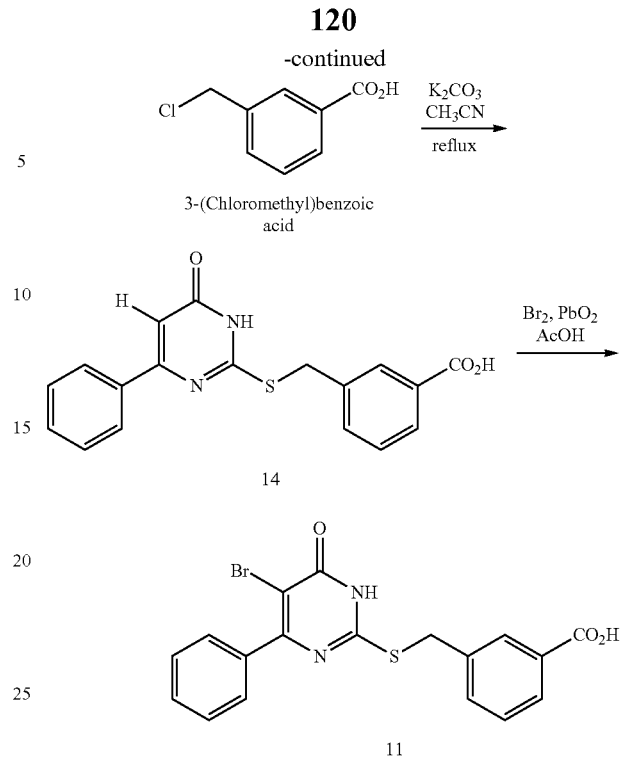

Example 19a: Preparation of Compound 14

To a stirred suspension of intermediate 12.2 (100 mg, 0.43 mmol) and K$_2$CO$_3$ (178 mg, 1.29 mmol) in CH$_3$CN (15 mL) was added 3-(chloromethyl)benzoic acid (74 mg, 0.43 mmol). Stirring was continued overnight at reflux. The volatiles were removed under vacuo. The crude was taken up with water, washed with EtOAc, acidified to pH 3 and extracted with EtOAc (3×50 mL). Titration with a mixture of Et$_2$O/Acetone afforded compound 14 (30 mg, 0.088 mmol) as white solid. Yield 21%. $^1$H NMR (400 MHz, DMSO) δ 4.59 (s, 2H), 6.69 (s, 1H), 7.41 (m, 1H), 7.46 (m, 3H), 7.71 (d, J=7.5 Hz, 1H), 7.81 (d, J=7.74 Hz, 1H), 8.06 (m, 3H), 12.85 (s, 2H). $^{13}$C NMR (100 MHz, DMSO) δ 33.8, 127.3, 127.3, 128.5, 129.1, 129.2, 130.1, 131.0, 131.3, 131.5, 133.6, 136.3, 138.8, 167.5.

Example 19b: Preparation of Compound 11

To a stirred solution of compound 14 (100 mg, 0.29 mmol) in acetic acid (5 mL) was added lead dioxide (77.2 mg, 0.32 mmol) and bromine (0.02 mL, 0.32 mmol). Stirring was continued for 6 hrs at room temperature. The mixture was poured in a solution of Na$_2$S$_2$O$_5$ and was extracted with EtOAc (3×20 mL). The collected organic phases were washed with water and brine, and then they were dried over Na$_2$SO$_4$. Titration with a mixture of Et$_2$O/Acetone afforded compound 11 (40 mg, 0.09 mmol) as white solid. Yield 33%. $^1$H NMR (400 MHz, DMSO) δ 4.44 (s, 2H), 7.42 (t, J=7.6 Hz, 1H), 7.48 (m, 3H), 7.61-7.65 (m, 3H), 7.82 (d, J=7.5 Hz, 1H), 8.0 (s, 1H), 13.1 (m, 2H). $^{13}$C NMR (100 MHz, DMSO) δ 33.9, 128.4, 128.6, 129.14, 129.3, 129.3, 129.3, 130.1, 130.2, 131.3, 133.9, 138.1, 138.4, 167.5. HPLC: 94.2%

Scheme 20: Preparation of Compound 12

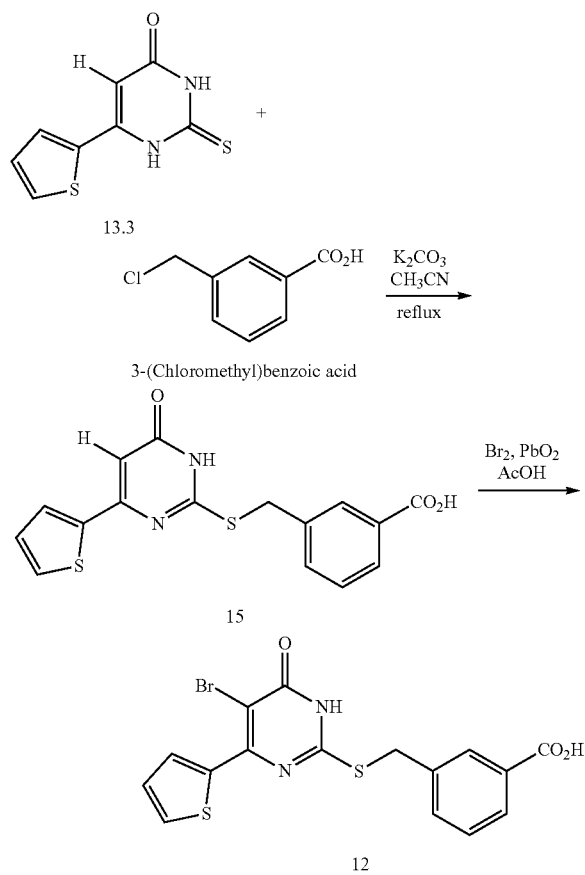

Example 20a: Preparation of Compound 15

To a stirred suspension of intermediate 13.3 (235 mg, 1.11 mmol) and K$_2$CO$_3$ (460 mg, 3.33 mmol) in CH$_3$CN (15 mL) was added 3-(chloromethyl)benzoic acid (190 mg, 1.11 mmol). Stirring was continued overnight at reflux. The volatiles were removed under vacuo. The crude was taken up with water, washed with EtOAc, acidified to pH 3 and extracted with EtOAc (3×50 mL). Titration with a mixture of Et$_2$O/Acetone afforded compound 15 (150 mg, 0.44 mmol) as white solid. Yield 39%. $^1$H NMR (400 MHz, DMSO) δ 4.55 (s, 2H), 6.64 (s, 1H), 7.19 (dd, J=4.9 Hz, J=3.8 Hz, 1H), 7.43 (t, J=7.7 Hz, 1H), 7.74 (d, J=7.6 Hz, 1H), 7.77 (d, J=4.9 Hz, 1H), 7.81 (d, J=7.8 Hz, 1H), 7.90 (d, J=3.6 Hz, 1H), 8.08 (s, 1H), 12.80 (s, 2H). $^{13}$C NMR (100 MHz, DMSO) δ 33.5, 101.6, 128.1, 128.6, 129.1, 129.1, 130.1, 131.1, 131.4, 133.7, 138.9, 141.7, 167.4.

Example 20b: Preparation of Compound 12

To a stirred solution of compound 15 (134 mg, 0.39 mmol) in acetic acid (5 mL) was added lead dioxide (102 mg, 0.42 mmol) and bromine (0.022 mL, 0.42 mmol). Stirring was continued for 6 hrs at room temperature. The mixture was poured in a solution of Na$_2$S$_2$O$_5$ and was extracted with EtOAc (3×20 mL). The collected organic phases were washed with water and brine, and then they were dried over Na$_2$SO$_4$. The crude of reaction was subjected to flash chromatography purification eluting with CH$_2$Cl$_2$/MeOH (10% for product). Compound 12 (45 mg, 0.11 mmol) was obtained as white solid. Yield 27%. $^1$H NMR (400 MHz, DMSO) δ 4.56 (s, 2H), 7.27 (t, J=3.5 Hz, 1H), 7.44 (t, J=7.6 Hz, 1H), 7.72 (d, J=7.5 Hz, 1H), 7.82 (d, J=7.7 Hz, 1H), 7.92 (d, J=4.5 Hz), 8.07 (s, 1H), 8.33 (d, J=2.9 Hz, 1H), 13.1 (m, 2H). $^{13}$C NMR (100 MHz, DMSO) δ 33.8, 128.6, 128.7, 128.7, 129.2, 130.1, 131.4, 132.3, 132.8, 133.6, 138.3, 141.1, 152.1, 158.5, 159.6, 167.4. HPLC: 95.2%

Scheme 21: Preparation of Compound 13

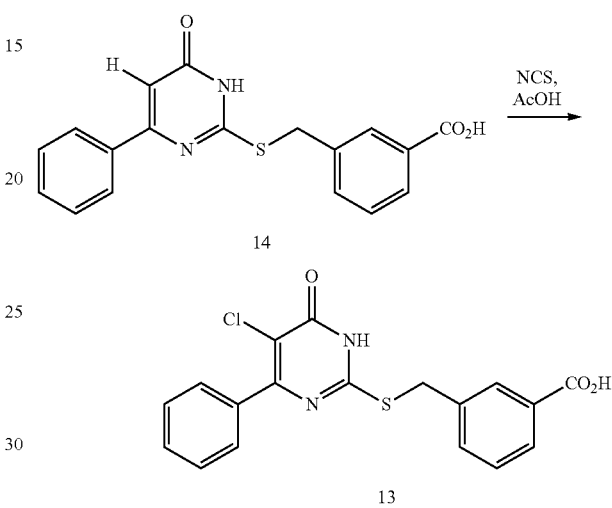

Example 21: Preparation of Compound 13

To a stirred solution of compound 14 (100 mg, 0.29 mmol) in acetic acid (5 mL) was added lead dioxide (55.8 mg, 0.35 mmol) and N-chlorosuccinimmide (47 mg, 0.35 mmol). Stirring was continued for 6 hrs at room temperature. The mixture was poured in water and was extracted with EtOAc (3×20 mL). The collected organic phases were washed with water and brine, and then they were dried over Na$_2$SO$_4$. Titration with a mixture of Et$_2$O/acetone afforded compound 13 (40 mg, 0.1 mmol) as white solid. Yield 37%. $^1$H NMR (400 MHz, DMSO) δ 4.47 (s, 2H), 7.43 (t, J=7.7 Hz, 1H), 7.49 (m, 3H), 7.64 (d, J=7.2 Hz, 1H), 7.71 (m, 2H), 7.83 (d, J=7.5 Hz, 1H), 8.02 (s, 1H), 13.1 (s, 1H), 13.25 (s, 1H); $^{13}$C NMR (100 MHz, DMSO) δ 33.9, 128.4, 128.4, 128.6, 129.1, 129.4, 130.2, 131.3, 131.3, 133.8, 136.5, 138.3, 167.5. HPLC: 95.3%

Scheme 22: Preparation of Compound 22

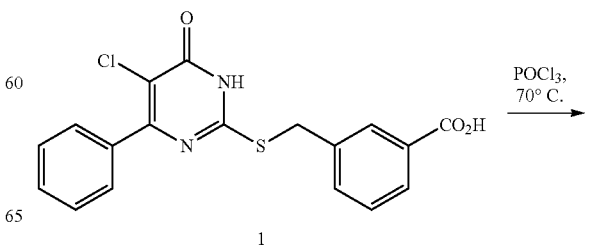

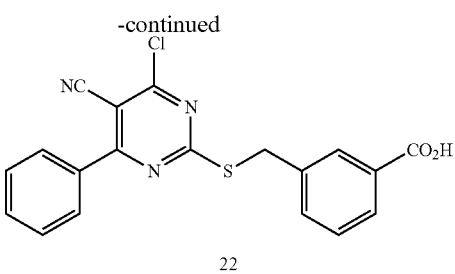

22

Example 22: Preparation of Compound 22

A stirred suspension of compound 1 (160 mg, 0.44 mmol) and POCl₃ (3 mL) was heated at 70° C. for 6 h. The white suspension turned red. The excess of POCl₃ was carefully destroyed with crushed ice and then water. The mixture was extracted with EtOAc (3×20 mL). The collected organic phase were washed with brine, dried over Na₂SO₄ and evaporated. Flash chromatography purification (gradient CH₂Cl₂/MeOH) afforded the title compound 22 (60 mg, 0.16 mmol) as white solid. Yield 36%. $^1$H NMR (400 MHz, DMSO) δ 4.58 (s, 2H), 7.44 (t, J=7.7 Hz, 1H), 7.58-7.62 (m, 2H), 7.66 (d, J=7.17 Hz, 1H), 7.70 (d, J=7.7 Hz, 1H), 7.82 (d, J=7.7 Hz, 1H), 7.94 (d, J=7.1 Hz, 2H), 8.08 (s, 1H), 12.98 (s, 1H); $^{13}$C NMR (100 MHz, DMSO) δ 34.9, 102.5, 115.2, 128.7, 129.2, 129.2, 129.6, 129.6, 130.4, 131.4, 132.7, 133.9, 134.7, 138.0, 162.9, 167.5, 169.0, 174.3. HPLC: 98.8%

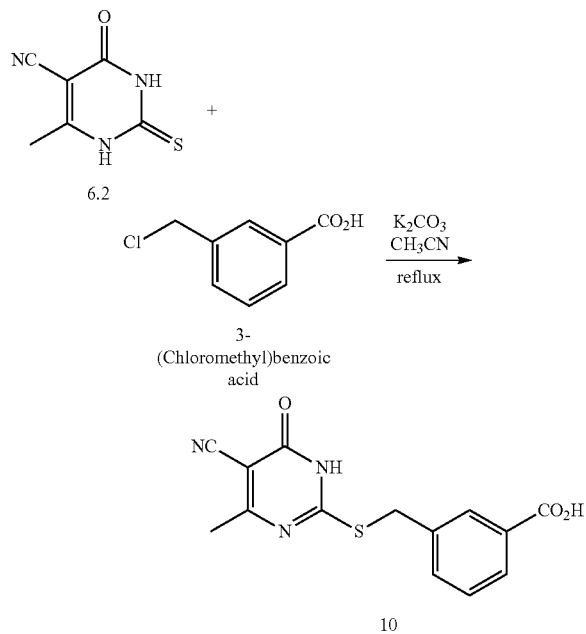

Example 23: Preparation of Compound 10

To a stirred suspension of intermediate 6.2 (145 mg, 0.86 mmol) and K₂CO₃ (599 mg, 4.33 mmol) in CH₃CN (15 mL) was added 3-(chloromethyl)benzoic acid (148 mg, 0.86 mmol). Stirring was continued overnight at reflux. The volatiles were removed under vacuo. The crude was taken up with water, washed with EtOAc, acidified to pH 3 and extracted with EtOAc (3×50 mL). The crude of reaction was purified by flash chromatography, eluting with (CH₂Cl₂/MeOH+ACOH 3%) affording the title compound 10 (60 mg, 0.2 mmol) as white solid. Yield 23%. $^1$H NMR (400 MHz, DMSO) δ 2.44 (s, 3H), 4.49 (s, 2H), 7.45 (t, J=7.6 Hz, 1H), 7.68 (d, J=7.4 Hz, 1H), 7.82 (d, J=7.6 Hz, 1H), 8.05 (m, 1H), 13.1 (s, 1H); $^{13}$C NMR (100 MHz, DMSO) δ 23.3, 33.9, 95.3, 115.6, 128.7, 129.1, 130.6, 131.2, 134.1, 138.0, 161.1, 165.7, 167.4, 170.9. HPLC 96.5%

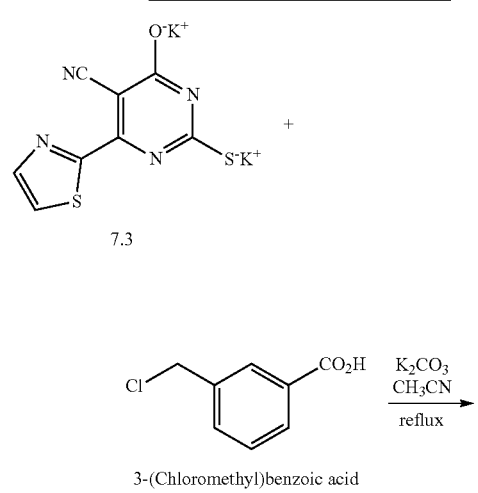

Example 24: Preparation of Compound 5

To a stirred suspension of intermediate 7.3 (414 mg, 1.27 mmol) and K₂CO₃ (526 mg, 3.81 mmol) in CH₃CN (20 mL) was added 3-(chloromethyl)benzoic acid (217 mg, 1.27 mmol). Stirring was continued overnight at reflux. The volatiles were removed under vacuo. The crude was taken up with water, washed with EtOAc, acidified to pH 3 and extracted with EtOAc (3×50 mL). The title compound 5 has been obtained (260 mg, 0.7 mmol) as pure light yellow solid after titration with a mixture of Et₂O/Acetone. Yield 55%. $^1$H NMR (400 MHz, DMSO) δ 4.62 (s, 2H), 7.45 (m, 1H), 7.74 (d, J=5.9 Hz, 1H), 7.82 (d, J=6.1 Hz, 1H), 8.08 (s, 1H), 8.21 (d, J=7.2 Hz, 2H), 12.9 (s, 1H); $^{13}$C NMR (100 MHz, DMSO) δ 34.0, 90.5, 114.9, 127.7, 128.8, 129.3, 130.1, 131.4, 133.7, 138.1, 146.2, 156.7, 161.9, 163.8, 166.5, 167.4. HPLC 96.5%

Scheme 25: Preparation of Compound 19

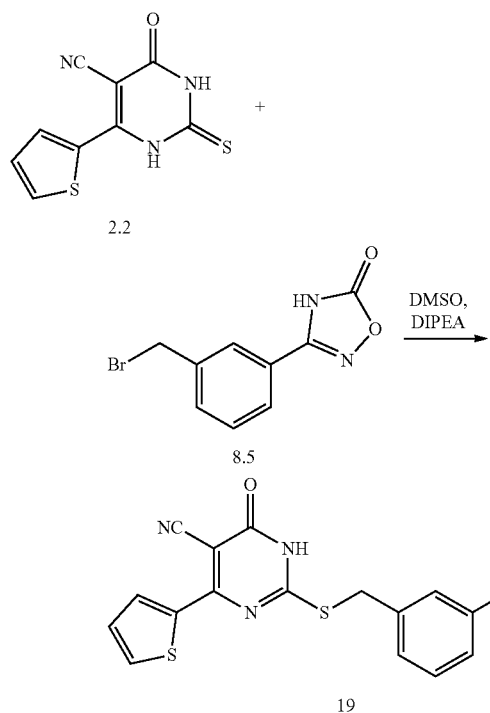

Example 25: Preparation of Compound 19

To a stirred suspension of intermediate 2.2 (100 mg, 0.42 mmol) and DIPEA (0.07 mL, 0.47 mmol) in DMSO (5 mL) was added intermediate 8.5 (120 mg, 0.47 mmol). Stirring was continued overnight at room temperature. The crude was poured in water, washed with EtOAc then acidified to pH 3 and extracted with EtOAc (3×50 mL). The title compound 19 has been obtained (65 mg, 0.15 mmol) as pure orange solid after flash chromatography purification eluting with $CH_2Cl_2$/MeOH (10% for product). Yield 38%. $^1$H NMR (400 MHz, DMSO) δ 4.37 (s, 2H), 7.20 (t, J=4 Hz, 1H), 7.45 (t, J=7.6 Hz, 1H), 7.63 (t, J=7.2 Hz, 2H), 7.75 (d, J=4.3 Hz, 1H), 7.88 (s, 1H), 8.07 (d, J=3 Hz, 1H); $^{13}$C NMR (100 MHz, DMSO) δ 33.7, 85.7, 120.4, 124.9, 125.4, 126.7, 128.7, 128.8, 129.5, 131.1, 132.3, 140.6, 142.2, 159.1, 159.9, 163.3, 170.4, 171.3. HPLC 94.1%.

Scheme 26: Preparation of Compound 18

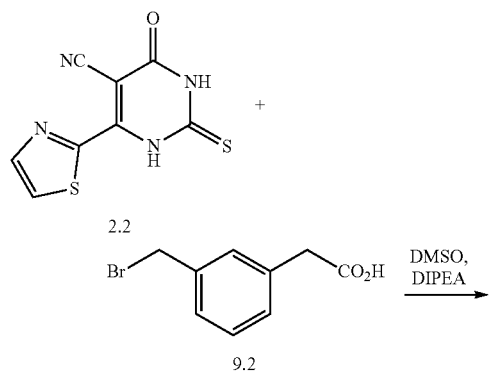

Example 26: Preparation of Compound 18

To a stirred suspension of intermediate 2.2 (500 mg, 0. mmol) and DIPEA (0.4 mL, 2.12 mmol) in DMSO (5 mL) was added intermediate 9.2 (487 mg, 2.12 mmol). Stirring was continued overnight at room temperature. The crude was poured in water, washed with EtOAc then acidified to pH 3 and extracted with EtOAc (3×50 mL). The title compound 18 has been obtained (200 mg, 0.52 mmol) as pure yellowish solid after flash chromatography purification eluting with $CH_2Cl_2$/MeOH (10% for product) and titration with a mixture of $Et_2O$/Acetone. Yield 25%. $^1$H NMR (400 MHz, DMSO) δ 3.49 (s, 2H), 4.53 (s, 2H), 7.16 (d, J=6.8 Hz, 1H), 7.26 (t, J=7.2 Hz, 1H), 7.36 (m, 3H), 8.05 (d, J=4.4 Hz, 1H), 8.27 (s, 1H), 12.13 (s, 1H); $^{13}$C NMR (100 MHz, DMSO) δ 34.3, 40.9, 88.5, 116.8, 127.6, 128.9, 129.1, 129.8, 130.4, 131.9, 135.2, 135.8, 137.0, 139.9, 159.1, 161.6, 165.7, 172.9. HPLC 95.8%.

Scheme 27: Preparation of Compound 17

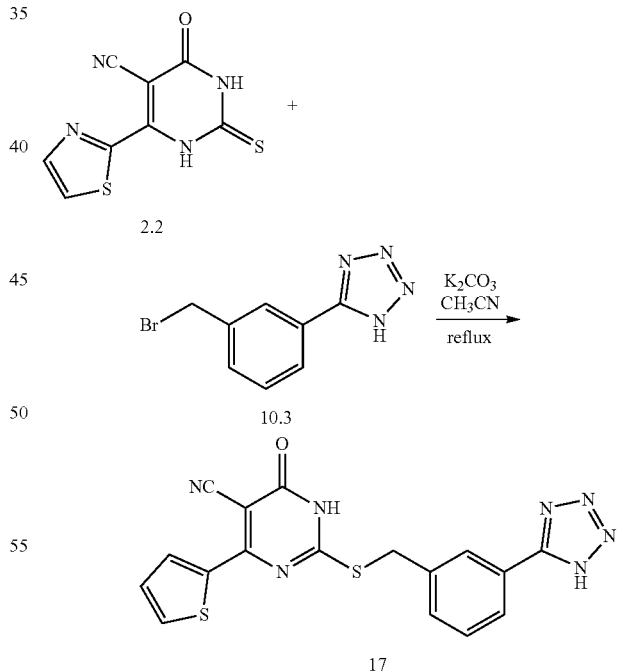

Example 27: Preparation of Compound 17

To a stirred suspension of intermediate 2.2 (160 mg, 0.66 mmol) and DIPEA (0.09 mL, 0.55 mmol) in DMSO (3 mL) was added intermediate 10.3 (171 mg, 0.55 mmol). Stirring was continued overnight at room temperature. The crude was poured in water, washed with EtOAc then acidified to pH 3 and extracted with EtOAc (3×50 mL). The title compound 17 has been obtained (90 mg, 0.22 mmol) as pure orange solid after flash chromatography purification eluting with $CH_2Cl_2$/MeOH (5% for product) and prior titration with a mixture of $Et_2O$/Acetone. Yield 23%. $^1$H NMR (400 MHz, DMSO) δ 4.59 (s, 2H), 7.29 (t, J=4.6 Hz, 1H), 7.54 (t, J=7.6 Hz, 1H), 7.68 (t, J=7.8 Hz, 1H), 7.91 (d, J=7.7 Hz, 1H), 7.96 (d, J=4.9 Hz, 1H), 8.16 (s, 1H), 8.22 (d, J=3.8 Hz, 1H); $^{13}$C NMR (100 MHz, DMSO) δ 33.9, 88.9, 117.6, 125.0, 126.2, 127.9, 129.6, 129.9, 131.2, 131.9, 134.4, 139.3, 140.4, 155.8, 159.1, 163.8, 167.0. HPLC 96.2%.

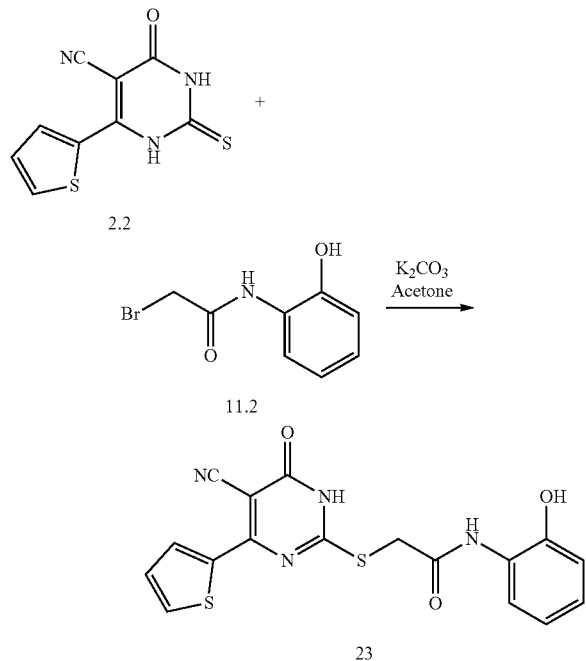

Scheme 28: Preparation of Compound 23

Example 28: Preparation of Compound 23

To a stirred suspension of intermediate 2.2 (150 mg, 0.63 mmol) and $K_2CO_3$ (96.6 mg, 0.70 mmol) in acetone (10 mL) was added intermediate 11.2 (173 mg, 0.72 mmol). Stirring was continued overnight at room temperature. The volatiles were removed under vacuo. The crude was taken up with water, acidified to pH 3 and extracted with EtOAc (3×50 mL). The title compound 23 has been obtained (150 mg, 0.39 mmol) as pure orange solid after flash chromatography purification eluting with $CH_2Cl_2$/MeOH (5% for product) and prior titration with hot EtOAc. Yield 62%. $^1$H NMR (400 MHz, DMSO) δ 3.92 (s, 2H), 6.72 (t, J=7.7 Hz, 1H), 6.79 (d, J=7.6 Hz, 1H), 6.88 (t, J=7.3 Hz, 1H), 7.20 (t, J=4.26 Hz, 1H), 7.77 (d, J=4.7 Hz, 1H); 7.92 (d, J=7.8 Hz, 1H), 8.0 (d, J=3.5 Hz, 1H); 9.59 (s, 1H), 9.80 (s, 1H); $^{13}$C NMR (100 MHz, DMSO) δ 35.12, 86.2, 115.5, 119.2, 120.1, 121.0, 124.4, 127.0, 128.7, 129.2, 131.4, 141.8, 147.3, 159.2, 167.9, 169.1, 170.5. HPLC 97.7%.

II. Biological Activity

Example 29: Determination of ACMSD1 Inhibition

The activity of compounds 1-19 and 21-23 as inhibitors of ACMSD1 was determined by measuring the conversion of 3OH-Anthranilic Acid into product (i.e., ACMS) in a spectrophotometrical in vitro assay.

The pre-assay mixture consisting of 3-hydroxyanthranilic acid (3OH-HA), 3-hydroxyanthranilic acid, 3,4-diOxygenase (HAO), and a dialyzed crude extract of *E. coli* BL21 (DE3) cells expressing the recombinant enzyme, was incubated at 25° C. with monitoring of the increase in absorbance at 360 nm due to the formation of ACMS from 3OH-HA. After the reaction was completed within ~2 mins, an aliquot of ACMSD1 solution (prepared and purified from *Pichia Pastoris* overexpressing the recombinant enzyme) was added, and the decrease in absorbance at 360 nm was followed at 15 second intervals. The effect of ACMS concentration on the enzyme activity was investigated by varying 3OH-HA concentration from 2 to 20 μM. Kinetic parameters were calculated from the initial velocity data by using the Lineweaver-Burk plot.

The rate of the decrease in absorbance caused by ACMSD1 was calculated by subtracting that of the control reaction mixture without ACMSD from that described above. One unit of ACMSD activity was indicated as the amount of enzyme that converts 1 mmol of ACMS per minute at 25° C. The absence or a reduction of ACMSD1 activity (e.g., by using ACMSD inhibitors) results in a slow ACMS-spontaneous degradation (i.e., cyclization to form quinolic acid).

The enzymatic activity was determined at a HAA concentration of 10 μM in the presence of the compounds in Table 1 below. The compounds were tested at the concentration of about 5 μM and 10 μM and the $IC_{50}$ was calculated for compounds showing inhibitory activity higher than 50%. The results are shown in Table 1.

TABLE 1

| Compound No. | Structure | Activity hACMSD $IC_{50}$ |
|---|---|---|
| 1 | 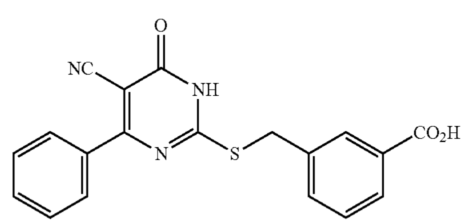 | 0.050 |

TABLE 1-continued

| Compound No. | Structure | Activity hACMSD IC$_{50}$ |
|---|---|---|
| 2 | 6-(furan-2-yl)-5-cyano-2-[(3-carboxybenzyl)thio]-pyrimidin-4(3H)-one | 0.066 |
| 3 | 6-(thiophen-3-yl)-5-cyano-2-[(3-carboxybenzyl)thio]-pyrimidin-4(3H)-one | 0.031 |
| 4 | 6-(thiophen-2-yl)-5-cyano-2-[(3-carboxybenzyl)thio]-pyrimidin-4(3H)-one | 0.012 |
| 5 | 6-(thiazol-2-yl)-5-cyano-2-[(3-carboxybenzyl)thio]-pyrimidin-4(3H)-one | 0.049 |
| 6 | 6-cyclohexyl-5-cyano-2-[(3-carboxybenzyl)thio]-pyrimidin-4(3H)-one | 0.077 |
| 7 | 6-(pyridin-4-yl)-5-cyano-2-[(3-carboxybenzyl)thio]-pyrimidin-4(3H)-one | 0.082 |
| 8 | 6-(4-chlorophenyl)-5-cyano-2-[(4-carboxybenzyl)thio]-pyrimidin-4(3H)-one | 0.082 |

TABLE 1-continued

| Compound No. | Structure | Activity hACMSD IC$_{50}$ |
|---|---|---|
| 9 | 4-(4-methylphenyl)-5-cyano-2-[(3-ethoxycarbonylbenzyl)thio]-6-oxo-1,6-dihydropyrimidine | 0.96 |
| 10 | 4-methyl-5-cyano-2-[(3-carboxybenzyl)thio]-6-oxo-1,6-dihydropyrimidine | 1.7 |
| 11 | 5-bromo-4-phenyl-2-[(3-carboxybenzyl)thio]-6-oxo-1,6-dihydropyrimidine | 0.071 |
| 12 | 5-bromo-4-(2-thienyl)-2-[(3-carboxybenzyl)thio]-6-oxo-1,6-dihydropyrimidine | 0.088 |
| 13 | 5-chloro-4-phenyl-2-[(3-carboxybenzyl)thio]-6-oxo-1,6-dihydropyrimidine | 0.136 |
| 14 | 4-phenyl-2-[(3-carboxybenzyl)thio]-6-oxo-1,6-dihydropyrimidine | 0.74 |
| 15 | 4-(2-thienyl)-2-[(3-carboxybenzyl)thio]-6-oxo-1,6-dihydropyrimidine | 0.76 |

TABLE 1-continued

| Compound No. | Structure | Activity hACMSD IC$_{50}$ |
|---|---|---|
| 16 | 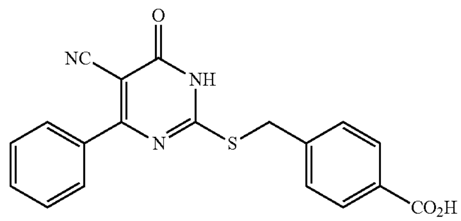 | 0.11 |
| 17 | 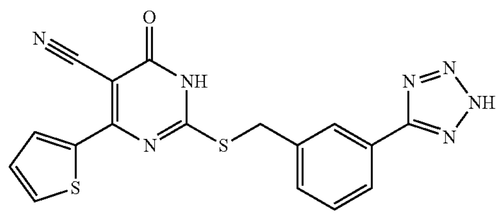 [SMILES: N#Cc1c(-c2cccs2)nc(SCc2cccc(-c3nn[nH]n3)c2)[nH]c1=O] | 0.005 |
| 18 | 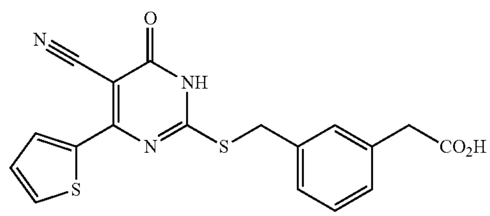 [SMILES: N#Cc1c(-c2cccs2)nc(SCc2cccc(CC(=O)O)c2)[nH]c1=O] | 0.010 |
| 19 | 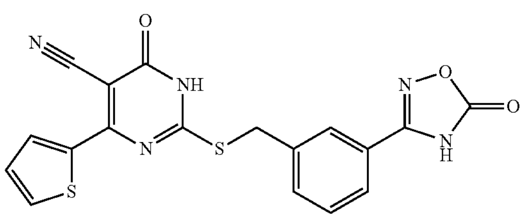 [SMILES: N#Cc1c(-c2cccs2)nc(SCc2cccc(-c3noc(=O)[nH]3)c2)[nH]c1=O] | 0.025 |
| 21 | 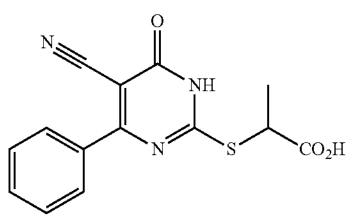 [SMILES: CC(Sc1nc(-c2ccccc2)c(C#N)c(=O)[nH]1)C(=O)O] | 1.99 |
| 22 | 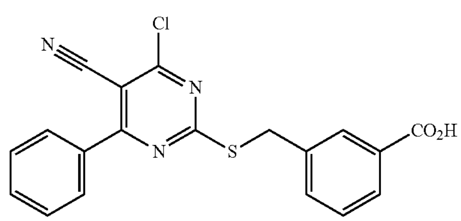 [SMILES: N#Cc1c(Cl)nc(SCc2cccc(C(=O)O)c2)nc1-c1ccccc1] | 1.1 |
| 23 | 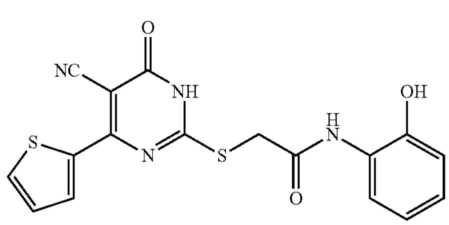 [SMILES: N#Cc1c(-c2cccs2)nc(SCC(=O)Nc2ccccc2O)[nH]c1=O] | 4.9 |

Example 30: Determination of ACMSD-1 Modulation in HEK293T Cells

HEK293T cells (ATCC) were seeded in six-well plates and transfected using Fugene HD to express transiently ACMSD. 24 hrs post transfection, the cells were stimulated for 48 hrs to 72 hrs with different concentrations of Compound 1 and then lysed to measure the ACMSD activity, by measuring the conversion of 3OH-Anthranilic Acid into product (i.e. α-amino-beta-carboxymuconate-ε-semialdehyde, ACMS) in a spectrophotometrical in vitro assay. The amount of the whole protein content in cell lysates was detected by Bradford analysis. This value was used to get the specificity activity of the enzyme normalized in all samples (mU/ml or $\Delta E/\Delta t$/mg of total protein).

ACMSD-1 enzyme is known to be expressed in liver, kidney and brain; available cell lines for these cell types were therefore tested to determine the expression levels of ACMSD. We determined that ACMSD-1 is not expressed in transformed cell lines from liver and kidney, such as HepG2, HEK293T, Hep3B etc. Transfection of ACMSD was performed to express the enzyme in different cellular backgrounds such as COS-7, HEK293T, and HepG2. The HEK293T cellular background proved to be the best system, with the highest protein production allowing robust measurement ACMSD1 enzyme activity. This is probably due to the better transfection efficacy observed in HEK293T.

Having determined the optimum stimulation time and transfection protocol cells were stimulated with different concentrations of Compound 1 (about 50 nM to about 5 uM). Compound 1 inhibited ACMSD-1 activity, in a dose dependent manner, in this over-expression cell-based assay.

Example 31: Determination of NAD$^+$ Content in Human Primary Hepatocytes Treated with Compound 4

The NAD$^+$ concentration or content was determined in human primary hepatocytes treated with Compound 4. Vehicle (NT) was used as a control.

At least three experiments were run treating primary hepatocytes with different concentrations of Compound 4 (0.5 µM and 5 µM) after 48 hrs from seeding. Compound 4 was replaced every 24 hrs, and then cells were directly harvested and lysed with ACN/H$_2$O (ratio 5:1). LCMS/MS was used to detect and measure NAD$^+$ concentration/content. Screening data showed that Compound 4 inhibits ACMSD-1 enzyme at concentrations as low as 0.5 µM and 5 µM. (FIG. 1)

Example 32: Determination of NAD$^+$ Content in Human Primary Hepatocytes Treated with Compound 1

The NAD$^+$ concentration or content was determined in human primary hepatocytes treated with Compound 1 and MEHP, a known ACMSD inhibitor. MEHP was used as a control.

Figure 3:
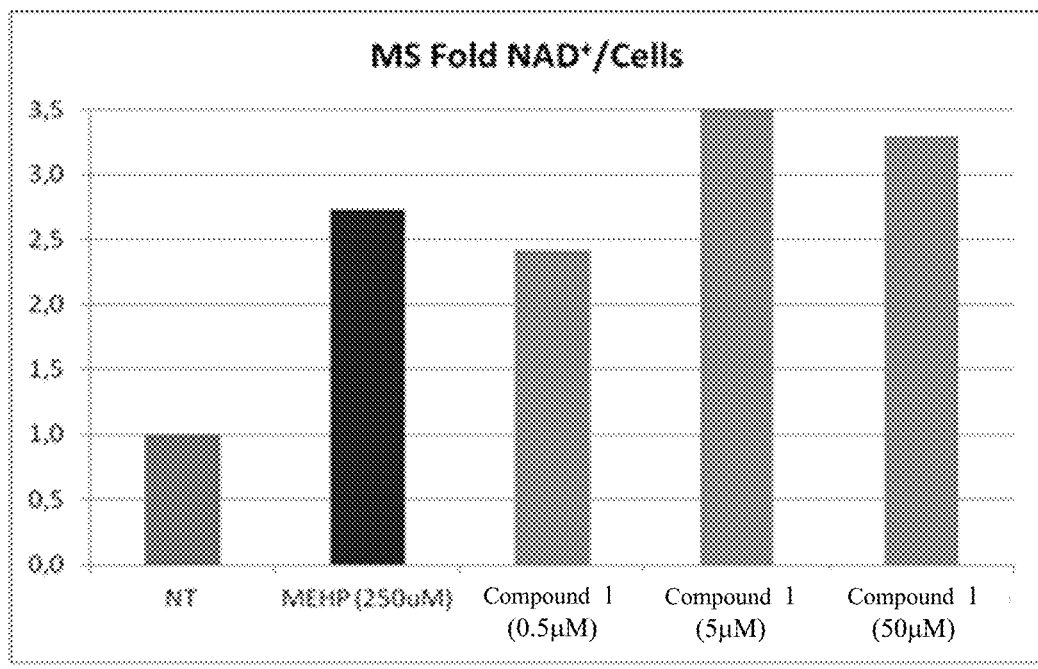
FIG. 3 is a graph of the measured $NAD^+$ content in human primary hepatocytes treated with various concentrations of Compound 1 and mono-(2-ethylhexyl)phthalate (MEHP), as a control.

At least three experiments were run treating primary hepatocytes with different concentrations of Compound 1 (0.5 µM, 5 µM, and 50 µM) after 48 hrs from seeding. Compound 1 was replaced every 24 hrs, and then cells were directly harvested and lysed with ACN/H$_2$O (ratio 5:1). LCMS/MS was used to detect and measure NAD$^+$ concentration/content. Screening data showed that 500 µM of MEHP inhibits 70% of purified ACMSD-1 enzyme, and that 0.5 µM of Compound 1 has similar inhibition activity as 250 µM of MEHP. (FIG. 3)

Example 33: Modulation of SOD2 Activity in AML-12 Cells and Murine Primary Hepatocytes The modulation of SOD-2 activity in AML-12 cells and murine primary hepatocytes treated with either Compound 1 or 17 was measured.

The mouse hepatocytes cell line AML-12 (alpha mouse liver 12) was obtained from ATCC and grown at 37° C. in a humidified atmosphere of 5% CO$_2$/95% air in Dulbecco's Modified Eagle Medium/Nutrient Mixture F-12 (DMEM/F-12) supplemented with 0.005 mg/ml insulin, 0.005 mg/ml transferrin, 5 ng/ml selenium, 40 ng/ml dexamethasone and 1% gentamycin. ACMSD inhibitor was initially diluted from powder in DMSO to a stock concentration of 1 mM. This stock was further diluted with water to a concentration of 100 µM which was used for the cell treatments.

Primary hepatocytes were prepared from 8-12-week-old C57BL/6J mice by collagenase perfusion method. Mouse livers were perfused with Hank's balanced salt solution (HBSS, KCl, 5.4 mM; KH$_2$PO$_4$, 0.45 mM; NaCl, 138 mM; NaHCO$_3$, 4.2 mM; Na$_2$HPO$_4$, 0.34 mM; glucose, 5.5 mM; HEPES, 1 M; EGTA, 50 mM; CaCl$_2$), 50 mM; pH 7.4). Livers were then washed at a rate of 5 ml/min through the portal vein. After washing, livers were perfused with collagenase (0.025%) solution. Cell viability was assessed by the trypan blue method. Isolated primary hepatocytes were plated with DMEM medium (Gibco) including 10% FCS, 10 units per ml penicillin and HEPES for buffering. The cells were maintained in culture at 37° C. in a humidified atmosphere of 5% CO$_2$/95% air. After 6-8 hrs of attachment, this medium was replaced with media containing different concentrations of an ACMSD inhibitor (i.e., Compound 1 or Compound 17) or with the corresponding concentration of DMSO (as a control). Primary hepatocytes were harvested about 24 hrs later if not indicated differently.

Primary hepatocytes or AML-12 cells were then lysed in a 20 mM HEPES buffer (Gibco), pH 7.2, containing 1 mM EGTA (Sigma), 210 mM mannitol (Sigma), and 70 mM sucrose (AMRESCO). Total protein concentration was determined using the Bradford assay (BioRad). SOD-2 activity was determined at indicated times after ACMSD inhibitor treatment by the SOD Assay Kit (Cayman Chemical) according to the manufacturer's instructions. In order to specifically detect the SOD2 activity 2 mM potassium cyanide was added to the assay, which inhibited both Cu/Zn-SOD and extracellular SOD, resulting in the detection of only Mn-SOD (SOD-2) activity. Absorbance was determined with a Victor X4 multi-label plate reader (Perkin-Elmer) at 450 nm. Results are expressed in U/ml/mg of protein according to the standard curve and measured protein concentration.

Figure 5A:
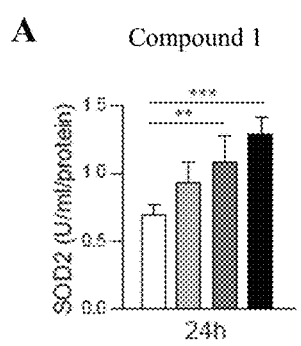
FIG. 5A is a graph showing the modulation of SOD2 activity in AML-12 cells treated for 24 hours with Compound 1.
Figure 5B:
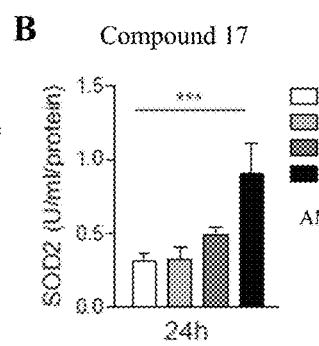
FIG. 5B shows a graph of the modulation of SOD2 activity in AML-12 cells treated for 24 hours with Compound 17.

The oxidative stress resistance pathway, which seemed to be induced upon ACSMD inhibition, was explored by measuring the activity of SOD2. The results showed that SOD2 was induced in a dose-dependent manner in both AML-12 and primary murine hepatocytes by both Compound 17 and Compound 1. In primary hepatocytes, which express ACMSD at significantly higher levels than AML-12, effects were observed at a dose of about 5 nM and reached a maximum at dose of about 50 nM. Both Compound 17 and Compound 1 were able to induce the activity of SOD2 in a dose-dependent manner. (FIG. 5A and FIG. 5B)

Example 34: Determination of NAD$^+$ Content in Murine Primary Hepatocytes

NAD$^+$ levels were determined in human primary hepatocytes treated with Compound 17.

NAD$^+$ was extracted using acidic extraction method. Samples were collected and homogenized in 70% ice-cold perchloric acid (HClO$_4$). After insoluble protein parts were pelleted by adding potassium carbonate (K$_2$CO$_3$), the samples were separated by high-performance liquid chromatography (HPLC) and analyzed by mass-spectrometry. The proteins in the pellet were quantified by Bradford assay and were used for normalization.

Figure 2:
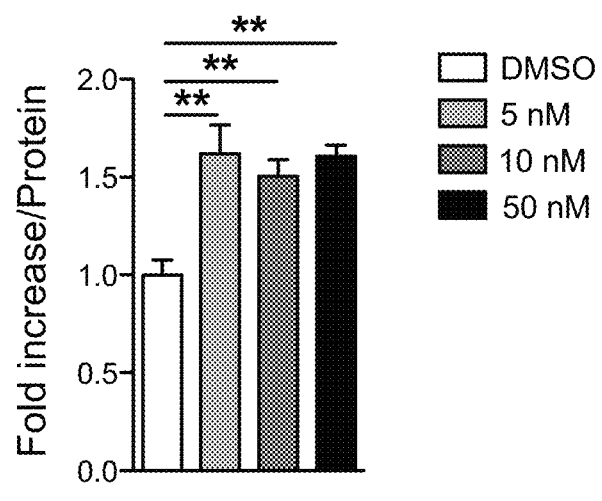
FIG. 2 is a graph of the measured $NAD^+$ levels in murine primary hepatocytes treated with different concentrations of Compound 17 for 24 hours and detected by LC-MS/MS. The data indicate an increase in $NAD^+$ levels in murine primary hepatocytes treated with Compound 17.

The exposure of primary hepatocytes to 5 nM, 10 nM and 50 nM of the ACMSD inhibitor Compound 17 for 24 hours induced a significant and dose-dependent increase in intracellular NAD$^+$ levels. A significant effect on NAD$^+$ levels was observed at concentrations as low as 5 nM concentration. (FIG. 2)

Example 35: RT-qPCR Analysis of SIRT1-Regulated Genes in AML-12 Cells, Hepa-1.6 Cells and Primary Murine Hepatocytes Treated with Compound 1 or 17

Gene expression of ACMSD and genes known to be regulated by SIRT1, (an enzyme that is strictly NAD$^+$ dependent) such as Pgc1a, Sod1, Sod2 (MnSOD), were analysed in AML-12 cells, Hepa-1.6 cells and primary murine hepatocytes treated with Compound 1 or 17.

Cells (AML-12, Hepa-1.6, HEK-293, primary human and murine hepatocytes) were treated with different concentrations of Compound 1 or Compound 17. Total RNA was extracted from cells using TRIzol (Invitrogen) according to the manufacturer's instructions. The RNA was treated with DNase, and 2 µg of RNA was used for reverse transcription (RT). 50× diluted cDNA was used for RT-quantitative PCR (RT-qPCR) reactions. The RT-qPCR reactions were performed using the Light-Cycler system (Roche Applied Science) and a qPCR Supermix (QIAGEN) with the indicated primers. The average of at least three technical repeats was used for each biological data point.

Figure 5C:
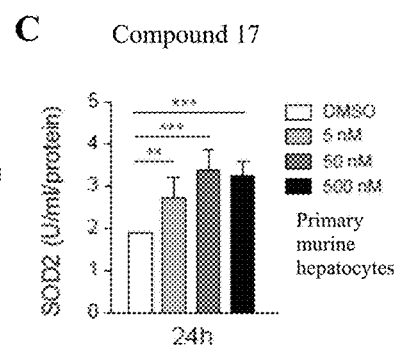
FIG. 5C shows a graph of the modulation of SOD2 activity in primary murine hepatocytes cells treated for 24 hours with Compound 17.

A dose-dependent increase in mRNA expression levels of genes known to be regulated by SIRT1, (an enzyme that is strictly NAD$^+$ dependent) such as Pgc1a, Sod2 (MnSOD), but not Sod1 (Cu—Zn SOD), was observed in primary mouse hepatocytes treated for 24 hrs with Compound 17 (5 nM-500 nM range). The observed increase in the gene expression was dose-dependent, which is in line with the dose-dependent increase in SOD2 enzymatic activity observed in Example 32 (FIG. 5). Sod2 mRNA levels were also increased in a dose-dependent manner in the AML-12 cells and Hepa-1.6 hepatic cell lines after 24 hrs of treatment with Compound 1. These changes in mRNA expression are compatible with the activation of SIRT1, subsequent to the induction in NAD$^+$ levels by inhibition of ACMSD1 activity by Compound 17. (FIG. 4 and FIG. 5)

Example 36: Modulation of Caspase 3/7 Activity in MDCK Cells

An in vitro study was performed to determine the effects of compounds of Formula (I), Formula (Ia), Formula (Ib), Formula (II), or Formula (III), or a pharmaceutically acceptable salt thereof, on Acute Kidney Injury in MDCK cells.

MDCK cells (MDCK (NBL-2) ATCC® CCL-34™) were cultured in base medium ATCC-formulated Eagle's Minimum Essential Medium, Catalog No. 30-2003 with fetal bovine serum (FBS) to a final concentration of 10%. 10,000 cells were plated into 96 wells and 24 hours after cell plating the medium was changed with fresh medium supplemented with 1% FBS. Cisplatin (50 µM for 16 hrs) was then used to induce cell injury. Different concentrations of Compound 18 (in 1% DMSO) were added in combination with cisplatin (FIG. 1) or 1 hour prior adding cisplatin (FIG. 2).

Caspase 3/7 activity (Promega) was determined according to standard procedures using a luminescent signal readout on a Victor V plate reader (PerkinElmer). Each experiment/condition was performed in triplicate.

Caspase activity was analyzed as percentage effect normalized to the cisplatin alone (100%) and vehicle treated cells as 0% of caspase activity. Data were analyzed by GraphPad Software. One-way analysis of variance (Dunnett's Multiple Comparison test) was used for statistical analyses.

As shown in FIG. 1, MDCK cells were treated with different concentrations of Compound 18 (0.01 µM to 100 µM) in combination with cisplatin (cisp). The EC$_{50}$ value was calculated as equal to 70 µM. Cells treated with Compound 18 decreased caspase activity in significant manner at a concentration of 100 µM compared to cells treated with cisplatin alone (p<0.001).

MDCK cells were also treated with different concentrations (1 µM to 125 µM) of Compound 18 one hour prior to the addition of cisplatin (cisp). As shown in FIG. 2, cells treated with Compound 18 decreased caspase activity in significant manner at a concentration of about 30 µM to about 125 µM compared to cells treated with cisplatin alone (p<0.001). The EC$_{50}$ value was calculated as equal to 30 µM.

Data show that Compound 18 decreases, in significant manner, the activity of caspase 3/7 induced by cisplatin (FIG. 1) the protective effect is particularly noteworthy if Compound 18 is added before insult with the injury agent (cisplatin) as shown in FIG. 2.

Example 37: Cytotoxicity and hERG Screening

Cytotoxicity: 20000 HePG2 and AML-12 cells were seeded in 96 well plate (Viewplate PerkinElmer). Dose-response of the compound in Table 2 was performed using HP D300 digital dispenser, ranging from 10 nM to 300 µM with constant DMSO 1% in medium. Cells were stimulated for 4 hrs at 37° C.; the supernatant was used to perform LDH release (Cytotox-one, Promega) as a measure of necrosis while the cells were lysed to detect ATP level for determining cell viability (Celltiter-glo, Promega) according to manufacturer's instructions.

The Predictor hERG assay kit (Invitrogen), containing membrane preparations from Chinese hamster ovary cells stably transfected with hERG potassium channel and a high-affinity red fluorescent hERG channel ligand (tracer), was used for the determination of hERG channel affinity binding of the test compounds in Table 2. Compounds that bind to the hERG channel protein (competitors) were identified by their ability to displace the tracer, resulting in a lower fluorescence polarization. The final concentration of DMSO in each well was maintained at 1%. The assays were performed according to the manufacturer's protocol (Invitrogen).

The results are shown in Table 2.

TABLE 2

| Compound | Compound Structure | Cytotoxicity AML-12 | Hep-G2 | hERG |
|---|---|---|---|---|
| 17 | 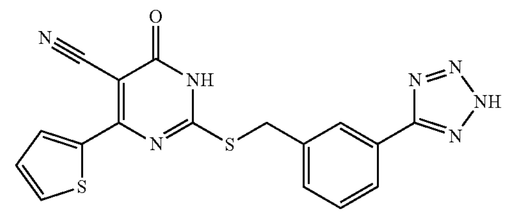 [SMILES: N#Cc1c(-c2cccs2)nc(SCc2cccc(-c3nn[nH]n3)c2)[nH]c1=O] | Not Toxic | Not Toxic | No Activity |
| 8 | 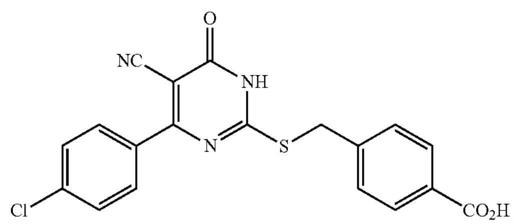 [SMILES: N#Cc1c(-c2ccc(Cl)cc2)nc(SCc2ccc(C(=O)O)cc2)[nH]c1=O] | Not Toxic | Not Toxic | No Activity |
| 4 | 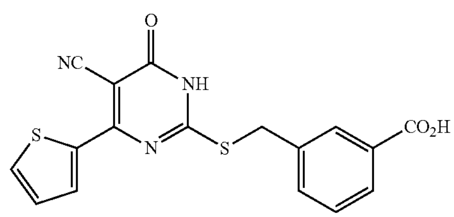 [SMILES: N#Cc1c(-c2cccs2)nc(SCc2cccc(C(=O)O)c2)[nH]c1=O] | Not Toxic | Not Toxic | No Activity |
| 19 | 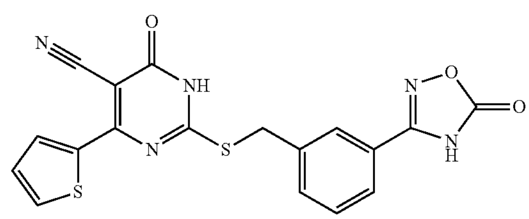 [SMILES: N#Cc1c(-c2cccs2)nc(SCc2cccc(-c3noc(=O)[nH]3)c2)[nH]c1=O] | Not Toxic | Not Toxic | No Activity |
| 5 | 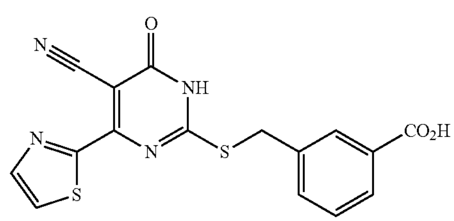 [SMILES: N#Cc1c(-c2nccs2)nc(SCc2cccc(C(=O)O)c2)[nH]c1=O] | Not Toxic | Not Toxic | No Activity |
| 1 | 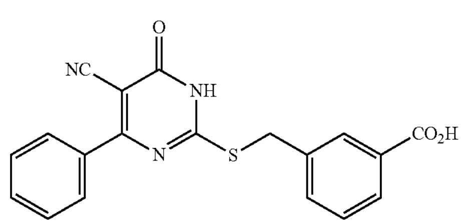 [SMILES: N#Cc1c(-c2ccccc2)nc(SCc2cccc(C(=O)O)c2)[nH]c1=O] | Not Toxic | Not Toxic | No Activity |

TABLE 2-continued

| Compound | Compound Structure | Cytotoxicity | | |
|---|---|---|---|---|
| | | AML-12 | Hep-G2 | hERG |
| 11 | [structure: 5-bromo-6-phenyl-2-((3-carboxybenzyl)thio)pyrimidin-4(3H)-one] | Not Toxic | Not Toxic | No Activity |

Example 38: *C. elegans* Experiments—ACMSD1 Silencing, Lifespan Assays, Mobility Assessment and GFP Fluorescence Quantification

*C. elegans* (*Caenorhabditis elegans*) strains were provided by the *Caenorhabditis* Genetics Center (University of Minnesota). Worms were maintained on Nematode Growth Medium (NGM) agar plates seeded with *E. coli* OP50 bacteria at 20° C., unless stated otherwise. The strains used for the experiments were the following: Bristol N2, NL2099 (rrf-3(pk1426)II), KN259 (huIs33[sod-3::GFP+pRF4(rol-6 (su1006))]).

Bacterial feeding RNAi experiments were carried out as follows: worms were grown on NGM agar plates containing Carbenicillin and IPTG at final concentrations of 25 μg/ml and 1 mM respectively and seeded with bacterial cultures taken from Ahringer library. Clones used were acmsd-1 (Y71D11A.3), sir-2.1 (R11A8.4), and daf-16 (R13H8.1). Clones were purchased from GeneService and their identity was confirmed by sequencing. For the double RNAi experiments bacterial cultures were mixed before seeding on NGM plates. The control RNAi in this kind of experiments was 50% diluted with control empty vector RNAi bacteria.

The nematode *Caenorhabditis elegans* was used as a model system to confirm the activation of the oxidative stress defense that we have observed in cells at the level of an intact organism. The effects of acmsd-1 RNAi were assessed in *C. elegans* by RT-qPCR. The total RNA was extracted from cells using TRIzol (Invitrogen) according to the manufacturer's instructions. RNA was treated with DNase, and 2 μg of RNA was used for reverse transcription (RT). 50× diluted cDNA was used for RT-quantitative PCR (RT-qPCR) reactions. The RT-qPCR reactions were performed using the Light-Cycler system (Roche Applied Science) and a qPCR Supermix (QIAGEN) with the indicated primers. The average of at least three technical repeats was used for each biological data point.

*C. elegans* lifespan assays were carried at 20° C. as follows. Animals were exposed to NAC (N-acetyl cysteine) at a final concentration of 5 mM from a 0.5 M aqueous stock from the young adult stage. Sodium pyruvate was added at a final concentration of 2.5 mM to NGM plates containing carbenicillin (100 1 g mL) and seeded with UV-killed OP50. After 5 days of RNAi treatment, worms were transferred to plates containing paraquat and seeded with acmsd-1 RNAi bacteria. Control animals were grown during the first 5 days of adulthood on RNAi bacteria containing the empty vector and then transferred to plates containing paraquat and seeded with acmsd-1 RNAi bacteria. Survival analyses were performed using the Kaplan-Meier method, and the significance of differences between survival curves was calculated using the log rank test. The statistical software used was XLSTAT 2007 (XLSTAT, Brooklyn, N.Y., USA), and all P-values <0.05 were considered significant. 100 worms were used per condition and scored every 2 days. The reasons for censoring were the «exploded vulva» phenotype or worms that crawled off the plate. Where indicated, paraquat was added on top of the agar plates at the indicated concentration. Once the paraquat solution was completely dried, L4 worms were transferred to these agar plates and monitored for 5-6 days every day. By day 6 all the paraquat tests were stopped because a small percentage in worm population could start to die naturally and rather than dying due to the paraquat effects.

The movement of worms was recorded for 45 seconds at days 1, 3, and 5 of adulthood using a Nikon DS-L2/DS-Fi1 camera and controller setup, attached to both a computer and a standard bright field microscope. For each condition five plates of worms, with 10 worms per plate were used. The movement of worms during aging was calculated by taking an integral of the speed value which was assessed by following the worm centroids with a modified version of the freely-available for the Parallel Worm Tracker for MAT-LAB.

Fluorescence intensity in worm strains expressing GFP-reporter proteins was quantified using Victor X4 plate reader (Perkin Elmer). The animals were prepared in the following way: eighty worms per condition (at the corresponding ages) were picked (20 worms per well of a black-walled 96-well plate) and placed into the M9 medium. Each experiment was repeated at least twice.

Figure 7A:
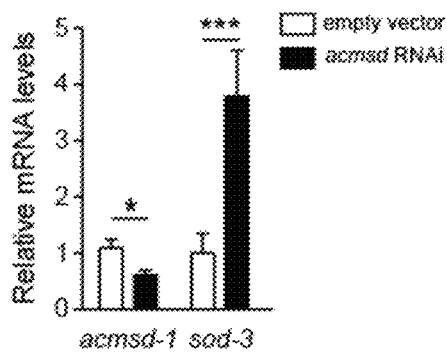
FIG. 7A is a graph of changes in acsmd-1 and sod-3 expression at mRNA levels measured in N2 wild type worms at day 2 of adulthood by acmsd-1 RNAi silencing in *Caenorhabditis elegans* (*C. elegans*).
Figure 7B:
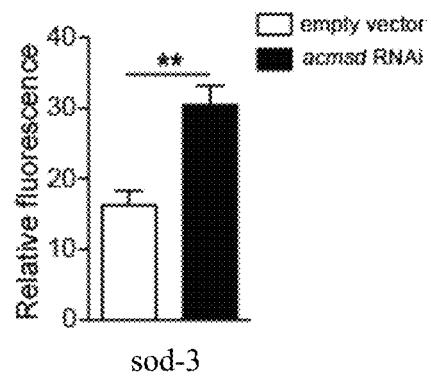
FIG. 7B is a graph of the induction of sod-3 expression at protein levels in N2 worms at day 3 of adulthood, quantified by using SOD-3 gfp reporter strain, after acmsd-1 RNAi silencing in *C. elegans*.
Figure 7C:
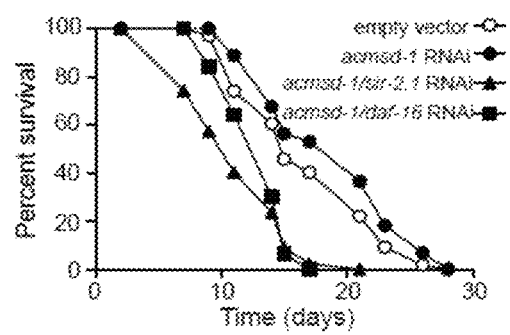
FIG. 7C is a graph showing the survival of worms upon downregulation of acmsd-1 by feeding a specific RNAi in *C. elegans*.

The expression level of acmsd-1 mRNA was significantly reduced confirming the efficacy of RNAi mediated gene knock-down (FIG. 7A). The worm ortholog of MnSOD, SOD-3, was induced at its mRNA level with concomitant downregulation of the acmsd-1 gene with RNAi. A significant increase at the protein level of SOD-3 was also observed at Day 3 of adulthood. (FIG. 7B) ACMSD downregulation improved worm lifespan and this improvement was SIR-2.1- and DAF-16-dependent. (FIG. 7C)

Figure 7D:
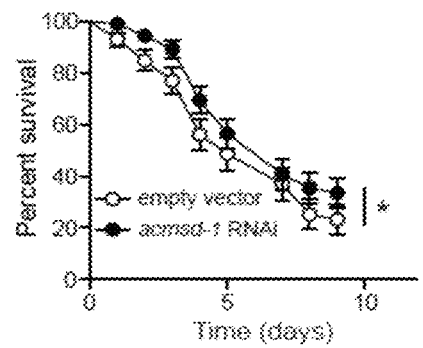
FIG. 7D is a graph showing that downregulation of acmsd-1 improves the stress-resistance of worms when they are exposed to paraquat-induced oxidative stress.
Figure 7E:
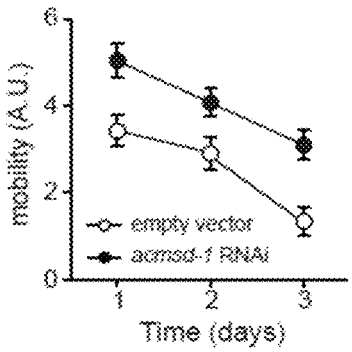
FIG. 7E is a graph showing the mobility of worms over time fed with acmsd-1 RNAi under paraquat-induced oxidative stress condition. As FIGS. 7C-7E show, reduced acmsd-1 expression improves the survival and fitness of worms under paraquat-induced oxidative stress.

Moreover, worms exposed to acmsd-1 RNAi lived longer and showed improved performance in mobility assays when treated with paraquat, a well-known ROS inducer that is widely used to mimic oxidative stress in *C. elegans*. (FIGS. 7D and 7E)

Figure 7F:
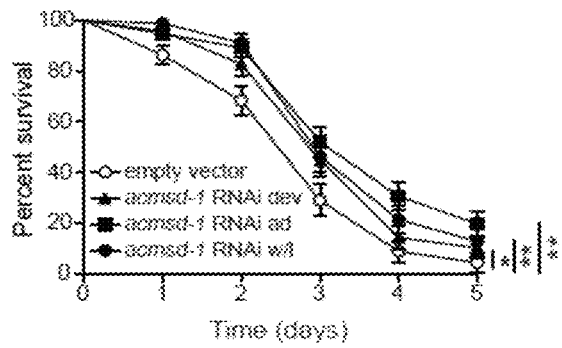
FIG. 7F is a graph that shows the survival of worms under paraquat-induced stress conditions when exposed to acmsd-1 RNAi during different stages of development.

The better survival at paraquat conditions was independent on the developmental stage at which worms were exposed to acmsd-1 RNAi. (FIG. 7F)

Figure 7G:
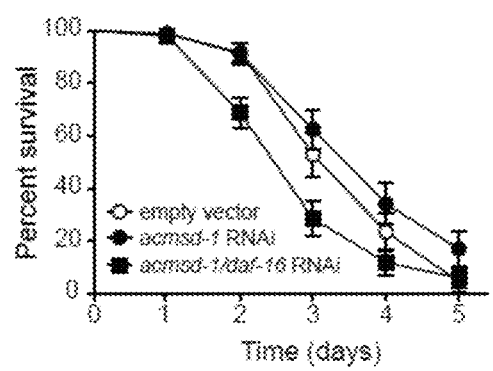
FIG. 7G is a graph showing worm survival under paraquat-induced stress conditions upon downregulation of acmsd-1 combined with daf-16 downregulation by feeding a specific RNAi in *C. elegans*.
Figure 8A:
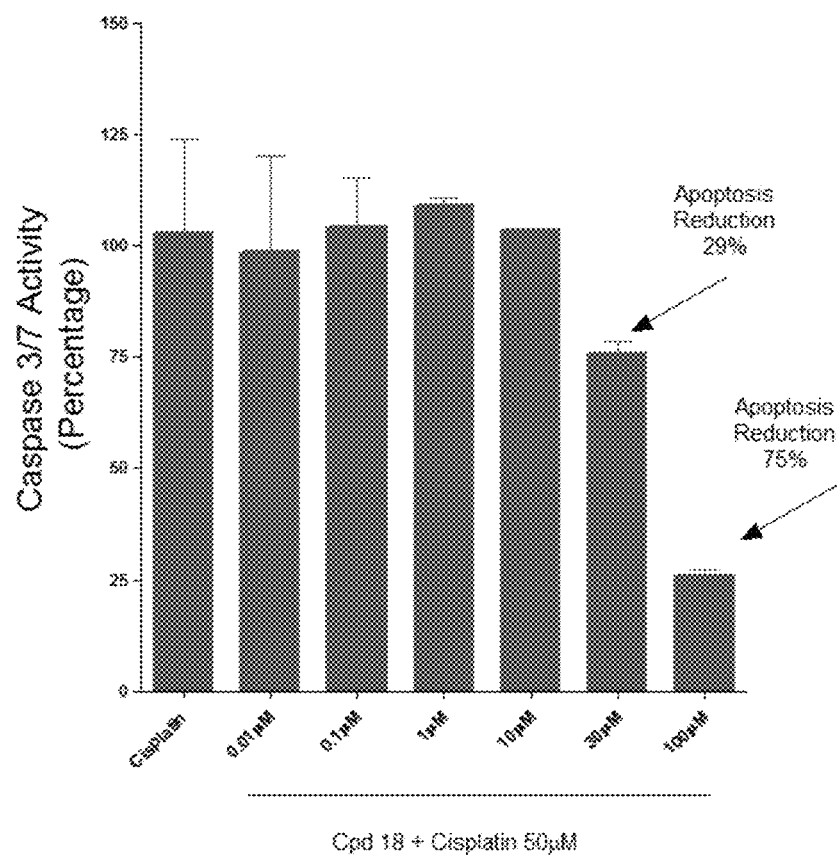
FIG. 8A is a graph of changes in caspase3/7 activity induced by cisplatin in MDCK cells when treated with different concentrations of Compound. 18 in combination with cisplatin.
Figure 8B:
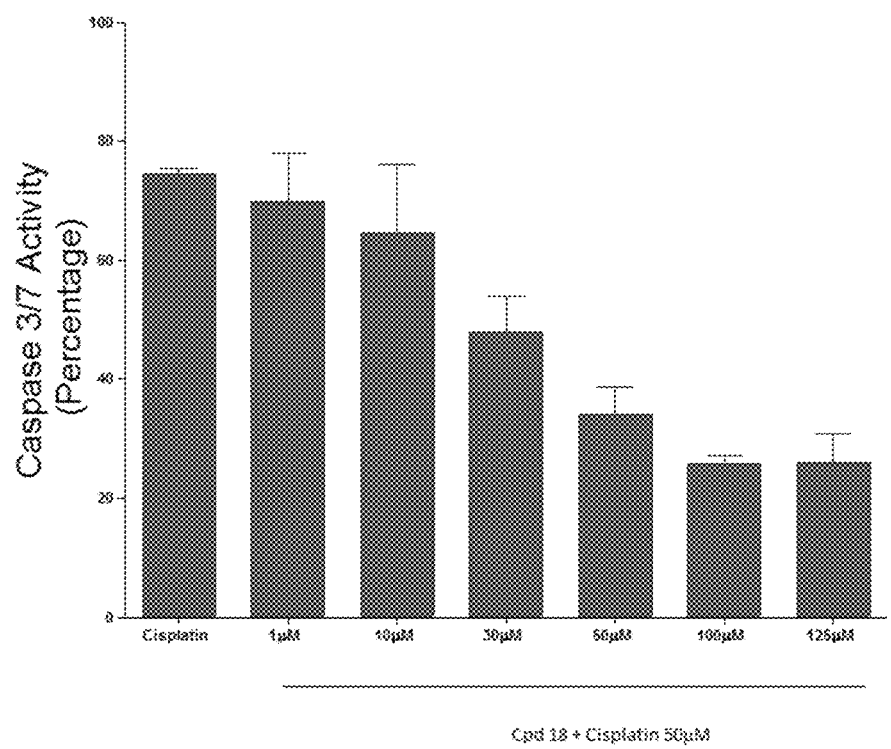
FIG. 8B is a graph of changes in caspase3/7 activity induced by cisplatin in MDCK cells when treated with different concentrations of Compound. 18 one hour prior to the addition of cisplatin.

This increase in lifespan under oxidative stress conditions was no longer observed when DAF-16, the worm ortholog of FoxO1, was downregulated, meaning that better oxidative stress resistance was DAF-16 dependent. (FIG. 7G)

Example 39: Study of the Anti-Diabetic Effects of Compounds of Formula (I), Formula (Ia), Formula (Ib), Formula (II), or Formula (III) in C57BL/6J and KK-Ay Mice A glucose tolerance test is performed on male C57BL/6J and KK-Ay mice to determine the effects of compounds of Formula (I), Formula (Ia), Formula (Ib), Formula (II), or Formula (III) on glucose and insulin levels.

Male C57BL/6J and KK-Ay mice, 6-7 weeks of age, are obtained, e.g., from Charles River Laboratories France and CLEA Japan, respectively. Mice are fed from the age of 8 weeks onwards with regular chow (CD-Harlan 2018), a high fat diet (HFD-Harlan 06414). A compound of Formula (I), Formula (Ia), Formula (Ib), Formula (II), or Formula (III), or a pharmaceutically acceptable salt thereof, is mixed with the HFD at 180 mg kg$^{-1}$ of food. On the basis of their daily food intake, this results in a daily dose of about 15 mg kg$^{-1}$ body weight. The mice are fasted for 4 hrs before blood and tissues are harvested for RNA isolation, lipid measurements and histology. Oxygen consumption is measured with the Oxymax apparatus (Columbus Instruments). Histological analysis and transmission electron microscopy are performed.

An oral glucose tolerance test is performed in the animals that are fasted overnight. Glucose is administered by gavage at a dose of 2 g/kg. An intraperitoneal insulin tolerance test is performed in animals fasted for 4 hrs. Insulin is injected at a dose of 0.75 U/kg body weight. Glucose is quantified with the Maxi Kit Glucometer 4 (Bayer Diagnostic) or Glucose RTU (bioMerieux Inc.) and plasma insulin concentrations are measured by ELISA (Cristal Chem Inc.). Statistical differences are determined by either ANOVA or Student's t-test.

Example 40: Study of the Anti-Diabetic and Obesity Effects of Compounds of Formula (I), Formula (Ia), Formula (Ib), Formula (II), or Formula (III) in db/db Mice with LepR Mutation A study of the anti-diabetic effects of the compounds of Formula (I), Formula (Ia), Formula (Ib), Formula (II), or Formula (III), or a pharmaceutically acceptable salt thereof, is conducted in genetically obese Leprdb/J (db/db) mice.

Animals are bred and housed in a temperature- and humidity-controlled environment in compliance with FELASA-protocols. From an age of three weeks, mice are fed a high-fat diet (HFD) (Harlan 06414). Most pharmacological studies are started in diabetic eight-week-old db/db and wild type (wt) references.

Subchronic Intervention db/db mice are treated once/day with a compound of Formula (I), Formula (Ia), Formula (Ib), Formula (II), or Formula (III), or a pharmaceutically acceptable salt thereof, for 14 days between 5-6 PM before dark-phase onset (6 PM). Blood samples are collected after 4 hrs of fasting the mice prior to the first dose and at 18±2 hrs after the last dose. Glucose concentrations of each blood sample are determined.

Acute Intervention Glucose

Initial blood samples are collected in random-fed db/db mice between 6-8 AM after light-phase-onset (6 AM), then compounds of Formula (I), Formula (Ia), Formula (Ib), Formula (II), or Formula (III), or a pharmaceutically acceptable salt thereof, are administered, diet-access is restricted, and the second blood sample is collected 4 hrs post-treatment. Thereafter, mice are subjected to an oral glucose tolerance test (OGTT1: 1 g glucose/kg body mass) and blood glucose concentrations are determined at 0.5, 1, 2, 3, and 4 hrs after each glucose challenge.

Euglycemic-Hyperinsulinemic Clamps Assay db/db mice receive a permanent jugular vein catheter under ketamine/xylazine anesthesia. For six to seven days, later (after 6 AM) food-access is restricted. Conscious mice are placed in oversized rat-restrainers and warmed by warming pads. Catheter-ends are then connected to syringes in CMA402-pumps (Axel Semrau, Sprockhoevel, Germany). After 110 minutes of primed-continuous [3-$^3$H]glucose infusion (1.85 kBq/min), a blood sample is collected to determine plasma insulin, glucose and [3-$^3$H]glucose concentrations and to calculate basal endogenous glucose appearance rates. The mice then receive vehicle or a compound of Formula (I), Formula (Ia), Formula (Ib), Formula (II), or Formula (III), or a pharmaceutically acceptable salt thereof, via gavage.

Subsequently, glucose-1 clamps are started with a [3-$^3$H] glucose infusion (3.7 kBq/min) containing insulin (36 pmol/kg*min$^{-1}$; Humulin®, Lilly, USA) causing a moderate net-increase in plasma insulin concentrations. Blood glucose concentrations are measured every 10 minutes and target glycemia is established by adjusting the rate of a 20% glucose infusion (GIR). At minute 120, 2-deoxy-D-[1-$^{14}$C] glucose (370 kBq) is given intravenously. Blood samples are collected at minute 30, 60, 90, 100, 110, 120, 122, 125, 130, and 140. The mice are then sacrificed (i.e., through an intravenous ketamine/xylazine-overdose). Gastrocnemius muscle and epididymal adipose tissue are collected, immediately snap-frozen in liquid nitrogen, and stored at −80° C. 2-[$^{14}$C]deoxyglucose-6-phosphate is extracted from the tissue and glucose uptake rates (Rg) are calculated.

Plasma [$^3$H]- and [$^{14}$C]-radioactivity is determined in deproteinized plasma after [$^3$H$_2$O] evaporation. Glucose fluxes under basal conditions and between glucose clamp minute 60 to 90 and 90 to 120 are estimated as follows: whole-body glucose disappearance rate (Rd)=[3-$^3$H]GIR (dpm/min)/plasma [3-$^3$H]glucose specific activity (dpm/min*mol); basal Endo Ra=[3-$^3$H]GIR (dpm/min)/plasma [3-$^3$H]glucose specific activity (dpm/min*mol); glucose-clamp Endo Ra=GIR-Rd. Ultima-Gold scintillation-cocktail, radioisotopes, and a Tri-Carb2910TR are obtained from Perkin Elmer (Germany).

Assays from Blood, Plasma, Urine

Blood samples are collected from lateral tail veins. Blood glucose is measured with a glucometer (Contour, Bayer Vital, Germany), urine and plasma glucose with a colorimetric Glucose LabAssay (Wako, Germany), and HbA1c with AlcNow+ (Bayer Vital) or Clover Analyzer (Inopia, South Korea).

Analyses of Disease Onset and Survival

Disease onset is defined as the last day of individual peak body weight before gradual loss occurs. The stages of disease are defined as follows: the early stage of disease is defined as the duration of time between peak body weight until loss of 10% of peak body weight. The late stage of disease is defined as the duration of time between 10% loss of peak body weight until the end stage of disease. The end stage of disease is defined as the day when an animal could no longer right itself within 30 s for three consecutive trials when placed on its side. Animals are euthanized at the end stage of disease.

Body Composition Measurements

Body weights are assessed weekly for at least 13 weeks. Brown adipose tissue (BAT) and gonadal white adipose tissue (WAT) are dissected and weighed at the indicated age.

Total lean mass, % of WAT and BMD (bone mineral density) are determined by DEXA (PIXImus DEXA; GE).

Indirect Calorimetry, Food Intake and Activity

Animals are initially weighed and acclimated to the test cage. Volume oxygen ($VO_2$) and volume carbon dioxide production ($VCO_2$) are measured every 20 min using the Oxymax Comprehensive Laboratory Animal Monitoring System (CLAMS) (Columbus Instruments) and are reported as average $VO_2$ per hour normalized to body weight (mL/h/kg). Using the CLAMS machine, activity counts by infrared beam interruptions and food intake are simultaneously measured. More specifically, food intake is measured by deducting the weight of powderized food pellets at the end of experimentation from the starting weight at the beginning of experimentation. To complement this experiment and to control for a novel environment that may affect feeding behaviour, we also perform a more 'manual' experiment, wherein a set weight of food pellets is placed at the same time each day into a clean home cage, which holds a mouse. The next day the weight of the remaining pellets is recorded and deducted from the starting weight. This experiment is performed for 14 days straight. The body weight of each mouse is also recorded daily. Results for each genotype are similar to that acquired from the CLAMS.

Statistical Analyses.

Considering a 1-β larger than 0.9 statistically powerful, we estimate appropriate group numbers from pilot studies a priori. One- or two-way Analyses of Variance (Bonferroni post-tests) or t-tests are performed.

Example 41: Study of the Effects of Compounds of Formula (I), Formula (Ia), Formula (Ib), Formula (II), or Formula (III) on Non-Alcoholic Fatty Liver Disease (NAFLD) and Non-Alcoholic Steatohepatitis (NASH) in Mice A study is performed to determine the effects of compounds of Formula (I), Formula (Ia), Formula (Ib), Formula (II), or Formula (III), or a pharmaceutically acceptable salt thereof, on non-alcoholic fatty liver disease (NAFLD) and non-alcoholic steatohepatitis (NASH) in male C57BL/6J fed a high fat and high sucrose diet.

Male C57BL/6J mice (The Jackson Laboratory, Bar Harbor, Me., USA) are housed under a 14 hrs light-10 hrs dark cycle at 21-23° C. and have ad libitum access to water during the entire experiment. From the age of 6 weeks, mice are fed a 'Western' HF-HSD with 44.6% of kcal derived from fat (of which 61% saturated fatty acids) and 40.6% of kcal derived from carbohydrates (primarily sucrose 340 g/kg diet) (TD.08811, 45% kcal Fat Diet, Harlan Laboratories Inc., Madison, Wis., USA) or normal chow diet (NCD) as control (V1534-000 ssniff R/M-H, ssniff Spezialdiaten GmbH, Soest, Germany). The animals are then treated with a compound of Formula (I), Formula (Ia), Formula (Ib), Formula (II), or Formula (III), or a pharmaceutically acceptable salt thereof, or a control for 4, 12 or 20 weeks (n=8 per group for every time point), after which they are sacrificed.

Body weight and food intake are monitored weekly on the same day. After sedation with sodium pentobarbital (intraperitoneal injection, 50 mg/kg body weight), total fat mass is analysed by dual-energy X-ray absorptiometry (DEXA) (PIXImus densitometer, Lunar Corp., Madison, Wis., USA). Intraperitoneal glucose tolerance test (IPGTT) is performed in 6 hrs fasted mice. Tail vein glucose levels are measured with a Bayer Contour glucometer immediately before (time point 0 min) and 15, 30, 60, 90 and 150 min after glucose administration (1 g glucose/kg body weight). Insulin resistance is calculated using the Homeostasis Model of Insulin Resistance (HOMA-IR) index: (fasting insulin (ng/mL)× fasting glucose (mg/dL))/405.

Sacrifice

After a 6 hrs fasting period, mice are anaesthetized with sodium pentobarbital (intraperitoneal injection, 50 mg/kg body weight) and sacrificed by blood sampling via cardiac puncture. Plasma is obtained by centrifugation of blood (6000 rpm for 5 min at 4° C.) that is collected in heparinised syringes. Tissues are either snap frozen in liquid nitrogen or stored at −80° C. together with the plasma until further biochemical and molecular analyses or preserved for histological analysis.

Histological Analyses

Liver samples are routinely fixed in buffered formalin (4%) and embedded in paraffin. Serial 4 mm thick sections are stained with H&E and picrosirius red to assess fibrosis. Frozen liver sections are stained with Oil Red O to assess lipid accumulation. All liver biopsies are analysed by an expert liver pathologist, blinded to the dietary condition or surgical intervention. Steatosis, activity and fibrosis are semiquantitatively scored according to the NASH-Clinical Research Network criteria. The amount of steatosis (percentage of hepatocytes containing fat droplets) is scored as 0 (<5%), 1 (5-33%), 2 (>33-66%) and 3 (>66%). Hepatocyte ballooning is classified as 0 (none), 1 (few) or 2 (many cells/prominent ballooning). Foci of lobular inflammation are scored as 0 (no foci), 1 (<2 foci per 200× field), 2 (2-4 foci per 200× field) and 3 (>4 foci per 200× field). Fibrosis is scored as stage F0 (no fibrosis), stage F1a (mild, zone 3, perisinusoidal fibrosis), stage F1b (moderate, zone 3, perisinusoidal fibrosis), stage F1c (portal/periportal fibrosis), stage F2 (perisinusoidal and portal/periportal fibrosis), stage F3 (bridging fibrosis) and stage F4 (cirrhosis). Diagnosis of NASH is based on accepted histological criteria. Severity of the disease is assessed using the NAS (NAFLD activity score) as the unweighted sum of scores of steatosis, hepatocyte ballooning and lobular inflammation. Percentage of fibrosis is quantitated by morphometry from digitalised sirius red stained sections using the Aperio system after tuning the threshold of fibrosis detection under visual control. Results are expressed as collagen proportional area.

Example 42: Study of the Effects of Compounds of Formula (I), Formula (Ia), Formula (Ib), Formula (II), or Formula (III) on Non-Alcoholic Fatty Liver Disease (NAFLD) and Non-Alcoholic Steatohepatitis (NASH) in Methionine and Choline Deficient Mice A study is performed to determine the effects of compounds of Formula (I), Formula (Ia), Formula (Ib), Formula (II), or Formula (III), or a pharmaceutically acceptable salt thereof, on non-alcoholic fatty liver disease (NAFLD) and non-alcoholic steatohepatitis (NASH) in male wildtype mice fed a methionine- and choline-deficient diet.

Wildtype mice housed in 12-hour light/dark cycles, with free access to food and water are used. At least 5 animals per time point are analysed. All experiments are repeated at least three times. For dietary treatment, 8-12 weeks old male mice weighing 25 g are either fed a methionine- and choline-deficient diet (MCD to induce NASH) or chow diet (as a control). Animal experiments and evaluation of NAFLD and NASH as described above in Example 40 for mice fed the high fat and high sucrose diet.

Example 43: Study of the Effects of Compounds of Formula (I), Formula (Ia), Formula (Ib), Formula (II), or Formula (III) on Atherosclerosis in High Cholesterol Fed LDL-R Knockout Mice A study is performed to determine the effects of compounds of Formula (I), Formula (Ia), Formula (Ib), Formula (II), or Formula (III), or a pharmaceutically acceptable salt thereof, on atherosclerosis in high cholesterol fed LDL-R knockout mice.

LDL-R knockout (KO) mice are backcrossed for ten generations with the C57BL/6J strain, yielding congenic C57BL/6J animals. The controls that are used are littermates in all experiments. The animals are treated with a compound of Formula (I), Formula (Ia), Formula (Ib), Formula (II), or Formula (III), or pharmaceutically acceptable salt thereof, or a control. Mice are sacrificed 12 weeks after the initiation of the atherogenic diet (TD94059; Harlan), after which the heart and aorta are perfused with PBS and subsequently fixed (Shandon Formal Fixx, Thermo Scientific). Atherosclerosis is assessed by an Oil red O staining of the aortic root and quantified with MetaMorph software. Biochemistry parameters are measured with the appropriate kits in the COBAS C111 (Roche). For the in vivo lipopolysaccharide (LPS) study, mice are intraperitoneally injected with 100 mg of LPS, and blood is taken from the tail vein. TNFα levels are quantified with Mouse TNFα ELISA Ready-SET-Go! (eBioscience) assay. Blood cell counts are determined with Advia2120 (Siemens Healthcare Diagnostics).

The Student's t test is used to calculate the statistical significance. In case of multiple testing (i.e., the comparison of more than two groups), this test is preceded by the ANOVA test. $P<0.05$ is considered statistically significant. Results represent the mean±SEM.

Example 44: Study of the Effects of Compounds of Formula (I), Formula (Ia), Formula (Ib), Formula (II), or Formula (III) on Inherited Mitochondrial Disease in Sco2$^{KO/KI}$ Mice A study is performed to determine the effects of compounds of Formula (I), Formula (Ia), Formula (Ib), Formula (II), or Formula (III), or a pharmaceutically acceptable salt thereof, on inherited mitochondrial disease in Sco2$^{KO/KI}$ mice.

Anti-COI, anti-COX5a, anti-Ndufa9, anti-SDH-HA, and anti-Core 2 are from Invitrogen; anti-GAPDH is from Millipore; anti-FoxO1 and anti-acetylated-FoxO1 are from Cell Signaling and Santa Cruz, respectively. Anti-mouse secondary antibodies are from Amersham. Chemicals are from Sigma. Oligonucleotides are from PRIMM, Italy.

Compounds of Formula (I), Formula (Ia), Formula (Ib), Formula (II), or Formula (III), or a pharmaceutically acceptable salt thereof, are dissolved in water and added to a standard powder diet (Mucedola, Italy) at the appropriate concentration of 50 mg/Kg/day. Pellets containing the compounds of Formula (I), Formula (Ia), Formula (Ib), Formula (II), or Formula (III), or a pharmaceutically acceptable salt thereof, or the vehicles are reconstituted by hand and kept frozen at −20° C. until needed. The diet supply is changed every three days, and only the amount needed is thawed at each time and administered ad libitum for one month. Sco2$^{KO/KI}$ mice are maintained in a temperature- and humidity-controlled animal-care facility, with a 12 hrs light/dark cycle and free access to water and food. Animals are sacrificed by cervical dislocation.

Morphological Analysis

For histochemical analysis, tissues are frozen in liquid-nitrogen precooled isopentane. Series of 8 mm thick sections are stained for COX and SDH.

Biochemical Analysis of MRC Complexes

Muscle quadriceps samples stored in liquid nitrogen are homogenized in 10 mM phosphate buffer (pH 7.4), and the spectrophotometric activity of cI, cII, cIII, and cIV, as well as CS, is measured as described. Note that in all panels the activity of cII is multiplied by 10 for visualization clarity.

NAD$^+$ Determination

NAD$^+$ is extracted using acidic and alkaline extraction methods, respectively. Tissue NAD$^+$ is analysed with mass spectrometry as previously described.

Example 45: Study of the Effects of Compounds of Formula (I), Formula (Ia), Formula (Ib), Formula (II), or Formula (III) on Inherited Mitochondrial Disease in Deletor Mice A study is performed to determine the effects of compounds of Formula (I), Formula (Ia), Formula (Ib), Formula (II), or Formula (III), or a pharmaceutically acceptable salt thereof, on inherited mitochondrial disease in Deletor mice.

The Deletor mouse model is generated in C57BL/6 congenic background and has been previously characterized (Tyynismaa et al, 2005); WT mice are littermates from the same congenic mouse strain C57BL/6J. Deletor and WT male mice are administered either chow diet (CD) or a compound of Formula (I), Formula (Ia), Formula (Ib), Formula (II), or Formula (III), or a pharmaceutically acceptable salt thereof, admixed with the CD at the appropriate concentration. The food pellets are manually prepared by mixing a compound of Formula (I), Formula (Ia), Formula (Ib), Formula (II), or Formula (III), or a pharmaceutically acceptable salt thereof, into the powdered food as described for the Sco2$^{KO/KI}$ mice in Example 43 and stored at −20° C. The mice are housed in standard animal facility, under a 12 hrs dark/light cycle. They have ad libitum access to food and water. The pre-manifestation group consists of 12 Deletors and 12 WT mice, and the post-manifestation group of 24 Deletors and 24 WT mice, receiving either a compound of Formula (I), Formula (Ia), Formula (Ib), Formula (II), or Formula (III), or a pharmaceutically acceptable salt thereof, or CD diet. During the intervention, the mice are regularly monitored for weight, food consumption, and physical endurance. Their exercise capability is measured twice by treadmill exercise test (Exer-6M Treadmill, Columbus Instrument) at the start and the end of the diet. The exercise test protocol consists of the initial running speed of 7 m/s which is increased every 2 min by 2 m/s and continued until the animal is unable to run or repeatedly falls from the belt at the stimulus site.

Oxygen consumption and carbon dioxide production, as well as spontaneous moving and feeding activities, are recorded by Oxymax Lab Animal Monitoring System (CLAMS; Columbus Instruments, OH, USA). The mice are kept in individual cages inside a CLAMS chamber for 3 days; the first day and night is a nonrecording adjustment period followed by a 24 hrs recording at thermoneutrality (+30° C.). The results of $O_2$ consumption and $CO_2$ production are used to calculate respiratory exchange rate and analysed separately from the light (inactive) and dark (active) periods of the day.

Morphologic Analysis

Tissue sections are prepared from the quadriceps, liver, and BAT. Samples are embedded with OCT Compound Embedding Medium (Tissue-Tek) and snap-frozen in 2-methylbutane in liquid nitrogen. Frozen sections (12 lm) from quadriceps are assayed for in situ histochemical COX and succinate dehydrogenase (SDH) activities simultaneously. The activities from the quadriceps sections, the COX-negative and the COX-negative plus SDH positive and normal fibres are calculated. Approximately 2000 fibres are counted from each mouse sample. The intensity of COX histochemical activity from quadriceps for both oxidative and non-oxidative fibres is measured with Image J software. Frozen sections (8 μm) from liver and BAT are stained with Oil Red O. For plastic embedding, quadriceps, liver, and BAT samples are fixed in 2.5% glutaraldehyde, treated with 1% osmium tetroxide, dehydrated in ethanol, and embedded in epoxy resin. Semi-thin (1 μm) sections are stained with methyl blue (0.5% w/v) and boric acid (1% w/v). The interesting areas for the ultrastructural analyses are selected by inspection of the light microscopic sections. For transmission electron microscopy, ultrathin (60-90 nm) sections are cut on grids and stained with uranyl acetate and lead citrate and viewed with a Transmission Electron Microscope. Crista content in both BAT and muscle is determined from electron micrographs, utilizing a 1 μm "intra-mitochondrial measuring stick," placed perpendicular to cristae. Skeletal muscle samples are also analysed for citrate synthase activity.

Example 46: Study of the Effects of Compounds of Formula (I), Formula (Ia), Formula (Ib), Formula (II), or Formula (III) on Kidney Disease A study is performed to determine the effects of compounds of Formula (I), Formula (Ia), Formula (Ib), Formula (II), or Formula (III), or a pharmaceutically acceptable salt thereof, on kidney disease in C57BL/6J WT mice. (Wei, Q., et al. "*Mouse model of ischemic acute kidney injury: technical notes and tricks*" American Journal of Physiology-Renal Physiology, 303(11), F1487-F1494)

C57BL/6J WT mice are purchased from Charles-River. All mice are fed a standard commercial diet while housed at an ambient temperature of 20-22° C. with a relative humidity of 50±5% under 12/12 hrs light-dark cycle in a specific pathogen-free facility. The experimental mice are 8 weeks old and are divided into four groups: control (n=5); cisplatin (20 mg/kg; Sigma Chemical, St Louis, Mo.; n=5); a compound of Formula (I), Formula (Ia), Formula (Ib), Formula (II), or Formula (III), or a pharmaceutically acceptable salt thereof, and cisplatin (n=5); and a compound of Formula (I), Formula (Ia), Formula (Ib), Formula (II), or Formula (III), or a pharmaceutically acceptable salt thereof, alone (40 mg/kg; n=5). The dose and time of cisplatin treatment for nephrotoxicity are chosen according to a published method. A compound of Formula (I), Formula (Ia), Formula (Ib), Formula (II), or Formula (III), or a pharmaceutically acceptable salt thereof, is administered orally once a day for 4 days. Cisplatin is injected once at 12 hrs after the first administration of a compound of Formula (I), Formula (Ia), Formula (Ib), Formula (II), or Formula (III), or a pharmaceutically acceptable salt thereof. The mice are sacrificed at 72 hrs after the single cisplatin injection.

Assays for Renal Functional Markers and Proinflammratory Cytokines

For renal function analysis, serum is isolated and stored at −80° C. until use. Serum creatinine and BUN levels are measured using an assay kit according to the manufacturer's instructions (BioVision, Milpitas, Calif.). In addition, the proinflammatory cytokines TNF-α, IL-1b, and IL-6 from serum or homogenates from kidney tissue are quantified by ELISA (Quantikine Kit; R&D Systems, Minneapolis, Minn.) according to the manufacturer's instructions. For measuring cytokines, kidney tissue is homogenized in phosphate buffered saline containing 0.05% Tween-20. Aliquots containing 300 mg of total protein are used. A metabolic cage is used for collecting urine to analyse the level of urinary cytokines. The sample size for each group is five.

Alternative Study of the Effects of Compounds of Formula (I), Formula (Ia), Formula (Ib), Formula (II), or Formula (III) on Kidney Disease Alternatively, C57BL/6J WT mice are numbered and kept in acclimatization for a period of 5-7 days before initiation of the experiment. (Wei, Q., et al. "*Mouse model of ischemic acute kidney injury: technical notes and tricks*" American Journal of Physiology-Renal Physiology, 303(11), F1487-F1494) Mice are randomized into different treatment groups based on their body weight. Different groups are maintained on Harlan diet 2916. Mice are then maintained on the respective diets for 10 days prior to bilateral Ischemic kidney injury. Body weight measurement is made once at randomization and once on day 7. Food consumption is evaluated once on day 7. Blood is collected by retro-orbital puncture under mild Isoflurane anesthesia and used for analysis of basal blood urea nitrogen levels (BUN) on day 9.

Mice are anesthetized with ketamine (80 mg/kg i.p) and/or Xylazine (10 mg/kg, i.p.) and placed on a surgical platform in a dorsal position. Both kidneys are exposed through flank incisions and renal pedicles are occluded using vascular clamps for 25 minutes. The clamp is then removed and the surgical site is sutured. 1 ml of physiological saline is administered intra-peritoneally after closing the wound to prevent dehydration. The sham-operated group is subjected to similar surgical procedures, except that the occluding clamp is not applied. Animals are monitored until recovery from anesthesia and returned to their home cage. Animals are observed every day for general clinical signs and symptoms and mortality.

One day prior to termination, animals are individually housed in metabolic cages for 12 h and urine is collected for estimation of urea, creatinine, sodium and potassium.

On days 12, 14, & 16 blood is collected by retro orbital puncture under mild isoflurane anesthesia and plasma is used for analysis of blood urea nitrogen levels (BUN) and serum creatinine. Animals are then euthanized by $CO_2$ inhalation and organs are collected. One kidney is fixed in 10% neutral buffered formalin and the other is flash frozen in liquid nitrogen, stored at −80° C. and used for the estimation of lipid peroxidation, GSH, MPO and SOD levels.

Histological Analysis and Neutrophil Counting

Mouse kidneys are fixed in 4% formaldehyde and embedded in paraffin wax. The 5-mm-thick sections are deparaffinised in xylene and rehydrated through graded concentrations of ethanol. H&E and PAS staining are performed using standard protocols. Images are collected and analysed using a light microscope (IX71, Olympus, Tokyo, Japan) with DP analyser software (DP70-BSW, Tokyo, Japan). Tubular damage in PAS-stained kidney sections is examined under a light microscope and scored based on the percentage of cortical tubular necrosis: 0=normal, 1=1-10, 2=11-25, 3=26-45, 4=46-75, and 5=76-100%. Slides are scored in a blinded manner, and results are means±s.d. of 10 representative fields/group. Severity criterion for tubular necrosis displaying the loss of the proximal tubular brush border and cast formation are used to classify samples. The sample size for each group is 10. Neutrophil infiltration is quantitatively assessed on PAS stained tissue by a renal pathologist by counting the number of neutrophils per high-power field (×400). At least 10 fields are counted in the outer stripe of the outer medulla for each slide.

All values are represented as mean±s.d. One-way analysis of variance is used to calculate the statistical significance of the results of all assays and P-values <0.05 are considered statistically significant.

Example 47: Study of the Effects of Compounds of Formula (I), Formula (Ia), Formula (Ib), Formula (II), or Formula (III) on Ischenia/Reperfusion-Induced Acute Kidney Injury A study is performed to determine the effects of compounds of Formula (I), Formula (Ia), Formula (Ib), Formula (II), or Formula (III), or a pharmaceutically acceptable salt thereof, on Ischemia/Reperfusion-induced (I/R-induced) Acute Kidney Injury in CD-1 (ICR) mice.

CD-1 (ICR) mice are purchased from Charles River Laboratory (Wilmington, Mass.). Mice are housed in a temperature- and humidity-controlled environment with a 12:12 hrs light-dark cycle and are allowed freely access to standard rodent chow (TekLad, Madison, Wis.) and tap water.

Mice are subjected to a midline back incision, and both renal pedicles are clamped for 45 min with microaneurysm clamps (00396-01; Fine Science Tools, Foster City, Calif.). After removal of the clamp, the kidneys are inspected for the restoration of blood flow. The animals are allowed to recover, and they are sacrificed 48 hrs after reperfusion. Mice are treated with 100 mg/kg of a compound of Formula (I), Formula (Ia), Formula (Ib), Formula (II), or Formula (III), or a pharmaceutically acceptable salt thereof, by oral gavage once per day. CD-1 mice are divided into four groups: (1) young mice with sham injury (n=4) (6-7 weeks old); (2) young mice with I/R injury (n=8); (3) adult mice with sham injury (n=4) (20-24 weeks old); and (4) adult mice with I/R injury (n=11). An additional 27 adult mice (20-24 weeks old) are randomized into two groups: 13 mice received a compound of Formula (I), Formula (Ia), Formula (Ib), Formula (II), or Formula (III), or a pharmaceutically acceptable salt thereof, and the other 14 mice received the vehicle as a control.

The serum creatinine level is measured using the QuantiChrom Creatinine Assay Kit (DICT-500, BioAssay Systems, Hayward, Calif.). BUN measurements are recorded using the Infinity Urea (Nitrogen) Liquid Stable Reagent (TR12421; ThermoTrace, Victoria, AU).

Evaluation of Renal Tissue

Kidneys are fixed in 4% paraformaldehyde, embedded in paraffin, and stained with hematoxylin and eosin (4 mm thick). Tubular injury is scored on a scale of 0-4 on the basis of the percentage of tubules with necrosis, dilatation, or cell swelling: 0, less than 5%; 1, 5-25%; 2, 25-50%; 3, 50-75%; and 4, over 75%. All high-power fields (×400) in the cortex and outer medulla are evaluated by a pathologist in a blinded manner.

All values are expressed as mean±s.e. Statistical analysis is carried out using GraphPad Prism 4.00 (San Diego, Calif.) with unpaired Student's t testing for two sets of data and an analysis of variance with a Bonferroni post-test for multiple groups. P<0.05 was considered significant.

Example 48: Determination of the Effects of Compounds 1 and 17 on FoxO1 Phosphorylation Levels AML-12 cells were treated with different concentrations of Compound 1 or Compound 17 for 24 hours. Cells were then lysed in lysis buffer (50 mM Tris, 150 mM KCl, EDTA 1 mM, NP40 1%) containing protease and phosphatase inhibitors, and analyzed by SDS-PAGE/western blot. Blocking and antibody incubations were done in 5% milk. Each protein present was detected with its specific antibody. Tubulin antibody was obtained from Sigma Inc, FoxO1 and phopho-FoxO1 (Ser256) antibodies were obtained from Cell Signaling. Antibody detection reactions were developed by enhanced chemiluminescence (Advansta, CA, USA) using x-ray films.

Figure 6A:
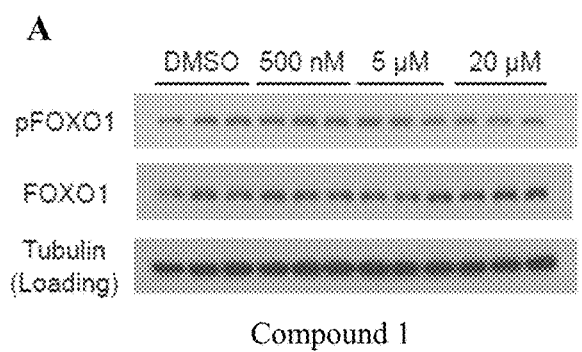
FIG. 6A is a gel showing the effect of Compound 1 on the FoxO1 phosphorylation levels.
Figure 6B:
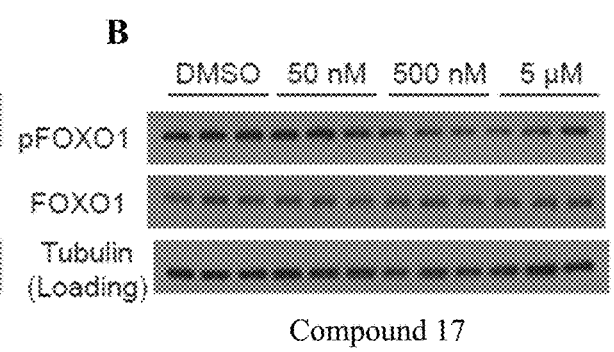
FIG. 6B is a gel showing the effect of Compound 17 on the FoxO1 phosphorylation levels.

FoxO1 phosphorylation at Ser256 results in its nuclear export and in inhibition of its transcription factor activity. A decrease in FoxO1 phosphorylation at Ser256 with increasing dose of Compound 1 and 17 was observed (FIG. 6), indicating an increase in nuclear-translocated FoxO1 and therefore increased FoxO1 transcriptional activity.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice of testing the present disclosure, suitable methods and materials are described below. All publications, patent applications, patents, and other references mentioned herein are hereby expressly incorporated by reference. The references cited herein are not admitted to be prior art of the claimed disclosure. In the case of conflict, the present specification, including definitions, will control. In addition, the materials, methods, and examples are illustrative only and are not intended to be limiting.

Example 49: Synthesis of Exemplified Compounds

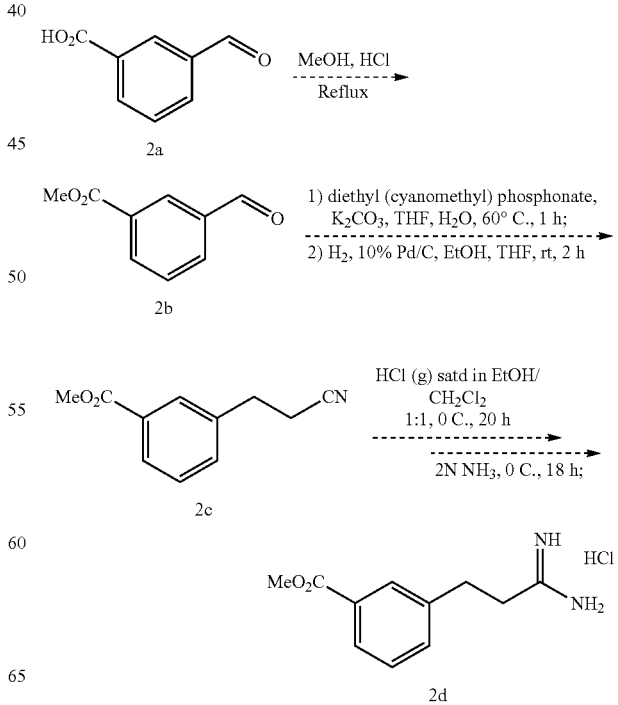

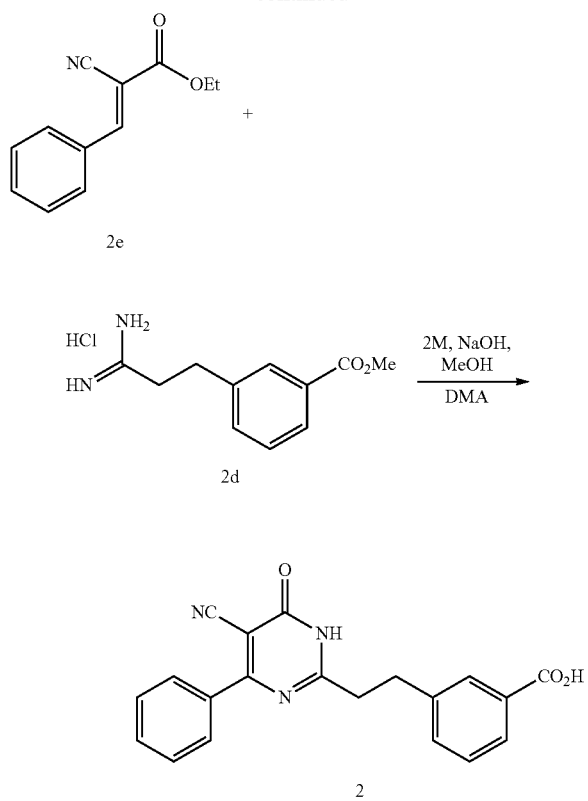

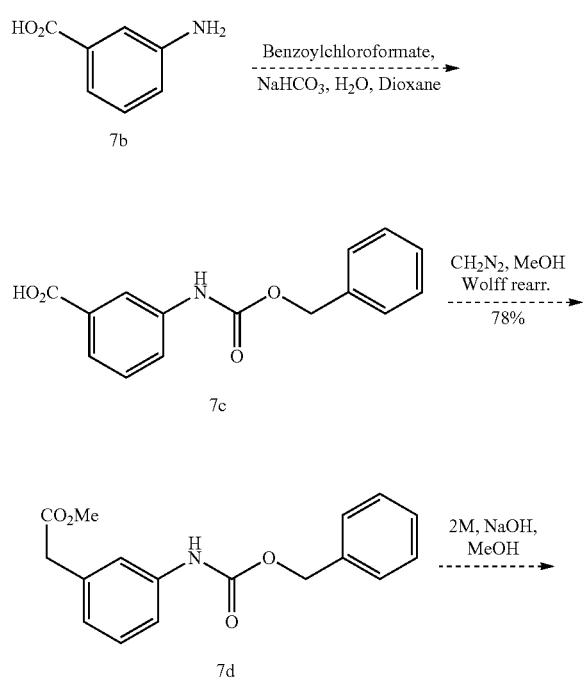

See, Hirose M, et al., "Design and synthesis of novel DFG-out RAF/vascular endothelial growth factor receptor 2 (VEGFR2) inhibitors: 3. Evaluation of 5-amino-linked thiazolo[5,4-d]pyrimidine and thiazolo[5,4-b]pyridine derivatives." *Bioorg. Med. Chem.* 2012, 15; 20(18):5600-15.

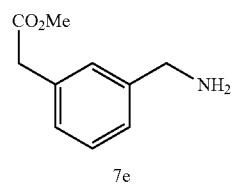

See, Clift M D, Silverman R B., "Synthesis and evaluation of novel aromatic substrates and competitive inhibitors of GABA aminotransferase," *Bioorg. Med. Chem. Lett.,* 2008, 15; 18(10):3122-5.

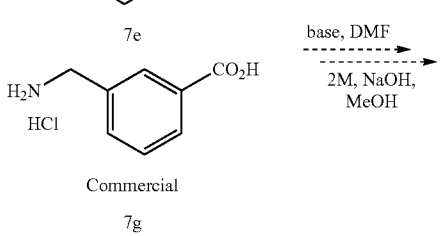

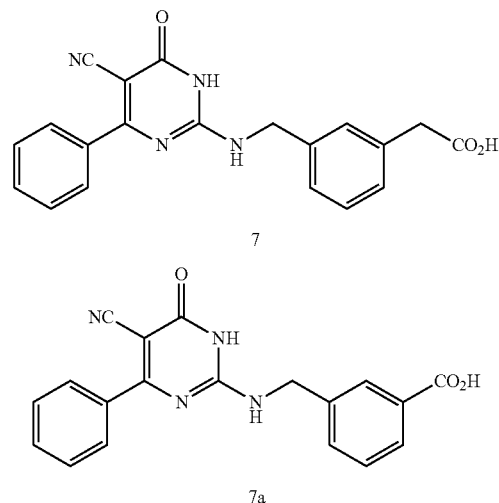

A. M. El-Reedy, A. O. Ayyad and A. S. Ali, "Azolopyrimidines and pyrimidoquinazolines from 4-chloropyrimidines," *J. Het. Chem.* 1989, 26, 313-16.
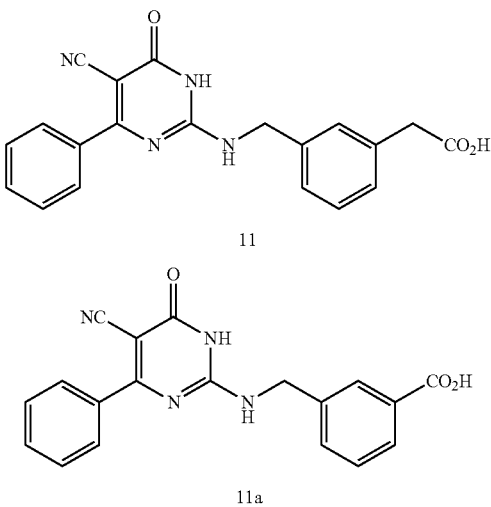
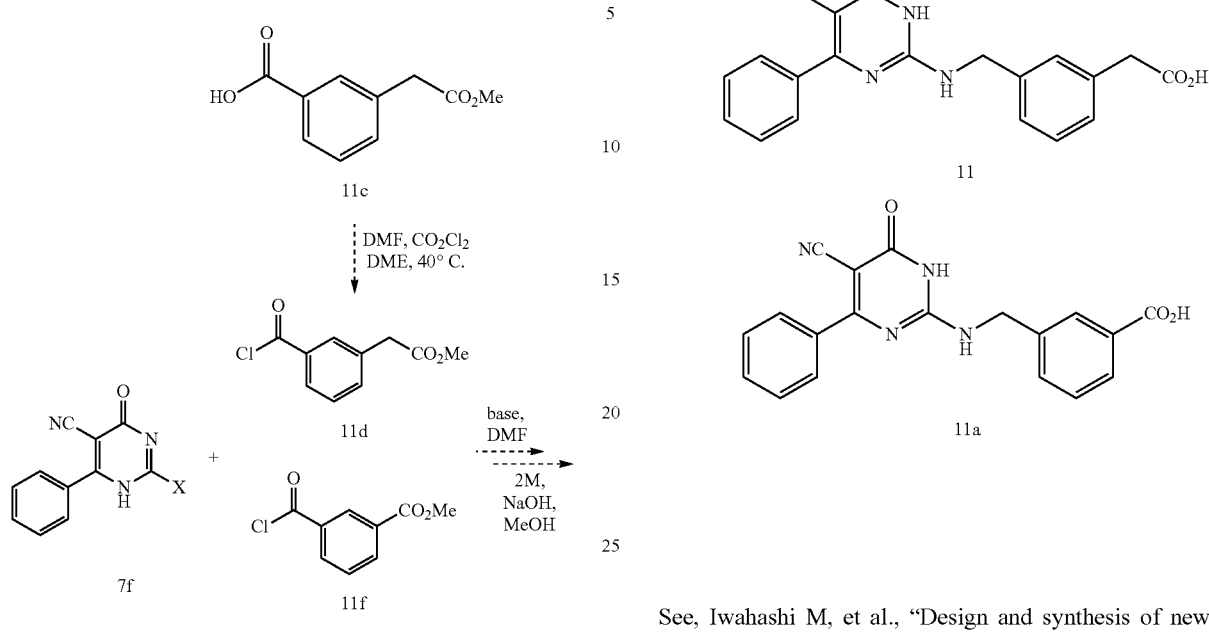
See, Iwahashi M, et al., "Design and synthesis of new prostaglandin $D_2$ receptor antagonists," *Bioorg. Med. Chem.* 2011, 19(18):5361-71.
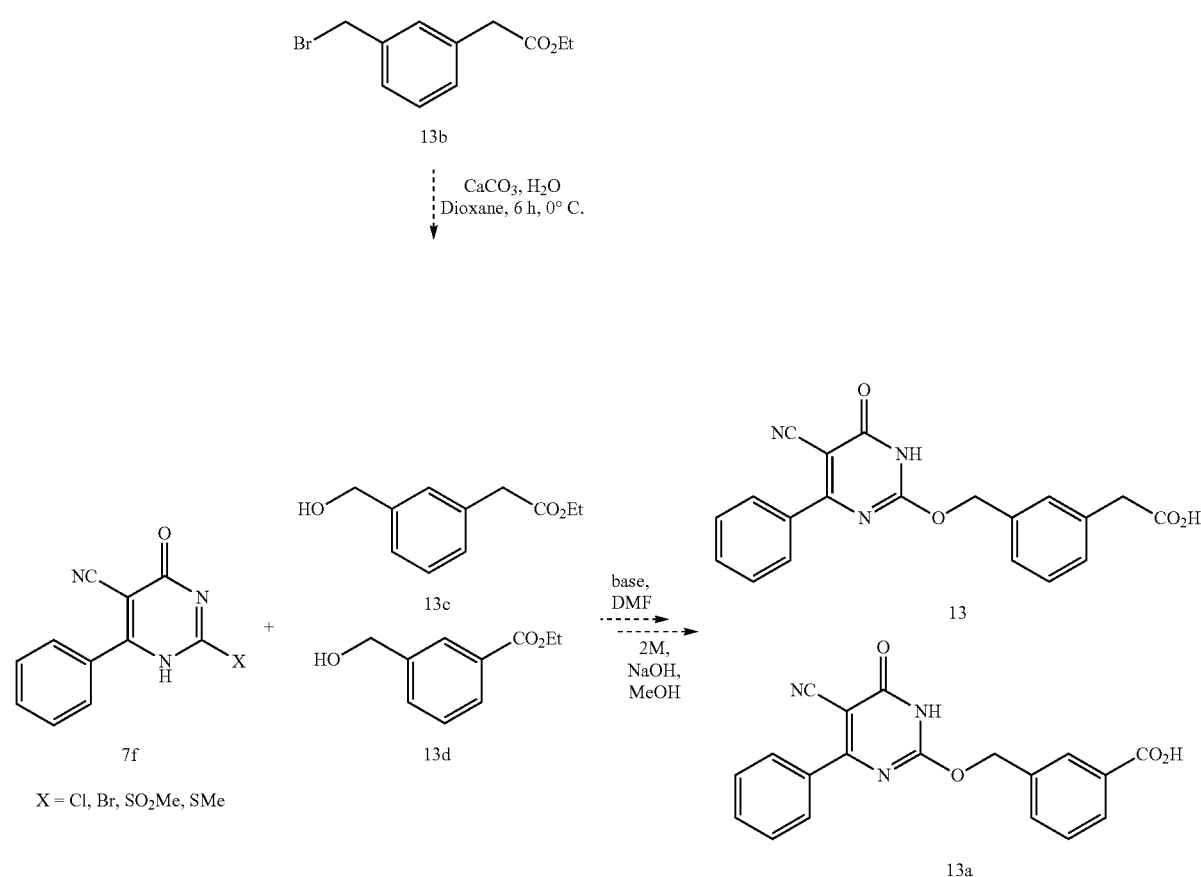

-continued

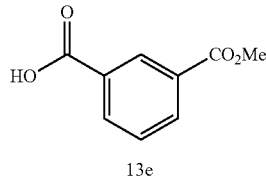

13e

See, U.S. 2008/004,302(A1); and U.S. Pat. No. 8,716,470 (B2).

EQUIVALENTS

Those skilled in the art will recognize, or be able to ascertain using no more than routine experimentation, many equivalents to the specific embodiments and methods described herein. Such equivalents are intended to be encompassed by the scope of the present disclosure.

The invention claimed is:

1. A compound of Formula (Ia)

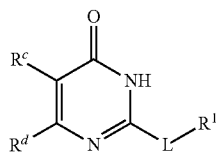

or a pharmaceutically acceptable salt, or tautomer thereof, wherein

L is —CH$_2$CH$_2$—, —CH$_2$C(O)—, —C(O)CH$_2$—, —NR$^2$CH$_2$—, —CH$_2$NR$^2$—, —OCH$_2$—, —CH$_2$O—, —SCH$_2$—, —CH$_2$S—, —S(O)CH$_2$—, —CH$_2$S(O)—, —CH$_2$S(O)$_2$—, or —S(O)$_2$CH$_2$—;

R$^1$ is C$_6$-C$_{10}$ aryl or heteroaryl, wherein the aryl and heteroaryl are substituted with R$^a$ and R$^b$, and optionally substituted with one or more R$^e$;

R$^2$ is H or C$_1$-C$_6$ alkyl;

one of R$^a$ and R$^b$ is hydrogen and the other is —(CH$_2$)$_r$CO$_2$R$^x$, —OCH$_2$CO$_2$R$^x$, —(CH$_2$)$_r$tetrazole, —(CH$_2$)$_r$oxadiazolone, —(CH$_2$)$_r$dihydrotetrazolone, —(CH$_2$)$_r$thiadiazolol, —(CH$_2$)$_r$ isoxazol-3-ol, —(CH$_2$)$_r$P(O)(OH)OR$^x$, —(CH$_2$)$_r$S(O)$_2$OH, —(CH$_2$)$_r$C(O)NHCN, or —(CH$_2$)$_r$ C(O)NHS(O)$_2$alkyl;

R$^c$ is C$_1$-C$_6$ alkyl, C$_1$-C$_6$ haloalkyl, halogen, —CN, —OR$^x$, —CO$_2$R$^x$, or NO$_2$;

R$^d$ is methyl, optionally substituted 5- to 10-membered aryl, optionally substituted 5- or 6-membered heteroaryl, or optionally substituted 5- or 6-membered carbocycle;

each R$^x$ is independently at each occurrence hydrogen or C$_1$-C$_6$ alkyl;

each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN; and r is 0 or 1;

with the proviso that R$^c$ is not —CN when L is —SCH$_2$— and R$^d$ is optionally substituted phenyl, R$^c$ is not C$_1$-C$_6$ alkyl when L is —SCH$_2$— and R$^d$ is methyl, and that R$^c$ is not —CN when L is —SCH$_2$— and R$^d$ is 2-furyl.

2. The compound of claim 1, wherein:

one of R$^a$ and R$^b$ is hydrogen and the other is CO$_2$R$^x$, CH$_2$CO$_2$R$^x$, tetrazole, or oxadiazolone;

R$^c$ is halogen, —CN, —OR$^x$, or C$_1$-C$_6$ alkyl;

R$^d$ is methyl, optionally substituted 5- to 10-membered aryl, optionally substituted 5- or 6-membered heteroaryl, or optionally substituted 5- or 6-membered carbocycle; and R$^x$ is hydrogen or C$_1$-C$_6$ alkyl;

each R$^e$ is independently C$_1$-C$_6$ alkyl, C$_2$-C$_6$ alkenyl, C$_2$-C$_6$ alkynyl, halogen, —OR$^y$, C$_1$-C$_6$ haloalkyl, —NHR$^z$, —OH, or —CN;

each R$^y$ and R$^z$ is independently hydrogen, C$_1$-C$_6$ alkyl, or C$_1$-C$_6$ haloalkyl;

with the proviso that R$^c$ is not hydrogen or —CN when R$^d$ is optionally substituted phenyl and that R$^c$ is not —CN when R$^d$ is 2-furyl.

3. The compound of claim 1, wherein R$^c$ is —CN or halogen.

4. The compound of claim 1, wherein R$^d$ is methyl, cyclohexyl, pyridinyl, thiazolyl, phenyl, or thienyl.

5. The compound of claim 1, wherein R$^d$ is methyl, cyclohexyl, pyridinyl, thiazolyl, thienyl, or optionally substituted phenyl.

6. The compound of claim 1, wherein R$^a$ is hydrogen, CH$_2$CO$_2$H, tetrazole, or oxadiazolone (1,2,4-oxadiazol-5 (4H)-one).

7. The compound of claim 1, wherein R$^b$ is hydrogen, CH$_2$CO$_2$H, tetrazole, or oxadiazolone (1,2,4-oxadiazol-5 (4H)-one).

8. The compound of claim 1, wherein the compound is selected from the group consisting of:

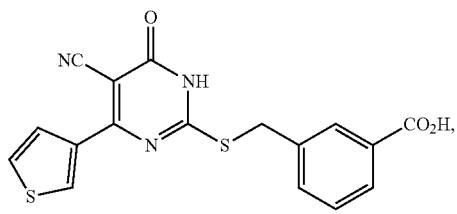

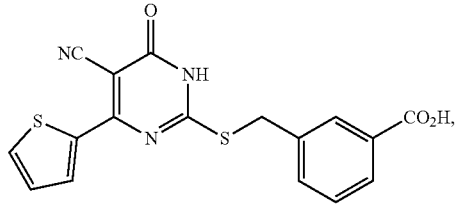

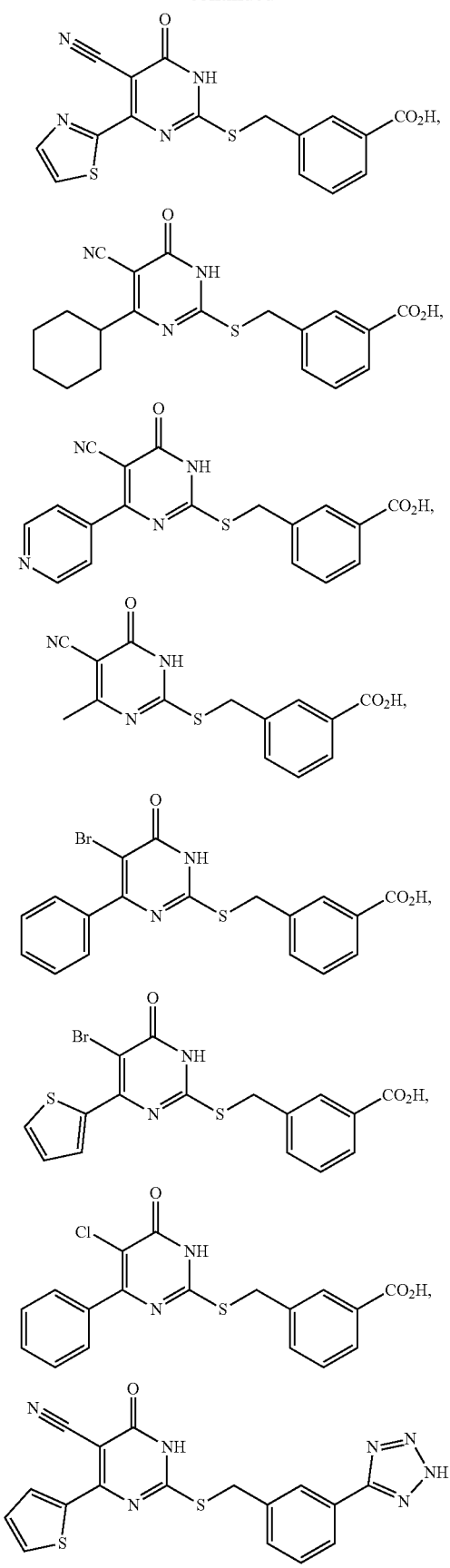

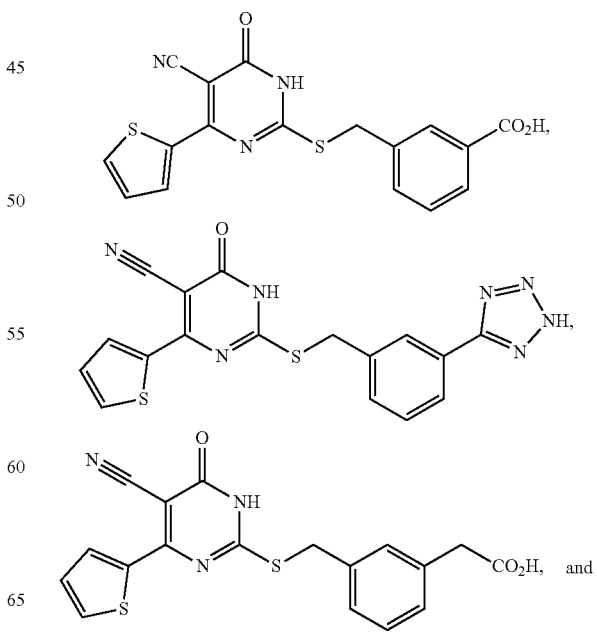

or a pharmaceutically acceptable salt thereof.

9. A pharmaceutical composition comprising a compound of claim 1, or a pharmaceutically acceptable salt thereof, and at least one of a pharmaceutically acceptable carrier, diluent, or excipient.

10. The pharmaceutical composition according to claim 9, which comprises one or more further therapeutic agents.

11. A method of treating a disease or disorder associated with reduced nicotinamide adenine dinucleotide ($NAD^+$) levels selected from the group consisting of a metabolic disorder, a neurodegenerative disease, a chronic inflammatory disease, a fatty liver disease, and a kidney disorder in a subject, the method comprising administering to the subject suffering from or susceptible to developing a disease or disorder associated with reduced $NAD^+$ levels a therapeutically effective amount of one or more compounds of claim 1.

12. The compound of claim 1, wherein the compound is selected from the group consisting of -continued

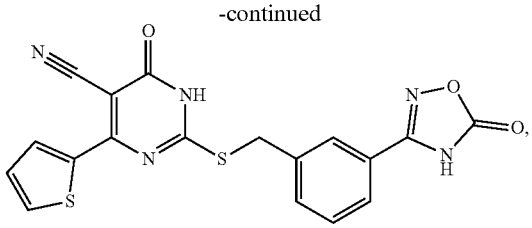

or a pharmaceutically acceptable salt thereof.

13. The compound of claim 1, wherein the compound is selected from the group consisting of

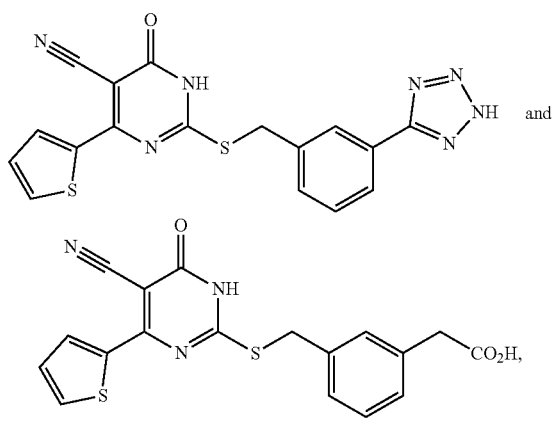

or a pharmaceutically acceptable salt thereof.

14. The compound of claim 1, wherein the compound is

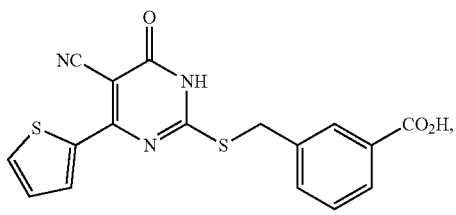 [SMILES: N#Cc1c(-c2cccs2)nc(SCc2cccc(C(=O)O)c2)[nH]c1=O]

or a pharmaceutically acceptable salt thereof.

15. The compound of claim 1, wherein the compound is

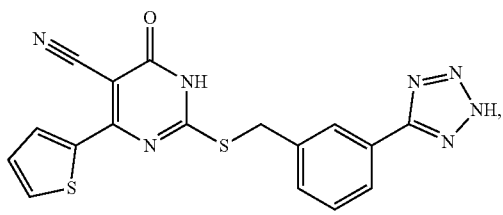 [SMILES: N#Cc1c(-c2cccs2)nc(SCc2cccc(-c3nn[nH]n3)c2)[nH]c1=O]

or a pharmaceutically acceptable salt thereof.

16. The compound of claim 1, wherein the compound is

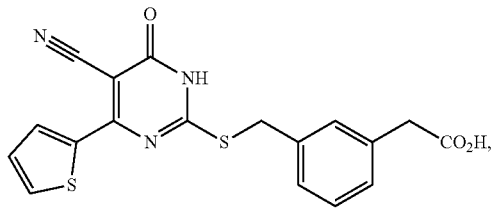 [SMILES: N#Cc1c(-c2cccs2)nc(SCc2cccc(CC(=O)O)c2)[nH]c1=O]

or a pharmaceutically acceptable salt thereof.

17. The compound of claim 1, wherein the compound is

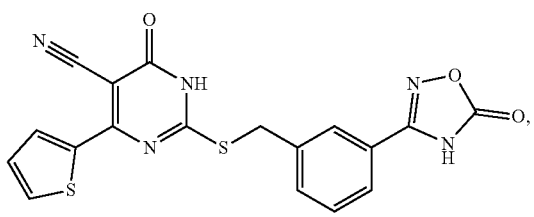 [SMILES: N#Cc1c(-c2cccs2)nc(SCc2cccc(-c3noc(=O)[nH]3)c2)[nH]c1=O]

or a pharmaceutically acceptable salt thereof.

* * * * *